US011802154B2

(12) United States Patent
Mack et al.

(10) Patent No.: US 11,802,154 B2
(45) Date of Patent: Oct. 31, 2023

(54) HUMANIZED ANTI-CD200 ANTIBODIES AND USES THEREOF

(71) Applicant: Alexion Pharmaceuticals, Inc., Boston, MA (US)

(72) Inventors: Taneisha Ann-Tanara Mack, East Hampton, CT (US); Douglas L. Sheridan, Branford, CT (US); Tadas Panavas, Madison, CT (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 414 days.

(21) Appl. No.: 16/954,562

(22) PCT Filed: Dec. 20, 2018

(86) PCT No.: PCT/US2018/066855
§ 371 (c)(1),
(2) Date: Oct. 20, 2020

(87) PCT Pub. No.: WO2019/126536
PCT Pub. Date: Jun. 27, 2019

(65) Prior Publication Data

US 2021/0230273 A1 Jul. 29, 2021

Related U.S. Application Data

(60) Provisional application No. 62/608,300, filed on Dec. 20, 2017.

(51) Int. Cl.
*C07K 16/28* (2006.01)
*G01N 33/68* (2006.01)

(52) U.S. Cl.
CPC ..... *C07K 16/2803* (2013.01); *G01N 33/6854* (2013.01); *C07K 2317/24* (2013.01); *C07K 2317/31* (2013.01); *C07K 2317/52* (2013.01); *C07K 2317/55* (2013.01); *C07K 2317/56* (2013.01); *C07K 2317/92* (2013.01); *C07K 2317/94* (2013.01); *G01N 2333/70503* (2013.01)

(58) Field of Classification Search
CPC ............ C07K 2317/94; C07K 2317/24; C07K 16/2803
USPC ...................................................... 424/133.1
See application file for complete search history.

(56) References Cited

U.S. PATENT DOCUMENTS

| | | | |
|---|---|---|---|
| 5,403,484 | A | 4/1995 | Ladner et al. |
| 5,595,721 | A | 1/1997 | Kaminski et al. |
| 6,090,382 | A | 7/2000 | Salfeld et al. |
| 6,258,562 | B1 | 7/2001 | Salfeld et al. |
| 6,338,851 | B1 | 1/2002 | Gorczynski |
| 6,652,858 | B2 | 11/2003 | Gorczynski et al. |
| 6,749,854 | B2 | 6/2004 | Gorczynski et al. |
| 6,955,811 | B2 | 10/2005 | Gorczynski et al. |
| 6,984,625 | B2 | 1/2006 | Gorczynski |
| 7,238,352 | B2 | 7/2007 | Gorczynski et al. |
| 7,368,535 | B2 | 5/2008 | Gorczynski et al. |
| 7,408,041 | B2 | 8/2008 | Bowdish et al. |
| 7,422,739 | B2 | 9/2008 | Anderson et al. |
| 7,427,665 | B2 | 9/2008 | Bowdish et al. |
| 7,435,412 | B2 | 10/2008 | Bowdish et al. |
| 7,435,415 | B2 | 10/2008 | Gelber |
| 7,435,803 | B2 | 10/2008 | Hansen et al. |
| 7,452,536 | B2 | 11/2008 | Gorczynski et al. |
| 7,598,353 | B2 | 10/2009 | Bowdish et al. |
| 7,714,110 | B2 | 5/2010 | Bowdish et al. |
| 7,887,798 | B2 | 2/2011 | Gorczynski et al. |
| 7,915,000 | B2 | 3/2011 | Bowdish et al. |
| 8,075,884 | B2 | 12/2011 | Bowdish et al. |
| 8,114,403 | B2 | 2/2012 | Bowdish et al. |
| 8,187,877 | B2 | 5/2012 | Bowdish et al. |
| 8,252,285 | B2 | 8/2012 | Rother et al. |
| 8,637,014 | B2 | 1/2014 | Rother et al. |
| 8,709,415 | B2 | 4/2014 | Bowdish et al. |
| 8,840,885 | B2 | 9/2014 | Bowdish et al. |
| 8,986,684 | B2 | 3/2015 | Wang |
| 8,999,328 | B2 | 4/2015 | Bowdish et al. |
| 9,000,133 | B2 | 4/2015 | Bowdish et al. |
| 9,085,623 | B2 | 7/2015 | Rother et al. |
| 9,150,661 | B2 | 10/2015 | Bowdish et al. |
| 9,180,186 | B2 | 11/2015 | Faas McKnight et al. |

(Continued)

FOREIGN PATENT DOCUMENTS

| | | |
|---|---|---|
| JP | H0246297 A | 2/1990 |
| WO | 85/03508 A1 | 8/1985 |

(Continued)

OTHER PUBLICATIONS

Burd et al (Nat Med. Dec. 2020 ; 26(12): 1852-1858. doi:10.1038/s41591-020-1089-8).*
Mehadevan et al (Journal for ImmunoTherapy of Cancer (2019) 7:227).*
MacCallum et al. (J. Mol. Biol. (1996) 262:732-745).*
Vajdos et al. ((2002) J. Mol. Biol. 320, 415-428).*
Wu et al. (J. Mol. Biol. (1999) 294, 151-162).*
Vajda et al., Current Opinion in Structural Biology, 67 pp. 226-231).*
Marks et al., J. Biol. Chem. 295(29) 9823-9837 (2020).*

(Continued)

*Primary Examiner* — Lynn A Bristol
(74) *Attorney, Agent, or Firm* — Nelson Mullins Riley & Scarborough LLP; Jane E. Remillard, Esq.; Jill Gorny Sloper, Esq.

(57) ABSTRACT

Provided herein are antibodies, or antigen binding portions thereof, that bind to CD200. Also provided are uses of these proteins in therapeutic applications, such as the treatment of cancer and in conjunction with organ transplantation. Also provided are nucleic acids encoding the heavy and/or light chain variable regions (or heavy and/or light chains) of the antibodies, vectors comprising the nucleic acids, and cells that produce the antibodies.

19 Claims, 13 Drawing Sheets

Specification includes a Sequence Listing.

(56) References Cited

U.S. PATENT DOCUMENTS

| | | | |
|---|---|---|---|
| 9,249,229 | B2 | 2/2016 | Bowdish et al. |
| 9,447,187 | B2 | 9/2016 | Wang et al. |
| RE46,323 | E | 2/2017 | Rother et al. |
| 9,862,767 | B2 | 1/2018 | Rother et al. |
| 2002/0168364 | A1 | 11/2002 | Gorczynski et al. |
| 2002/0192215 | A1 | 12/2002 | Hoek et al. |
| 2004/0018972 | A1 | 1/2004 | Gorczynski et al. |
| 2004/0054145 | A1 | 3/2004 | Gorczynski |
| 2004/0175692 | A1 | 9/2004 | Bowdish et al. |
| 2004/0198661 | A1 | 10/2004 | Bowdish et al. |
| 2005/0048069 | A1 | 3/2005 | Gorczynski et al. |
| 2005/0074452 | A1 | 4/2005 | Bowdish et al. |
| 2005/0107314 | A1 | 5/2005 | Gorczynski et al. |
| 2005/0118163 | A1 | 6/2005 | Mizushima et al. |
| 2005/0129690 | A1 | 6/2005 | Bowdish et al. |
| 2005/0169870 | A1 | 8/2005 | Truitt et al. |
| 2006/0057651 | A1 | 3/2006 | Bowdish et al. |
| 2006/0153846 | A1 | 7/2006 | Krause et al. |
| 2007/0036786 | A1 | 2/2007 | Tuaillon et al. |
| 2007/0065438 | A1 | 3/2007 | Liversidge et al. |
| 2009/0053222 | A1 | 2/2009 | Gorczynski et al. |
| 2010/0196374 | A1 | 8/2010 | Wang |
| 2010/0239598 | A1 | 9/2010 | Bowdish et al. |
| 2010/0285030 | A1 | 11/2010 | Bowdish et al. |
| 2010/0291085 | A1 | 11/2010 | Rother et al. |
| 2013/0158236 | A1 | 6/2013 | Bowdish et al. |
| 2013/0189258 | A1 | 7/2013 | Rother et al. |
| 2013/0202602 | A1 | 8/2013 | Faas McKnight et al. |
| 2014/0170143 | A1 | 6/2014 | Wang et al. |
| 2015/0368341 | A1 | 12/2015 | Bowdish et al. |
| 2016/0009803 | A1 | 1/2016 | Rother et al. |
| 2016/0033514 | A1 | 2/2016 | McKnight et al. |
| 2021/0087267 | A1* | 3/2021 | Miano .............. A61K 39/39591 |

FOREIGN PATENT DOCUMENTS

| | | | |
|---|---|---|---|
| WO | 94/28027 | A1 | 12/1994 |
| WO | 97/21450 | A1 | 6/1997 |
| WO | 99/24565 | A1 | 5/1999 |
| WO | 01/87336 | A1 | 11/2001 |
| WO | 02/11762 | A2 | 2/2002 |
| WO | 02/42332 | A2 | 5/2002 |
| WO | 02/059280 | A2 | 8/2002 |
| WO | 02/095030 | A2 | 11/2002 |
| WO | 2004/060295 | A2 | 7/2004 |
| WO | 2004/078938 | A2 | 9/2004 |
| WO | 2005/115453 | A2 | 12/2005 |
| WO | 2006/020266 | A2 | 2/2006 |
| WO | 2006/031370 | A2 | 3/2006 |
| WO | 2006/082515 | A2 | 8/2006 |
| WO | 2007/037795 | A2 | 4/2007 |
| WO | 2007/084321 | A2 | 7/2007 |
| WO | 2008/089022 | A2 | 7/2008 |
| WO | 2009/014744 | A1 | 1/2009 |
| WO | 2009/014745 | A1 | 1/2009 |
| WO | 2009/037190 | A2 | 3/2009 |
| WO | 2009/83602 | A1 | 7/2009 |
| WO | 2011/100538 | A1 | 8/2011 |
| WO | 2012/106634 | A1 | 8/2012 |
| WO | 2016/154290 | A1 | 9/2016 |
| WO | 2018/102594 | A1 | 6/2018 |
| WO | 2019/126536 | A1 | 6/2019 |
| WO | 2019126133 | A1 | 6/2019 |

OTHER PUBLICATIONS

Akbar et al., Cell Reports 34, 108856, Mar. 16, 2021.*

Lo et al., BMC Genomics vol. 22, Article No. 116.* clinicaltrials.gov/ct2/show/NCT02987504 (Jul. 18, 2018).*

Shao et al (Oncotarget, 2023, vol. 14, pp. 96-103).*

Almasri, Nidal M. et al., "Reduced Expression of CD20 Antigen as a Characteristic Marker for Chronic Lymphocytic Leukemia," American Journal of Hematology, vol. 40:259-263 (1992).

Banerjee, Debatri et al., "Blocking CD200-CD200 receptor axis augments NOS-2 expression and aggravates experimental autoimmune uveoretinitis in Lewis rats," Ocular Immunology and Inflammation, vol. 12(2):115-125 (2004).

Barclay, A. Neil et al., "CD200 and membrane protein interactions in the control of myeloid cells," Trends in Immunology, vol. 23(6):285-290 (2002).

Bello, Celeste et al., "Monoclonal Antibodies for B-Cell Lymphomas: Rituximab and Beyond," Hematology, pp. 233-242 (2007).

Borriello, Frank et al., "MRC OX-2 Defines a Novel T Cell Costimulatory Pathway," The Journal of Immunology, vol. 158:4548-4554 (1997).

Broderick, Cathryn et al., "Constitutive Retinal CD200 Expression Regulates Resident Microglia and Activation State of Inflammatory Cells during Experimental Autoimmune Uveoretinitis," American Journal of Pathology, vol. 161 (5):1669-1677 (2002).

Burge, Daniel J. et al., "Pharmacokinetic and Pharmacodynamic Properties of TRU-015, a CD20-Directed Small Modular Immunopharmaceutical Protein Therpeutic, in Patients with Rheumatoid Arthritis: A Phase I, Open-Label, Dose-Escalation ClinicalStudy," Clinical Therapeutics, vol. 30(10):1806-1816 (2008).

Chen, Dang-Xiao et al., "Synthetic peptides from the N-terminal regions of CD200 and CD200R1 modulate immunosuppressive and anti-inflammatory effects of CD200-CD200R1 interaction," International Immunology, vol. 17 (3):289-296 (2005).

Chen, Z. et al., "Cloning and characterization of the murine homologue of the rat/human MRC OX-2 gene," Biochimica et Biophysica Acta, vol. 1362:6-10 (1997).

Cheng, Dang-Xiao et al., "Discrete Monoclonal Antibodies Define Functionally Important Epitopes in the CD200 Molecule Responsible for Immunosuppression Function," Transplantation, vol. 79:282-288 (2005).

Cherwinski, Holly M. et al., "The CD200 Receptor Is a Novel and Potent Regulator of Murine and Human Mast Cell Function," The Journal of Immunology, vol. 174:1348-1356 (2005).

Chi, E. et al., "Physical stability of proteins in aqueous solution: mechanism and driving forces in nonnative protein aggregation," Pharmaceutical Research, vol. 20:1325-1336 (2003).

Cui, Weiguo et al., "CD200 and its receptor, CD200R, modulate bone mass via the differentiation of osteoclasts," PNAS, vol. 104(36):14436-14441 (2007).

Ebert, Ellen C. et al., "Selective Immunosuppressive Action of a Factor Produced by Colon Cancer Cells," Cancer Research, vol. 50:6158-6161 (1990).

Ennishi, D. et al., "CD5 expression is potentially predictive of poor outcome among biomarkers in patients with diffuse large B-cell lymphoma receiving rituximab plus Chop therapy," Annals of Oncology, vol. 19:1921-1926 (2008).

Fallarino, Francesca et al., "Murine Plasmacytoid Dendritic Cells Initiate the Immunosuppressive Pathway of Tryptophan Catabolism in Response to CD200 Receptor Engagement," The Journal of Immunology, vol. 173:3748-3754 (2004).

Frediberg, Jonathan W., "Unique Toxicities and Resistance Mechanisms Associated with Monoclonal Antibody Therapy," Hematology, pp. 329-334 (2005).

Gorczynski et al., "Breast Cancer Cell CD200 Expression Regulates Immune Response to EMT6 Tumor Cells in Mice," Breast Cancer Research and Treatment, vol. 123(2): 405-415 (2009).

Gorczynski, Laura et al., "Evidence That an Ox-2-Positive Cell Can Inhibit the Stimulation of Type 1 Cytokine Production by Bone Marrow-Derived B7-1 (and B7-2)-Positive Dendritic Cells," The Journal of Immunology, vol. 162:774-781 (1999).

Gorczynski, R. et al., "An immunoadhesin incorporating the molecule OX-2 is a potent immunosuppressant that prolongs Alto- and Xenograftsurvival," FASEB Journal, vol. 13(5):A983, Poster Presentation 712.35 (1999).

Gorczynski, R. et al., "Dendritic Cells Expressing TGFbeta/IL-10, and Cho Cells With OX-2, Increase Graft Survival," Transplantation Proceedings, vol. 33:1565-1566 (2001).

Gorczynski, R.M. et al., "A CD200FC Immunoadhesin Prolongs Rat Islet Xenograft Survival in Mice," Transplantation, vol. 73(12):1948-1953 (2002).

Gorczynski, R.M. et al., "Anti-Rat OX-2 Blocks Increased Small Intestinal Transplant Survival After Portal Vein Immunization," Transplantation Proceedings, vol. 31:577-578 (1999).

(56) References Cited

OTHER PUBLICATIONS

Gorczynski, R.M. et al., "Evidence for Persistent Expression of OX2 as a Necessary Component of Prolonged Renal Allograft Survival Following Portal Vein Immunization," Clinical Immunology, vol. 97(1):69-78 (2000).
Gorczynski, R.M. et al., "Evidence of a role for CD200 in regulation of immune rejection of leukaemic tumour cells in C57BL/6 mice," Clin. Exp. Immunol., vol. 126:220-229 (2001).
Gorczynski, R.M. et al., "Persistent expression of OX-2 is necessary for renal allograft survival," FASEB Journal, vol. 14(6):A1069, Poster Presentation No. 102.4 (2000).
Gorczynski, R.M. et al., "Structural and Functional Heterogeneity in the CD200R Family of Immunoregulatory Molecules and their Expression at the Feto-maternal interface," American Journal of Reproductive Immunology, vol. 52:147-163 (2004).
Gorczynski, R.M. et al., "Synergy in Induction of Increased Renal Allograft Survival after Portal Vein Infusion of Dendritic Cells Transduced to Expression TGFbeta and IL-10, along with Administration of Cho Cells Expressing the Regulatory Molecule OX-2," Clinical Immunology, vol. 95(3):182-189 (2000).
Gorczynski, Reg M., "Evidence for an Immunoregulatory Role of OX2 with Its Counter Ligand (OX2L) in the Regulation of Transplant Rejection, Fetal Loss, Autoimmunity and Tumor Growth," Archivum Immunologiae et Therapiae Experimentalis, vol. 49:303-309 (2001).
Gorczynski, Reginald et al., "CD200 Is a Ligand for All Members of the CD200R Family of Immunoregulatory Molecules," The Journal of Immunology, vol. 172:7744-7749 (2004).
Gorczynski, Reginald M. et al., "An Immunoadhesin Incorporating the Molecule OX-2 Is a Potent Immunosuppressant That Prolongs Allo-and Xenograft Survival," The Journal of Immunology, vol. 163:1654-1660 (1999).
Gorczynski, Reginald M. et al., "Anti-CD200R Amerliorates Collagen-Induced Arthritis in Mice," Clinical Immunology, vol. 104(3):256-264 (2002).
Gorczynski, Reginald M. et al., "Augmented Induction of CD4+ CD25+ Treg using Monoclonal Antibodies to CD200R," Transplantation, vol. 79:488-491 (2005).
Gorczynski, Reginald M. et al., "CD200 Immunoadhesin Suppresses Collagen-Induced Arthritis in Mice," Clinical Immunology, vol. 101(3):328-334 (2001).
Gorczynski, Reginald M. et al., "Increased Expression of the Novel Molecule OX-2 is Involved in Prolongation of Murine Renal Allograft Survival," Transplantation, vol. 65(8):1106-1114 (1998).
Gorczynski, Reginald M. et al., "Induction of Tolerance-Inducing Antigen-Presenting Cells in Bone Marrow Cultures in Vitro Using Monoclonal Antibodies to CD200R," Transplantation, vol. 77(8):1138-1144 (2004).
Gorczynski, Reginald M. et al., "Receptor Engagement on Cells Expressing a Ligand for the Tolerance-Inducing Molecule OX2 Induces an Immunoregulatory Population That Inhibits Alloreactivity in Vitro and in Vivo," The Journal of Immunology, vol. 165:485-486(2000).
Gorczynski, Reginald M., "CD200 and its receptors as targets for immunoregulation," Current Opinion in Investigational Drugs, vol. 6(5):483-488 (2005).
Gorczynski, Reginald M., "Transplant tolerance modifying antibody to CD200 receptor, but not CD200, alters cytokine production profile from stimulated macrophages," Eur. J. Immunol., vol. 31:2331-2337 (2001).
Hatherley, Deborah et al., "The CD200 and CD200 receptor cell surface proteins interact through their N-terminal immunoglobulin-like domains," Eur. J. Immunol., vol. 34:1688-1694 (2004).
Hernandez-Ilizaliturri, F.J. et al., "Strategies to overcoming rituximab-chemotherapy resistance by targeting the autophagy pathway using bortezomib in combination with the BCL-2 inhibitor obatoclax in non-Hodgkin's lymphomas (NHL)," Journal of Clinical Oncology, 2009 ASCO Annual Meeting Proceedings, vol. 27(15S), Poster Presentation No. 8543, 1 page (2009).
Hoek, R.M., et al., "Macrophage regulation by the B7.1/2 homologue OX2?" FASEB Journal, vol. 14(6):A1232, Poster Presentation No. 193.1 (2000).
Hoek, Robert M., "Down-Regulation of the Macrophage Lineage Through Interaction with OX2 (CD200)," Science, vol. 290(5497):1768-1771 (2000).
Holodick, Nichol E. et al., "Adult BM generates CD5+ B1 cells containing abundant N-region additions," Eur. J. Immunol., vol. 39(9):2383-2394 (2009).
Hutchings, N.J. et al., "Interactions of Cytoplasmic Region of OX2R are Consistent wtih an Inhibitory Function," Annual Congress of the British Society for Immunology, vol. 101(Suppl. 1), Poster Presentation No. 10.6, 1 page (2000).
International Preliminary Report on Patentability, PCT/US2018/066174, dated Jun. 23, 2020, 14 pages.
International Preliminary Report on Patentability. PCT/US2018/066855, dated Jun. 23, 2020, 8 pages.
International Search Report and Written Opinion, PCT/US2018/066174, dated Jun. 4, 2019, 22 pages.
International Search Report and Written Opinion. PCT/US2018/066855, dated Mar. 27, 2019, 12 pages.
Jorgensen, G. et al., "Recent trends in stabilising peptides and proteins in pharmaceutical formulation considerations in the choice of excipients," Expert Opinion on Drug Delivery, vol. 6 (11):66-108 (2009).
U.S. Appl. No. 16/954,868, filed Jun. 17, 2020, Dino Miano.
U.S. Appl. No. 13/521,671, filed Apr. 17, 2013, Susan Faas McKnight.
U.S. Appl. No. 14/827,693, filed Aug. 17, 2015, Susan Faas McKnight.
U.S. Appl. No. 13/983,415, filed Nov. 26, 2013, Yi Wang.
U.S. Appl. No. 14/739,862, filed Jun. 15, 2015, Russell P. Rother.
U.S. Appl. No. 13/578,367, filed Jan. 18, 2013, Russell P. Rother.
U.S. Appl. No. 12/452,772, filed Apr. 5, 2010, Yi Wang.
U.S. Appl. No. 14/080,457, filed Nov. 14, 2013, Russell P. Rother.
U.S. Appl. No. 13/533,546, filed Jun. 26, 2012, Russell P. Rother.
U.S. Appl. No. 12/670,379, filed Jul. 20, 2010, Russell P. Rother.
U.S. Appl. No. 12/087,683, filed Jan. 14, 2009, Katherine S. Bowdish.
U.S. Appl. No. 13/311,910, filed Dec. 6, 2011, Katherine S. Bowdish.
U.S. Appl. No. 13/771,911, filed Feb. 20, 2013, Katherine S. Bowdish.
U.S. Appl. No. 10/379,151, filed Mar. 4, 2003, Katherine S. Bowdish.
U.S. Appl. No. 10/433,207, filed May 30, 2003, Katherine S. Bowdish.
U.S. Appl. No. 12/286,759, filed Sep. 30, 2008, Katherine S. Bowdish.
U.S. Appl. No. 13/029,021, filed Feb. 16, 2011, Katherine S. Bowdish.
U.S. Appl. No. 10/736,188, filed Dec. 15, 2003, Katherine S. Bowdish.
U.S. Appl. No. 10/894,672, filed Jul. 20, 2004, Katherine S. Bowdish.
U.S. Appl. No. 12/221,134, filed Jul. 30, 2008, Katherine S. Bowdish.
U.S. Appl. No. 12/221,122, filed Jul. 30, 2008, Katherine S. Bowdish.
U.S. Appl. No. 12/715,303, filed Mar. 1, 2010, Katherine S. Bowdish.
U.S. Appl. No. 13/344,195, filed Jan. 5, 2012, Katherine S. Bowdish.
U.S. Appl. No. 10/996,316, filed Nov. 23, 2004, Katherine S. Bowdish.
U.S. Appl. No. 11/171,567, filed Jun. 30, 2005, Katherine S. Bowdish.
U.S. Appl. No. 11/985,322, filed Nov. 13, 2007, Katherine S. Bowdish.
U.S. Appl. No. 13/072,470, filed Mar. 25, 2011, Katherine S. Bowdish.
U.S. Appl. No. 14/630,262, filed Feb. 24, 2015, Katherine S. Bowdish.
U.S. Appl. No. 13/521,671, Jun. 23, 2020.
U.S. Appl. No. 13/521,671, Mar. 11, 2015.
U.S. Appl. No. 13/521,671, Nov. 10, 2014.
U.S. Appl. No. 14/827,693, Apr. 3, 2018.
U.S. Appl. No. 14/827,693, Aug. 16, 2017.

(56) References Cited

OTHER PUBLICATIONS

U.S. Appl. No. 14/827,693, May 24, 2017.
U.S. Appl. No. 13/983,415, May 6, 2016.
U.S. Appl. No. 13/983,415, Dec. 24, 2015.
U.S. Appl. No. 13/983,415, Aug. 24, 2015.
U.S. Appl. No. 13/983,415, May 22, 2015.
U.S. Appl. No. 14/739,862, Nov. 1, 2017.
U.S. Appl. No. 14/739,862, Sep. 25, 2017.
U.S. Appl. No. 14/739,862, Jun. 7, 2017.
U.S. Appl. No. 13/578,367, Jun. 11, 2015.
U.S. Appl. No. 13/578,367, Mar. 5, 2015.
U.S. Appl. No. 13/578,367, Jul. 7, 2014.
U.S. Appl. No. 13/578,367, Feb. 20, 2014.
U.S. Appl. No. 12/452,772, Nov. 12, 2014.
U.S. Appl. No. 12/452,772, Mar. 13, 2014.
U.S. Appl. No. 12/452,772, May 25, 2012.
U.S. Appl. No. 12/452,772, Oct. 13, 2011.
U.S. Appl. No. 12/452,772, Aug. 4, 2011.
U.S. Appl. No. 12/670,379, Mar. 26, 2012.
U.S. Appl. No. 12/670,379, Oct. 19, 2011.
U.S. Appl. No. 12/670,379, Jul. 26, 2011.
U.S. Appl. No. 13/533,546, Sep. 23, 2013.
U.S. Appl. No. 13/533,546, May 2, 2013.
U.S. Appl. No. 13/533,546, Mar. 14, 2013.
U.S. Appl. No. 14/080,457, Oct. 14, 2016.
U.S. Appl. No. 12/087,683, Aug. 5, 2011.
U.S. Appl. No. 12/087,683, May 24, 2011.
U.S. Appl. No. 12/087,683, Jan. 4, 2011.
U.S. Appl. No. 12/087,683, Sep. 23, 2010.
U.S. Appl. No. 13/311,910, Dec. 13, 2013.
U.S. Appl. No. 13/311,910, Jul. 1, 2013.
U.S. Appl. No. 13/771,911, Oct. 23, 2014.
U.S. Appl. No. 13/771,911, Jul. 18, 2014.
U.S. Appl. No. 10/379,151, Jun. 4, 2008.
U.S. Appl. No. 10/379,151, Mar. 19, 2008.
U.S. Appl. No. 10/379,151, Sep. 24, 2007.
U.S. Appl. No. 10/379,151, Mar. 28, 2007.
U.S. Appl. No. 10/379,151, Jul. 13, 2006.
U.S. Appl. No. 10/379,151, Mar. 27, 2006.
U.S. Appl. No. 10/736,188, Apr. 3, 2008.
U.S. Appl. No. 10/736,188, Jul. 30, 2007.
U.S. Appl. No. 10/736,188, Jul. 26, 2006.
U.S. Appl. No. 10/894,672, Sep. 18, 2015.
U.S. Appl. No. 10/894,672, May 22, 2015.
U.S. Appl. No. 10/894,672, Feb. 24, 2014.
U.S. Appl. No. 10/894,672, Dec. 23, 2013.
U.S. Appl. No. 10/894,672, Dec. 28, 2009.
U.S. Appl. No. 10/894,672, May 12, 2009.
U.S. Appl. No. 10/894,672, Oct. 15, 2008.
U.S. Appl. No. 10/894,672, Mar. 19, 2008.
U.S. Appl. No. 10/894,672, Nov. 7, 2007.
U.S. Appl. No. 10/894,672, May 14, 2007.
U.S. Appl. No. 10/894,672, Feb. 1, 2007.
U.S. Appl. No. 12/221,134, May 29, 2009.
U.S. Appl. No. 12/221,134, Feb. 25, 2009.
U.S. Appl. No. 12/221,122, Dec. 1, 2009.
U.S. Appl. No. 12/221,122, Jul. 24, 2009.
U.S. Appl. No. 12/221,122, Apr. 30, 2009.
U.S. Appl. No. 12/221,122, Jan. 23, 2009.
U.S. Appl. No. 12/715,303, Oct. 26, 2011.
U.S. Appl. No. 12/715,303, Jul. 11, 2011.
U.S. Appl. No. 12/715,303, Nov. 8, 2010.
U.S. Appl. No. 12/715,303, Jul. 22, 2010.
U.S. Appl. No. 13/344,195, May 22, 2015.
U.S. Appl. No. 13/344,195, Apr. 9, 2014.
U.S. Appl. No. 13/344,195, Dec. 2, 2013.
U.S. Appl. No. 13/344,195, Oct. 8, 2013.
U.S. Appl. No. 10/996,316, May 28, 2008.
U.S. Appl. No. 10/996,316, May 19, 2008.
U.S. Appl. No. 10/996,316, May 12, 2008.
U.S. Appl. No. 10/996,316, Feb. 8, 2008.
U.S. Appl. No. 10/996,316, Nov. 7, 2007.
U.S. Appl. No. 10/996,316, May 14, 2007.
U.S. Appl. No. 10/996,316, Feb. 21, 2007.
U.S. Appl. No. 11/171,567, May 14, 2007.
U.S. Appl. No. 11/171,567, Feb. 14, 2007.
U.S. Appl. No. 11/985,322, Nov. 30, 2010.
U.S. Appl. No. 11/985,322, Jul. 30, 2010.
U.S. Appl. No. 11/985,322, Oct. 5, 2009.
U.S. Appl. No. 11/985,322, Jun. 11, 2009.
U.S. Appl. No. 13/072,470, Nov. 25, 2014.
U.S. Appl. No. 13/072,470, Jul. 17, 2014.
U.S. Appl. No. 13/072,470, Feb. 28, 2014.
U.S. Appl. No. 13/072,470, Jun. 22, 2012.
U.S. Appl. No. 13/072,470, Jan. 27, 2012.
U.S. Appl. No. 13/072,470, Sep. 8, 2011.
U.S. Appl. No. 10/433,207, Mar. 25, 2008.
U.S. Appl. No. 10/433,207, Oct. 31, 2007.
U.S. Appl. No. 10/433,207, May 2, 2007.
U.S. Appl. No. 10/433,207, Jul. 12, 2006.
U.S. Appl. No. 10/433,207, Mar. 29, 2006.
U.S. Appl. No. 12/286,759, Feb. 21, 2012.
U.S. Appl. No. 12/286,759, Oct. 21, 2011.
U.S. Appl. No. 12/286,759, May 20, 2011.
U.S. Appl. No. 13/029,021, May 14, 2014.
U.S. Appl. No. 13/029,021, Nov. 21, 2013.
U.S. Appl. No. 13/029,021, Jul. 20, 2012.
U.S. Appl. No. 13/029,021, Feb. 16, 2012.
U.S. Appl. No. 14/630,262, May 19, 2016.
Kausar, Fariha et al., "Ocrelizumab: a step forward in the evolution of B-cell therapy," Expert Opin. Biol. Ther., vol. 9 (7):889-895 (2009).
Kretz-Rommel and Bowdish, "Rationale for anti-CD200 immunotherapy in B-CLL and other hematologic malignancies: new concepts in blocking immune suppression," Expert Opinion on Biological Therapy, vol. 8(1), pp. 5-15 (2008).
Kretz-Rommel, A. et al., "Blockade of CD200 in the presence or absence of antibody effector function: implications for anti-CD200 therapy," J Immuno., vol. 180:699-705 (2008).
Kretz-Rommel, Anke et al., "CD200 Expression on Tumor Cells Suppresses Antitumor Immunity: New Approaches to Cancer Immunotherapy," The Journal of Immunology, vol. 178:5595-5605 (2007).
Kretz-Rommel, Anke et al., "The Immuno-Regulatory Protein CD200 Is Overexpressed in a Subset of B-Cell Chronic Lymphocytic Leukemias and Plays a Role in Down-Regulating the TH1 Immune Response," J. Immunother., vol. 27 (6):S46 (2004).
Levene, Adam P. et al., "Therapeutic monoclonal antibodies in oncology," Journal of the Royal Society of Medicine, vol. 98:146-152 (2005).
Lian, D. et al., "Synergy of Novel Anti-CD200 Antibody and Cyclosporine Enhances Myeloid-Derived Suppressor Cell Frequency and Leads to Long-Term Heart Allograft Survival," American Journal of Transplantation, vol. 11, Poster Board No. Session: P110.5-IV, p. 476, XP002739069, Apr. 4, 2011.
Mahadevan et al., American Society of Hematology (ASH) 52nd Annual Meeting and Exposition, Abstract 2465, 4 pages (2010).
Mahadevan, D. M.D. et al., "First-in-Human Phase I Dose Escalation Study of a Humanized Anti-CD200 Antibody (Samalizumab) in Patients with Advanced Stage B Cell Chronic Lymphocytic Leukemia (B-CLL) or Multiple Myeloma (MM)," Blood, vol. 116(21):2465-2467 (2010).
Marti, G.E. et al., "CD20 and CD5 Expression in B-Chronic Lymphocytic Leukemia," Ann. N.Y. Acad. Sci., vol. 651:480-483 (1992).
McWhirter, John R. et al., "Antibodies selected from combinatorial libraries block a tumor antigen that plays a key role in immunomodulation," PNAS, vol. 103(4):1041-1046 (2006).
Milani, Cannon et al., "Veltuzumab, an anti-CD20 mAb for the treatment of non-Hodgkin's lymphoma, chronic lymphocytic leukemia and immune thrombocytopenia purpura," Current Opinion in Molecular Therapeutics, vol. 11 (2):200-207 (2009).

(56) References Cited

OTHER PUBLICATIONS

Morschhauser, Franck et al., "Humanized Anti-CD20 Antibody, Veltuzumab, in Refractory/Recurrent Non-Hodgkin's Lymphoma: Phase I/II Results," Journal of Clinical Oncology, vol. 27(20):3346-3353 (2009).
Nathan, Carl et al., "Putting the brakes on innate immunity: a regulatory role for CD200?" Nature Immunology, vol. 2 (1):17-19 (2001).
Pallasch et al., "Disruption of T cell suppression in chronic lymphocytic leukemia by CD200 blockade," Leukemia Research, vol. 33(3), pp. 460-464 (2009).
Petermann, Kimberly B. et al., "CD200 is induced by ERK and is a potential therapeutic target in melanoma," The Journal of Clinical Investigation, vol. 117(12):3922-3929 (2007).
Preston, Sandy et al., "The leukocyte/neuron cell surface antigen OX2 binds to a ligand on macrophages," Eur. J. Immunol., vol. 27(8):1911-1918 (1997).
Ragheb, Rafik et al., "Preparation and functional properties of monoclonal antibodies to human, mouse and rat OX-2," Immunology Letters, vol. 68:311-315 (1999).
Ragheb, Rafik F.A. et al., "Exploration of OX-2 function in tolerance induction and graft acceptance using an anti-mouse OX-2 monoclonal antibody," Masters Abstracts International, vol. 38(4):971-972 (2000).
Ravandi et al., "Chronic lymphocytic leukemia (B-CLL) occurring with human immunodeficiency virus (HIV) infection: implications," Leukemia Research, vol. 27: 853-857 (2003).
Reddy, N.M. et al., Rituximab resistance and its association with changes in the internal domain of CD20 antigen and down-regulation of pro-apoptotic protein Bax and Bak in both rituximab-resistant cell lines (RRCL) and diffuse large B-cell lymphoma(DLBCL) patient (pt) samples, Journal of Clinical Oncology, 2006 ASCO Annual Meeting Proceedings, vol. 24(18S), Poster Presentation No. 17509 (2006).
Rijkers, Eva S.K. et al., "The inhibitory CD200R is differentially expressed on human and mouse T and B lymphocytes," Molecular Immunology, vol. 45:1126-1135 (2008).
Romagnani, Sergio, "Short Analytical Review, TH1 and TH2 in Human Diseases," Clinical Immunology and Immunopathology, vol. 80(3):225-235 (1996).
Rosenblum, Michael D. et al., "CD200 is a novel p53-target gene involved in apoptosis-associated immune tolerance," Blood, vol. 103(7):2691-2698 (2004).
Sequence alignment, 2015, 1 page.
Simelyte et al., "CD200-Fc, a novel antiarthritic biological agent that targets proinflammatory cytokine expression in the joint of mice with collagen-induced arthritis," Arthritis & Rheumatism, vol. 58(4), pp. 1038-1043 (2008).
Supplementary European Search Report for EP 11 73 2296, dated Sep. 30, 2013.
Taylor, Neil et al., "Enhanced Tolerance to Autoimmune Uveitis in CD200-Deficient Mice Correlates with a Pronounced Th2 Switch in Response to Antigen Challenge," The Journal of Immunology, vol. 174:143-154 (2005).
Tedder, Thomas F. et al., "Isolation and structure of a cDNA encoding the B1 (CD20) cell-surface antigen of human B lymphocytes," Proc. Natl. Acad. Sci. USA, vol. 85:208-212 (1988).
Teeling, Jessica L. et al., "The Biological Activity of Human CD20 Monoclonal Antibodies Is Linked to Unique Epitopes on CD20," The Journal of Immunology, vol. 177:362-371 (2006).
Transplantation Tech., Inc. WO02095030, "Modulation of CD200 Receptors as a Novel Method of Immunosuppression," Expert Opin. Ther. Patents, vol. 13(5):711-715 (2003).
Wang W. et al., "Antibody Structure Instability, and Formulation," Journal of Pharmaceutical Sciences, American Pharmaceutical Association, US,vol. 96 (1): 1-26(2007).
Wang W.,"Instability, stabilization, and formulation of liquid protein pharmaceuticals," International Journal of Pharmaceutics,vol. 185 (2):129-188 (1999).
Warne, I., "Development of high concentration protein biopharmaceuticals: The use of platform approaches in formulation development," European Journal of Pharmaceutics and Biopharmaceutics, vol. 78 (2):208-212 (2011).
Wright, G.J. et al., "The lymphoid/neuronal OX-2 glycoprotein Interacts with a novel protein expressed by macrophages," Tissue Antigens, vol. 55(Suppl. 1):11, Poster Presentation A. 9 (2000).
Wright, Gavin J. et al., "Lymphoid/Neuronal Cell Surface OX2 Glycoprotein Recognizes a Novel Receptor on Macrophages Implicated in the Control of Their Function," Immunity, vol. 13:233-242 (2000).
Zhang, Shuli et al., "Molecular Mechanisms of CD200 Inhibition of Mast Cell Activation," The Journal of Immunology, vol. 173:6786-6793 (2004).
Wright, Gavin J. et al.,]\"Characterization of the CD200 Receptor Interactions with CD200 Family in Mice and Humans and Their," J. Immunol., vol. 171:3034-3046 (2003).

* cited by examiner

VH

| | FR1 | CDR1 | FR2 | CDR2 | FR3 | CDR3 | FR4 |
|---|---|---|---|---|---|---|---|
| C2aB7 | EVQLQQSGPELVKPGASLKMSCKAS | GYSFTDYIIL | WVKQNHGKSLEWIG | HIDPYYGSSNYNLKFKG | KATLTVDKSSSTAYMQLNSLTSEDSAVYYCGR | SKRDYFDY | WGQGTTLTVSS |
| ALXN6000 | QVQLQQSGSELKKPGASVKISCKAS | GYSFTDYIIL | WVRQNPGKGLEWIG | HIDPYYGSSNYNLKFKG | RVTITADQSTTTAYMELSSLRSEDTAVYYCGR | SKRDYFDY | WGQGTTLTVSS |
| Ec (1-46) | QVQLVQSGAEVKKPGASVKVSCKAS | GYSFTDYIIL | WVRQAPGQGLEWMG | HIDPYYGSSNYNLKFKG | RVTMTRDTSTSTVYMELSSLRSEDTAVYYCAR | SKRDYFDY | WGQGTLVTVSS |
| IGHV1-69 | QVQLVQSGAEVKKPGSSVKVSCKAS | GYSFTDYIIL | WVRQAPGQGLEWMG | HIDPYYGSSNYNLKFKG | RVTITADESTSTAYMELSSLRSEDTAVYYCAR | SKRDYFDY | WGQGTLVTVSS |
| IGHV1-18 | QVQLVQSGAEVKKPGASVKVSCKAS | GYSFTDYIIL | WVRQAPGQGLEWMG | HIDPYYGSSNYNLKFKG | RVTMTTDTSTSTAYMELRSLRSDDTAVYYCAR | SKRDYFDY | WGQGTLVTVSS |
| IGHV1-2 | QVQLVQSGAEVKKPGASVKVSCKAS | GYSFTDYIIL | WVRQAPGQGLEWMG | HIDPYYGSSNYNLKFKG | RVTMTRDTSISTAYMELSRLRSDDTAVYYCAR | SKRDYFDY | WGQGTLVTVSS |
| IGHV1-3 | QVQLVQSGAEVKKPGASVKVSCKAS | GYSFTDYIIL | WVRQAPGQRLEWMG | HIDPYYGSSNYNLKFKG | RVTITRDTSASTAYMELSSLRSEDTAVYYCAR | SKRDYFDY | WGQGTLVTVSS |
| IGHV1-8 | QVQLVQSGAEVKKPGASVKVSCKAS | GYSFTDYIIL | WVRQATGQGLEWMG | HIDPYYGSSNYNLKFKG | RVTMTRNTSISTAYMELSSLRSEDTAVYYCAR | SKRDYFDY | WGQGTLVTVSS |
| IGHV5-10-1 | EVQLVQSGAEVKKPGESLRISCKGS | GYSFTDYIIL | WVRQMPGKGLEWMG | HIDPYYGSSNYNLKFKG | HVTISADKSISTAYLQWSSLKARTPPCITVRD | SKRDYFDY | WGQGTLVTVSS |
| IGHV1-45 | QMQLVQSGAEVKKTGSSVKVSCKAS | GYSFTDYIIL | WVRQAPGQALEWMG | HIDPYYGSSNYNLKFKG | RVTITRDRSMSTAYMELSSLRSEDTAMYYCAR | SKRDYFDY | WGQGTLVTVSS |
| IGHV1-58 | QMQLVQSGPEVKKPGTSVKVSCKAS | GYSFTDYIIL | WVRQARGQRLEWIG | HIDPYYGSSNYNLKFKG | RVTITRDMSTSTAYMELSSLRSEDTAVYYCAA | SKRDYFDY | WGQGTLVTVSS |
| IGHV7-4-1 | QVQLVQSGSELKKPGASVKVSCKAS | GYSFTDYIIL | WVRQAPGQGLEWMG | HIDPYYGSSNYNLKFKG | RFVFSLDTSVSTAYLQISSLKAEDTAVYYCAR | SKRDYFDY | WGQGTLVTVSS |

VK

| | | | | | | | |
|---|---|---|---|---|---|---|---|
| c2aB7_VK | DIQMTQSPSSMYASLGERVTITC | KASQDINSYLS | WFQQKPGKSPKTLIY | RANRLVD | GVPSRFSGSGSGQDYSLTISSLEYEDMGIYYC | LQYDEFPYT | FGGGTKLEIK |
| ALXN6000 | DIQMTQSPSSLSASIGDRVTITC | KASQDINSYLS | WFQQKPGKAPKLLIY | RANRLVD | GVPSRFSGSGSGTDYTLTISSLQPEDFAVYYC | LQYDEFPYT | FGGGTKLEIK |
| Ec (1-39) | DIQMTQSPSSLSASVGDRVTITC | KASQDINSYLS | WYQRKPGKAPKLLIY | RANRLVD | GVPSRFSGSGSGTDFTLTISSLQPEDFATYYC | LQYDEFPYT | FGQGTKVEIK |
| IGKV1-16 | DIQMTQSPSSLSASVGDRVTITC | KASQDINSYLS | WFQQKPGKAPKSLIY | RANRLVD | GVPSRFSGSGSGTDFTLTISSLQPEDFATYYC | LQYDEFPYT | FGQGTKLEIK |
| IGKV1D-33 | DIQMTQSPSSLSASVGDRVTITC | KASQDINSYLS | WYQQKPGKAPKLLIY | RANRLVD | GVPSRFSGSGSGTDFTFTISSLQPEDIATYYC | LQYDEFPYT | FGQGTKLEIK |
| IGKV1-12 | DIQMTQSPSSVSASVGDRVTITC | KASQDINSYLS | WYQQKPGKAPKLLIY | RANRLVD | GVPSRFSGSGSGTDFTLTISSLQPEDFATYYC | LQYDEFPYT | FGQGTKLEIK |

FIG. 1

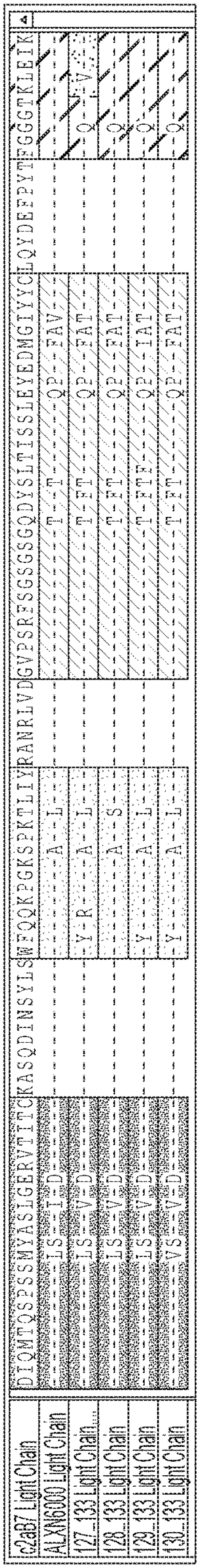
FIG. 3A
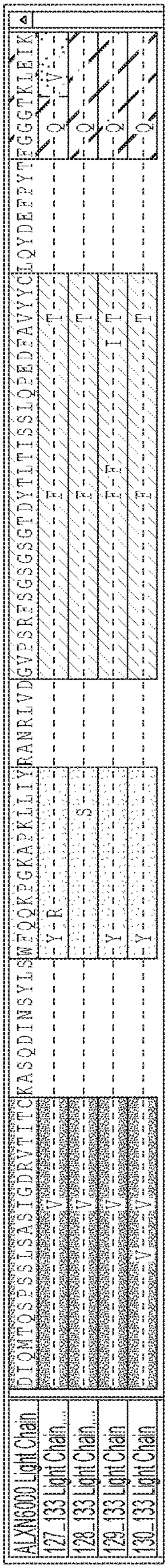
FIG. 3B
| | | | | | | | | | | | |
|---|---|---|---|---|---|---|---|---|---|---|---|
| | | FAB | hG2/G4 | | | TPP hG2/G$ | | | | | |
| TPP-100 | c2aB7 | pRAA131 | pRAA113 | pRAA125 | VR1 | TTP308 | | | | | |
| TPP-101 | ALXN6000 | pRAA132 | pRAA114 | pRAA126 | VR2 | TTP309 | | | | | |
| | | | | | | | | | | | |
| | | | | | | | | | | | |
| | pRAA133 | pRAA134 | pRAA135 | pRAA136 | pRAA137 | pRAA138 | pRAA139 | pRAA140 | pRAA141 | pRAA142 | FAB |
| pRAA127 | TPP-102 | TPP-106 | TPP-110 | TPP-114 | TPP-118 | TPP-122 | TPP-126 | TPP-130 | TPP-134 | TPP-138 | |
| pRAA128 | TPP-103 | TPP-107 | TPP-111 | TPP-115 | TPP-119 | TPP-123 | TPP-127 | TPP-131 | TPP-135 | TPP-139 | |
| pRAA129 | TPP-104 | TPP-108 | TPP-112 | TPP-116 | TPP-120 | TPP-124 | TPP-128 | TPP-132 | TPP-136 | TPP-140 | |
| pRAA130 | TPP-105 | TPP-109 | TPP-113 | TPP-117 | TPP-121 | TPP-125 | TPP-129 | TPP-133 | TPP-137 | TPP-141 | |
FIG. 4

| | | Light Chain | Light Chain | Light Chain | Light Chain | Light Chain | Light Chain | Light Chain | Light Chain | Light Chain | Light Chain |
|---|---|---|---|---|---|---|---|---|---|---|---|
| | | **pME022** | **pME023** | **pME024** | **pME025** | **pME026** | **pME027** | **pME028** | **pME029** | **pME030** | **pRAA128** |
| Heavy Chain | **pME001** | TPP-542 | TPP-563 | TPP-584 | TPP-605 | TPP-626 | TPP-647 | TPP-668 | TPP-689 | TPP-710 | TPP-731 |
| Heavy Chain | **pME002** | TPP-543 | TPP-564 | TPP-585 | TPP-606 | TPP-627 | TPP-648 | TPP-669 | TPP-690 | TPP-711 | TPP-732 |
| Heavy Chain | **pME003** | TPP-544 | TPP-565 | TPP-586 | TPP-607 | TPP-628 | TPP-649 | TPP-670 | TPP-691 | TPP-712 | TPP-733 |
| Heavy Chain | **pME004** | TPP-545 | TPP-566 | TPP-587 | TPP-608 | TPP-629 | TPP-650 | TPP-671 | TPP-692 | TPP-713 | TPP-734 |
| Heavy Chain | **pME005** | TPP-546 | TPP-567 | TPP-588 | TPP-609 | TPP-630 | TPP-651 | TPP-672 | TPP-693 | TPP-714 | TPP-735 |
| Heavy Chain | **pME006** | TPP-547 | TPP-568 | TPP-589 | TPP-610 | TPP-631 | TPP-652 | TPP-673 | TPP-694 | TPP-715 | TPP-736 |
| Heavy Chain | **pME007** | TPP-548 | TPP-569 | TPP-590 | TPP-611 | TPP-632 | TPP-653 | TPP-674 | TPP-695 | TPP-716 | TPP-737 |
| Heavy Chain | **pME008** | TPP-549 | TPP-570 | TPP-591 | TPP-612 | TPP-633 | TPP-654 | TPP-675 | TPP-696 | TPP-717 | TPP-738 |
| Heavy Chain | **pME009** | TPP-550 | TPP-571 | TPP-592 | TPP-613 | TPP-634 | TPP-655 | TPP-676 | TPP-697 | TPP-718 | TPP-739 |
| Heavy Chain | **pME010** | TPP-551 | TPP-572 | TPP-593 | TPP-614 | TPP-635 | TPP-656 | TPP-677 | TPP-698 | TPP-719 | TPP-740 |
| Heavy Chain | **pME011** | TPP-552 | TPP-573 | TPP-594 | TPP-615 | TPP-636 | TPP-657 | TPP-678 | TPP-699 | TPP-720 | TPP-741 |
| Heavy Chain | **pME012** | TPP-553 | TPP-574 | TPP-595 | TPP-616 | TPP-637 | TPP-658 | TPP-679 | TPP-700 | TPP-721 | TPP-742 |
| Heavy Chain | **pME013** | TPP-554 | TPP-575 | TPP-596 | TPP-617 | TPP-638 | TPP-659 | TPP-680 | TPP-701 | TPP-722 | TPP-743 |
| Heavy Chain | **pME014** | TPP-555 | TPP-576 | TPP-597 | TPP-618 | TPP-639 | TPP-660 | TPP-681 | TPP-702 | TPP-723 | TPP-744 |
| Heavy Chain | **pME015** | TPP-556 | TPP-577 | TPP-598 | TPP-619 | TPP-640 | TPP-661 | TPP-682 | TPP-703 | TPP-724 | TPP-745 |
| Heavy Chain | **pME016** | TPP-557 | TPP-578 | TPP-599 | TPP-620 | TPP-641 | TPP-662 | TPP-683 | TPP-704 | TPP-725 | TPP-746 |
| Heavy Chain | **pME017** | TPP-558 | TPP-579 | TPP-600 | TPP-621 | TPP-642 | TPP-663 | TPP-684 | TPP-705 | TPP-726 | TPP-747 |
| Heavy Chain | **pME018** | TPP-559 | TPP-580 | TPP-601 | TPP-622 | TPP-643 | TPP-664 | TPP-685 | TPP-706 | TPP-727 | TPP-748 |
| Heavy Chain | **pME019** | TPP-560 | TPP-581 | TPP-602 | TPP-623 | TPP-644 | TPP-665 | TPP-686 | TPP-707 | TPP-728 | TPP-749 |
| Heavy Chain | **pME020** | TPP-561 | TPP-582 | TPP-603 | TPP-624 | TPP-645 | TPP-666 | TPP-687 | TPP-708 | TPP-729 | TPP-750 |
| Heavy Chain | **pME021** | TPP-562 | TPP-583 | TPP-604 | TPP-625 | TPP-646 | TPP-667 | TPP-688 | TPP-709 | TPP-730 | TPP-751 |
| Heavy Chain | **pRAA137** | TPP-753 | TPP-754 | TPP-755 | TPP-756 | TPP-757 | TPP-758 | TPP-759 | TPP-760 | TPP-761 | TPP-752 |

FIG. 7

HUMANIZED ANTI-CD200 ANTIBODIES AND USES THEREOF

RELATED APPLICATIONS

This application is a 35 U.S.C. 371 national stage filing of International Application No. PCT/US2018/066855, filed on Dec. 20, 2018, which claims priority to U.S. Provisional Application No. 62/608,300, filed on Dec. 20, 2017. The contents of the aforementioned applications are incorporated herein by reference.

SEQUENCE LISTING

The instant application contains a Sequence Listing which has been submitted electronically in ASCII format and is hereby incorporated by reference in its entirety. Said ASCII copy, created on Jun. 17, 2020, is named AXJ_242US_Sequence_Listing.txt and is 515,449 bytes in size.

BACKGROUND

CD200 is a highly conserved, type I transmembrane glycoprotein expressed on various cell types, including particularly on cells of the immune system (e.g., T-cells, B-cells, and dendritic cells (Barclay et al., *TRENDS Immunol.* 2002: 23)) as well as certain cancer cells. The protein interacts with its receptor CD200R on myeloid cells and sub-populations of T cells (Wright et al., *J. Immunol.* 2003 (171): 3034-3046 and Wright et al., *Immunity* 2000 (13): 233-242); the CD200:CD200R interaction delivers an immunomodulatory signal to cells and induces immunosuppression including apoptosis-associated immune tolerance (Rosenblum et al., 2004 *Blood* (103): 2691-2698).

Anti-CD200 targeted therapy has been proposed as an immunotherapeutic treatment for cancer, autoimmune disorders and for prolonging allograft survival (e.g., U.S. Pat. Nos. 7,408,041; 9,085,623; and U.S. Pat. Publ. No. 2014/0170143). For example, in an animal model of CLL, anti-CD200 antibody administration resulted in nearly complete tumor growth inhibition (Kretz-Rommel et al., *J. Immunol.* 2007; 178:5595-5605). CD200 knockout animal studies as well as experiments using antagonist anti-CD200 antibodies and recombinant CD200-Fc fusion proteins have also demonstrated that CD200 is an immunosuppressive agent in autoimmune disorders and during transplantation (e.g., Hoek et al., *Science* 2000; 290-1771; Gorczynski et al., *J Immunol* 1999; 163:1654-1660).

In early clinical trials for or adult patients with advanced stage B-cell chronic lymphocytic leukemia (B-CLL) or multiple myeloma (MM), samalizumab (ALXN6000), a humanized, anti-human CD200 antibody, was well tolerated at all doses studied, exhibited a dose-dependent biological and pharmacokinetic response, and exhibited initial evidence of anti-tumor activity (Mahadevan et al., 52nd American Society of Hematology (ASH) Annual Meeting and Exposition 2010, Abstract 2465). Initial pharmaceutical formulations of samalizumab were limited to 5 mg/ml and had stability issues at 4° C., with a propensity to aggregate. The drug concentration thus limited the maximum dose or weight/size of the patient. Additionally, samalizumab had a half-life of approximately 18 days. Given the promising properties of samalizumab, anti-CD200 antibodies which share the binding specificity of samalizumab, but have enhanced properties, including but not limited to improved potency, higher concentration, decreased infusion volume, decreased infusion time, increased half-life, and/or improved stability, are highly desirable.

SUMMARY

Provided herein are re-engineered anti-CD200 antibodies with improved properties, such as improved binding affinity, occupancy, and ligand blocking, over anti-CD200 antibodies, e.g., samalizumab.

In one aspect, provided herein is an isolated antibody which binds to human CD200 and comprises heavy and light chain variable regions, wherein the heavy chain variable region comprises the amino acid sequence set forth in SEQ ID NO: 20, and the light chain variable region comprises the amino acid sequence set forth in SEQ ID NO: 21, wherein the antibody has at least one amino acid substitution in the heavy chain variable region at a position selected from the group consisting of: A9, V11, K12, V18, V20, R38, A40, P41, P43, R44, M48, R67, V68, I70, R72, T174, A76, E82, S84, R87, and A97, and/or at least one amino acid substitution in the light chain variable region at a position selected from the group consisting of: S12, T69, F71, T72, Q79, P80, F83, A84, and T85, wherein the numbering is according to the amino acid sequence in SEQ ID NO: 20 for the heavy chain variable region and SEQ ID NO: 21 for the light chain variable region. In some embodiments, the alanine at position 97 of the heavy chain variable region is substituted with glycine and/or the alanine at position n84 of the light chain variable region is substituted with glycine.

In another aspect, provided herein is an isolated antibody which binds to human CD200 and comprises heavy and light chain variable region sequences selected from the group consisting of: SEQ ID NOs: 23 and 24; SEQ ID NOs: 26 and 27; SEQ ID NOs: 29 and 30; SEQ ID NOs: 32 and 33; SEQ ID NOs: 35 and 36; SEQ ID NOs: 38 and 39; SEQ ID NOs: 41 and 42; SEQ ID NOs: 44 and 45; SEQ ID NOs: 47 and 48; SEQ ID NOs: 50 and 51; SEQ ID NOs: 53 and 54; SEQ ID NOs: 56 and 57; SEQ ID NOs: 59 and 60; SEQ ID NOs: 62 and 63; SEQ ID NOs: 65 and 66; SEQ ID NOs: 68 and 69; SEQ ID NOs: 71 and 72; SEQ ID NOs: 74 and 75; SEQ ID NOs: 77 and 78; SEQ ID NOs: 80 and 81; SEQ ID NOs: 83 and 84; SEQ ID NOs: 86 and 87; SEQ ID NOs: 89 and 90; SEQ ID NOs: 92 and 93; SEQ ID NOs: 95 and 96; SEQ ID NOs: 98 and 99; SEQ ID NOs: 101 and 102; SEQ ID NOs: 104 and 105; SEQ ID NOs: 107 and 108; SEQ ID NOs: 110 and 111; SEQ ID NOs: 113 and 114; SEQ ID NOs: 116 and 117; SEQ ID NOs: 119 and 120; SEQ ID NOs: 122 and 123; SEQ ID NOs: 125 and 126; SEQ ID NOs: 128 and 129; SEQ ID NOs: 131 and 132; SEQ ID NOs: 134 and 135; SEQ ID NOs: 137 and 138; SEQ ID NOs: 140 and 141; SEQ ID NOs: 143 and 144; SEQ ID NOs: 146 and 147; SEQ ID NOs: 149 and 150; SEQ ID NOs: 152 and 153; SEQ ID NOs: 155 and 156; SEQ ID NOs: 158 and 159; SEQ ID NOs: 161 and 162; SEQ ID NOs: 164 and 165; SEQ ID NOs: 167 and 168; SEQ ID NOs: 170 and 171; SEQ ID NOs: 173 and 174; SEQ ID NOs: 176 and 177; and SEQ ID NOs: 179 and 180.

In another aspect, provided herein is an isolated antibody which binds to human CD200 and comprises heavy and light chain sequences selected from the group consisting of: SEQ ID NOs: 181 and 182, SEQ ID NOs: 183 and 184, and SEQ ID NOs: 185 and 186.

In some embodiments, the antibodies bind to human CD200 with a $K_D$ of $10^{-7}$M or less (e.g., $10^{-8}$M or less, or $10^{-9}$M or less), as determined, e.g., by plasmon surface resonance, such as Biacore. In some embodiments, the antibody binds to human CD200 with a $K_D$ between $10^{-7}$M and $10^{-11}$M, e.g., between $10^{-8}$M and $10^{-11}$M or between $10^{-9}$M and $10^{-11}$M.

In some embodiments, the antibodies further comprise a constant region. In some embodiments, the antibody is selected from the group consisting of an IgG1, IgG2, IgG3, IgG4, IgM, IgA1, IgA2, IgA, IgD, or IgE antibody. In some embodiments, the antibody is a humanized antibody.

In some embodiments, the antibodies comprise a modified Fc constant region with no effector function or decreased effector function (e.g., ADCC, CDC, or binding to one or more Fc receptors) relative to the effector function of the corresponding unmodified Fc constant region, e.g., a G2/G4 constant region comprising the amino acid sequence of SEQ ID NO: 4. In some embodiments, the antibody has an ADCC activity or CDC activity equal to or less than the ADCC activity or CDC activity of the antibody with a G2/G4 Fc constant region comprising the amino acid sequence of SEQ ID NO: 4. In some embodiments, the modified Fc constant region comprises (i) the CH1 and hinge regions of an IgG2 antibody; (ii) the CH2 and CH3 regions of an IgG4 antibody; or (iii) the CH1 and hinge regions of an IgG2 antibody and the CH2 and CH3 regions of an IgG4 antibody. In some embodiments, the modified Fc constant region lacks a hinge region.

In some embodiments, the antibodies are selected from the group consisting of a Fab fragment, a $F(ab')_2$ fragment, a Fab' fragment, an scFv fragment, a minibody, a diabody, or a triabody.

In some embodiments, the antibodies further comprise a detectable or therapeutic moiety.

In some embodiments, the antibodies further comprise a second binding specificity (e.g., bispecific antibodies).

In another aspect, provided herein are compositions (e.g., pharmaceutical compositions) comprising the anti-CD200 antibodies or bispecific antibodies described herein. In some embodiments, the composition comprises a carrier (e.g., a pharmaceutically acceptable carrier).

In another aspect, provided herein are kits comprising the anti-CD200 antibodies or bispecific antibodies described herein and instructions for use.

In another aspect, provided herein are nucleic acids and vectors (e.g., expression vectors) encoding the heavy and/or light chain variable region, or heavy and/or light chains, or antigen-binding portions thereof, of the anti-CD200 antibodies described herein, as well as host cells comprising the nucleic acids or vectors. In some embodiments, the nucleic acid comprises the nucleotide sequence selected from the group consisting of: SEQ ID NOs: 187-234.

In another aspect, provided herein is a method of treating cancer (e.g., a solid tumor or liquid tumor) comprising administering to a subject in need thereof a therapeutically effective amount of an anti-CD200 antibody or bispecific antibody described herein. In some embodiments, the cancer comprises cancer cells that express CD200. In some embodiments, the cancer cells overexpress CD200 relative to normal cells of the same histological type as the cells from which the cancer cells are derived. In some embodiments, the cancer comprises cancer cells that express CD5. In some embodiments, the cancer is resistant to anti-CD20 antibody therapy. In some embodiments, the subject is immunocompetent.

Exemplary cancers include neural crest cell cancer, plasma cell cancer, a lymphoma, leukemia, ovarian cancer, skin cancer, liver cancer, lung cancer, renal cancer, breast cancer, colon cancer, pancreatic cancer, thyroid cancer, testicular cancer, cervical cancer, head and neck cancer, a cancer of the eye, stomach cancer, prostate cancer, neuroblastoma, and myeloma. In one embodiment, the cancer is chronic lymphocytic leukemia (CLL) or acute myelogenous leukemia (AML). In another embodiment, the cancer is B cell CLL. In another embodiment, the cancer is multiple myeloma.

In some embodiments, the methods described herein further comprise administering a second agent (e.g., anti-cancer agent such as a chemotherapeutic agent) or therapy (e.g., anti-cancer therapy such as radiation therapy).

In another aspect, provided herein is a method of treating an autoimmune disease comprising administering to a subject in need thereof a therapeutically effective amount of an anti-CD200 antibody or bispecific antibody described herein. Exemplary autoimmune diseases include rheumatoid arthritis, inflammatory bowel disease (including ulcerative colitis and Crohn's disease), systemic lupus erythematosus, multiple sclerosis, Hashimoto's thyroiditis, pernicious anemia, Addison's disease, type I diabetes, dermatomyositis, Sjogren's syndrome, lupus erythematosus, myasthenia gravis, Reiter's syndrome, Grave's disease, psoriasis, and autoimmune hemolytic anemia.

In another aspect, provided herein is a method of inhibiting an immune response in a subject who has received or will receive a cell, tissue, or organ transplant, wherein said method comprises administering to the subject an effective amount of an anti-CD200 antibody or bispecific antibody described herein. In some embodiments, the method further comprises administering an immunosuppressive or immunomodulatory drug. In some embodiments, the immune response is a humoral response or antibody-mediated response. In some embodiments, the method prevents graft rejection or promotes graft survival. In some embodiments, the method comprises administering the antibody, or antigen-binding fragment, prior to receiving the cell, tissue, or organ transplant. In some embodiments, the method comprises administering the antibody, or antigen-binding fragment thereof, during a rejection episode (e.g., acute or chronic humoral rejection of a grafted cell, tissue, or organ) of the transplant. In some embodiments, the subject is a recipient of a hematopoietic cell or bone marrow transplant, an allogeneic transplant of pancreatic islet cells, or a solid organ transplant selected from the group consisting of: a heart, a kidney-pancreas, a kidney, a liver, a lung, and a pancreas.

In another aspect, provided herein is a method for prolonging the survival of an allograft, the method comprising administering to a recipient mammal in need thereof an anti-CD200 antibody or bispecific antibody described herein in an amount and with a frequency effective to prolong the survival of the allograft in the recipient mammal, wherein the recipient mammal is presensitized to the allograft.

In another aspect, provided herein is a method for transplanting an allograft organ into a recipient mammal (e.g., a human), the method comprising:

(a) prior to transplantation of an allograft organ into a recipient mammal, administering an anti-CD200 antibody or bispecific antibody described herein as a single agent to the recipient mammal, wherein the recipient mammal is presensitized to the allograft organ;

(b) transplanting the allograft organ into the recipient mammal; and (c) administering the antibody as a single agent to the recipient mammal following transplantation of the allograft organ.

In another aspect, provided herein is a method of detecting CD200 in a sample comprising contacting the sample with an anti-CD200 antibody or bispecific antibody described herein under conditions that allow for formation of a complex between the antibody, or antigen binding portion thereof, and CD200, and detecting the formation of the complex.

BRIEF DESCRIPTION OF THE DRAWINGS

FIG. 1 shows an alignment of heavy and light chain variable region sequences of samalizumab (ALXN6000) (SEQ ID NOs:11 and 12, respectively) and c2aB7 (SEQ ID NOs:16 and 17, respectively) with re-humanized heavy (SEQ ID NOs: 235-244) and light chain (SEQ ID NOs: 245-248) variable region sequences.

FIGS. 3A and 3B are alignments highlighting differences in sequences between samalizumab (SEQ ID NO: 12) and c2aB7 (SEQ ID NO: 17) and the re-humanized light chain variable region sequences (SEQ ID NOs: 250, 252, 254, and 256).

FIG. 4 is a schematic of different combinations of re-humanized heavy and light chain variable region sequences for generating anti-CD200 Fabs.

FIG. 7 is a schematic of different combinations of back-mutated heavy and light chains to generate Fabs for use in the Octet assay to test binding affinity.

DETAILED DESCRIPTION

I. Overview

Figure 2A:
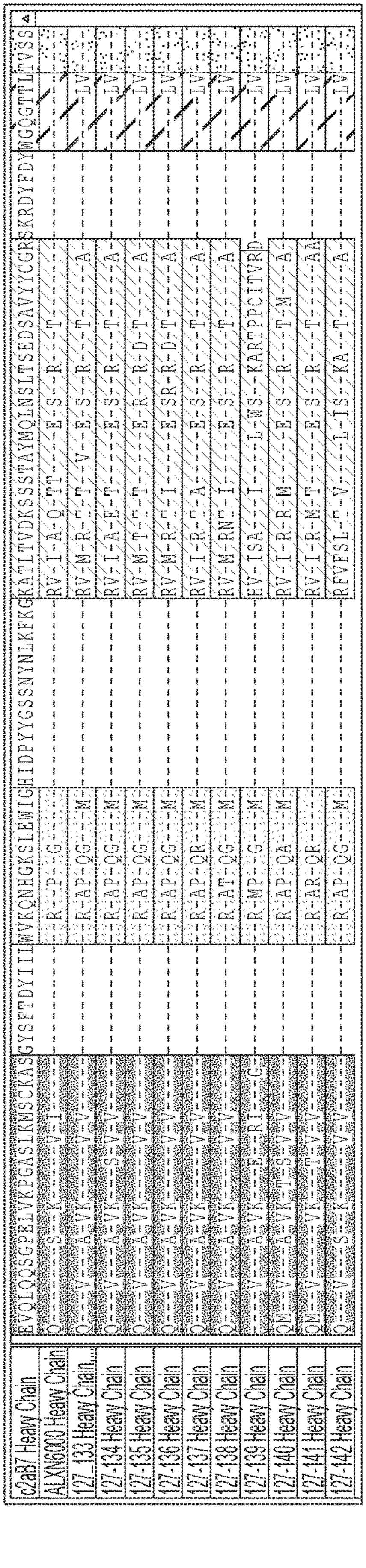
FIGS. 2A and 2B are alignments highlighting differences in sequences between samalizumab (SEQ ID NO: 11) and c2aB7 (SEQ ID NO: 16) and the re-humanized heavy chain variable region sequences (SEQ ID NOs: 249, 257, 265, 273, 281, 287, 295, 303, 311, and 319).

Provided herein are antibodies with high binding affinity for CD200 that are useful for therapeutic use, e.g., for treating cancer and autoimmune diseases, for use in transplantation, and for prolonging the survival of allografts. Also provided are nucleic acids encoding the antibodies, methods of making the antibodies, immunoconjugates and multispecific molecules comprising such antibodies, and pharmaceutical compositions comprising the antibodies.

II. Definitions

In order that the present description may be more readily understood, certain terms are first defined. Additional definitions are set forth throughout the detailed description. Unless defined otherwise, all technical and scientific terms used herein have the same meaning as commonly understood by one of ordinary skill in the art, and conventional methods of immunology, protein chemistry, biochemistry, recombinant DNA techniques and pharmacology are employed.

As used herein, the singular forms "a", "an" and "the" include plural referents unless the context clearly dictates otherwise. The use of "or" or "and" means "and/or" unless stated otherwise. Furthermore, use of the term "including" as well as other forms, such as "include", "includes", and "included", is not limiting.

The term "about" as used herein when referring to a measurable value such as an amount, a temporal duration and the like, is encompasses variations of up to ±10% from the specified value. Unless otherwise indicated, all numbers expressing quantities of ingredients, properties such as molecular weight, reaction conditions, etc., used herein are to be understood as being modified by the term "about".

The terms "CD200", "OX-2" and "OX-2/CD200" are used interchangeably herein and refers to the highly conserved type I transmembrane glycoprotein having an amino acid sequence of the full-length precursor human CD200 isoform A (SEQ ID NO:1; Genbank Accession No. NP005935.2), the full-length human CD200 isoform B (SEQ ID NO: 2; Genbank Accession No. NP001004196.2), or the full-length human CD200 of SEQ ID NO: 3 (Genbank Accession No. CAA28943.1; FIG. 3 of McCaughan et al. (1987) *Immunogenetics* 25:329-335).

The term "CD200 antagonist" as used herein includes any agent that is capable of inhibiting the activity, function and/or the expression of CD200 or its receptor. In certain embodiments, the antagonist disrupts the interaction of CD200 and CD200R. In other embodiments, the CD200 antagonist is capable of decreasing the immunosuppressive effects of CD200 or is capable of targeting CD200-expressing cells for depletion or elimination.

The term "antibody" as used herein refers to polypeptides comprising at least one antibody derived antigen binding site (e.g., VH/VL region or Fv, or CDR), and includes whole antibodies and any antigen binding fragments (i.e., "antigen-binding portions") or single chains thereof. Antibodies include known forms of antibodies. For example, the antibody can be a human antibody, a humanized antibody, a bispecific antibody, or a chimeric antibody. A whole "antibody" refers to a glycoprotein comprising at least two heavy (H) chains and two light (L) chains inter-connected by disulfide bonds, in which each heavy chain is comprised of a heavy chain variable region (abbreviated herein as $V_H$) and a heavy chain constant region; and each light chain is comprised of a light chain variable region (abbreviated herein as VL) and a light chain constant region. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The antibody also can be of any of the following isotypes: IgG1, IgG2, IgG3, IgG4, IgM, IgA1, IgA2, IgAsec, IgD, and IgE. The antibody may be a naturally occurring antibody or may be an antibody that has been altered by a protein engineering technique (e.g., by mutation, deletion, substitution, conjugation to a non-antibody moiety). For example, an antibody may include one or more variant amino acids (compared to a naturally occurring antibody) which change a property (e.g., a functional property) of the antibody. For example, numerous such alterations are known in the art which affect, e.g., half-life, effector function, and/or immune responses to the antibody in a patient. The term antibody also includes artificial or engineered polypeptide constructs which comprise at least one antibody-derived antigen binding site.

The term "antigen-binding portion" of an antibody, as used herein, refers to one or more fragments of an antibody that retain the ability to specifically bind to an antigen (e.g., CD200), e.g., a Fab, Fab'2, scFv, SMIP, Affibody®, nanobody, or a domain antibody. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). In one embodiment of the invention, the formulation contains an antigen-binding portions described in U.S. Pat. Nos. 6,090,382 and 6,258,562, each incorporated by reference herein.

The term "monoclonal antibody," as used herein, includes an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Monoclonal antibodies are advantageous in that they may be synthesized by a hybridoma culture, essentially uncontaminated by other immunoglobulins. The modifier "monoclonal" indicates the character of the antibody as being amongst a substantially homogeneous population of antibodies, and is not to be construed as requiring production of the antibody by any particular method. The monoclonal antibodies to be used in accordance with the formulations disclosed herein may be made by the hybridoma method first described by Kohler, et al., (1975) *Nature* 256: 495 or other methods known in the art. A "polyclonal antibody" is an antibody which was produced among or in the presence of one or more other, non-identical antibodies. In general, polyclonal antibodies are produced from a B-lymphocyte in the presence of several other B-lymphocytes which produced non-identical antibodies. Usually, polyclonal antibodies are obtained directly from an immunized animal.

A "human" antibody (HuMAb) refers to an antibody having variable regions in which both the framework and CDR regions are derived from human germline immunoglobulin sequences.

A "humanized" antibody refers to an antibody in which some, most or all of the amino acids outside the CDR domains of a non-human antibody are replaced with corresponding amino acids derived from human immunoglobulins.

A "chimeric antibody" refers to an antibody in which the variable regions are derived from one species and the constant regions are derived from another species, such as an antibody in which the variable regions are derived from a mouse antibody and the constant regions are derived from a human antibody.

An "isolated" antibody or antigen binding fragment is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified to greater than 95% by weight of antibody, and in some embodiments, to greater than 99% by weight.

An "Fc region," "Fc domain," or "Fc" refers to the C-terminal region of the heavy chain of an antibody. Thus, an Fc region comprises the constant region of an antibody excluding the first constant region immunoglobulin domain (e.g., CH1 or CL).

An "antigen" is an entity (e.g., a proteinaceous entity or peptide) to which an antibody binds.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

As used herein, "isotype" refers to the antibody class (e.g., IgG1, IgG2, IgG3, IgG4, IgM, IgA1, IgA2, IgD, and IgE antibody) that is encoded by the heavy chain constant region genes.

A "native sequence Fc region" or "native sequence Fc" comprises an amino acid sequence that is identical to the amino acid sequence of an Fc region found in nature.

The term "pharmaceutical formulation" refers to preparations which are in such form as to permit the biological activity of the active ingredients to be unequivocally effective, and which contain no additional components which are significantly toxic to the subjects to which the formulation would be administered.

As used herein, the terms "specific binding," "selective binding," "selectively binds," and "specifically binds," refer to antibody binding to an epitope on a predetermined antigen but not to other antigens. Typically, the antibody (i) binds with an equilibrium dissociation constant ($K_D$) of approximately less than $10^{-7}$ M, such as approximately less than 10-s M, $10^{-9}$ M or $10^{-10}$ M or even lower when determined by, e.g., surface plasmon resonance (SPR) technology in a BIACORE® 2000 surface plasmon resonance instrument using the predetermined antigen, e.g., recombinant human CD200, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Accordingly, unless otherwise indicated, an antibody that "specifically binds to human CD200" refers to an antibody that binds to soluble or cell bound human CD200 with a $K_D$ of $10^{-7}$ M or less, such as approximately less than $10^{-8}$ M, $10^{-9}$ M or $10^{-10}$ M or even lower.

The term "epitope" or "antigenic determinant" refers to a site on an antigen to which an immunoglobulin or antibody specifically binds. Epitopes can be formed both from contiguous amino acids (usually a linear epitope) or noncontiguous amino acids juxtaposed by tertiary folding of a protein (usually a conformational epitope).

The term "binds to the same epitope" with reference to two or more antibodies means that the antibodies bind to the same segment of amino acid residues, as determined by a given method. Techniques for determining whether an antibody binds to the same epitope as another antibody include, for example, epitope mapping methods, such as, x-ray analyses of crystals of antigen:antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. In certain embodiments, an antibody competes with, and inhibits binding of another antibody to a target by at least 10%, 20%, 30%, 40%, 50%, 60%, 70%, 80%, 90% or 100%.

The term "surface plasmon resonance", as used herein, refers to an optical phenomenon that allows for the analysis of real-time biospecific interactions by detection of alterations in protein concentrations within a biosensor matrix, for example using the Biacore™ system (Pharmacia Biosensor AB, Uppsala, Sweden and Piscataway, N.J.). For further descriptions, see Jonsson, U., et al. (1993) *Ann. Biol. Clin.* 51:19-26; Jonsson, U., et al. (1991) *Biotechniques* 11:620-627; Johnsson, B., et al. (1995) *J. Mol. Recognit.* 8:125-131; and Johnsson, B., et al. (1991) *Anal. Biochem.* 198:268-277.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e., $k_d/k_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system or flow cytometry and Scatchard analysis.

The term "$EC_{50}$" in the context of an in vitro or in vivo assay using an antibody or antigen binding fragment thereof, refers to the concentration of an antibody or an antigen-binding portion thereof that induces a response that is 50% of the maximal response, i.e., halfway between the maximal response and the baseline.

The term "nucleic acid molecule," as used herein, is intended to include DNA molecules and RNA molecules. A nucleic acid molecule may be single-stranded or double-stranded, and may be cDNA.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms, "plasmid" and "vector" may be used interchangeably. However, other forms of expression vectors, such as viral vectors (e.g., replication defective retroviruses, adenoviruses and adeno-associated viruses), which serve equivalent functions are also contemplated.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

Also provided are "conservative sequence modifications" of the sequences set forth herein, i.e., nucleotide and amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997)).

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, usually at least about 90% to 95%, and more preferably at least about 98% to 99.5% of the amino acids.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the XBLAST program, score=50, wordlength=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. *Current Protocols in Molecular Biology*, Greene Publishing and Wiley Interscience, New York (1987).

Nucleic acids, e.g., cDNA, may be mutated, in accordance with standard techniques, to provide gene sequences. For coding sequences, these mutations may affect the corresponding amino acid sequence as desired. In particular, DNA sequences substantially homologous to or derived from native V, D, J, constant, switches and other such sequences described herein are contemplated (where "derived" indicates that a sequence is identical or modified from another sequence).

The term "inhibition" as used herein, refers to any statistically significant decrease in biological activity, including partial and full blocking of the activity. For example, "inhibition" can refer to a statistically significant decrease of about 10%, 20%, 30%, 40%, 50%, 60%, 70%, 80%, 90%, 95%, 96%, 97%, 98%, 99%, or 100% in biological activity.

As used herein, the term "inhibits growth" of a tumor includes any measurable decrease in the growth of a tumor, e.g., the inhibition of growth of a tumor by at least about 10%, for example, at least about 20%, at least about 30%, at least about 40%, at least about 50%, at least about 60%, at least about 70%, at least about 80%, at least about 90%, at least about 99%, or about 100%.

The terms "treat," "treating," and "treatment," as used herein, refer to therapeutic measures described herein. The methods of "treatment" employ administration to a subject the combination disclosed herein in order to cure, delay, reduce the severity of, or ameliorate, one or more symptoms of the disease or disorder or recurring disease or disorder, or in order to prolong the survival of a subject beyond that expected in the absence of such treatment.

The term "patient" includes human and other mammalian subjects that receive either prophylactic or therapeutic treatment.

As used herein, the term "subject" includes any human or non-human animal. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc.

The terms "effective amount" or "therapeutically effective amount" are used interchangeably, and refer to an amount of formulation or antibody effective to alleviate or ameliorate symptoms of disease or to prolong the survival of the subject being treated. Determination of a therapeutically effective amount is within the capability of those skilled in the art, especially in light of the detailed disclosure provided herein. Therapeutically effective dosages may be determined by using in vitro and in vivo methods.

The term "prophylaxis" refers to decreasing the likelihood of, or prevention of, a disease or condition (e.g., cancer, autoimmune disease, allograft rejection).

As used herein, the term "chronically" (e.g., to chronically administer a compound), or similar terms, refers to a method of administration in which an agent (e.g., an anti-CD200 antibody) is administered to a subject in an amount and with a frequency sufficient to maintain an effective amount of the agent in the subject for at least seven (e.g., at least eight, nine, 10, 11, 12, 13, 14, 15, 16, 17, 18, 19, 20, 21, 22, 23, 24). In some embodiments, an agent can be chronically administered to a subject for at least one (e.g., at least two, three, four, five, or six) month(s). In some embodiments, an agent can be chronically administered to a subject for a year or more.

An "immune response" refers to a biological response within a vertebrate against foreign agents, which response protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune response or reaction includes, e.g., activation or inhibition of a T cell, e.g., an effector T cell or a Th cell, such as a CD4+ or CD8+ T cell, or the inhibition of a Treg cell.

"Immunotherapy" refers to the treatment of a subject afflicted with, or at risk of contracting or suffering a recurrence of, a disease by a method comprising inducing, enhancing, suppressing or otherwise modifying an immune response. "Immunostimulating therapy" or "immunostimulatory therapy" refers to a therapy that results in increasing (inducing or enhancing) an immune response in a subject for, e.g., treating cancer. "Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

As used herein, "administering" refers to the physical introduction of a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intra-arterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually, or topically. Administering can also be performed, for example, once, a plurality of times, and/or over one or more extended periods.

As used herein, the term "T cell-mediated response" refers to a response mediated by T cells, including effector T cells (e.g., $CD8^+$ cells) and helper T cells (e.g., $CD4^+$ cells). T cell mediated responses include, for example, T cell cytotoxicity and proliferation. As used herein, the term "cytotoxic T lymphocyte (CTL) response" refers to an immune response induced by cytotoxic T cells. CTL responses are mediated primarily by $CD8^+$ T cells.

As used herein, the terms "inhibits" or "blocks" (e.g., referring to inhibition/blocking of CD200 binding or activity) are used interchangeably and encompass both partial and complete inhibition/blocking.

As used herein, "cancer" refers a broad group of diseases characterized by the uncontrolled growth of abnormal cells in the body. Unregulated cell division may result in the formation of malignant tumors or cells that invade neighboring tissues and may metastasize to distant parts of the body through the lymphatic system or bloodstream. As used herein, the term includes pre-malignant as well as malignant cancers.

As used herein, the term "hematological malignancy" includes a lymphoma, leukemia, myeloma, or a lymphoid malignancy, as well as a cancer of the spleen and the lymph nodes. Exemplary lymphomas include both B cell lymphomas and T cell lymphomas.

An "autoimmune disorder," as used herein, refers to a disease state in which, via the action of white blood cells (e.g., B cells, T cells, macrophages, monocytes, or dendritic cells), a pathological immune response (e.g., pathological in duration and/or magnitude) has been generated in a host organism against a substance or a tissue that is normally present within the host organism. Autoimmune diseases are characterized by increased inflammation due to immune system activation against self-antigens.

The terms "allograft", "homograft" and "allogeneic graft" refer to the transplant of an organ or tissue from one individual to another of the same species with a different genotype, including transplants from cadaveric, living related, and living unrelated donors. A graft transplanted from one individual to the same individual is referred to as an "autologous graft" or "autograft". A graft transplanted between two genetically identical or syngeneic individuals is referred to as a "syngeneic graft". A graft transplanted between individuals of different species is referred to as a "xenogeneic graft" or "xenograft".

The term "sample" refers to tissue, body fluid, or a cell (or a fraction of any of the foregoing) taken from a patient or a subject.

Various aspects described herein are described in further detail in the following subsections.

III. Anti-CD200 Antibodies

Provided herein are optimized anti-CD200 antibodies (e.g., isolated humanized antibodies) that are characterized by particular structural and/or functional features. In part, the disclosure pertains to humanized versions of the murine C2aB7 antibody, which include at least one back-mutation in the framework region of the humanized antibody to a residue corresponding to the C2aB7 parental sequence, as described below and in the Examples.

The heavy and light chain variable region sequences of the C2aB7 antibody are set forth in SEQ ID NOs: 16 and 17, respectively. The heavy and light chain CDR1-3 sequences of the C2aB7 antibody and samalizumab are set forth in SEQ ID NOs: 5-7 and 8-10, respectively.

Suitable human germline sequences for humanization of antibodies are well known in the art, and include, for example, Ec (1-46), IGHV1-69, IGHV1-18, IGHV1-2, IGHV1-3, IGHV1-8, IGHV5-$10^{-1}$, IGHV1-45, IGHV1-58, IGFV7-4-1, Ec (1-39), IGKV1-16, IGKV1D-33, and IGKV1-12.

In one aspect, provided herein are humanized versions of the murine c2aB7 antibody (referred to herein also as humanized antibodies). These antibodies comprise the heavy and light chain CDR sequences of the C2aB7 antibody, but differ in framework region sequences. Accordingly, provided herein are humanized antibodies that bind to human CD200 and comprise the heavy and light chain variable regions selected from the group consisting of:

(a) SEQ ID NOs: 249 and 250;
(b) SEQ ID NOs: 251 and 252;
(c) SEQ ID NOs: 253 and 254;
(d) SEQ ID NOs: 255 and 256;
(e) SEQ ID NOs: 257 and 258;
(f) SEQ ID NOs: 259 and 260;
(g) SEQ ID NOs: 261 and 262;
(h) SEQ ID NOs: 263 and 264;
(i) SEQ ID NOs: 265 and 266;
(j) SEQ ID NOs: 267 and 268;
(k) SEQ ID NOs: 269 and 270;
(l) SEQ ID NOs: 271 and 272;
(m) SEQ ID NOs: 273 and 274;
(n) SEQ ID NOs: 275 and 276;
(o) SEQ ID NOs: 277 and 278;
(p) SEQ ID NOs: 279 and 280;
(q) SEQ ID NOs: 281 and 282;
(r) SEQ ID NOs: 20 and 21;
(s) SEQ ID NOs: 283 and 284;
(t) SEQ ID NOs: 285 and 286;
(u) SEQ ID NOs: 287 and 288;
(v) SEQ ID NOs: 289 and 290;
(w) SEQ ID NOs: 291 and 292;
(x) SEQ ID NOs: 293 and 294;
(y) SEQ ID NOs: 295 and 296;
(z) SEQ ID NOs: 297 and 298;
(aa) SEQ ID NOs: 299 and 300;
(bb) SEQ ID NOs: 301 and 302;
(cc) SEQ ID NOs: 303 and 304;
(dd) SEQ ID NOs: 305 and 306;
(ee) SEQ ID NOs: 307 and 308;
(ff) SEQ ID NOs: 309 and 310;
(gg) SEQ ID NOs: 311 and 312;
(hh) SEQ ID NOs: 313 and 314;
(ii) SEQ ID NOs: 315 and 316;
(jj) SEQ ID NOs: 317 and 318;
(kk) SEQ ID NOs: 319 and 320;
(ll) SEQ ID NOs: 321 and 322;
(mm) SEQ ID NOs: 323 and 324; and
(nn) SEQ ID NOs: 325 and 326.

In another aspect, back-mutations are introduced into the humanized antibodies described herein, wherein at least 1 amino acid (e.g., 1, 2, 3, 4, or 5 or more amino acids) at a position(s) in the framework regions of the humanized antibody that differs from the amino acid at the corresponding position(s) in the parental C2aB7 antibody is substituted with the amino acid(s) at the corresponding position(s) in the parental C2aB7 antibody, with the proviso that the humanized antibody does not comprise the heavy and light chain variable region sequences of the C2aB7 antibody. Accordingly, provided herein are antibodies that bind to human CD200 and comprise the heavy and light chain variable regions selected from the group consisting of:

(a) SEQ ID NOs: 249 and 250;
(b) SEQ ID NOs: 251 and 252;
(c) SEQ ID NOs: 253 and 254;
(d) SEQ ID NOs: 255 and 256;
(e) SEQ ID NOs: 257 and 258;
(f) SEQ ID NOs: 259 and 260;
(g) SEQ ID NOs: 261 and 262;
(h) SEQ ID NOs: 263 and 264;
(i) SEQ ID NOs: 265 and 266;
(j) SEQ ID NOs: 267 and 268;
(k) SEQ ID NOs: 269 and 270;
(l) SEQ ID NOs: 271 and 272;
(m) SEQ ID NOs: 273 and 274;
(n) SEQ ID NOs: 275 and 276;
(o) SEQ ID NOs: 277 and 278;
(p) SEQ ID NOs: 279 and 280;
(q) SEQ ID NOs: 281 and 282;
(r) SEQ ID NOs: 20 and 21;
(s) SEQ ID NOs: 283 and 284;
(t) SEQ ID NOs: 285 and 286;
(u) SEQ ID NOs: 287 and 288;
(v) SEQ ID NOs: 289 and 290;
(w) SEQ ID NOs: 291 and 292;
(x) SEQ ID NOs: 293 and 294;
(y) SEQ ID NOs: 295 and 296;
(z) SEQ ID NOs: 297 and 298;
(aa) SEQ ID NOs: 299 and 300;
(bb) SEQ ID NOs: 301 and 302;
(cc) SEQ ID NOs: 303 and 304;
(dd) SEQ ID NOs: 305 and 306;
(ee) SEQ ID NOs: 307 and 308;
(ff) SEQ ID NOs: 309 and 310;
(gg) SEQ ID NOs: 311 and 312;
(hh) SEQ ID NOs: 313 and 314;
(ii) SEQ ID NOs: 315 and 316;
(jj) SEQ ID NOs: 317 and 318;
(kk) SEQ ID NOs: 319 and 320;
(ll) SEQ ID NOs: 321 and 322;
(mm) SEQ ID NOs: 323 and 324; and
(nn) SEQ ID NOs: 325 and 326, wherein at least 1 amino acid at a position(s) (e.g., 1, 2, 3, 4, or 5 or more amino acids) in the framework regions of the heavy chain variable region and/or light chain variable region that differs from the amino acid at the corresponding position(s) in the parental C2aB7 antibody is substituted with the amino acid(s) at the corresponding position(s) in the C2aB7 antibody, with the proviso that the antibody does not comprise the heavy and light chain variable region sequences of the C2aB7 antibody.

In one aspect, provided herein is an antibody that binds to human CD200 and comprises heavy and light chain variable region sequences set forth in SEQ ID NOs: 20 and 21, wherein the antibody has 1, 2, 3, 4, or 5 or more amino acid substitutions in the heavy chain variable region framework regions at a position selected from the group consisting of: A9, V11, K12, V18, V20, R38, A40, P41, P43, R44, M48, R67, V68, I70, R72, T174, A76, E82, S84, R87, and A97, and/or 1, 2, 3, 4, 5 or more amino acid substitutions in the light chain variable region framework regions at a position selected from the group consisting of: S12, T69, F71, T72, Q79, P80, F83, A84, and T85, wherein the numbering is according to the amino acid sequence in SEQ ID NO: 20 for the heavy chain variable region and SEQ ID NO: 21 for the light chain variable region. In some embodiments, the amino acid substitutions in the heavy chain variable region framework regions are selected from the group consisting of: A9P, V11L, K12V, V18L, V20M, R38K, A40N, P41H, Q43K, R44S, M48I, R67K, V68A, I70L, R72V, T174K, A76S, E82Q, S84N, R87T, and A97G. In some embodiments, the amino acid substitutions in the light chain variable region framework regions are selected from the group consisting of: S12Y, T69Q, F71Y, T72S, Q79E, P80Y, F83M, A84G, and T85I.

In some embodiments, the heavy chain variable region framework regions have 1 amino acid substitution selected from the group consisting of: A9P, V11L, K12V, V18L, V20M, R38K, A40N, P41H, Q43K, R44S, M48I, R67K, V68A, I70L, R72V, T174K, A76S, E82Q, S84N, R87T, and A97G. Accordingly, in one embodiment, the antibody comprises heavy and light chain variable region sequences set forth in SEQ ID NOs: 20 and 21, wherein alanine at position 97 of the heavy chain variable region is substituted with glycine, wherein the numbering is according to the amino acid sequence of the heavy chain variable region set forth in SEQ ID NO: 20.

In some embodiments, the light chain variable region framework regions have 1 amino acid substitution selected from the group consisting of 512Y, T69Q, F71Y, T72S, Q79E, P80Y, F83M, A84G, and T85I. Accordingly, in one embodiment, the antibody comprises heavy and light chain variable region sequences set forth in SEQ ID NOs: 20 and 21, wherein alanine at position 84 of the light chain variable region is substituted with glycine, wherein the numbering is according to the amino acid sequence of the light chain variable region set forth in SEQ ID NO: 21.

In some embodiments, the heavy chain variable region framework regions have 1 amino acid substitution and the light chain variable region framework regions have 1 amino acid substitution. Accordingly, in one embodiment, the antibody comprises a heavy chain variable region comprising the amino acid sequence set forth in SEQ ID NO: 20, and a light chain variable region comprises the amino acid sequence set forth in SEQ ID NO: 21, wherein alanine at position 97 of the heavy chain variable region is substituted with glycine, and alanine at position 84 of the light chain variable region is substituted with glycine, wherein the numbering is according to the amino acid sequence of the heavy and light chain variable region sequences set forth in SEQ ID NOs: 20 and 21.

In one aspect, provided herein are antibodies that bind to human CD200 and comprise the heavy and light chain variable region sequences selected from the group consisting of: SEQ ID NOs: 23 and 24; SEQ ID NOs: 26 and 27; SEQ ID NOs: 29 and 30; SEQ ID NOs: 32 and 33; SEQ ID NOs: 35 and 36; SEQ ID NOs: 38 and 39; SEQ ID NOs: 41 and 42; SEQ ID NOs: 44 and 45; SEQ ID NOs: 47 and 48; SEQ ID NOs: 50 and 51; SEQ ID NOs: 53 and 54; SEQ ID NOs: 56 and 57; SEQ ID NOs: 59 and 60; SEQ ID NOs: 62 and 63; SEQ ID NOs: 65 and 66; SEQ ID NOs: 68 and 69; SEQ ID NOs: 71 and 72; SEQ ID NOs: 74 and 75; SEQ ID NOs: 77 and 78; SEQ ID NOs: 80 and 81; SEQ ID NOs: 83 and 84; SEQ ID NOs: 86 and 87; SEQ ID NOs: 89 and 90; SEQ ID NOs: 92 and 93; SEQ ID NOs: 95 and 96; SEQ ID NOs: 98 and 99; SEQ ID NOs: 101 and 102; SEQ ID NOs: 104 and 105; SEQ ID NOs: 107 and 108; SEQ ID NOs: 110 and 111; SEQ ID NOs: 113 and 114; SEQ ID NOs: 116 and 117; SEQ ID NOs: 119 and 120; SEQ ID NOs: 122 and 123; SEQ ID NOs: 125 and 126; SEQ ID NOs: 128 and 129; SEQ ID NOs: 131 and 132; SEQ ID NOs: 134 and 135; SEQ ID NOs: 137 and 138; SEQ ID NOs: 140 and 141; SEQ ID NOs: 143 and 144; SEQ ID NOs: 146 and 147; SEQ ID NOs: 149 and 150; SEQ ID NOs: 152 and 153; SEQ ID NOs: 155 and 156; SEQ ID NOs: 158 and 159; SEQ ID NOs: 161 and 162; SEQ ID NOs: 164 and 165; SEQ ID NOs: 167 and 168; SEQ ID NOs: 170 and 171; SEQ ID NOs: 173 and 174; SEQ ID NOs: 176 and 177; and SEQ ID NOs: 179 and 180.

In another aspect, provided herein are antibodies that bind to human CD200 and comprise the heavy and light chain sequences selected from the group consisting of: SEQ ID NOs: 181 and 182, SEQ ID NOs: 183 and 184, and SEQ ID NOs: 185 and 186.

In some embodiments, the anti-CD200 antibodies described herein bind to the same epitope on human CD200 as samalizumab.

In some embodiments, the anti-CD200 antibodies described herein block the interaction between CD200 and CD200 receptor (CD200R).

In some embodiments, the anti-CD200 antibodies described herein bind to a human CD200 polypeptide expressed on the surface of a cell.

In some embodiments, the anti-CD200 antibodies described herein bind to human CD200 with a $K_D$ of about $10^{-7}$M or less, about $10^{-8}$ M or less, about $10^{-9}$ M or less, about $10^{-10}$ M or less, about $10^{-11}$ M or less, about $10^{-12}$ M or less, about $10^{-7}$ M to about $10^{-12}$ M, about $10^{-7}$ M to about $10^{-11}$ M, about $10^{-7}$ M to about $10^{-10}$ M, about $10^{-8}$ M to about $10^{-12}$ M, about $10^{-9}$M to about $10^{-12}$ M, about $10^{-10}$ M to about $10^{-12}$ M, about $10^{-10}$ M to about $10^{-11}$M, about $10^{-9}$ M to about $10^{-11}$ M, or about $10^{-10}$ M to about $10^{-11}$ M.

In some embodiments, the anti-CD200 antibodies described herein bind with a higher affinity to human CD200 than an antibody comprising the heavy and light chain variable region sequences of samalizumab, as assessed, e.g., by surface plasmon resonance (SPR) or bio-layer interferometry binding assay, such as the Octet assay described herein.

Standard assays to evaluate the binding ability of the antibodies toward human CD200 are known in the art, including for example, ELISAs, Western blots, and RIAs. Suitable assays are also described in detail in the Examples. The binding kinetics (e.g., binding affinity) of the antibodies also can be assessed by standard assays known in the art, such as by surface plasmon resonance (Biacore™ analysis) and the Octet® assay (described in the Examples). Assays to evaluate the effects of the antibodies on functional properties of CD200 are described in further detail infra and in the Examples.

In some embodiments, the anti-CD200 antibodies described herein are more stable (as assessed, e.g., by aggregation, mechanical stability) than an antibody comprising the heavy and light chain variable region sequences of samalizumab (e.g., can be formulated at higher concentrations in solution, less aggregation, less precipitation in solution), as assessed by, e.g., SEC and/or thermal stability.

Assays for determining the stability of antibodies are well known in the art (e.g., SEC, thermal stability, measurement of activity and/or purity as a function of time, etc.), and described in the Examples.

In some embodiments, the anti-CD200 antibodies described herein have about the same or lower hydrophobicity than an antibody comprising the heavy and light chain variable region sequences of samalizumab, as assessed, e.g., by HPLC-HIC. In some embodiments, the anti-CD200 antibodies have a higher hydrophobicity than an antibody comprising the heavy and light chain variable region sequences of the C2aB7 antibody. In some embodiments, the anti-CD200 antibodies have a higher hydrophobicity than an antibody comprising the heavy and light chain variable region sequences of the C2aB7 antibody, and about the same or lower hydrophobicity than an antibody comprising the heavy and light chain variable region sequences of samalizumab. Assays for determining the hydrophobicity of an antibody are well known in the art (e.g., HPLC-HIC, solubility, solvent/solute requirements, measurement of activity and/or purity as a function of time, etc.), and described in the Examples.

In some embodiments, the anti-CD200 antibodies described herein comprise a modified Fc constant region which has reduced effector function (e.g., antibody-dependent cell-mediated cytotoxicity (ADCC), complement dependent cytotoxicity (CDC), and/or binding to one or more Fc receptors) relative to the effector function of the corresponding unmodified Fc constant region, as described in further detail infra. In some embodiments, the anti-CD200 antibodies described herein have no effector function.

In some embodiments, the modified Fc constant region is a G2/G4 constant region. In another embodiment, the modified Fc constant region comprises (i) the CH1 and hinge regions of an IgG2 antibody; (ii) the CH2 and CH3 regions of an IgG4 antibody; or (iii) the CH1 and hinge regions of an IgG2 antibody and the CH2 and CH3 regions of an IgG4 antibody. In another embodiment, the modified Fc constant region lacks a hinge region. In some embodiments, the modified Fc constant region is a G2/G4 constant region comprising the amino acid sequence set forth in SEQ ID NO: 4.

An antibody that exhibits one or more of the functional properties described above (e.g., biochemical, immunochemical, cellular, physiological or other biological activities, or the like) as determined according to methodologies known to the art and described herein, will be understood to relate to a statistically significant difference in the particular activity relative to that seen in the absence of the antibody (e.g., or when a control antibody of irrelevant specificity is present). Preferably, the anti-CD200 antibody-induced increases in a measured parameter effects a statistically significant increase by at least 10% of the measured parameter, more preferably by at least 20%, 30%, 40%, 50%, 60%, 70%, 80%, 90%, 95%, or 100% (i.e., 2 fold), 3 fold, 5 fold or 10 fold. Conversely, anti-CD200 antibody-induced decreases in a measured parameter effects a statistically significant decrease by at least 10%, 20%, 30%, 40%, 50%, 60%, 70%, 80%, 90%, 95%, 97%, 98%, 99%, or 100%.

In some embodiments, a VH domain of the anti-CD200 antibodies described herein is linked to a constant domain to form a heavy chain, e.g., a full-length heavy chain. In some embodiments, the VH domain is linked to the constant domain of a human immunoglobulin, e.g., IgG1, IgG2, IgG3, IgG4, IgM, IgA1, IgA2, IgAsec, IgD, and IgE, or variants thereof (e.g., variants comprising Fc regions with reduced or no effector function). Similarly, a VL domain of the anti-CD200 antibodies described herein described herein is linked to a constant domain to form a light chain, e.g., a full-length light chain.

The anti-CD200 antibodies disclosed herein include all known forms of antibodies and other protein scaffolds with antibody-like properties. For example, the antibody can be a humanized antibody, bispecific antibody, an immunoconjugate, a chimeric antibody, or a protein scaffold with antibody-like properties, such as fibronectin or ankyrin repeats. The antibody also can be a Fab, Fab'$_2$, scFv, affibody, avimer, nanobody, or a domain antibody. Full-length antibodies can be prepared from $V_H$ and $V_L$ sequences using standard recombinant DNA techniques and nucleic acids encoding the desired constant region sequences can be operatively linked to the variable region sequences.

IV. Antibodies with Altered Effector Function

In some embodiments, the anti-CD200 antibodies described herein have altered effector function. Effector functions involving the constant region of the target-specific antibody may be modulated by altering the properties of the constant or Fc region. Altered effector functions include, for example, a modulation in one or more of the following activities: ADCC, CDC, apoptosis, binding to one or more Fc-receptors, and pro-inflammatory responses. Modulation refers to an increase, decrease, or elimination of an activity compared to the activity of a second antibody. In certain embodiments, the second antibody is an antibody with effector function, e.g., an antibody having a native sequence Fc or constant region.

A variant constant region with altered FcR binding affinity and/or ADCC activity and/or altered CDC activity is a polypeptide which has either enhanced or diminished FcR binding activity and/or ADCC activity and/or CDC activity compared to the native or parent polypeptide or to a polypeptide comprising a native sequence or constant region. A polypeptide variant which displays increased binding to an FcR binds at least one FcR with greater affinity than the parent polypeptide. A polypeptide variant which displays decreased binding to an FcR binds at least one FcR with lower affinity than a parent polypeptide. Such variants which display decreased binding to an FcR may possess little or no appreciable binding to an FcR, e.g., 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the binding to the FcR as compared to the level of binding of a native sequence immunoglobulin constant or Fc region to the FcR. Similarly, a variant anti-CD200 antibody that displays altered ADCC and/or CDC activity may exhibit either increased or reduced ADCC and/or CDC activity compared to the native or parent polypeptide. For example, in some embodiments, the anti-CD200 antibody comprising a variant constant region can exhibit approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the ADCC and/or CDC activity of the native form of the constant region. An anti-CD200 antibody comprising a variant constant region displaying reduced ADCC and/or CDC may exhibit reduced or no ADCC and/or CDC activity.

A native sequence Fc or constant region comprises an amino acid sequence identical to the amino acid sequence of an Fc or constant chain region found in nature. A variant or altered Fc or constant region comprises an amino acid sequence which differs from that of a native sequence heavy chain region by virtue of at least one amino acid modification, insertion, or deletion. In certain embodiments, the variant or altered constant region has at least one amino acid substitution, insertion, and/or deletion, compared to a native sequence constant region or to the constant region of a parent polypeptide, e.g. from about 1 to about 100 amino acid substitutions, insertions, and/or deletions in a native sequence constant region or in the constant region of the parent polypeptide. In some embodiments, the variant or altered constant region herein will possess at least about 70% homology (similarity) or identity with a native sequence constant region and/or with a constant region of a parent polypeptide, and in some instances at least about 75% and in other instances at least about 80% homology or identity therewith, and in other embodiments at least about 85%, 90% or 95% homology or identity therewith. The variant or altered constant region may also contain one or more amino acid deletions or insertions. Additionally, the variant constant region may contain one or more amino acid substitutions, deletions, or insertions that results in altered post-translational modifications, including, for example, an altered glycosylation pattern.

Antibodies with altered or no effector functions may be generated by engineering or producing antibodies with variant constant, Fc, or heavy chain regions; recombinant DNA technology and/or cell culture and expression conditions may be used to produce antibodies with altered function and/or activity. For example, recombinant DNA technology may be used to engineer one or more amino acid substitutions, deletions, or insertions in regions (such as, for example, Fc or constant regions) that affect antibody function including effector functions. Alternatively, changes in post-translational modifications, such as, e.g. glycosylation patterns, may be achieved by manipulating the cell culture and expression conditions by which the antibody is produced. Suitable methods for introducing one or more substitutions, additions, or deletions into an Fc region of an antibody are well known in the art and include, e.g., standard DNA mutagenesis techniques as described in, e.g., Sambrook et al. (1989) "Molecular Cloning: A Laboratory Manual, 2nd Edition," Cold Spring Harbor Laboratory Press, Cold Spring Harbor, N.Y.; Harlow and Lane (1988); Borrebaek, *Antibody Engineering—A practical guide* (1992); Johne et al., *J Immunol Methods* 160:191-198 (1993), International Publication No. WO 06/53301; and U.S. Pat. No. 7,704,497.

Accordingly, certain aspects and methods described herein relate to anti-CD200 antibodies with altered effector functions that comprise one or more amino acid substitutions, insertions, and/or deletions in the Fc or constant region. In some embodiments, such a variant anti-CD200 antibody exhibits reduced or no effector function. In some embodiments, a variant antibody comprises a hybrid constant region, or a portion thereof, such as a G2/G4 hybrid constant region (see e.g., Burton et al. (1992) *Adv Immun* 51:1-18; Canfield et al. (1991) *J Exp Med* 173:1483-1491; and Mueller et al. (1997) *Mol Immunol* 34(6):44'-452). For example (and in accordance with Kabat numbering), the IgG1 and IgG4 constant regions contain G249G25o residues whereas the IgG2 constant region does not contain residue 249, but does contain G250. In a G2/G4 hybrid constant region, where the 249-250 region comes from the G2 sequence, the constant region can be further modified to introduce a glycine residue at position 249 to produce a G2/G4 fusion having $G_{249}/G_{250}$. An exemplary G2/G4 hybrid constant region is described in U.S. Pat. No. 8,075,884. For example, in one embodiment, the G2/G4 hybrid constant region comprises the amino acid sequence set forth in SEQ ID NO: 4.

In addition to using a G2/G4 construct as described above, anti-CD200 antibodies with reduced effector function may be produced by introducing other types of changes in the amino acid sequence of certain regions of the antibody. Such amino acid sequence changes include but are not limited to the Ala-Ala mutation described in, e.g., International Publication Nos. WO 94/28027 and WO 98/47531; and Xu et al. (2000) *Cell Immunol* 200:16-26. Thus, in some embodiments, anti-CD200 antibodies with mutations within the constant region including the Ala-Ala mutation may be used to reduce or abolish effector function. According to these embodiments, the constant region of an anti-CD200 antibody comprises a mutation to an alanine at position 234 or a mutation to an alanine at position 235. Additionally, the constant region may contain a double mutation: a mutation to an alanine at position 234 and a second mutation to an alanine at position 235. In one embodiment, the anti-CD200 antibody comprises an IgG4 framework, wherein the Ala-Ala mutation would describe a mutation(s) from phenylalanine to alanine at position 234 and/or a mutation from leucine to alanine at position 235. In another embodiment, the anti-CD200 antibody comprises an IgG 1 framework, wherein the Ala-Ala mutation would describe a mutation(s) from leucine to alanine at position 234 and/or a mutation from leucine to alanine at position 235. An anti-CD200 antibody may alternatively or additionally carry other mutations, including the point mutation K322A in the CH2 domain (Hezareh et al. (2001) *J Virol* 75:12161-8).

Additional substitutions that, when introduced into a heavy chain constant region, result in decreased effector function are set forth in, e.g., Shields et al. (2001) *J Biol Chem* 276(9):6591-6604. See particularly Table 1 ("Binding of human IgG1 variants to human FcRn and FcγR) of Shields et al., the disclosure of which is incorporated herein by reference in its entirety. By screening a library of anti-IgE antibodies, each antibody of the library differing by one or more substitutions in the heavy chain constant region, for binding to a panel of Fc receptors (including FcRn, FcγRI, FcγRIIA, FcγRIIB, and FcγRIIIA), the authors identified a number of substitutions that modulate specific Fc-Fc receptor interactions. For example, a variant IgG2a heavy chain constant region in which the CH2 domain contains a D265A substitution (heavy chain amino acid numbering according to Kabat et al.) results in a complete loss of interaction between the variant constant region and IgG Fc receptors FcγRIIB, FcγRIII, FcγRI, and FcγRIV. Shields et al. (2001) at page 6595, Table 1. See also Baudino et al. (2008) *J Immunol* 181:6664-6669.

Changes within the hinge region also affect effector functions. For example, deletion of the hinge region may reduce affinity for Fc receptors and may reduce complement activation (Klein et al. 1981 *PNAS USA* 78: 524-528). The present disclosure therefore also relates to antibodies with alterations in the hinge region.

In some embodiments, anti-CD200 antibodies may be modified to either enhance or inhibit complement dependent cytotoxicity (CDC). Modulated CDC activity may be achieved by introducing one or more amino acid substitutions, insertions, or deletions in an Fc region of the antibody (see, e.g., U.S. Pat. No. 6,194,551). Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See Caron et al., *J. Exp Med.* 176:1191-1195 (1992) and Shopes, B. *J. Immunol.* 148:2918-2922 (1992), WO 99/51642, Duncan & Winter, *Nature* 322: 738-40 (1988); U.S. Pat. Nos. 5,648,260; 5,624,821; and WO 94/29351. Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

In some embodiments, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. Unless otherwise specified throughout the specification, numbering of the residues in the Fc region is that of the EU index as in Kabat (WO 00/42072). The effector ligand to which affinity is altered can be, for example, an Fc receptor or the C1 component of complement (see, e.g., U.S. Pat. Nos. 5,624,821 and 5,648,260). In another embodiment, one or more amino acids selected from amino acid residues 329, 331 and 322 can be replaced with a different amino acid residue such that the antibody has altered C1q binding and/or reduced or abolished complement dependent cytotoxicity (CDC) (see, e.g., U.S. Pat. No. 6,194,551). In another example, one or more amino acid residues within amino acid positions 231 and 239 are altered to thereby alter the ability of the antibody to fix complement (see, e.g., International Publication WO 94/29351).

In some embodiments, the Pc region may be modified to increase antibody dependent cellular cytotoxicity (ADCC) and/or to increase the affinity for an Fcγ receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 379, 330, 331, 332, 333, 334, 335, 337, 338, 340, 360, 373, 376, 378, 382, 388, 389, 398, 414, 416, 419, 430, 433, 434, 435, 436, 437, 438 or 439. Exemplary substitutions include 236A, 239D, 239E, 268D, 267E, 268E, 268F, 324T, 332D, and 332E. Exemplary variants include 239D/332E, 236A/332E, 236A/239D/332E, 268F/324T, 267E/268F, 267E/324T, and 267E/268F/324T. Other modifications for enhancing FcγR and complement interactions include but are not limited to substitutions 298A, 333A, 334A, 326A, 247I, 339D, 339Q, 280H, 290S, 298D, 298V, 243L, 292P, 300L, 396L, 305I, and 396L. These and other modifications are reviewed in Strohl, 2009, Current Opinion in Biotechnology 20:685-691.

Fe modifications that increase binding to an Fey receptor include amino acid modifications at any one or more of amino acid positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 324, 327, 329, 330, 335, 337, 3338, 340, 360, 373, 376, 379, 382, 388, 389, 398, 414, 416, 419, 430, 434, 435, 437, 438 or 439 of the Fc region.

Other Fe modifications that can be made to Fes are those for reducing or ablating binding to FcγR and/or complement proteins, thereby reducing or ablating Fe-mediated effector functions such as ADCC, ADCP, and CDC. Exemplary modifications include but are not limited substitutions, insertions, and deletions at positions 234, 235, 236, 237, 267, 269, 325, and 328, wherein numbering is according to the EU index. Exemplary substitutions include but are not limited to 234G, 235G, 236R, 237K, 267R, 269R, 325L, and 328R, wherein numbering is according to the EU index. An Fc variant may comprise 236R/328R. Other modifications for reducing FcγR and complement interactions include substitutions 297A, 234A, 235A, 237A, 318A, 228P, 236E, 268Q, 309L, 3305, 331 S, 2205, 2265, 229S, 238S, 233P, and 234V, as well as removal of the glycosylation at position 297 by mutational or enzymatic means or by production in organisms such as bacteria that do not glycosylate proteins. These and other modifications are reviewed in Strohl, *Current Opinion in Biotechnology* 20:685-691 (2009).

Optionally, the Fc region may comprise a non-naturally occurring amino acid residue at additional and/or alternative positions known to one skilled in the art (see, e.g., U.S. Pat. Nos. 5,624,821; 6,277,375; 6,737,056; 6,194,551; 7,317, 091; 8,101,720; International Publication Nos. WO 00/42072; WO 01/58957; WO 02/06919; WO 04/016750; WO 04/029207; WO 04/035752; WO 04/074455; WO 04/099249; WO 04/063351; WO 05/070963; WO 05/040217, WO 05/092925 and WO 06/020114).

Fe variants that enhance affinity for an inhibitory receptor FcγRIIb may also be used. Such variants may provide an Fc fusion protein with immunomodulatory activities related to FcγRIIb$^+$ cells, including for example B cells and monocytes. In one embodiment, the Fe variants provide selectively enhanced affinity to FcγRIIb relative to one or more activating receptors. Modifications for altering binding to FcγRIIb include one or more modifications at a position selected from the group consisting of 234, 235, 236, 237, 239, 266, 267, 268, 325, 326, 327, 328, and 332, according to the EU index. Exemplary substitutions for enhancing FcγRIIb affinity include but are not limited to 234D, 234E, 234F, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. Exemplary substitutions include 235Y, 236D, 239D, 266M, 267E, 268D, 268E, 328F, 328W, and 328Y. Other Fe variants for enhancing binding to FcγRIIb include 235Y/267E, 236D/267E, 239D/268D, 239D/267E, 267E/268D, 267E/268E, and 267E/328F.

In certain embodiments, the antibody is modified to increase its biological half-life. For example, this may be done by increasing the binding affinity of the Fc region for FcRn. For example, one or more of more of following residues can be mutated: 252, 254, 256, 433, 435, and/or 436, as described in U.S. Pat. No. 6,277,375. Specific exemplary substitutions include one or more of the following: T252L, T254S, and/or T256F. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Other exemplary variants that increase binding to FcRn and/or improve pharmacokinetic properties include substitutions at positions 259, 308, 428, and 434, including for example 2591, 308F, 428L, 428M, 434S, 434H, 434F, 434Y, and 434M. Other variants that increase Fc binding to FcRn include: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 286A, 305A, 307A, 307Q, 311A, 312A, 376A, 378Q, 380A, 382A, 434A (Shields et al, Journal of Biological Chemistry, 2001, 276(9):6591-6604), 252F, 252T, 252Y, 252W, 254T, 256S, 256R, 256Q, 256E, 256D, 256T, 309P, 311S, 433R, 433S, 433I, 433P, 433Q, 434H, 434F, 434Y, 252Y/254T/256E, 433K/434F/436H, 308T/309P/311S (Dall'Acqua et al., *J. Immunol.,* 2002, 169:5171-5180, Dall'Acqua et al., 2006, *J. of Biol. Chem.* 281:23514-23524). Other modifications for modulating FcRn binding are described in Yeung et al., 2010, *J Immunol,* 182:7663-7671. In certain embodiments, hybrid IgG isotypes with particular biological characteristics may be used. For example, an IgG1/IgG3 hybrid variant may be constructed by substituting IgG1 positions in the CH2 and/or CH3 region with the amino acids from IgG3 at positions where the two isotypes differ. Thus a hybrid variant IgG antibody may be constructed that comprises one or more substitutions, e.g., 274Q, 276K, 300F, 339T, 356E, 358M, 384S, 392N, 397M, 4221, 435R, and 436F. In other embodiments described herein, an IgG1/IgG2 hybrid variant may be constructed by substituting IgG2 positions in the CH2 and/or CH3 region with amino acids from IgG1 at positions where the two isotypes differ. Thus a hybrid variant IgG antibody may be constructed that comprises one or more substitutions, e.g., one or more of the following amino acid substitutions: 233E, 234L, 235L, –236G (referring to an insertion of a glycine at position 236), and 327A.

Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A, which has been shown to exhibit enhanced FcγRIIIa binding and ADCC activity (Shields et al., 2001). Other IgG1 variants with strongly enhanced binding to FcγRIIIa have been identified, including variants with S239D/I332E and S239D/I332E/A330L mutations which showed the greatest increase in affinity for FcγRIIIa, a decrease in FcγRIIb binding, and strong cytotoxic activity in cynomolgus monkeys (Lazar et al., 2006). Introduction of the triple mutations into antibodies such as alemtuzumab (CD52-specific), trastuzumab (HER2/neu-specific), rituximab (CD20-specific), and cetuximab (EGFR-specific) translated into greatly enhanced ADCC activity in vitro, and the S239D/I332E variant showed an enhanced capacity to deplete B cells in monkeys (Lazar et al., 2006). In addition, IgG1 mutants containing L235V, F243L, R292P, Y300L, and P396L mutations which exhibited enhanced binding to FcγRIIIa and concomitantly enhanced ADCC activity in transgenic mice expressing human FcγRIIIa in models of B cell malignancies and breast cancer have been identified (Stavenhagen et al., 2007; Nordstrom et al., 2011). Other Fc mutants that may be used include: S298A/E333A/L334A, S239D/I332E, S239D/I332E/A330L, L235V/F243L/R292P/Y300L/P396L, and M428L/N434S.

In some embodiments, an Fc is chosen that has reduced binding to FcγRs. An exemplary Fc, e.g., IgG1 Fc, with reduced FcγR binding comprises the following three amino acid substitutions: L234A, L235E and G237A. In some embodiments, an Fc is chosen that has reduced complement fixation. An exemplary Fc, e.g., IgG1 Fc, with reduced complement fixation has the following two amino acid substitutions: A330S and P331S. In some embodiments, an Fc is chosen that has essentially no effector function, i.e., it has reduced binding to FcγRs and reduced complement fixation. An exemplary effectorless Fc (e.g., IgG1 Fc) comprises the following five mutations: L234A, L235E, G237A, A330S and P331S.

Another potential means of modulating effector function of antibodies includes changes in glycosylation, which is summarized in, e.g., Raju (2003) *BioProcess International* 1(4):44-53. According to Wright and Morrison, the microheterogeneity of human IgG oligosaccharides can affect biological functions such as CDC and ADCC, binding to various Fc receptors, and binding to C1q protein. (1997) *TIBTECH* 15:26-32. Glycosylation patterns of antibodies can differ depending on the producing cell and the cell culture conditions (Raju, supra). Such differences can lead to changes in both effector function and pharmacokinetics. See, e.g., Israel et al. (1996) *Immunology* 89(4):573-578; Newkirk et al. (1996) *Clin Exp Immunol* 106(2):259-64. Differences in effector function may be related to the IgG's ability to bind to the Fcγ receptors (FcγRs) on the effector cells. Shields et al. have shown that IgG, with variants in amino acid sequence that have improved binding to FcγR, can exhibit up to 100% enhanced ADCC using human effector cells ((2001) *J Biol Chem* 276(9):6591-604). While these variants include changes in amino acids not found at the binding interface, both the nature of the sugar component as well as its structural pattern may also contribute to the differences observed. In addition, the presence or absence of fucose in the oligosaccharide component of an IgG can improve binding and ADCC. See, e.g., Shields et al. (2002) *J Biol Chem* 277(30):26733-40. An IgG that lacked a fucosylated carbohydrate linked to $Asn^{297}$ exhibited normal receptor binding to the FcγRI receptor. In contrast, binding to the FcγRIIIA receptor was improved 50-fold and accompanied by enhanced ADCC, especially at lower antibody concentrations.

Shinkawa et al. demonstrated that an antibody to the human IL-5 receptor produced in a rat hybridoma showed more than 50% higher ADCC when compared to the antibody produced in Chinese hamster ovary cells (CHO) (Shinkawa et al. (2003) Biol Chem 278(5):3466-73). Monosaccharide composition and oligosaccharide profiling showed that the rat hybridoma-produced IgG had a lower content of fucose than the CHO-produced protein. The authors concluded that the lack of fucosylation of an IgG 1 has a critical role in enhancement of ADCC activity.

A different approach was taken by Umana et al. who changed the glycosylation pattern of chCE7, a chimeric IgG1 anti-neuroblastoma antibody ((1999) *Nat Biotechnol* 17(2):176-80). Using tetracycline, they regulated the activity of a glycosyltransferase enzyme (GnTIII) which bisects oligosaccharides that have been implicated in ADCC activity. The ADCC activity of the parent antibody was barely above background level. Measurement of ADCC activity of the chCE7 produced at different tetracycline levels showed an optimal range of GnTIII expression for maximal chCE7 in vitro ADCC activity. This activity correlated with the level of constant region-associated, bisected complex oligosaccharide. Newly optimized variants exhibited substantial ADCC activity. Similarly, Wright and Morrison produced antibodies in a CHO cell line deficient in glycosylation and showed that antibodies produced in this cell line were incapable of complement-mediated cytolysis ((1994) *J Exp Med* 180:1087-1096). Thus, as known alterations that affect effector function include modifications in the glycosylation pattern or a change in the number of glycosylated residues, the present disclosure relates to a CD200 antibody wherein glycosylation is altered to either enhance or decrease effector function(s) including ADCC and CDC. Altered glycosylation includes a decrease or increase in the number of glycosylated residues as well as a change in the pattern or location of glycosylated residues.

Still other approaches exist for the altering effector function of antibodies. For example, antibody-producing cells can be hypermutagenic, thereby generating antibodies with randomly altered nucleotide and polypeptide residues throughout an entire antibody molecule (see WO 2005/011735). Hypermutagenic host cells include cells deficient in DNA mismatch repair. Antibodies produced in this manner may be less antigenic and/or have beneficial pharmacokinetic properties. Additionally, such antibodies may be selected for properties such as enhanced or decreased effector function(s).

It is further understood that effector function may vary according to the binding affinity of the antibody. For example, antibodies with high affinity may be more efficient in activating the complement system compared to antibodies with relatively lower affinity (Marzocchi-Machado et al. (1999) *Immunol Invest* 28:89-101). Accordingly, an antibody may be altered such that the binding affinity for its antigen is reduced (e.g., by changing the variable regions of the antibody by methods such as substitution, addition, or deletion of one or more amino acid residues). An anti-CD200 antibody with reduced binding affinity may exhibit reduced effector functions, including, for example, reduced ADCC and/or CDC.

V. Nucleic Acids

Also provided herein are nucleic acid molecules that encode the antibodies described herein. The nucleic acids may be present in whole cells, in a cell lysate, or in a partially purified or substantially pure form. Accordingly, also provided herein are host cells comprising these nucleic acid molecules, as well as expression vectors comprising these nucleic acid molecules. A nucleic acid described herein can be, for example, DNA or RNA and may or may not contain intronic sequences. In a certain embodiments, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

In some embodiments, provided herein are nucleic acid molecules that encode the VH and/or VL sequences, or heavy and/or light chain sequences, of any of the anti-CD200 antibodies described herein. For example, in some embodiments, provided are nucleic acids comprising a nucleotide sequence selected from the group consisting of SEQ ID NOs: 187-234. In some embodiments, provided are nucleic acids encoding the heavy and/or light chain variable region, or heavy and/or light chain, or antigen-binding portion thereof, within the nucleotide sequence selected from the group consisting of SEQ ID NOs: 187-234. Host cells comprising the nucleotide sequences (e.g., nucleic acid molecules) described herein are encompassed herein.

Once DNA fragments encoding variable region segments are obtained, these DNA fragments can be further manipulated by standard recombinant DNA techniques, for example, to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2 and/or CH3). The sequences of human heavy chain constant region genes are known in the art (see e.g., Kabat, E. A., el al. (1991) *Sequences of Proteins of Immunological Interest*, Fifth Edition, U.S. Department of Health and Human Services, NIH Publication No. 91-3242) and DNA fragments encompassing these regions can be obtained by standard PCR amplification.

The heavy chain constant region can be an IgG1, IgG2, IgG3, IgG4, IgA, IgE, IgM or IgD constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991)) and DNA fragments encompassing these regions can be obtained by standard PCR amplification. The light chain constant region can be a kappa or lambda constant region.

In some embodiments, nucleic acid molecules encoding the heavy and light chain variable regions, or heavy and light chains, are present in a single expression vector. In some embodiments, nucleic acid molecules encoding the heavy and light chain variable regions, or heavy and light chains, are present in multiple expression vectors which can be introduced into a host cell together such that the heavy and light chain variable regions, or heavy and light chains, are co-expressed in the cell.

scFv genes can be created by operatively linking the VH- and VL-encoding DNA fragments to another fragment encoding a flexible linker known in the art such that the VH and VL sequences can be expressed as a contiguous single-chain protein, with the VL and VH regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Also provided herein are nucleic acid molecules with conservative substitutions (i.e., substitutions that do not alter the resulting amino acid sequence upon translation of nucleic acid molecule), e.g., for codon optimization.

VI. Methods of Production

Suitable methods for producing an antibody (e.g., an anti-CD200 antibody) or antigen-binding fragments thereof, in accordance with the disclosure are known in the art (see, e.g., U.S. Pat. Nos. 7,427,665; 7,435,412; and 7,408,041, the disclosures of each of which are incorporated herein by reference in their entirety) and described herein. Recombinant techniques may be used to produce antibodies based on the sequence of the monoclonal antibodies.

Recombinant DNA technology can be used to modify one or more characteristics of the antibodies produced in non-human cells. Thus, chimeric antibodies can be constructed in order to decrease the immunogenicity thereof in diagnostic or therapeutic applications. Moreover, immunogenicity can be minimized by humanizing the antibodies by CDR grafting and, optionally, framework modification. See U.S. Pat. Nos. 5,225,539 and 7,393,648, the contents of each of which are incorporated herein by reference.

Recombinant DNA technology can be used to produce the antibodies according to established procedure, including procedures in bacterial or preferably mammalian cell culture. The selected cell culture system preferably secretes the antibody product.

In some embodiments, the process for the production of an antibody disclosed herein includes culturing a host, e.g., *E. coli* or a mammalian cell (e.g., CHO cell), which has been transformed with a hybrid vector. The vector includes one or more expression cassettes containing a promoter operably linked to a first DNA sequence encoding a signal peptide linked in the proper reading frame to a second DNA sequence encoding the antibody protein (e.g., the heavy and/or light chain variable region, or the heavy and light chain, of an anti-CD200 antibody described herein). The antibody protein is then collected and isolated. Optionally, the expression cassette may include a promoter operably linked to a polycistronic (e.g., bicistronic) DNA sequence encoding antibody proteins each individually operably linked to a signal peptide in the proper reading frame.

Large quantities of the desired antibodies can also be obtained by multiplying mammalian cells in vivo. Multiplication of mammalian host cells in vitro is carried out in suitable culture media, which include the customary standard culture media (such as, for example Dulbecco's Modified Eagle Medium (DMEM) or RPMI 1640 medium), optionally replenished by a mammalian serum (e.g. fetal calf serum), or trace elements and growth sustaining supplements (e.g. feeder cells such as normal mouse peritoneal exudate cells, spleen cells, bone marrow macrophages, 2-aminoethanol, insulin, transferrin, low density lipoprotein, oleic acid, or the like). Multiplication of host cells which are bacterial cells or yeast cells is likewise carried out in suitable culture media known in the art. For example, for bacteria suitable culture media include medium LE, NZCYM, NZYM, NZM, Terrific Broth, SOB, SOC, 2×YT, or M9 Minimal Medium. For yeast, suitable culture media include medium YPD, YEPD, Minimal Medium, or Complete Minimal Dropout Medium.

In vitro production provides relatively pure antibody preparations and allows scale-up production to give large amounts of the desired antibodies. Techniques for bacterial cell, yeast, plant, or mammalian cell cultivation are known in the art and include homogeneous suspension culture (e.g., in an airlift reactor or in a continuous stirrer reactor), and immobilized or entrapped cell culture (e.g., in hollow fibers, microcapsules, on agarose microbeads or ceramic cartridges).

The foregoing, and other, techniques are discussed in, for example, Kohler and Milstein, (1975) *Nature* 256:495-497; U.S. Pat. No. 4,376,110; Harlow and Lane, *Antibodies: a Laboratory Manual*, (1988) Cold Spring Harbor, the disclosures of which are all incorporated herein by reference. Techniques for the preparation of recombinant antibody molecules are described in the above references and also in, e.g.: WO 97/08320; U.S. Pat. Nos. 5,427,908; 5,508,717; Smith (1985) *Science* 225:1315-1317; Parmley and Smith (1988) *Gene* 73:305-318; De La Cruz et al. (1988) *J. Biol. Chem.* 263:4318-4322; U.S. Pat. Nos. 5,403,484; 5,223,409; WO 88/06630; WO 92/15679; U.S. Pat. Nos. 5,780,279; 5,571,698; 6,040,136; Davis et al. (1999) *Cancer Metastasis Rev.* 18(4):421-5; and Taylor et al. (1992) *Nucleic Acids Research* 20: 6287-6295; Tomizuka et al. (2000) *Proc. Natl. Acad. Sci. USA* 97(2): 722-727, the contents of each of which are incorporated herein by reference in their entirety.

For isolation of the antibodies, the immunoglobulins in the culture supernatants or in the ascitic fluid may be concentrated, e.g., by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g., affinity chromatography with one or more surface polypeptides derived from a CD200-expressing cell line or synthetic CD200 fragment peptides, or with Protein-A or -G.

The antibodies and fragments thereof can be "chimeric." Chimeric antibodies and antigen-binding fragments thereof comprise portions from two or more different species (e.g., mouse and human). Chimeric antibodies can be produced with mouse variable regions of desired specificity spliced into human constant domain gene segments (for example, U.S. Pat. No. 4,816,567). In this manner, non-human antibodies can be modified to make them more suitable for human clinical application (e.g., methods for treating or preventing a cancer in a human subject).

The monoclonal antibodies of the present disclosure include "humanized" forms of the non-human (e.g., mouse) antibodies (e.g., humanized form of C2aB7). Humanized or CDR-grafted mAbs are particularly useful as therapeutic agents for humans because they are not cleared from the circulation as rapidly as mouse antibodies and do not typically provoke an adverse immune reaction. Generally, a humanized antibody has one or more amino acid residues introduced into it from a non-human source. These non-human amino acid residues are often referred to as "import" residues, which are typically taken from an "import" variable domain. Methods of preparing humanized antibodies are generally well known in the art. For example, humanization can be essentially performed following the method of Winter and co-workers (see, e.g., Jones et al. (1986) *Nature* 321:522-525; Riechmann et al. (1988) *Nature* 332:323-327; and Verhoeyen et al. (1988) *Science* 239:1534-1536), by substituting rodent CDRs or CDR sequences for the corresponding sequences of a human antibody. Also see, e.g., Staelens et al. (2006) *Mol Immunol* 43:1243-1257.

In some embodiments, humanized forms of non-human (e.g., mouse) antibodies are human antibodies (recipient antibody) in which hypervariable (CDR) region residues of the recipient antibody are replaced by hypervariable region residues from a non-human species (donor antibody) such as a mouse, rat, rabbit, or non-human primate having the desired specificity, affinity, and binding capacity. In some instances, framework region residues of the human immunoglobulin are also replaced by corresponding non-human residues (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function.

In certain embodiments, de-immunized anti-CD200 antibodies are provided. De-immunized antibodies are those modified so as to render the antibody non-immunogenic, or less immunogenic, to a given species. De-immunization can be achieved by modifying the antibody utilizing any of a variety of techniques known to those skilled in the art (see, e.g., International Publication Nos. WO 04/108158 and WO 00/34317). For example, an antibody may be de-immunized by identifying potential T cell epitopes and/or B cell epitopes within the amino acid sequence of the antibody and removing one or more of the potential T cell epitopes and/or B cell epitopes from the antibody, for example, using recombinant techniques. The modified antibody may then optionally be produced and tested to identify antibodies that have retained one or more desired biological activities, such as, for example, binding affinity, but have reduced immunogenicity. Methods for identifying potential T cell epitopes and/or B cell epitopes may be carried out using techniques known in the art, such as, for example, computational methods (see e.g., International Publication No. WO 02/069232), in vitro or in silico techniques, and biological assays or physical methods (such as, for example, determination of the binding of peptides to MHC molecules, determination of the binding of peptide:MHC complexes to the T cell receptors from the species to receive the antibody, testing of the protein or peptide parts thereof using transgenic animals with the MHC molecules of the species to receive the antibody, or testing with transgenic animals reconstituted with immune system cells from the species to receive the antibody, etc.). In various embodiments, the de-immunized antibodies (e.g., deimmunized anti-CD200 antibodies) described herein include de-immunized antigen-binding fragments, Fab, Fv, scFv, Fab' and F(ab')2, monoclonal antibodies, murine antibodies, engineered antibodies (such as, for example, chimeric, single chain, CDR-grafted, humanized, fully human antibodies, and artificially selected antibodies), synthetic antibodies, and semi-synthetic antibodies.

In some embodiments, a recombinant DNA comprising an insert coding for a heavy chain variable domain and/or for a light chain variable domain of an anti-CD200 antibody, or for a heavy chain and/or for a light chain expressing cell line is produced. The term "DNA" includes coding single stranded DNAs, double stranded DNAs consisting of said coding DNAs and of complementary DNAs thereto, or these complementary (single stranded) DNAs themselves.

Furthermore, a DNA encoding a heavy chain variable domain and/or a light chain variable domain of anti-CD200 antibodies, or a heavy chain and/or a light chain of anti-CD200 antibodies, can be enzymatically or chemically synthesized to contain the authentic DNA sequence coding for a heavy chain variable domain and/or for the light chain variable domain, or for a heavy chain and/or for a light chain, or a mutant thereof. A mutant of the authentic DNA is a DNA encoding a heavy chain variable domain and/or a light chain variable domain, or a heavy chain and/or a light chain, of the above-mentioned antibodies in which one or more amino acids are deleted, inserted, or exchanged with one or more other amino acids. Preferably said modification(s) are outside the CDRs of the heavy chain variable domain and/or of the light chain variable domain of the antibody in humanization and expression optimization applications.

The term mutant DNA also embraces silent mutants wherein one or more nucleotides are replaced by other nucleotides with the new codons coding for the same amino acid(s). The term mutant sequence also includes a degenerate sequence. Degenerate sequences are degenerate within the meaning of the genetic code in that an unlimited number of nucleotides are replaced by other nucleotides without resulting in a change of the amino acid sequence originally encoded. Such degenerate sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Recombinant DNAs including an insert coding for a heavy chain murine variable domain of an anti-CD200 antibody or a CD200-expressing cell line fused to a human constant domain IgG, for example γ1, γ2, γ3 or γ4, in particular embodiments γ1 or γ4, may be used. Recombinant DNAs including an insert coding for a light chain murine variable domain of an antibody fused to a human constant domain κ or λ, preferably κ, are also provided.

Another embodiment pertains to recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA sequence encoding a peptide facilitating the purification of the antibody and/or a cleavage site and/or a peptide spacer and/or an agent. The DNA coding for an agent is intended to be a DNA coding for the agent useful in diagnostic or therapeutic applications. Thus, agent molecules which are toxins or enzymes, especially enzymes capable of catalyzing the activation of prodrugs, are particularly indicated. The DNA encoding such an agent has the sequence of a naturally occurring enzyme or toxin encoding DNA, or a mutant thereof, and can be prepared by methods known in the art.

Accordingly, the monoclonal antibodies can be naked antibodies that are not conjugated to other agents, for example, a therapeutic agent or detectable label.

Alternatively, the monoclonal antibody can be conjugated to an agent such as, for example, at least one of a cytotoxic agent, a small molecule, a hormone, an enzyme, a growth factor, a cytokine, a ribozyme, a peptidomimetic, a chemical, a prodrug, a nucleic acid molecule including coding sequences (such as antisense, RNAi, gene-targeting constructs, etc.), or a detectable label (e.g., an NMR or X-ray contrasting agent, fluorescent molecule, etc.). In certain embodiments, an anti-CD200 antibody or an antigen-binding fragment (e.g., Fab, Fv, single-chain scFv, Fab', and $F(ab')_2$) is linked to a molecule that increases the half-life of the antibody or antigen-binding fragment.

Several possible vector systems are available for the expression of cloned heavy chain and light chain genes in mammalian cells. One class of vectors relies upon the integration of the desired gene sequences into the host cell genome. Cells which have stably integrated DNA can be selected by simultaneously introducing selectable marker drug resistance genes such as *E. coli* gpt (Mulligan and Berg (1981) *Proc Natl Acad Sci USA,* 78:2072) or Tn5 neo (Southern and Berg (1982) *Mol Appl Genet.* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA,* 79:7147), polyoma virus (Deans et al. (1984) *Proc Natl Acad Sci USA* 81:1292), or SV40 virus (Lusky and Botchan (1981) *Nature* 293:79).

Since an immunoglobulin cDNA is comprised only of sequences representing the mature mRNA encoding an antibody protein, additional gene expression elements regulating transcription of the gene and processing of the RNA are required for the synthesis of immunoglobulin mRNA. These elements may include splice signals, transcription promoters, including inducible promoters, enhancers, and termination signals. cDNA expression vectors incorporating such elements include those described by Okayama and Berg (1983) *Mol Cell Biol* 3:280; Cepko et al. (1984) *Cell* 37:1053; and Kaufman (1985) *Proc Natl Acad Sci USA* 82:689.

VII. Multispecific Antibodies

Also contemplated are multispecific antibodies. In the therapeutic embodiments of the present disclosure, bispecific antibodies are contemplated. Bispecific antibodies are monoclonal antibodies that have binding specificities for at least two different antigens. In the present case, one of the binding specificities is for the CD200 antigen on a cell (such as, e.g., an immune cell), the other one is for any other antigen, and preferably for a cell-surface protein or receptor or receptor subunit.

Methods for making multispecific antibodies, such as bispecific antibodies, are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello (1983) *Nature* 305:537-539). Antibody variable domains with the desired binding specificities (antibody-antigen combining sites) can be fused to immunoglobulin constant domain sequences. The fusion preferably is with an immunoglobulin heavy-chain constant domain, including at least part of the hinge, $C_H2$, and $C_H3$ regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, e.g., Suresh et al. (1986) *Methods in Enzymology* 121:210; International Publication No. WO 96/27011; Brennan et al. (1985) *Science* 229:81; Shalaby et al. *J Exp Med* (1992) 175:217-225; Kostelny et al. (1992) *J Immunol* 148(5):1547-1553; Hollinger et al. (1993) *Proc. Natl. Acad. Sci. USA* 90:6444-6448; Gruber et al. (1994) *J Immunol* 152:5368; and Tutt et al. (1991) *J Immunol* 147:60. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. See, e.g., Kostelny et al. (1992) *J Immunol* 148(5):1547-1553. The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) *Proc Natl Acad Sci USA* 90:6444-6448 has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See, e.g., Gruber et al. (1994) *J Immunol* 152:5368. Alternatively, the antibodies can be "linear antibodies" as described in, e.g., Zapata et al. (1995) *Protein Eng* 8(10):1057-1062. Briefly, these antibodies comprise a pair of tandem Fd segments ($V_H$-$C_H1$-$V_H$-$C_H1$) which form a pair of antigen binding regions. Linear antibodies can be bispecific or monospecific. The disclosure also embraces variant forms of bispecific antibodies such as the tetravalent dual variable domain immunoglobulin (DVD-Ig) molecules described in Wu et al. (2007) *Nat Biotechnol* 25(11):1290-1297. The DVD-Ig molecules are designed such that two different light chain variable domains (VL) from two different parent antibodies are linked in tandem directly or via a short linker by recombinant DNA techniques, followed by the light chain constant domain. Methods for generating DVD-Ig molecules from two parent antibodies are further described in, e.g., International Publication Nos. WO 08/024,188 and WO 07/024,715, the disclosures of each of which are incorporated herein by reference in their entirety.

VIII. Immunoconjugates

The anti-CD200 antibodies described herein can be modified following their expression and purification. The modifications can be covalent or non-covalent modifications. Such modifications can be introduced into the antibodies by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies.

In some embodiments, the antibodies can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, or a luminescent label. Suitable heterologous polypeptides include, e.g., an antigenic tag (e.g., FLAG, polyhistidine, hemagglutinin (HA), glutathione-S-transferase (GST), or maltose-binding protein (MBP)) for use in purifying the antibodies or fragments. Heterologous polypeptides also include polypeptides that are useful as diagnostic or detectable markers, for example, luciferase, green fluorescent protein (GFP), or chloramphenicol acetyl transferase (CAT). Suitable radioactive labels include, e.g., $^{32}P$, $^{33}P$ $^{14}C$ $^{125}I$, $^{131}I$, $^{35}S$, and $^{3}H$. Suitable fluorescent labels include, without limitation, fluorescein, fluorescein isothiocyanate (FITC), green fluorescence protein (GFP), DyLight™ 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase. Heterologous polypeptides can be incorporated into the anti-CD200 antibodies as fusion proteins. Methods for generating nucleic acids encoding an antibody-heterologous polypeptide fusion protein are well known in the art of antibody engineering and described in, e.g., Dakappagari et al. (2006) *J Immunol* 176:426-440.

In some embodiments, the heterologous polypeptide is one that is toxic to a cell. For example, the toxic polypeptide can be selected from the group consisting of *Pseudomonas* exotoxin (PE), bryodin, gelonin, aspergillin, restrictocin, angiogenin, saporin, abrin, a prokaryotic ribonuclease, a eukaryotic ribonuclease, ricin, pokeweed antiviral protein (PAP), a pro-apoptotic polypeptide, a ribosomal inhibitory protein, or a biologically active fragment of any of the foregoing.

Pro-apoptotic polypeptides include, e.g., Bax, Bad, Bak, Bim, Bik, Bok, Hrk, FasL, TRAIL, and TNF-α, and pro-apoptotic, biologically-active fragments thereof.

In some embodiments, an anti-CD200 antibody described herein can be conjugated to a small molecule or radioactive agent that is toxic to a cell. For example, an anti-CD200 antibody can be conjugated to at least one toxic small molecule selected from the group consisting of cisplatin, carboplatin, procarbazine, mechlorethamine, cyclophosphamide, calicheamicin, camptothecin, adriamycin, ifosfamide, melphalan, chlorambucil, bisulfan, nitrosurea, dactinomycin, daunorubicin, doxorubicin, bleomycin, platinum, plicomycin, monomethyl auristatin, auristatin E, mitomycin, etoposide, verampil, podophyllotoxin, tamoxifen, taxol, transplatinum, 5-fluorouracil, vincristine, vinblastine, methotrexate, or an analog of any of the aforementioned. The antibody or fragment can be conjugated to a radioactive agent that is toxic to a cell. Such radioactive agents include, e.g., $^{90}Y$, $^{186}Re$, $^{188}Re$, $^{64}Cu$, $^{67}Cu$, $^{212}Pb$, $^{212}Bi$, $^{213}Bi$, $^{123}I$, $^{125}I$, $^{131}I$, $^{111}In$, $^{211}At$, $^{32}O$, $^{177}Lu$, $^{47}Sc$, $^{105}Rh$, $^{109}Pd$, $^{153}Sm$, or $^{199}Au$.

Two proteins (e.g., an anti-CD200 antibody and a heterologous moiety) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α (2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of the antibody. Alternatively, the radioactive label can be included as part of a larger molecule (e.g., $^{125}I$ in meta-[$^{125}I$]iodophenyl-N-hydroxysuccinimide ([$^{125}I$]mIPNHS) which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA) which is in turn bound to the protein backbone. Methods of conjugating the radioactive labels or larger molecules/chelates containing them to the anti-CD200 antibodies described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an anti-CD200 antibody) are known in the art of protein chemistry. For example, fluorophores can be conjugated to free amino groups (e.g., of lysines) or sulfhydryl groups (e.g., cysteines) of proteins using succinimidyl (NHS) ester or tetrafluorophenyl (TFP) ester moieties attached to the fluorophores. In some embodiments, the fluorophores can be conjugated to a heterobifunctional cross-linker moiety such as sulfo-SMCC. Suitable conjugation methods involve incubating an antibody protein, or fragment thereof, with the fluorophore under conditions that facilitate binding of the fluorophore to the protein. See, e.g., Welch and Redvanly (2003) *Handbook of Radiopharmaceuticals: Radiochemistry and Applications*, John Wiley and Sons (ISBN 0471495603).

In some embodiments, the anti-CD200 antibodies described herein can be modified, e.g., with a moiety that improves the stabilization and/or retention of the antibodies in circulation, e.g., in blood, serum, or other tissues. For example, the antibody or fragment can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476. The stabilization moiety can improve the stability, or retention of, the antibody (or fragment) by at least 1.5 (e.g., at least 2, 5, 10, 15, 20, 25, 30, 40, or 50 or more) fold.

In some embodiments, the anti-CD200 antibodies described herein can be glycosylated. In some embodiments, an antibody or antigen-binding fragment thereof described herein can be subjected to enzymatic or chemical treatment, or produced from a cell, such that the antibody or fragment has reduced or absent glycosylation. Methods for producing antibodies with reduced glycosylation are known in the art and described in, e.g., U.S. Pat. No. 6,933,368; Wright et al. (1991) *EMBO J* 10(10):2717-2723; and Co et al. (1993) *Mol Immunol* 30:1361.

IX. Kits

Provided herein are kits comprising the anti-CD200 antibodies, multispecific molecules, or immunoconjugates described herein, optionally contained in a single vial or container, and include instructions for use, e.g., in treating or diagnosing a disease such as cancer or an autoimmune disease. The kits may include a label indicating the intended use of the contents of the kit. The term label includes any writing, marketing materials or recorded material supplied on or with the kit, or which otherwise accompanies the kit.

Such kits may comprise the antibody, multispecific molecule, or immunoconjugate in unit dosage form, such as in a single dose vial or a single dose pre-loaded syringe.

X. Compositions/Formulations

Provided herein are compositions (e.g., pharmaceutical compositions) comprising an anti-CD200 antibody described herein. Such compositions can be formulated for, e.g., administration to a human to treat cancer or an autoimmune disorder, or for administering to a patient undergoing transplantation. The pharmaceutical compositions will generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt. See, e.g., Berge et al. (1977) *J Pharm Sci* 66:1-19.

The compositions can be formulated according to standard methods. Pharmaceutical formulation is a well-established art, and is described in, e.g., Gennaro (2000) *Remington: The Science and Practice of Pharmacy,* $20^{th}$ Edition, Lippincott, Williams & Wilkins (ISBN: 0683306472); Ansel et al. (1999) *Pharmaceutical Dosage Forms and Drug Delivery Systems,* $7^{th}$ Edition, Lippincott Williams & Wilkins Publishers (ISBN: 0683305727); and Kibbe (2000) *Handbook of Pharmaceutical Excipients American Pharmaceutical Association,* $3^{rd}$ Ed. (ISBN: 091733096X). In some embodiments, a composition can be formulated, for example, as a buffered solution at a suitable concentration and suitable for storage at 2-8° C. In some embodiments, a composition can be formulated for storage at a temperature below 0° C. (e.g., −20° C. or −80° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes, and suppositories. The preferred form depends, in part, on the intended mode of administration and therapeutic application. For example, compositions containing an anti-CD200 antibody described herein, intended for systemic or local delivery, can be in the form of injectable or infusible solutions. Accordingly, the compositions can be formulated for administration by a parenteral mode (e.g., intravenous, subcutaneous, intraperitoneal, or intramuscular injection). "Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intra-arterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion (see below).

The compositions can be formulated as a solution, microemulsion, dispersion, liposome, or other ordered structure suitable for stable storage at high concentration. Sterile injectable solutions can be prepared by incorporating an antibody described herein in the required amount in an appropriate solvent with one or a combination of ingredients enumerated above, as required, followed by filtered sterilization. Generally, dispersions are prepared by incorporating an anti-CD200 antibody described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of the antibody described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts and gelatin.

In certain embodiments, the anti-CD200 antibodies described herein can be prepared with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. (See, e.g., J. R. Robinson (1978) *Sustained and Controlled Release Drug Delivery Systems*, Marcel Dekker, Inc., New York.)

In some embodiments, the anti-CD200 antibodies described herein can be formulated in a composition suitable for intrapulmonary administration (e.g., for administration via nebulizer) to a mammal such as a human. Methods for preparing such compositions are well known in the art and described in, e.g., U.S. Patent Application Publication No. 2008/0202513; U.S. Pat. Nos. 7,112,341 and 6,019,968; and International Publication Nos. WO 00/061178 and WO 06/122257, the disclosures of each of which are incorporated herein by reference in their entirety. Dry powder inhaler formulations and suitable systems for administration of the formulations are described in, e.g., U.S. Patent Application Publication No. 2007/0235029, International Publication No. WO 00/69887; and U.S. Pat. No. 5,997,848.

In some embodiments, the anti-CD200 antibodies described herein can be modified, e.g., with a moiety that improves its stabilization and/or retention in circulation, e.g., in blood, serum, or other tissues. The stabilization moiety can improve the stability, or retention of, the antibody by at least 1.5 (e.g., at least 2, 5, 10, 15, 20, 25, 30, 40, or 50 or more) fold.

In some embodiments, the anti-CD200 antibodies described herein can be formulated with one or more additional active agents useful for treating, e.g., cancer, or ameliorating a symptom thereof. For example, an anti-CD200 antibody can be formulated with an anti-CD20 therapeutic agent (e.g., an anti-CD20 antibody, e.g., as described in US 2013/0189258), a genotoxic agent or a chemotherapeutic agent, or one or more kinase inhibitors. The genotoxic or chemotherapeutic agent can be, but is not limited to at least one of: carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, podophyllotoxin, taxol, satraplatinum, 5-fluorouracil, vincristin, vinblastin, methotrexate, ara-C, taxotere, gemcitabine, cisplatin (CDDP), adriamycin (ADR), or an analog of any of the aforementioned. Kinase inhibitors include, e.g., one or more of: trastuzumab, gefitinib, erlotinib, imatinib mesylate, or sunitinib malate. Additional agents are known in the art and described herein.

When the anti-CD200 antibody is to be used in combination with a second active agent, or when two or more different anti-CD200 antibodies are to be used, the agents can be formulated separately or together. For example, the respective pharmaceutical compositions can be mixed, e.g., just prior to administration, and administered together or can be administered separately, e.g., at the same or different times.

As described above, a composition can be formulated such that it includes a therapeutically effective amount of an anti-CD200 antibody or the composition can be formulated to include a sub-therapeutic amount of the antibody and a sub-therapeutic amount of one or more additional active agents such that the components in total are therapeutically effective for treating a cancer or an autoimmune disorder. In some embodiments, a composition can be formulated to include two or more anti-CD200 antibodies, each at sub-therapeutic doses, such that the antibodies in combination are at a concentration that is therapeutically effective for treating a cancer or an autoimmune disorder in a human.

Compositions comprising an anti-CD200 antibody can be formulated for prolonging the survival of an allograft organ in a mammal by, e.g., delaying graft rejection, as described in U.S. Pat. No. 9,447,187.

Also provided herein are liquid pharmaceutical formulations comprising an anti-CD200 antibodies described herein, in an amount suitable for therapeutic use that is stable at 2-8° C. for an extended period of time (e.g., at least 12, 15, 18, 21 or 24 months). Suitable formulations for the anti-CD200 antibodies described herein, as well as methods for preparing the formulations, are further described in the co-pending application entitled "Liquid Formulations of Anti-CD200 Antibodies," filed on Dec. 20, 2017, the entire contents of which are incorporated herein by reference.

Accordingly, in one aspect, provided herein are liquid formulations comprising (i) at least one anti-CD200 antibody described herein, (ii) a non-ionic surfactant, (iii) a polyol, and (iv) a citrate buffer at a pH of about 5.0 to about 5.5.

In certain embodiments, the concentration of the anti-CD200 antibody in the citrate buffered liquid formulation is between about 2 mg/mL and about 20 mg/mL; or is between about 5 mg/mL and about 10 mg/mL. In certain embodiments, the polyol in the liquid pharmaceutical citrate buffered formulation is a sugar alcohol, for example, mannitol, and is present at a concentration of at least 1.0% (w/v), between about 1.0% and about 5% (w/v), or between about 1% and about 3% mannitol. In certain embodiments, the non-ionic surfactant in the liquid pharmaceutical citrate buffered formulation is a polysorbate (e.g., Polysorbate 20, Polysorbate 40, Polysorbate 60, Polysorbate 80 or a combination of one or more thereof), and is present at a concentration between about 0.001% and 1.0% (w/v); about 0.01% and 0.05% (w/v). In certain embodiments, the non-ionic surfactant is Polysorbate 80 at a concentration between about 0.02% and 0.04% (w/v). In certain embodiments, the concentration of the citrate buffer in the liquid pharmaceutical formulation is sufficient to maintain a pH between 5.0 and 5.5. In certain embodiments, the pH of the citrate buffered formulation is about 5.2. In certain embodiments, the concentration of the citrate buffer in the liquid pharmaceutical formulation is between about 10 mM and 100 mM; or between about 25 mM and 75 mM. In certain embodiments the concentration of the citrate buffer in the liquid pharmaceutical formulation is about 50 mM. In certain embodiments, the concentration of the citrate buffer is 75 mM. In certain embodiments, the liquid pharmaceutical citrate buffered formulation comprises a tonicity agent. In certain embodiments, the tonicity agent contributes to maintaining the osmolality of the formulation between about 340 mOsm/kg and about 575 mOsm/kg. In some embodiments, the tonicity agent is NaCl. In certain embodiments, the concentration of the NaCl in the liquid citrate buffered pharmaceutical formulation is between about 25 mM and about 200 mM; or between about 75 mM and about 150 mM.

In certain embodiments, the liquid formulation exhibits low to undetectable levels of antibody precipitation, aggregation and/or degradation, with little to no loss of biological activity during manufacture, transportation and storage at 2-8° C. for extended periods of at least 12 months, at least 18 months, and/or at least 24 months. In certain embodiments, at least 95%, at least 97%, or at least 98% o of the anti-CD200 antibody molecules or antigen-binding fragments in the liquid pharmaceutical formulation are monomers after storage at 2-8° C. for 24 months.

In particular embodiments, the liquid formulation comprises:

a. about 5 mg/ml to about 10 mg/ml of an anti-CD200 antibody described herein;
b. about 1% to about 3% mannitol;
c. about 0.01% to about 0.05% polysorbate;
d. about 25 mM to about 75 mM citrate buffer to a pH of 5.0 to 5.5; and
e. about 75 mM to about 150 mM NaCl.

In other particular embodiments, the liquid formulation consists essentially of:

a. about 5 mg/ml to about 10 mg/ml of an anti-CD200 antibody described herein;
b. about 1% to about 3% mannitol;
c. about 0.01% to about 0.05% polysorbate;
d. about 25 mM to about 75 mM citrate buffer to a pH of 5.0 to 5.5; and
e. about 75 mM to about 150 mM NaCl.

In other particular embodiments, the liquid formulation comprises:

a. about 5 mg/ml to about 10 mg/ml of an anti-CD200 antibody described herein;
b. about 1% to about 3% mannitol;
c. about 0.01% to about 0.05% polysorbate;
d. about 50 mM citrate buffer to a pH of 5.0 to 5.5; and
e. about 75 mM to about 150 mM NaCl.

In one embodiment, the polysorbate is polysorbate 80. In one embodiment, the formulation comprises about 0.02% polysorbate 80. In another embodiment, the osmolality of the formulation is about 350 mOsm/kg to about 525 mOsm/kg.

In one particular embodiment, the liquid formulation comprises:

a. about 5 mg/ml of an anti-CD200 antibody described herein;
b. about 1% mannitol;
c. about 0.02% polysorbate 80;
d. about 50 mM citrate buffer to a pH of about 5.5; and
e. about 75 mM NaCl.

In one particular embodiment, the liquid formulation comprises:

a. about 5 mg/ml of an anti-CD200 antibody described herein;
b. about 3% mannitol;
c. about 0.02% polysorbate 80;
d. about 50 mM citrate buffer to a pH of about 5.5; and
e. about 75 mM NaCl.

In one particular embodiment, the liquid formulation comprises:

a. about 5 mg/ml of an anti-CD200 antibody described herein;
b. about 1% mannitol;
c. about 0.02% polysorbate 80;
d. about 50 mM citrate buffer to a pH of about 5.25; and
e. about 75 mM NaCl.

In one particular embodiment, the liquid formulation comprises:

a. about 5 mg/ml of an anti-CD200 antibody described herein;
b. about 3% mannitol;
c. about 0.02% polysorbate 80;
d. about 50 mM citrate buffer to a pH of about 5.5; and
e. about 75 mM NaCl.

In one particular embodiment, the liquid formulation comprises:

a. about 5 mg/ml of an anti-CD200 antibody described herein;
b. about 1% mannitol;
c. about 0.02% polysorbate 80;
d. about 50 mM citrate buffer to a pH of about 5.0; and
e. about 75 mM NaCl.

In one particular embodiment, the liquid formulation comprises:

a. about 5 mg/ml of an anti-CD200 antibody described herein;
b. about 3% mannitol;
c. about 0.02% polysorbate 80;
d. about 50 mM citrate buffer to a pH of about 5.0; and
e. about 75 mM NaCl.

In one particular embodiment, the liquid formulation comprises:

a. about 10 mg/ml of an anti-CD200 antibody described herein;
b. about 1% mannitol;
c. about 0.02% polysorbate 80;
d. about 50 mM citrate buffer to a pH of about 5.25; and
e. about 75 mM NaCl.

In one particular embodiment, the liquid formulation comprises:

a. about 10 mg/ml of an anti-CD200 antibody described herein;
b. about 3% mannitol;
c. about 0.02% polysorbate 80;
d. about 50 mM citrate buffer to a pH of about 5.25; and
e. about 75 mM NaCl.

In one particular embodiment, the liquid formulation comprises:

a. about 10 mg/ml of an anti-CD200 antibody described herein;
b. about 1% mannitol;
c. about 0.02% polysorbate 80;
d. about 50 mM citrate buffer to a pH of about 5.00; and
e. about 75 mM NaCl.

In one particular embodiment, the liquid formulation comprises:

a. about 10 mg/ml of an anti-CD200 antibody described herein;
b. about 3% mannitol;
c. about 0.02% polysorbate 80;
d. about 50 mM citrate buffer to a pH of about 5.00; and
e. about 75 mM NaCl.

In another aspect, provided herein are liquid formulations comprising (i) at least one anti-CD200 antibody described herein, (ii) a non-ionic surfactant, (iii) at least one neutral amino acid with a non-charged side chain (e.g., glycine), and (iv) an acetate buffer at a pH of about 5.0 to about 6.0.

In some embodiments, the antibody concentration in the acetate buffered formulation at least about 20 mg/ml, for example, between about 20 mg/ml to about 100 mg/ml. In some embodiments, the concentration of the antibody in the acetate buffered formulation is between about 20 to about 75 mg/ml. In other embodiments, the concentration of the antibody in the acetate buffered formulation is between about 25 to about 50 mg/ml. In some embodiments, the concentration of the antibody in the acetate buffered formulation is suitable for subcutaneous (SC) delivery. In some embodiments, the neutral amino acid in the acetate buffered formulation is alanine, glycine, isoleucine, leucine, methionine, phenylalanine, proline, valine or a combination thereof. In some embodiments, the neutral amino acid in the acetate buffered formulation is glycine, proline, arginine, lysine or leucine. In certain embodiments, the neutral amino acid in the acetate buffered formulation is glycine. In some embodiments, the concentration of the neutral amino acid in the acetate buffered formulation is at least 200 mM, for example, between about 200 mM and 500 mM. In some embodiments, the concentration of the neutral amino acid is between 250 mM and 350 mM. In certain embodiments, the non-ionic surfactant in the liquid pharmaceutical citrate buffered formulation is a polysorbate (e.g., Polysorbate 20, Polysorbate 40, Polysorbate 60, Polysorbate 80 or a combination of one or more thereof), and is present at a concentration between about 0.001% and 1.0% (w/v); about 0.01% and 0.05% (w/v). In certain embodiments, the surfactant is present in the acetate buffered formulation in an amount of 0.02% or about 0.06% (w/v). In one embodiment, the polysorbate is present in the acetate buffered formulation in an amount of 0.05% (w/v). The liquid acetate buffered formulations provided herein are at a pH of between about 5.0 to about 6.0. Suitable acetate buffers include sodium acetate, sodium acetate dehydrate, trisodium acetate, dibasic sodium phosphate or sodium phosphate heptahydrate. In certain embodiments, the acetate buffer is a sodium acetate buffer. In certain embodiments, the pH of the acetate buffered formulation is about 5.25-5.5. In one embodiment, the pH of the acetate buffered formulation is about 5.5. In some embodiments, the concentration of the acetate buffer in the formulation is about 5 mM to 50 mM. In some embodiments, the concentration of the acetate buffer in the formulation is about 5 mM to about 25 mM, or about 5 mM to about 10 mM. In some embodiments, the concentration of the acetate buffer in the formulation is about 10 mM.

In particular embodiments, the liquid formulation comprises:

(a) about 20 mg/ml to about 100 mg/ml of at least one anti-CD200 antibody described herein;
(b) about 200 mM to 500 mM of at least one neutral amino acid with a non-charged side chain;
(c) about 0.01% to about 0.1% polysorbate; and
(d) about 5 mM to about 20 mM acetate buffer to a pH of 5.0 to 6.0.

In other particular embodiments, the acetate buffered formulation comprises:

a) about 50 mg/ml of at least one anti-CD200 antibody described herein;
(b) about 250 mM to about 350 mM glycine;
(c) about 0.02% to about 0.0.5% polysorbate; and
(d) about 10 mM acetate buffer to a pH of 5.0 to 6.0.

In certain embodiments, the liquid formulation comprises:

a. about 50 mM of at least one anti-CD200 antibody described herein;

b. about 10 mM Na acetate;
c. 290 mM L-glycine; and
d. 0.05% (w/v) Polysorbate 80, wherein the formulation has a pH of about 5.5 and is stable at 2-8° C. for at least six months and up to at least 2 years.

The liquid anti-CD200 antibody formulations provided herein are stable under standard shipping and storage conditions. The stability of the formulations is determined, for example, as described in the Examples. In some embodiments, the formulation is considered stable if the anti-CD200 antibody or antigen binding fragment remains soluble (i.e., shows no visible precipitation upon visual inspection) at 2-8° C. for at least 9 months, at least 12 months, at least 15 months, at least 18 months, at least 21 months, or at least 24 months.

In related embodiments, both the citrate buffered and acetate buffered formulations provided herein demonstrate low to undetectable levels of aggregation. In some embodiments, the formulation contains no more than about 5%, no more than about 4%, no more than about 3%, no more than about 2%, no more than about 1% and no more than about 0.5% aggregation by weight of protein as measured by gel permeation high-performance liquid chromatography (GP-HPLC). SEC-HPLC, or static light scattering (SLS) techniques. In certain embodiments, at least 95% of the anti-CD200 antibody molecules in the formulation are present as a monomer at 2-8° C. for 24 months. In some embodiments, at least 97% of the anti-CD200 antibody molecules in the formulation are present as a monomer at 2-8° C. for 24 months. In some embodiments, at least 98% of the anti-CD200 antibody molecules in the formulation are present as a monomer at 2-8° C. for 24 months.

XI. Methods of Use

Provided herein are methods for treating cancer, autoimmune disorders, and for preventing or inhibiting allograft rejection by administering to a subject in need thereof an anti-CD200 antibody described herein in an effective amount (e.g., a therapeutically effective amount). In certain embodiments, the disease or disorder is associated with the upregulation of OX-2/CD200.

A. Cancer

In one aspect, provided are methods of treating cancer by administering to a subject in need thereof an anti-CD200 antibody described herein. Methods of using anti-CD200 antibodies for the treatment of cancer have been described, for example, in U.S. Pat. Nos. 7,435,412; 8,709,415; and 9,085,623, the contents of which are hereby incorporated by reference.

Cancers that can be treated with the anti-CD200 antibodies described herein include, but are not limited to, lung cancer (e.g., small-cell lung cancer, non-small cell lung cancer), breast cancer, colon cancer, colorectal cancer, pancreatic cancer, kidney cancer, gastric cancer, salivary gland carcinoma, liver cancer (e.g., hepatic carcinoma), bone cancer, hematological cancer, neural tissue cancer (e.g., neuroblastoma), glial cell tumors such as glioblastoma and neurofibromatosis, melanoma, thyroid cancer, endometrial carcinoma, ovarian cancer, testicular cancer, prostate cancer, cervical cancer, vaginal cancer, bladder cancer and various types of head and neck cancer. Also included are cancers derived from neural crest cells and any cancers that express CD200.

In certain embodiments, this disclosure provides a method for treating hematological malignancies, such as, for example, a lymphoma, leukemia, myeloma or a lymphoid malignancy, as well as a cancer of the spleen and the lymph nodes. Exemplary lymphomas include both B cell lymphomas and T cell lymphomas. B-cell lymphomas include both Hodgkin's lymphomas and most non-Hodgkin's lymphomas. Non-limiting examples of B cell lymphomas include diffuse large B-cell lymphoma, follicular lymphoma, mucosa-associated lymphatic tissue lymphoma, small cell lymphocytic lymphoma (overlaps with chronic lymphocytic leukemia), mantle cell lymphoma (MCL), Burkitt's lymphoma, mediastinal large B cell lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis. Non-limiting examples of T cell lymphomas include extranodal T cell lymphoma, cutaneous T cell lymphomas, anaplastic large cell lymphoma, and angioimmunoblastic T cell lymphoma. Hematological cancers also include leukemia, such as, but not limited to, secondary leukemia, chronic lymphocytic leukemia (CLL), acute myelogenous leukemia (AML), chronic myelogenous leukemia (CML), and acute lymphoblastic leukemia (ALL). Hematological cancers further include myelomas, such as, but not limited to, multiple myeloma and smoldering multiple myeloma. Other hematological and/or B cell- or T-cell-associated cancers are encompassed by the term hematological cancer.

In some embodiments, the subject treating according to the methods provided herein has a tumor or hematological malignancy comprising cancer cells overexpress CD200 relative to normal cells of the same histological type as the cells from which the cancer cells are derived. Methods of determining the expression of CD200 are well-known and described, for example, in U.S. Pat. Nos. 7,435,412; 8,709,415; and 9,085,623.

In particular embodiments, provided herein are methods of treating chronic lymphocytic leukemia (CLL) by administering an anti-CD200 antibody described herein. "CLL", as used herein, refers to chronic lymphocytic leukemia involving any lymphocyte, including but not limited to various developmental stages of B cells and T cells, including but not limited to B cell CLL. B-CLL, as used herein, refers to leukemia with a mature B cell phenotype which is $CD5^+$, $CD23^+$, $CD20^{dim+}$, $sIg^{dim+}$ and arrested in G0/G1 of the cell cycle.

In certain embodiments, a patient can have a cancer that is suspected of being resistant or is likely to become resistant to an anti-CD20 therapy. One biomarker useful in assessing whether a cancer is likely to become resistant to an anti-CD20 therapeutic agent such as rituximab is the presence or concentration of $CD5^+$ cancer cells in the population (see, U.S. Pat. No. 9,085,623). In some embodiments, the anti-CD20 therapeutic agent is an anti-CD20 antibody such as, but not limited to, rituximab, ofatumumab, TRU-015, veltuzumab, ocrelizumab, or AME-133v. In some embodiments, the methods comprise treating a subset of CLL patients that are refractory to treatment with anti-CD20 therapy (e.g., rituximab-resistant).

For instance, the formulations described herein can be administered as a therapeutic to cancer patients or autoimmune disease patients, especially, but not limited to CLL, AML, and solid tumor patients.

The anti-CD200 antibodies described herein can also be administered in combination with other immunomodulatory compounds, vaccines, or chemotherapy. As used herein, adjunctive or combined administration (co-administration) includes simultaneous administration of the formulation with the immunomodulatory compound, vaccine or chemotherapy, in the same or different dosage form, or separate administration of the compounds (e.g., sequential administration). Thus, the anti-CD200 antibodies described herein and immunomodulatory compounds, vaccines or chemotherapy, can be simultaneously administered in a single formulation. Alternatively, the anti-CD200 antibodies described herein and immunomodulatory compounds, vaccines or chemotherapy, can be formulated for separate administration and are administered concurrently or sequentially.

Illustrative examples of suitable immunomodulatory therapies include the administration of agents that block negative regulation of T cells or antigen presenting cells (e.g., anti-CTLA4 antibodies, anti-PD-L1 antibodies, anti-PDL-2 antibodies, anti-PD-1 antibodies and the like) or the administration of agents that enhance positive co-stimulation of T cells (e.g., anti-CD40 antibodies or anti 4-1BB antibodies). Furthermore, immunomodulatory therapy could be cancer vaccines such as dendritic cells loaded with tumor cells, tumor RNA or tumor DNA, tumor protein or tumor peptides, patient derived heat-shock proteins (hsp's) or general adjuvants stimulating the immune system at various levels such as CpG, Luivac, Biostim, Ribomunyl, Imudon, Bronchovaxom or any other compound activating receptors of the innate immune system (e.g., toll-like receptors). Also, immunomodulatory therapy could include treatment with cytokines such as IL-2, GM-CSF, and IFN-gamma.

Accordingly in some embodiments, the methods of treatment provided herein enhance the immune response to cancer cells by the administration of an anti-CD200 antibody described herein (or a composition (or formulation) comprising the antibodies), alone or in combination with one of the previously mentioned immunomodulatory therapies. For example, in certain embodiments, the formulations provided herein may be used in combination with a monoclonal antibody (e.g., rituximab, trastuzumab, alemtuzumab, cetuximab, or bevacizumab), including a conjugated monoclonal antibody (e.g., gemtuzumab ozogamicin, ibritumomab tiuxetan, or tositumomab).

In other embodiments, existing regulatory T cells are eliminated with reagents such as anti-CD25 or cyclophosphamide before starting anti-CD200 antibody treatment. Also, therapeutic efficacy of myeloablative therapies followed by bone marrow transplantation or adoptive transfer of T cells reactive with CLL cells is enhanced by treatment with an anti-CD200 antibody described herein. Furthermore, treatment with an anti-CD200 antibody described herein can substantially enhance efficacy of cancer vaccines such as dendritic cells loaded with CLL cells or proteins, peptides or RNA derived from such cells, patient-derived heat-shock proteins, tumor peptides or protein. In other embodiments, an anti-CD200 antibody described herein can be used in combination with an immuno-stimulatory compound, such as CpG, toll-like receptor agonists or any other adjuvant, anti-CTLA-4 antibodies, and the like.

In other embodiments, efficacy of the anti-CD200 antibody is improved by blocking of immunosuppressive mechanisms with, e.g., anti-PDL1 and/or 2 antibodies, anti-PD1 antibodies, anti-IL-10 antibodies, or anti-IL-6 antibodies. In yet other embodiments, efficacy of an anti-CD200 antibody described herein (or formulation comprising the antibody) is improved by administration of agents that increase NK cell number or T-cells, e.g., the small molecule inhibitor IMiDs, thalidomide, or thalidomide analogs. In certain embodiments, the methods described herein further comprise administering one or more additional therapeutics with an anti-CD200 antibody described herein.

Non-limiting examples of cytotoxic compounds include therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy a-emitters. Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin, for example. Procedures for preparing enzymatically active polypeptides of the immunotoxins are described in WO 84/03508 and WO 85/03508, which are hereby incorporated by reference. Certain cytotoxic moieties are derived from adriamycin, chlorambucil, daunomycin, methotrexate, neocarzinostatin, and platinum, for example.

Furthermore, combined administration of an anti-CD200 antibody described herein with chemotherapeutics could be particularly useful to reduce overall tumor burden, to limit angiogenesis, to enhance tumor accessibility, to enhance susceptibility to ADCC, to result in increased immune function by providing more tumor antigen, or to increase the expression of the T cell attractant LIGHT. When an anti-CD200 antibody described herein is administered to a subject in combination with another conventional anti-neoplastic agent, either concomitantly or sequentially, the anti-CD200 antibody may be shown to enhance the therapeutic effect of either agent alone. These chemotherapeutic antitumor compounds may be categorized by their mechanism of action into groups, including, for example, the following classes of agents: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as *vinca* alkaloids (vinblastine, vincristine, and vinorelbine), microtubule disruptors such as taxane (paclitaxel, docetaxel), vincristine, vinblastine, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); immunomodulatory agents (thalidomide and analogs thereof such as lenalidomide (Revlimid, CC-5013) and CC-4047 (Actimid)), cyclophosphamide; anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylprednisolone, prednisone, and prenisolone); growth factor signal transduction kinase inhibitors; mitochondrial dysfunction inducers and caspase activators; and chromatin disruptors.

B. Autoimmune Disorders

In another aspect, the disclosure relates to methods of treating patients with autoimmune disorders by administering a liquid formulation provided herein to a subject in need thereof. Methods of treating autoimmune disorders by administering an anti-CD200 antibody are described for example, in U.S. Pat. Nos. 8,637,014 and 9,085,623.

Examples of autoimmune disease include but are not limited to, psoriasis, pancreatitis, type I diabetes (IDDM), Graves' Disease, inflammatory bowel disease (IBD), Crohn's Disease, ulcerative colitis, irritable bowel syndrome, multiple sclerosis, rheumatoid arthritis, reactive arthritis, enteropathic arthritis, spondyloarthropathy, autoimmune myocarditis, Kawasaki disease, celiac disease, uveitis, Behcet's disease, coronary artery disease, chronic obstructive pulmonary disease (COPD), interstitial lung disease, inflammatory muscle disease (polymyositis, dermatomyositis), microscopic polyangiitis, autoimmune aplastic anemia, autoimmune thyroiditis, autoimmune hepatitis, Wegener's syndrome, diverticulosis, systemic lupus erythematosus, ankylosing spondylitis, scleroderma, systemic sclerosis, psoriatic arthritis, osteoarthritis, atopic dermatitis, vitiligo, graft vs. host disease (GVHD), cutaneous T cell lymphoma (CTCL), Sjogren's syndrome, glomerulonephritis, IgA nephropathy, autoimmune nephritis, pemphigus vulgaris, myasthenia gravis, autoimmune hearing loss, neuromyelitis optica, Goodpasture's syndrome, cryoglobulinemia, Guillain Bane syndrome, chronic inflammatory demyelinating polyneuropathy (CIDP), autoimmune hemolytic anemia, idiopathic thrombocytopenic purpura (ITP), CAD (or cold hemagglutinin disease or CHD/CHAD), transplant rejection, PCH (known as the "Donath-Landsteiner antibody"), MG (express antibodies to nicotinic acetylcholine receptor, AChR), highly sensitized transplant patients, antiphospholipid syndrome, allergy, and asthma, and other autoimmune diseases, or other diseases mediated by CD200.

A human "at risk of developing an autoimmune disorder" refers to a human with a family history of autoimmune disorders (e.g., a genetic predisposition to one or more inflammatory disorders) or one exposed to one or more autoimmune disorder/autoantibody-inducing conditions. For example, a human exposed to a shiga toxin is at risk for developing typical HUS. Humans with certain cancers (e.g., liquid tumors such as multiple myeloma or chronic lymphocytic leukemia) can pre-dispose patients to developing certain autoimmune hemolytic diseases. For example, PCH can follow a variety of infections (e.g., syphilis) or neoplasms such as non-Hodgkin's lymphoma. In another example, CAD can be associated with HIV infection, *Mycoplasma* pneumonia infection, non-Hodgkin's lymphoma, or Waldenstrom's macroglobulinemia. In yet another example, autoimmune hemolytic anemia is a well-known complication of human chronic lymphocytic leukemia, approximately 11% of CLL patients with advanced disease will develop AIHA. As many as 30% of CLL may be at risk for developing AIHA. See, e.g., Diehl et al. (1998) *Semin Oncol* 25(1):80-97 and Gupta et al. (2002) *Leukemia* 16(10):2092-2095.

A human "suspected of having an autoimmune disorder" is one who presents with one or more symptoms of an autoimmune disorder. Symptoms of autoimmune disorders can vary in severity and type with the particular autoimmune disorder and include, but are not limited to, redness, swelling (e.g., swollen joints), joints that are warm to the touch, joint pain, stiffness, loss of joint function, fever, chills, fatigue, loss of energy, pain, fever, pallor, icterus, urticarial dermal eruption, hemoglobinuria, hemoglobinemia, and anemia (e.g., severe anemia), headaches, loss of appetite, muscle stiffness, insomnia, itchiness, stuffy nose, sneezing, coughing, one or more neurologic symptoms such as dizziness, seizures, or pain. From the above it will be clear that not all humans are "suspected of having an autoimmune disorder."

Methods for detecting the presence or amount of an autoimmune disorder-associated autoantibody in a human are well known in the art and are described in, e.g., Burbelo et al. (2009) *J Transl Med* 7:83; Hanke et al. (2009) *Arthritis Res Ther* 11(1):R22; Hoch et al., *Nat Med.* 7(3):365-8 (2001); Vernino et al. (2008) *J Neuroimmunol* 197(1):63-69; Sokol et al., *Acta Haematol.* 68(4):268-77 (1982); and Littleton et al., *Mol Cell Proteomics* 8(7):1688-1696 (2009).

In some embodiments, an anti-CD200 antibody described herein is administered to a subject in an amount and with a frequency to maintain a reduced concentration (or a reduced expression or production) of the autoimmune disorder-associated autoantibody. Methods for detecting expression or a change in concentration of autoantibodies are well known in the art (e.g., Western blot, immunohistochemistry, and flow cytometry techniques) and described herein. Through an iterative process, a medical practitioner can determine the appropriate dose amount, and frequency of administration of each dose, required to maintain a reduced concentration of the autoimmune disorder-associated autoantibodies in the patient. For example, a medical practitioner can administer to a patient with an autoimmune disorder such as AIHA one or more (e.g., one, two, three, four, five, six, seven, eight, nine, or 10 or more or, e.g., at least two, at least three, four, five, six, seven, or eight or more) times the liquid formulation provided herein comprising an anti-CD200 antibody described herein in an amount that reduces (or is at least expected to reduce) the concentration of autoantibodies in the human. The at least two doses should be spaced apart in time by at least one (e.g., at least two, three, four, five, six, seven, eight, nine, 10, 11, 12, 13, or even 14) day(s). Biological samples (e.g., blood samples) containing the autoantibodies are obtained from the patient at various times, e.g., prior to the first anti-CD200 antibody administration, between the first dose and at least one additional dose, and at least one biological sample collection following the second dose. In some embodiments, biological samples may be collected at least two times between doses and/or at least one time after the final dose administered to the patient. The autoantibodies in each biological sample obtained are then interrogated for relative titer of the autoimmune-disease associated autoantibody to determine whether the amount and/or the frequency of administration of the anti-CD200 antibody are sufficient to maintain a reduced concentration of the autoantibody in the patient. The medical practitioner (and/or a computer) can determine an anti-CD200 antibody dosing schedule for the patient that is sufficient to maintain a reduced concentration of autoimmune disorder-associated autoantibodies in the patient over the course of the treatment.

In some embodiments, administration of an anti-CD200 antibody described herein to the human reduces the autoantibody concentration by at least 5 (e.g., at least 6, 7, 8, 9, 10, 11, 12, 13, 14, 15, 16, 17, 18, 19, 20, 25, 30, 35, 40, 45, 50, 55, 60, 65, 70, 75, 80, or 85 or more) %. In some embodiments, the anti-CD200 antibody can be chronically administered to the human. For example, the anti-CD200 antibody can be chronically administered a patient with MG to maintain a reduced concentration of anti-AChR antibodies in the blood of the patient for a prolonged period of time. Accordingly, a patient chronically treated with an anti-CD200 antibody described herein can be treated for a period of time that is greater than or equal to 2 weeks (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks; 1, 2, 3, 4, 5, 6, 7, 8, 9, 10, 11, or 12 months; or 1, 1.5, 2, 2.5, 3, 3.5, 4, 4.5, 5, 5.5, 6, 6.5, 7, 7.5, 8, 8.5, 9, 9.5, 10, 10.5, or 12 years, or for the remainder of the patient's life).

An anti-CD200 antibody described herein can be co-administered with one or more additional therapeutic agents useful for treating or preventing an inflammatory condition. The one or more agents include, e.g., a non-steroidal anti-inflammatory drug (NSAID), a disease-modifying anti-rheumatic drug (DMARD), a biological response modifier, or a corticosteroid. Biological response modifiers include, e.g., an anti-TNF agent (e.g., a soluble TNF receptor or an antibody specific for TNF such as adulimumab, infliximab, or etanercept). In some embodiments, the one or more additional therapeutic agents can be, e.g., steroids, anti-malarials, aspirin, non-steroidal anti-inflammatory drugs, immunosuppressants, cytotoxic drugs, corticosteroids (e.g., prednisone, dexamethasone, and prednisolone), methotrexate, methylprednisolone, macrolide immunosuppressants (e.g., sirolimus and tacrolimus), mitotic inhibitors (e.g., azathioprine, cyclophosphamide, and methotrexate), fungal metabolites that inhibit the activity of T lymphocytes (e.g., cyclosporine), mycophenolate mofetil, glatiramer acetate, and cytotoxic and DNA-damaging agents (e.g., chlorambucil or any other DNA-damaging agent described herein or known in the art).

In some embodiments, an anti-CD200 antibody described herein (or formulations comprising the antibodies) may be combined with antibody treatments including daclizumab, a genetically engineered human IgG1 monoclonal antibody that binds specifically to the a-chain of the interleukin-2 receptor, as well as various other antibodies targeting immune cells or other cells. Such combination therapies may be useful in the treatment of type 1 diabetes, rheumatoid arthritis, lupus, and idiopathic thrombocytopenic purpura, and other autoimmune indications.

C. Cell and Tissue Transplants

Further provided are methods of inhibiting an immune response to a tissue or cell transplant in a subject by administering an anti-CD200 antibody described herein. Methods of inhibiting allograft rejection using anti-CD200 antibodies have been described, for example, in U.S. Pat. No. 8,252,285 and US 2014/0170143.

The formulations as described herein may be used to inhibit or prevent a humoral immune response in recipients of various kinds of transplanted cells, tissues, and organs. For example, a graft may be autologous, allogeneic, or xenogeneic to the recipient. The graft may be a cell, tissue, or organ graft, including, but not limited to, bone marrow grafts, peripheral blood stem cell grafts, skin grafts, arterial and venous grafts, pancreatic islet cell grafts, and transplants of the kidney, liver, pancreas, thyroid, and heart. In one embodiment, the autologous graft is a bone marrow graft, an arterial graft, a venous graft, or a skin graft. In another embodiment, the allograft is a bone marrow graft, a corneal graft, a kidney transplant, a heart transplant, a liver transplant, a lung transplant, a pancreatic transplant, a pancreatic islet cell transplant, or a combined transplant of a kidney and pancreas. In another embodiment, the graft is a xenograft, preferably wherein the donor is a pig. Further, an anti-CD200 antibody, used alone or in combination with a second agent, may also be used to suppress a deleterious immune response to a non-biological graft or implant, including, but not limited to, an artificial joint, a stent, or a pacemaker device.

In certain embodiments, the graft recipient is a recipient of a hematopoietic cell or bone marrow transplant, an allogeneic transplant of pancreatic islet cells, or a solid organ transplant selected from the group consisting of a heart transplant, a kidney-pancreas transplant, a kidney transplant, a liver transplant, a lung transplant, and a pancreas transplant. Additional examples of grafts include but are not limited to allotransplanted cells, tissues, or organs such as vascular tissue, eye, cornea, lens, skin, bone marrow, muscle, connective tissue, gastrointestinal tissue, nervous tissue, bone, stem cells, cartilage, hepatocytes, or hematopoietic cells.

In some embodiments, provided are methods for the treatment and prevention of graft versus host disease (GVHD) and graft rejection in patients by administering an anti-CD200 antibody described herein. In some embodiments, the antibodies (or formulations) can be used in methods for treating or preventing an acute or a chronic humoral rejection in a transplant recipient. In other embodiments, the antibodies (or formulations) can be used in methods of treating patients who have received or will receive a transplant (e.g., a xenotransplant or allotransplant).

In some embodiments, an anti-CD200 antibody described herein may be administered to a patient prior to a transplant or allograft procedure, or after the procedure in order to decrease or eliminate CD200-positive immune cells that could reduce acceptance of the transplanted organ, tissue, or cell. In certain embodiments where the graft recipient is human, an allograft may be MHC mismatched. In certain embodiments, the MHC mismatched allograft is an HLA mismatched allograft. In further embodiments, the recipient is ABO mismatched to the allograft.

In some embodiments, a method of prolonging or promoting graft survival by administering an anti-CD200 antibody described herein increases graft survival in the recipient by at least about 15%, by at least about 20%, by at least about 25%, by at least about 30%, by at least about 40%, or by at least about 50%, compared to the graft survival observed in a control recipient. A control recipient may be, for example, a graft recipient that does not receive a therapy post-transplant or that receives a monotherapy following transplant.

In some embodiments, an anti-CD200 antibody described herein is administered to the recipient mammal for at least seven (e.g., at least eight, nine, 10, 11, 12, 13, 14, 15, 16, 17, 18, 19, 20, 21, 22, 23, 24, 25, 26, 27, 28, 29, 30, 31) days following transplantation of the allograft into the recipient mammal. In some embodiments, an anti-CD200 antibody described herein is administered at least once per day for up to seven (e.g., up to eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) days following transplantation of the allograft into the recipient mammal. In some embodiments, an anti-CD200 antibody described herein is administered at least once per day for at least seven, but less than 30 (e.g., less than 29, 28, 27, 26, 25, 24, 23, 22, 21, 20, 19, 18, 17, 16, 15, 14, 13, 12, 11, 10, 9, or 8) days following transplantation of the allograft into the recipient mammal. In some embodiments of any of the methods described herein, an anti-CD200 antibody described herein is administered to the recipient mammal once every two days. In some embodiments of any of the methods described herein, an anti-CD200 antibody described herein can be administered at least once a week. In some embodiments of any of the methods described herein, an anti-CD200 antibody described herein can be administered at least once every two weeks (e.g., at least once every 12, 13, 14, 15, or 16 days).

In certain embodiments, a method of promoting graft survival by administering an anti-CD200 antibody described herein promotes long-term graft survival, wherein the long-term graft survival is selected from among: at least about 6 months post-transplant, at least about 1 year post transplant; at least about 5 years post-transplant; at least about 7.5 years post-transplant; and at least about 10 years post-transplant. In certain embodiments, the therapies described herein promote accommodation of the graft and the graft survives for the remaining life-time of the recipient.

In some embodiments, an anti-CD200 antibody described herein is therapeutically effective as a single-agent therapy (such therapy is also referred to herein as a "monotherapy") to substantially prolong the survival of an allograft (e.g., a renal transplant) in the transplant recipient.

In other embodiments, an anti-CD200 antibody described herein is used in combination with lower doses of traditional therapeutic drugs than would be possible in the absence of the anti-CD200 antibody. In another embodiment, the antibodies (and formulations) and methods of the disclosure obviate the need for a more severe form of therapy, such as radiation therapy, high-dose immunomodulatory therapy, or splenectomy. Combination treatments are discussed in more detail in the previous section related to autoimmune disorders and include, for example, one or more of adriamycin, azathiopurine, busulfan, cyclophosphamide, cyclosporine A, Cytoxan, fludarabine, 5-fluorouracil, methotrexate, mycophenolate mofetil, a nonsteroidal anti-inflammatory, rapamycin, sirolimus, and tacrolimus. Other examples include antibodies such as, e.g., OKT3™ (muromonab-CD3), CAMPATH™-1G, CAMPATH™-1H (alemtuzumab), or CAMPATH™-1M, SIMULEC™ (basiliximab), ZENAPAX™ (daclizumab), RITUXAN™ (rituximab), and anti-thymocyte globulin.

In some embodiments, an immunomodulatory treatment method such as plasmapheresis, splenectomy, or immunoadsorption, can be used in combination with an anti-CD200 antibody described herein. In embodiments where an anti-CD200 antibody described herein is administered to a transplant recipient to inhibit a humoral immune response, the antibody may be administered to a transplant recipient prior to or following transplantation, alone or in combination with one or more therapeutic agents or regimens for the treatment or prevention of GVHD and graft rejection. For example, an anti-CD200 antibody described herein may be used to deplete alloantibodies from a transplant recipient prior to or following transplantation of an allogeneic graft.

In additional embodiments of inhibiting graft rejection, the immunomodulatory or immunosuppressive agent is one or more agents selected from the group consisting of adriamycin, azathiopurine, busulfan, cyclophosphamide, cyclosporine A, fludarabine, 5-fluorouracil, methotrexate, mycophenolate mofetil, 6-mercaptopurine, a corticosteroid, a nonsteroidal anti-inflammatory, sirolimus (rapamycin), and tacrolimus (FK-506). In alternative embodiments, the immunomodulatory or immunosuppressive agent is an antibody selected from the group consisting of muromonab-CD3, alemtuzumab, basiliximab, daclizumab, rituximab, anti-thymocyte globulin, and IVIg.

In particular embodiments, an anti-CD200 antibody described herein is administered in conjunction with at least one inhibitor of cellular immune function. Such inhibitors include, but are not limited to, cyclosporine A, tacrolimus, rapamycin, anti-T cell antibodies, daclizumab, and muromonab-CD3. In certain embodiments, a combination of an anti-CD200 antibody and an inhibitor of cellular immune function increases survival of a graft compared to the survival observed in a control graft recipient (e.g., a recipient receiving no treatment or a recipient receiving monotherapy, such as an inhibitor of cellular immune function). Increased survival includes, for example, at least about 15%, at least about 20%, at least about 25%, at least about 30%, at least about 40%, or at least about 50% increase in survival time (measured in days, months, or years, for example).

The present invention is further illustrated by the following examples which should not be construed as further limiting. The contents of Sequence Listing, figures and all references, patents and published patent applications cited throughout this application are expressly incorporated herein by reference.

EXAMPLES

Commercially available reagents referred to in the Examples below were used according to manufacturer's instructions unless otherwise indicated. Unless otherwise noted, the present invention uses standard procedures of recombinant DNA technology, such as those described hereinabove and in the following textbooks: Sambrook et al., supra; Ausubel et al., *Current Protocols in Molecular Biology* (Green Publishing Associates and Wiley Interscience, N.Y., 1989); Innis et al., *PCR Protocols: A Guide to Methods and Applications* (Academic Press, Inc.: N.Y., 1990); Harlow et al., *Antibodies: A Laboratory Manual* (Cold Spring Harbor Press: Cold Spring Harbor, 1988); Gait, *Oligonucleotide Synthesis* (IRL Press: Oxford, 1984); Freshney, Animal Cell Culture, 1987; Coligan et al., *Current Protocols in Immunology,* 1991.

Example 1: Re-Humanization of the Murine Anti-CD200 Antibody c2aB7

The anti-CD200 antibody samalizumab has very high aggregation potential which limited its formulation to no more than 5 mg/ml, which raised concerns about efficacious dosing and manufacturing, particularly for patients with larger body size. This Example describes the rational two-step re-humanization of the parental murine antibody of samalizumab, c2aB7, with the aim of identifying antibodies that aggregate less than (i.e., are more soluble) and bind with higher affinity to human CD200 than samalizumab, and finally which also have good manufacturability.

Figure 2B:
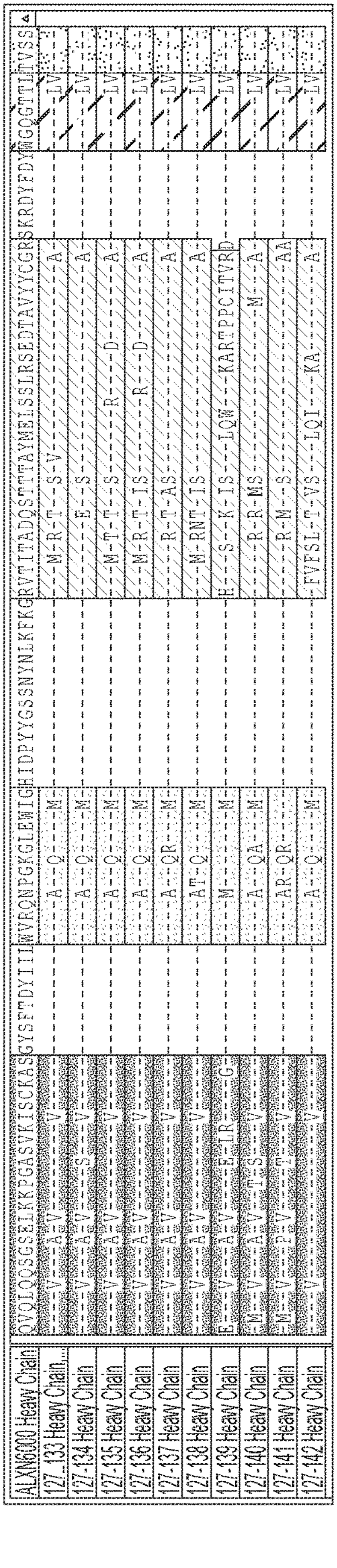

FIG. 1 shows an alignment of the heavy and light chain variable region sequences of samalizumab and C2aB7 with 10 different re-humanized heavy chain variable region sequences and 4 different re-humanized light chain variable region sequences. FIGS. 2A and 2B are alignments that highlight differences in sequences between C2aB7 and samalizumab and the 10 re-humanized heavy chain variable region sequences, respectively. FIGS. 3A and 3B are alignments that highlight differences in sequences between C2aB7 and samalizumab and the 4 re-humanized light chain variable region sequences, respectively. FIG. 4 shows the expression matrix of different combinations of re-humanized heavy and light chain variable region sequences.

Example 2: Affinity Assay of Re-Humanized Fab Antibodies

The various Fabs shown in the matrix of FIG. 4 were tested for binding to human CD200 using a bio-layer interferometry binding assay (OCTET®, Pall ForteBio LLC, Menlo Park, CA). Briefly, all samples were diluted in 1× kinetics buffer and dispensed into polypropylene 96-well black flat-bottom plates (Greiner Bio-One) at a volume of 200 µl per well. Anti-human IgG Fc (AHC) coated biosensor tips (Pall ForteBio, Menlo Park, CA) were pre-wetted with 1× kinetics buffer [10 mM sodium phosphate (pH 7.4), 140 mM sodium chloride, 0.05% Tween® 20, and 0.01% BSA]. The biosensors were then transferred to the Octet® HTX for kinetic screening of antigen binding. Biosensors were then transferred into fresh assay buffer for 60 s to collect a baseline read and then dipped into wells containing the antigen recombinant human CD200 Fc Chimera 50 nM for 300 s followed by another 60 s baseline read to remove any nonspecific protein. A single concentration of antibody (10 µg/ml) was then associated onto the human CD200 Fc antigen and dissociated in assay buffer for 300 s. All measurements were performed at 30° C. with agitation at 1000 rpm.

Figure 5:
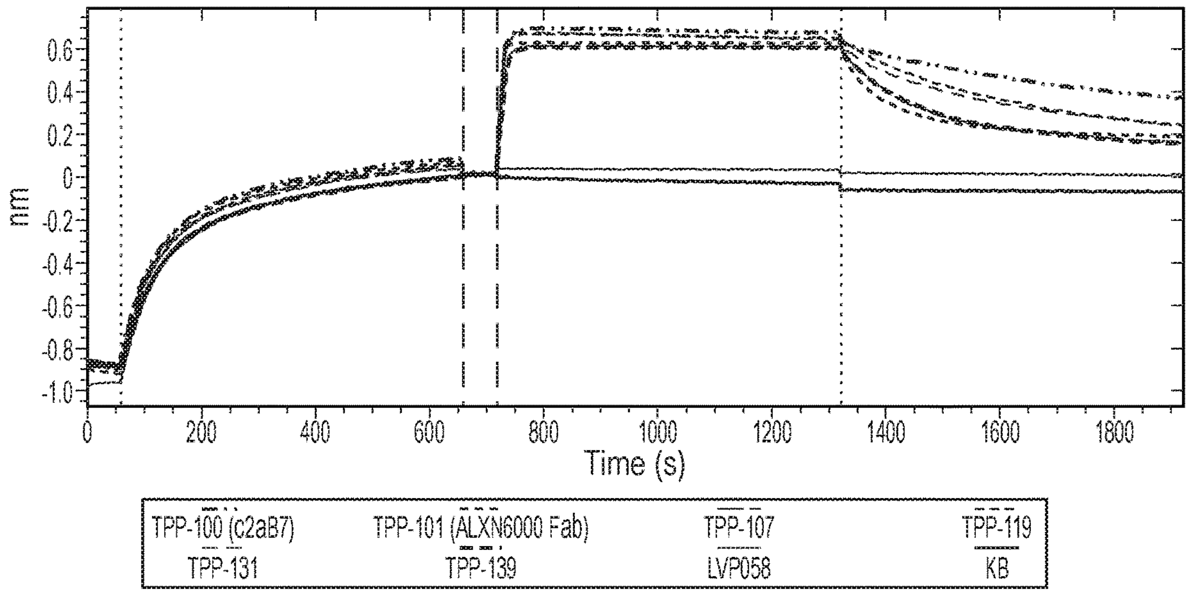
FIG. 5 is a sensorgram showing the affinity of various anti-CD200 Fabs for human CD200.

As shown in FIG. 5, TPP-100, TPP-119, and TPP-131 showed higher affinity for human CD200 than TPP-101. TPP-119 had lowered affinity when compared to the mouse parental c2aB7, TPP-100. However, TPP-119 showed better expression levels compared to TPP-131. As a result, TPP-119 was back-mutated to attempt to create a higher affinity antibody while maintaining expression levels.

The binding of Fabs to human CD200 was also tested by surface plasmon resonance (SPR) (BIACORE®, GE Healthcare). The kinetics of samalizumab Fab and other comparative Fabs binding to CD200 was determined on a Biacore™ 3000 instrument using an anti-Fc human capture method at pH 7.4. Anti-Fc-Human (KPL #01-10$^{-20}$) diluted to 0.1 mg/mL in 10 mM sodium acetate pH 5.0, was immobilized on two flow cells of a CM5 chip for 8 minutes by amine coupling. Recombinant CD200 Fc Chimera Protein was diluted to 1 µg/mL in running buffer (HBS-EP, pH 7.4). The diluted CD200 Fc Chimera Protein was then injected on one flow cell of a CM5 chip followed by injections of varying concentrations of Fabs on both cells. The second flow cell was used as a reference surface. The surface was regenerated each cycle with 20 mM HCl, 0.01% P20 (200 µL injection @100 µl/min). The data was processed with a 1:1 *Langmuir* model using BIAevaluation 4.1 software with 'double referencing'. The resulting binding affinities of Fabs are summarized in Table 1.

TABLE 1

Summary of Fab binding affinities to human CD200 by SPR

| Fab Sample | Corresponding mAb | $k_a$ (1/Ms) | $k_d$ (1/s) 1 | $K_D$ (M) | Chi$^2$ |
|---|---|---|---|---|---|
| TPP-100 (C2aB7) | TTP-308 | 1.51e6 | 7.39e−4 | 4.88e−10 | 0.09 |
| TPP-101 (ALXN6000 Fab) | TTP-309 | 2.67e6 | 0.0148 | 5.53e−9 | 0.95 |
| TPP-103 | | 6.94e5 | 7.04e−3 | 1.01e−8 | 0.59 |
| TPP-107 | | 8.85e5 | 4.1e−3 | 4.64e−9 | 0.73 |
| TPP-111 | | 1.23e6 | 6.25e−3 | 5.08e−9 | 0.39 |
| TPP-115 | | 1.31e6 | 5.3e−3 | 4.04e−9 | 0.11 |
| TPP-119 | TTP-305 | 1.28e6 | 1.59e−3 | 1.24e−9 | 0.06 |
| TPP-123 | | 1.12e6 | 4.87e−3 | 4.36e−9 | 0.26 |
| TPP-131 | | 2.65e6 | 2.35e−3 | 8.87e−10 | 0.07 |
| TPP-135 | | 9.3e5 | 0.0146 | 1.57e−8 | 0.36 |
| TPP-139 | | 9.93e5 | 3.68e−3 | 3.71e−9 | 1.05 |

Example 3: Expression of Fabs

In this Example, the expression levels of the Fabs in FIG. 4 were assessed. Briefly, plasmids encoding each Fab were transfected into Expi293™ cells and cultured in Expi293™ Expression Medium (Thermo Fisher) in a humidified 8% $CO_2$ incubator at 37° C. and 120 rpm. On the day of transfection, cells were centrifuged and resuspended to a density of 2.5×10$^6$ cells/mL in 100% fresh medium. Expi293™ transfections were performed according to the manufacturer's protocol. The Expi293™ Expression System Kit (Thermo Fisher), which contains transfection enhancers and ExpiFectamine™ 293 Transfection Kit reagent, was used for all Expi293™ transfections. ExpiFectamine™ 293 Transfection Kit reagent and plasmid DNA were separately diluted in Opti-MEM™ complexation medium (Thermo Fisher). Following a 5-minute incubation, ExpiFectamine™ 293 Transfection Kit and DNA mixtures were combined and incubated for an additional 20 minutes. The ExpiFectamine™ 293 Transfection Kit DNA Opti-MEM™ mixture was then added to cells. Enhancer 1 and Enhancer 2 were added to transfected cultures 16-18 hours post-transfection. Expi293™ transfections were harvested on day 4 post-transfection. Cell cultures were centrifuged at 1900×g for 15 minutes at room temperature and the supernatants were filtered through a 0.2 µm PES filter. Fab expression levels were quantified using the Octet® HTX. All samples were dispensed into polypropylene 96-well black flat-bottom plates at a volume of 200 µl per well. Anti-human Fab CH1 (FAB) coated biosensor tips—(Pall ForteBio LLC, Menlo Park, CA) were pre-wetted with of Expi293™ media. The biosensors and sample plate were then transferred to the Octet® HTX for quantitation. Measurements were performed at 30° C. with agitation at 1000 rpm.

Table 2 summarizes the expression levels of the various Fabs. While several of the Fabs showed similar or higher expression than both the parental and samalizumab Fabs (bolded), most showed lower expression.

TABLE 2

| Expression levels of Fabs | |
|---|---|
| Fab | Concentration (μg/ml) |
| TPP-100 (parental C2aB7) | 281 |
| TPP-101 (samalizumab Fab) | 356.7 |
| TPP-102 | 353.4 |
| TPP-103 | 302.3 |
| TPP-104 | 166.4 |
| TPP-105 | 311.2 |
| TPP-106 | 365.7 |
| TPP-107 | 178.7 |
| TPP-108 | 154.5 |
| TPP-109 | 486.7 |
| TPP-110 | 271.2 |
| TPP-111 | 242.8 |
| TPP-112 | 131.4 |
| TPP-113 | 418.6 |
| TPP-114 | 354.3 |
| TPP-115 | 293.1 |
| TPP-116 | 170.8 |
| TPP-117 | 369.1 |
| TPP-118 | 372.8 |
| TPP-119 | 276.2 |
| TPP-120 | 174.6 |
| TPP-121 | 408.5 |
| TPP-122 | 161.4 |
| TPP-123 | 226.6 |
| TPP-124 | 95.8 |
| TPP-126 | 274.3 |
| TPP-125 | 2.68 |
| TPP-127 | 2.65 |
| TPP-128 | 2.61 |
| TPP-129 | 2.88 |
| TPP-130 | 6.02 |
| TPP-131 | 127.6 |
| TPP-132 | 6.32 |
| TPP-133 | 25.6 |
| TPP-134 | 106.4 |
| TPP-135 | 297.2 |
| TPP-136 | 59.9 |
| TPP-137 | 351.3 |
| TPP-138 | 374.1 |
| TPP-139 | 431.1 |
| TPP-140 | 198 |
| TPP-141 | 444 |

Example 4: Stability of Fabs

This Example describes the assessment of Fab stability using differential scanning fluorimetry. Briefly, Differential Scanning Fluorimetry (DSF) monitored thermal unfolding of the proteins in the presence of a fluorescent dye (SYPRO™ Orange Protein Gel Stain) and using a real-time PCR instrument (Bio-Rad CFX96™). For the analysis of anti-CD200 antibodies, samples were diluted in PBS, pH 7.4 to 2 μM with a final volume of 50 μl. SYPRO™ Orange Protein Gel Stain was diluted to 10× concentration by serial dilution in PBS H 7.4. Samples were combined with SYPRO™ Orange Protein Gel Stain for a final concentration of 1 μM. 25 μl of this mixture was added to a white-walled PCR plate and the temperature was increased from 40° C. to 95° C. at 0.5° C./s with constant image capture. Data analysis was performed using the software Bio-Rad CFX96™ Manager 3.0. The melt peak plot represents the negative first derivative of the melt curve transition (50%) point on the slope of the raw data. Melting temperature is defined as 50% intact and 50% unfolded protein, and the assay control protein BB5.1 is consistent with previous results.

In this assay, a melting temperature >65° C. correlates with a thermally stable antibody. As shown in Table 3, all Fabs selected and tested were thermally stable.

TABLE 3

| Stability of Fabs by DSF | |
|---|---|
| Sample | Tm (° C.) n = 4 |
| TPP-100 | 79 |
| TPP-101 | 81.5 |
| TPP-103 | 84.5 |
| TPP-107 | 86 |
| TPP-111 | 86 |
| TPP-115 | 83 |
| TPP-119 | 82.5 |
| TPP-123 | 81 |
| TPP-131 | 75 |
| TPP-135 | 84.5 |
| TPP-139 | 83 |
| BB5.1 | 72 |

*BB5.1 is an assay control protein

Example 5: Back-Mutations to TPP-119 to Improve Affinity of Fabs for Human CD200

Figure 6A:
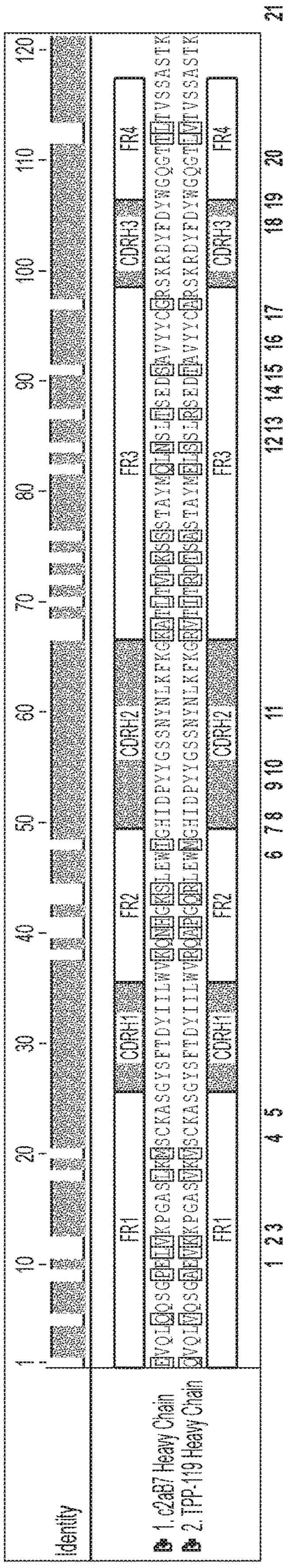
FIGS. 6A and 6B is an alignment showing the positions at which back-mutations were made in TPP-119 heavy (amino acids 213-333 of SEQ ID NO: 19) and light (amino acids 1-109 of SEQ ID NO: 19) chain variable region sequences, respectively.
Figure 6B:
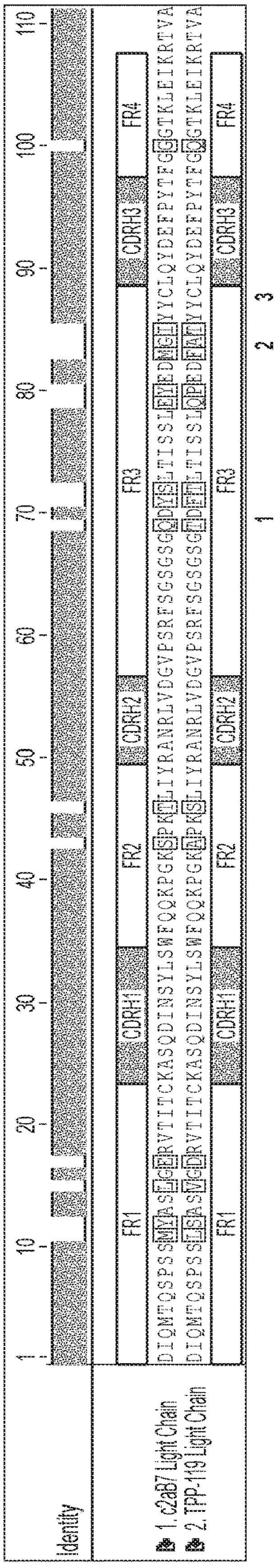

The Fab TPP-119 was chosen for further optimization based on its favorable properties (binding affinity, expression levels, and stability) based on its expression and binding affinity data as shown by Octet® and Biacore™. FIGS. 6A and 6B show the back-mutations (mutations to corresponding c2aB7 sequence) that were made in the heavy and light chain variable regions, respectively, of TPP-119. Single amino acid back-mutations were made, resulting in 21 different VH regions and 9 different VL regions, as shown in Tables 4 and 5.

TABLE 4

| VH region mutations | | |
|---|---|---|
| Plasmid | Mutation | Framework |
| pME001 | A9P | FR1 |
| pME002 | V11L | |
| pME003 | K12V | |
| PME004 | V18L | |
| PME005 | V20M | |
| pME006 | R38K | FR2 |
| PME007 | A40N | |
| pME008 | P41H | |
| PME009 | Q43K | |
| pME010 | R44S | |
| pME011 | M48I | |
| PME012 | R67K | FR3 |
| pME013 | V68A | |
| pME014 | I70L | |
| pME015 | R72V | |
| pME016 | TT74K | |
| pME017 | A76S | |
| PME018 | E82Q | |
| PME019 | S84N | |
| pME020 | R87T | |
| pME021 | A97G | |
| PRAA137 | Parental TPP-119 | |

TABLE 5

| VL region mutations | | |
|---|---|---|
| Plasmid | Mutation | Framework |
| PME022 | S12Y | FR1 |
| pME023 | T69Q | FR3 |
| PME024 | F71Y | |
| pME025 | T72S | |
| PME026 | Q79E | |
| PME027 | P80Y | |
| pME028 | F83M | |
| PME029 | A84G | |
| PME030 | T85I | |
| pRAA128 | Parental TPP-119 | |

Figure 8:
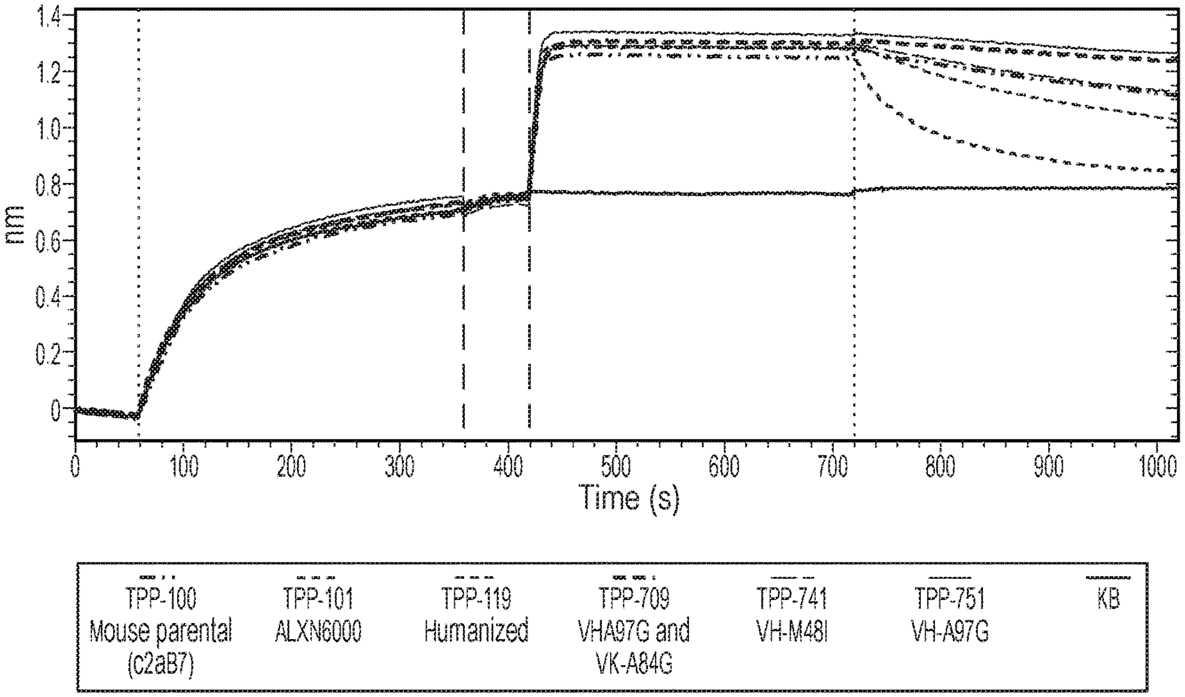
FIG. 8 is a sensorgram showing the affinity of back-mutated anti-CD200 Fabs for human CD200.

FIG. 7 summarizes the matrix of various combinations of the back-mutated heavy and light chains used for the Octet® assay. Table 5 summarizes the binding affinities of the various Fabs with back-mutated heavy chain or heavy/light chains for human CD200 relative to TPP-199 using the Octet® assay described in Example 2. Fabs in FIG. 7 that are not listed in Table 6 had lower binding affinity for human CD200 than TPP-199 (data not shown). As shown in Table 6 and FIG. 8, numerous Fabs exhibited better binding to CD200 compared to TPP-119, where the binding affinity ranges are defined as:

$+=k_d(1/s)$ of 1.5$e$-3 to 1.7$e$-3

$++=k_d(1/s)$ of 1.8$e$-3 to 1.9$e$-4

$+++=k_d(1/s)$ of >2.0$e$-4

TABLE 6

| Binding affinity of Fabs to human CD200 | | | | | |
|---|---|---|---|---|---|
| TPP-119 | + | TPP-542 | ++ | TPP-559 | +++ |
| TPP-548 | + | TPP-545 | ++ | TPP-562 | +++ |
| TPP-560 | + | TPP-550 | ++ | TPP-688 | +++ |
| TPP-561 | + | TPP-552 | ++ | TPP-709 | +++ |
| TPP-564 | + | TPP-556 | ++ | TPP-730 | +++ |
| TPP-575 | + | TPP-557 | ++ | TPP-741 | +++ |
| TPP-579 | + | TPP-563 | ++ | TPP-751 | +++ |
| TPP-669 | + | TPP-571 | ++ | | |
| TPP-671 | + | TPP-572 | ++ | | |
| TPP-686 | + | TPP-573 | ++ | | |
| TPP-690 | + | TPP-578 | ++ | | |
| TPP-697 | + | TPP-583 | ++ | | |
| TPP-712 | + | TPP-604 | ++ | | |
| TPP-714 | + | TPP-678 | ++ | | |
| TPP-718 | + | TPP-720 | ++ | | |
| TPP-719 | + | TPP-741 | ++ | | |
| TPP-721 | + | TPP-753 | ++ | | |
| TPP-722 | + | TPP-759 | ++ | | |
| TPP-724 | + | | | | |
| TPP-727 | + | | | | |
| TPP-733 | + | | | | |
| TPP-735 | + | | | | |
| TPP-738 | + | | | | |
| TPP-749 | + | | | | |
| TPP-750 | + | | | | |
| TPP-752 | + | | | | |
| TPP-756 | + | | | | |
| TPP-757 | + | | | | |
| TPP-758 | + | | | | |
| TPP-760 | + | | | | |

A selected panel of back-mutated Fabs were also tested for their affinity to human CD200 by SPR. Human CD200 was captured by Anti Fc (Human) on a CM5 chip followed by injections of TPP Fabs to obtain kinetics (this orientation minimized avidity that could potentially be caused by CD200 dimers). As shown in Table 7, TPP-709, TPP-741, and TPP-751 (Fabs corresponding to TPP-1143, TPP-1141, and TPP-1142 mAbs, respectively) all showed higher affinity for CD200 than samalizumab, with TPP-709 and TPP-751 (corresponding to TPP-1143 and TPP-1142 mAbs) showing an approximately 45-fold better affinity ($K_D$ of 104 and 132 pM) compared to samalizumab (TPP-101 Fab) and 3-fold better affinity than the mouse parental c2aB7 antibody (TPP-100 Fab).

TABLE 7

| Fab affinity for human CD200 by Biacore ™ M | | | | | |
|---|---|---|---|---|---|
| Sample (Fab) | Corresponding mAb | $k_a$ (1/Ms) | $k_d$ (1/s) 1 | $K_D$ (M) | $Chi^2$ |
| TPP-100 | TPP308 (c2aB7 mouse parental) | 1.69e6 | 7.47e-4 | 4.42e-10 | 0.11 |
| TPP-101 | Samalizumab TTP309 | 2.91e6 | 1.75e-2 | 6.01e-9 | 0.07 |
| TPP-119 | TPP305 | 1.37e6 | 1.74e-3 | 1.27e-9 | 0.12 |
| TPP-709 | TPP1143 | 1.82e6 | 2.40e-4 | 1.32e-10 | 0.08 |
| TPP-741 | TPP1141 | 1.74e6 | 7.07e-4 | 4.07e-10 | 0.18 |
| TPP-751 | TPP1142 | 2.11e6 | 2.20e-4 | 1.04e-10 | 0.18 |

Example 6: Expression of Back-Mutated Fabs

The expression levels of back-mutated Fabs were tested as described in Example 3. The Table 8 Fabs quantification was accomplished using the commercially available LabChip. The protein express chip was prepared according to the manufacturer's protocol. Samples were denatured at 100° C. for 5 minutes and ran in the The LabChip® GXII Touch™ using the Protein Express 200 assay. As shown in Table 8, Fab expression levels varied greatly, up to more than an order of magnitude difference in expression levels between constructs.

TABLE 8

| Fab protein expression levels | |
|---|---|
| Protein | Concentration (ng/μl) |
| TPP-542 | 15.17 |
| TPP-545 | 13.65 |
| TPP-550 | 10.51 |
| TPP-552 | 14.79 |
| TPP-556 | 15.47 |
| TPP-557 | 7.85 |
| TPP-559 | 0.56 |
| TPP-560 | 10.51 |
| TPP-562 | 15.54 |
| TPP-753 | 19.65 |
| TPP-563 | 5.48 |
| TPP-571 | 4.31 |
| TPP-572 | 0.04 |
| TPP-573 | 2.53 |
| TPP-578 | 0.04 |
| TPP-583 | 13.63 |
| TPP-604 | 6.19 |
| TPP-669 | 75.65 |
| TPP-678 | 61.84 |
| TPP-688 | 63.06 |
| TPP-759 | 41.19 |
| TPP-690 | 44.09 |
| TPP-709 | 75.82 |
| TPP-712 | 103.73 |
| TPP-720 | 74.07 |
| TPP-721 | 47.1 |
| TPP-730 | 76.49 |
| TPP-733 | 93.31 |

TABLE 8-continued

| Fab protein expression levels | |
|---|---|
| Protein | Concentration (ng/μl) |
| TPP-735 | 84.34 |
| TPP-741 | 72.7 |
| TPP-751 | 80.88 |

Example 7: Engineering Fabs into Monoclonal Antibodies

The back-mutated Fabs TPP-709, TPP-741, and TPP-751 were engineered into monoclonal antibody format by adding the human G2G4 Fc (effectorless) at the C-terminus of the heavy chain. The resulting mAbs were named TPP-1141, TPP-1142, and TPP-1143, as shown in Table 9. The heavy chain-Fc was cloned in frame with the Esp3I sites in mammalian expression vector pVEK001. This was synthesized by standard commercial methods and paired with the appropriate light chain construct for transfection/expression. Table 9 provides a summary of the newly engineered anti-CD200 antibodies and their relationships with the back-mutated Fabs. Electrospray ionization-time of flight (ESI-TOF) confirmed molecular weight consistent with theoretical molecular weight with glycans within experimental error.

TABLE 9

| Engineering summary table | | |
|---|---|---|
| Name | Fab Protein | mAb Protein |
| Mouse parental c2aB7 | TPP-100 | TPP-308 |
| Samalizumab | TPP-101 | TPP-309 |
| TPP-119 humanized | TPP-119 | TPP-305 |
| TPP-119 VH M48I | TPP-741 | TPP-1141 |
| TPP-119 VH A97G | TPP-751 | TPP-1142 |
| TPP-119 VH A97G and VK A84G | TPP-709 | TPP-1143 |

Example 8: Binding Properties of Engineered Anti-CD200 Antibodies

Figure 9:
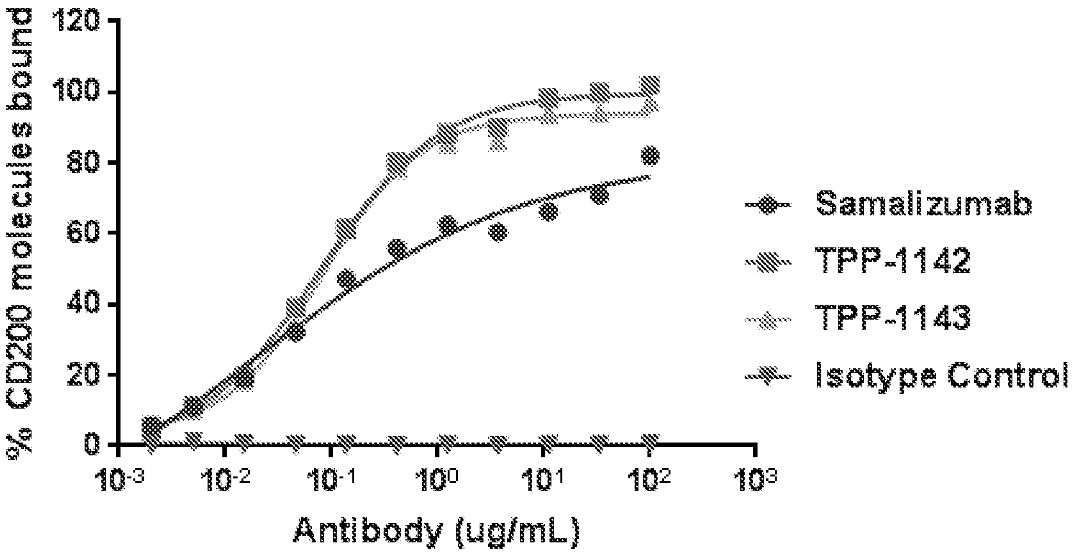
FIG. 9 is a graph comparing CD200 binding between samalizumab, TPP-1142, TPP-1143, and isotype control.

In this Example, the binding properties of the newly-engineered anti-CD200 antibodies were compared to samalizumab using a cell surface CD200 binding assay. Briefly, CD200 expressing Raji cells were incubated with increasing concentrations of the indicated labelled anti-CD200 antibodies. The binding of labelled antibodies to cells was detected by flow cytometry. As shown in FIG. 9, TPP-1142 and TPP-1143 showed improved binding to cell surface CD200 compared to samalizumab.

Figure 10:
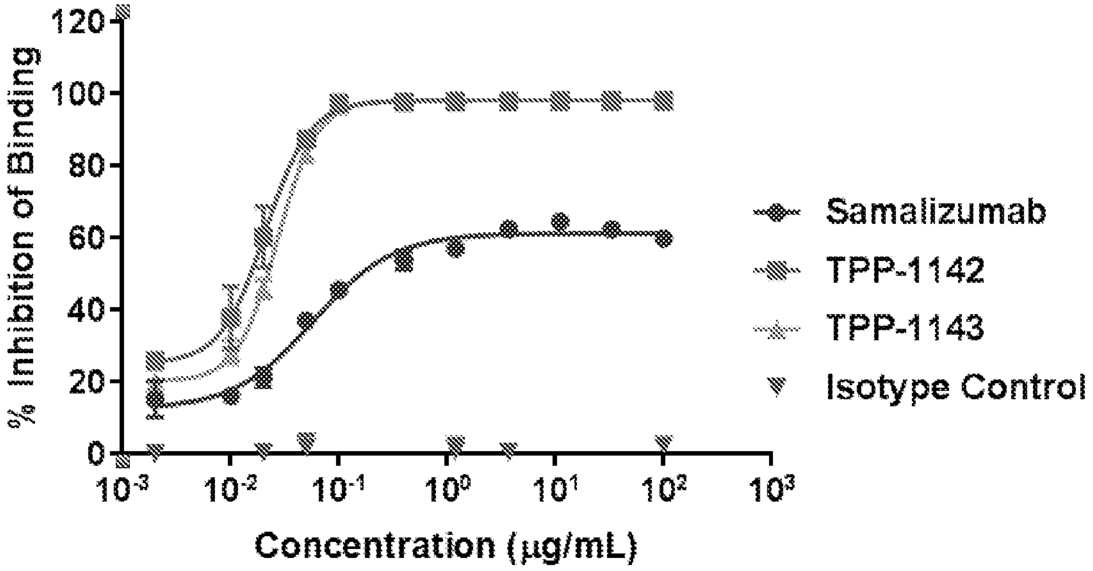
FIG. 10 is a graph comparing the inhibition of CD200 binding to CD200R between samalizumab, TPP-1142, TPP-1143, and isotype control.

Next, the abilities of the newly-engineered anti-CD200 antibodies to antagonize CD200R were compared with that of samalizumab using CD200+ Raji cells. Briefly, CD200+ Raji cells were incubated with increasing concentrations of the samalizumab, TPP-1142, TPP-1143, or isotype control prior to incubation with labelled CD200R-Fc fusion protein. Binding of labeled CD200R-Fc was detected by flow cytometry. As shown in FIG. 10 and Table 10, TPP-1142 and TPP-11143 more effectively inhibited the binding of CD200 to CD200R compared to samalizumab.

TABLE 10

| EC50 values for inhibition of CD200:CD200R interaction | | | |
|---|---|---|---|
| Antibody | Samalizumab (EC50) | TPP-1142 (EC50) | TPP-1143 (EC50) |
| Mean ± SD (mg/mL) | 0.069 ± 0.012 | 0.034 ± 0.014 | 0.028 (n = 1) |
| Mean ± SD (nmoles/L) | 0.460 ± 0.080 | 0.226 ± 0.093 | 0.186 (n = 1) |
| Maximal inhibition at 100 mg/mL antibody (mean + SD) | 62.90 ± 0.99% | 99.99 ± 0.18% | 98.89% |

Whole-blood receptor occupancy studies were performed to demonstrate dose-dependent target occupancy for the test molecules on B cell and T cell populations in whole blood. Total CD200 binding was assessed with an antibody to CD200 (1B2) that binds CD200 at a site that is non-competitive with TPP-1143 or samalizumab. This antibody was labeled with Alexa-647. B cell populations were stained with CD-19-FITC and T cell populations were stained with CD3-PE and their occupancy was quantitated as follows.

Therapeutic Antibody Binding in Whole Blood: Unlabeled TPP-1143 and samalizumab (anti-CD200 antibodies) or an isotype control antibody mAb were pre-diluted in PBS at dose concentrations ranging from 100 to 0.005 μg/ml in FACS tubes at twice the final concentration with enough volume for triplicate samples per dose. Whole blood (including sodium heparin as anticoagulant) was added at 250 μL/FACs tube and sealed. Tubes were incubated at 25° C. in a temperature-controlled cabinet overnight to allow therapeutic antibody binding.

FACS Antibody Staining: Cells were blocked with Fc blocking reagent for 30 min. Red blood cells were lysed with hemolytic buffer; remaining cells were spun 800×g for 5 minutes, and the resulting cell pellet was washed twice with PBS. After final wash, cell pellets were resupended into 200 μL PBS. Cells were stained with a fixable LIVE/DEAD™ dye for 20 minutes protected from light, and then neutralized and washed with FACS buffer. After the final wash the cells were resuspended in 100 μL wash with FcR block. Labeled antibody cocktail mixes were prepared CD3-PE/CD19-FITC/Alexa-647 or CD3-PE/CD19-FITC/1B2-647 in blocking buffer as well as appropriate controls (single color and FMO). The appropriate amount of antibody was added and incubated with cells protected from light for 30 minutes at room temperature. After incubation cells were washed, spun 800×g for 5 minutes and resuspended into 150 μL DPBS. Cells were fixed with an equal volume of 1% PFA for 15 minutes at 4° C., washed once with 3 ml PBS, resuspended into 200 μL PBS, transferred to V-bottom plates, and stored at 4° C. until analysis.

FACS Analysis: Data was acquired on an automated cell analyzer (BD Fortessa) by gating on lymphocytes, and single live cells followed by B cell (CD19+-FITC) and T cells (CD3-PE) populations. Two independent runs were performed for each antibody titration and samples were run in triplicate. Percent receptor occupancy was calculated from the MFI (median fluorescence intensity) according to the following formula:

$$RO=(((1B2\text{-}AF647\ MFI*K_{corr})\cdot SAM\text{-}A647\ MFI)/(1B2\cdot AF647\ MFI*K_{corr}))*100\%$$

Figure 11A:
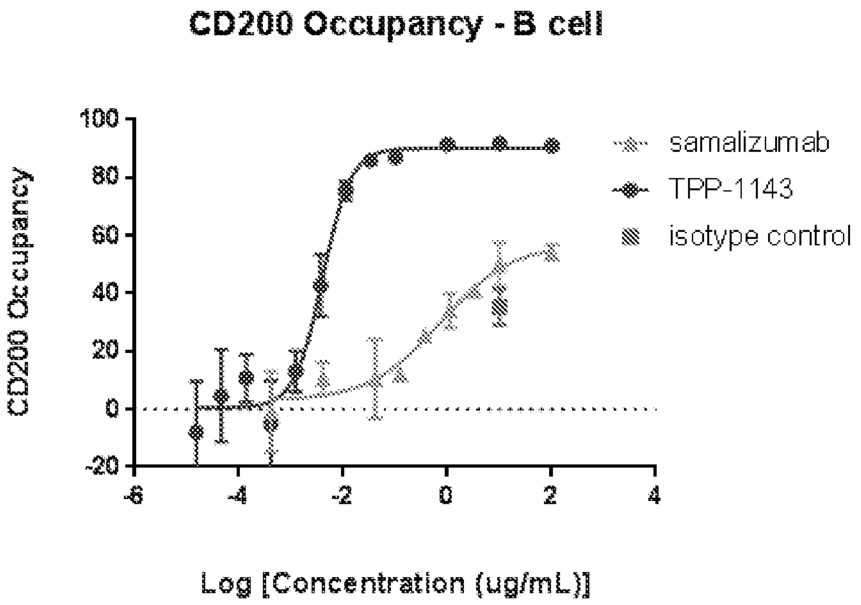
FIGS. 11A and 11B are graphs comparing CD200 occupancy in B cells and T cells, respectively, between samalizumab, TPP-1143, and isotype control. The graphs show the average of two replicate experiments +/−the SEM (standard error of the mean), where each individual experiment had triplicate data points per concentration of antibody.
Figure 11B:
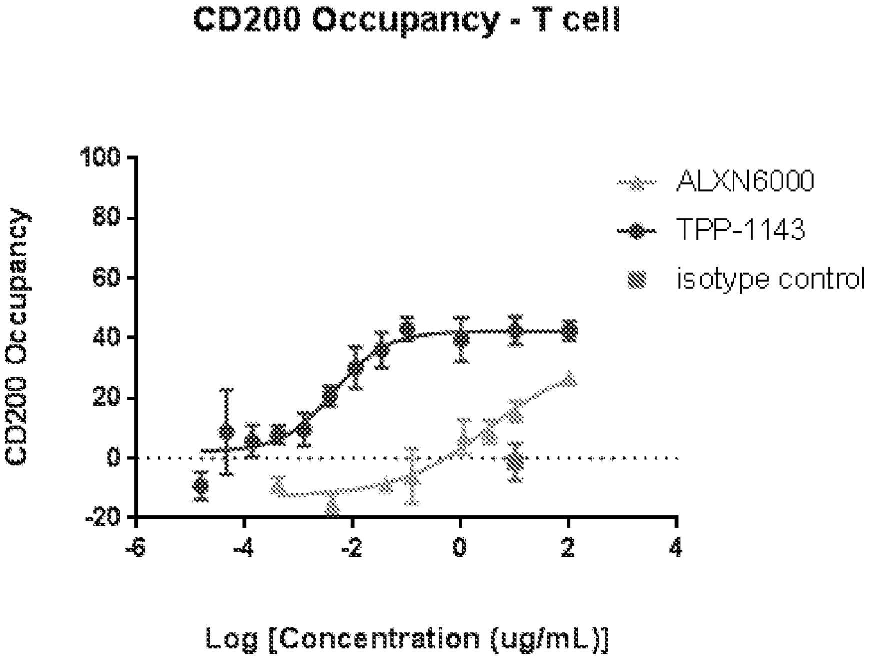

With respect to saturation of CD200, as shown in FIGS. 11A and 11B, TPP-1143 showed improved saturation of CD200 (occupancy) compared to samalizumab in both B cells (FIG. 11A) and T cells (FIG. 11B) in whole blood samples. B cells were more sensitive to CD200 saturation than T cells due to higher CD200 expression. TPP-1143 showed superior binding saturation kinetics compared to samalizumab.

Example 9: Stability of Anti-CD200 Monoclonal Antibodies

In this Example, the solubility of the engineered anti-CD200 antibodies described in Example 7 were tested by SEC. Samples were concentrated to approximately 50 mg/mL in 10 mM Sodium Acetate, 290 mM Glycine, and 0.05% PS-80 at pH5.5. SEC was performed on an ACQUITY UPLC® BEH200, 1.7 μm, 4.6×150 mm column with an isocratic elution with 1×PBS at flowrate of 0.4 mL/min for 8 min. SEC was performed both before and after concentration.

In later runs, precipitation occurred in the dialysis step into 10 mM Sodium Acetate, 290 mM Glycine, pH5.5 buffer without PS-80. The antibodies were stable when placed into 1×PBS buffer. The final products of TPP-1142 (5.33 mg/mL) and TPP-1143 (6.45 mg/mL) were successfully stored in 1×PBS. SEC-HPLC results indicated over 30% aggregation in both antibodies in 1×PBS.

Table 11 summarizes the SEC data. Samalizumab, TPP-1142, and TPP-1143 showed no notable decline in main peak % after concentration. Moreover, TPP-1142 and TPP-1143 were able to be concentrated to 50 mg/ml in buffer without precipitation, which was an improvement compared to samalizumab.

TABLE 11

| Soluble aggregation by SEC | | | |
|---|---|---|---|
| Name | Sample Name (IgG) | Main peak % pre-concentrating | Main peak% post-concentrating |
| Newly humanized (Fab TPP-119) | TPP-305 | 95.67 | 92.35 |
| Mouse parental c2aB7 (Fab TPP-100) | TPP-308 | 95.67 | 97.44 |
| Samalizumab (Fab TPP-101) | TPP-309 | 94.68 | 94.44 |
| vH M48I (Fab TPP-741) | TPP-1141 | 94.1 | 90.77 |
| vH A97G (Fab TPP-751) | TPP-1142 | 96.97 | 95.34 |
| TPP-709 vH A97G and vK A84G (Fab TPP-709) | TPP-1143 | 95.4 | 95.22 |

Figure 12:
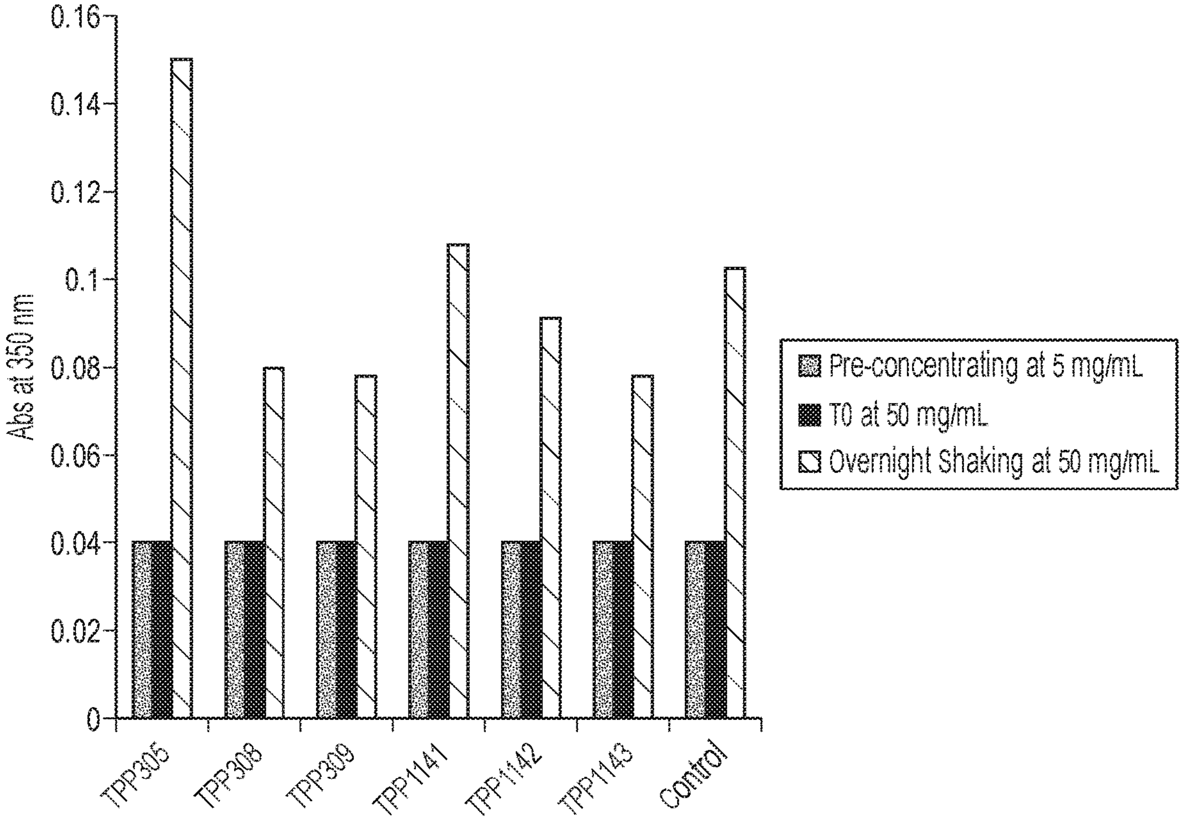
FIG. 12 is a bar graph showing the stability (level of insoluble aggregation) of the indicated Fabs under various conditions (pre-concentration (5 mg/mL), concentrating to 50 mg/mL, and overnight shaking at 50 mg/mL), as determined by absorbance at 350 nm.

Aggregation and mechanical stability of the anti-CD200 antibodies were also tested by assessing absorbance at 350 nm, which correlates with the level of insoluble aggregation. The turbidity was evaluated at 350 nm absorbance on a 96 well UV transparent plate with 80 μL in each well. As shown in FIG. 12, TPP-308, TPP-309, and TPP-1143 all had lower 350 nm absorption values than a control mAb, indicating the antibodies were more stable than the control after overnight shaking at 1000 rpm at room temperature, in terms of mechanical stability, indicating suitability for manufacturability.

The anti-CD200 antibodies were next tested for thermal stability. The thermal stability was tested by differential scanning fluorimetry (DSF). The protein melting curve was recorded by fluorescence signal change after binding with SYPRO™ Orange Protein Gel Stain as temperature ramped from 30.0° C. to 95.0° C. $T_{onset}$ was determined as the temperature when the fluorescence signal started rising from baseline.

Figure 13:
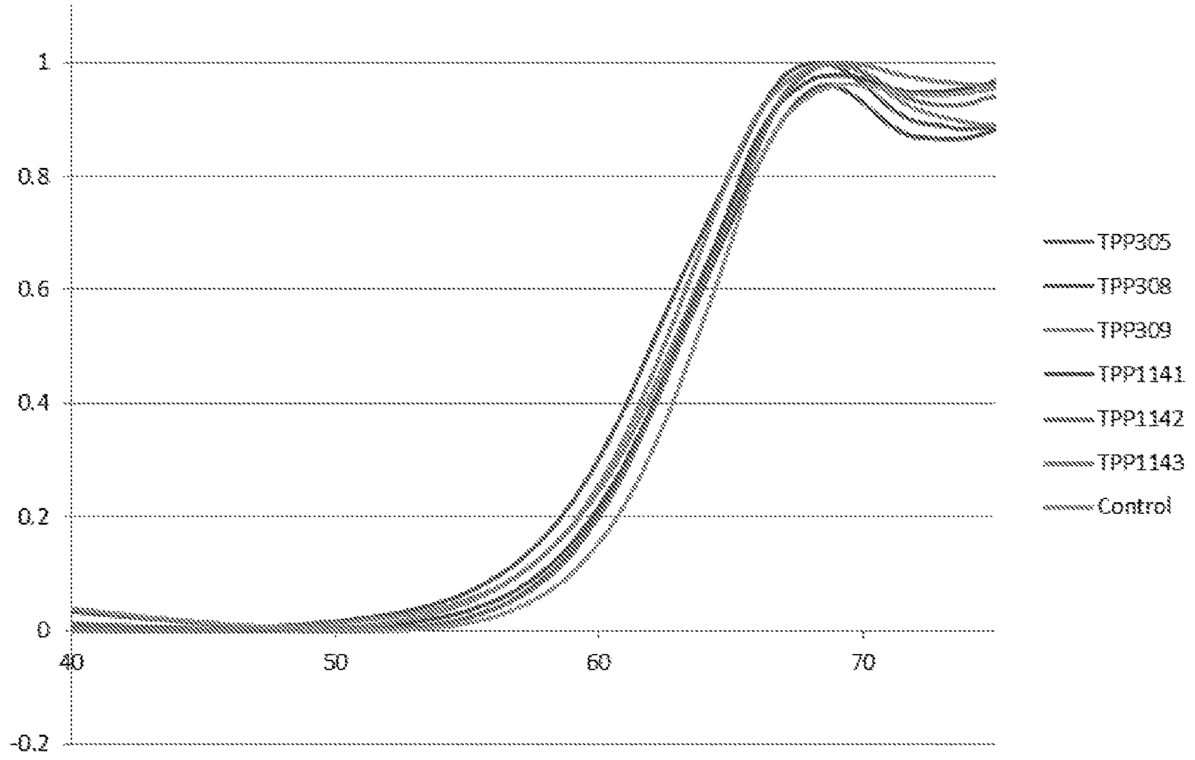
FIG. 13 is a graph depicting the thermal sensitivity of the indicated antibodies.

As shown in FIG. 13, all antibodies showed comparable good thermal stability, with a $T_{onset}$>51'3° C.

Example 10: Assessment of Hydrophobicity of Anti-CD200 Antibodies by HPLC-HIC

In this Example, the hydrophobicity of anti-CD200 antibodies was assessed by high pressure liquid chromatography-hydrophobic interaction chromatography (HPLC-HIC). Strong hydrophobicity leads to self-association under salt conditions, potentially posing formulation challenges. HPLC-HIC was performed on a ProPac™ HIC-10 HPLC Columns, 5 μm, 4.6×100 mm column with a gradient elution starting with 0.9 M sodium sulfate in 1×PBS for 1 min followed by a linear gradient to 1×PBS for 20 min.

Figure 14:
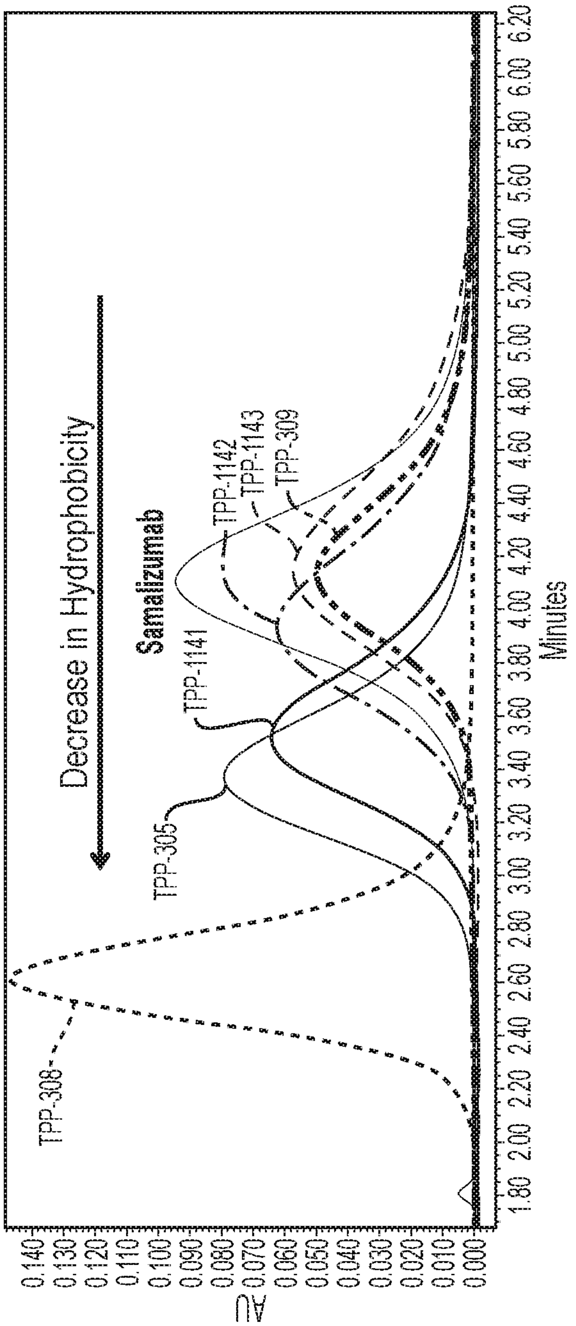
FIG. 14 is a graph showing the hydrophobicity of the indicated antibodies, as determined by HPLC-HIC.

As shown in FIG. 14, all tested antibodies were confirmed to be either less hydrophobic than, or of comparable hydrophobicity to, samalizumab, which was a necessary prerequisite for proceeding with further testing given the aggregation potential of samalizumab. TPP-308 was the least hydrophobic among the antibodies tested.

TABLE 12

| Summary Table of Sequences | | |
|---|---|---|
| SEQ ID | Description | Sequence |
| 1 | Precursor human CD200 isoform A | MERLVIRMPFSHLSTYSLVWVMAAVVLCTAQVQVVTQDEREQLYTPASLK CSLQNAQEALIVTWQKKKAVSPENMVTFSENHGVVIQPAYKDKINITQLG LQNSTITFWNITLEDEGCYMCLFNTFGFGKISGTACLTVYVQPIVSLHYK FSEDHLNITCSATARPAPMVFWKVPRSGIENSTVTLSHPNGTTSVTSILH IKDPKNQVGKEVICQVLHLGTVTDFKQTVNKGYWFSVPLLLSIVSLVILL VLISILLYWKRHRNQDREP |
| 2 | Human CD200 isoform B | MERLTLTRTIGGPLLTATLLGKTTINDYQVIRMPFSHLSTYSLVWVMAAV VLCTAQVQVVTQDEREQLYTPASLKCSLQNAQEALIVTWQKKKAVSPENM VTFSENHGVVIQPAYKDKINITQLGLQNSTITFWNITLEDEGCYMCLFNT FGFGKISGTACLTVYVQPIVSLHYKFSEDHLNITCSATARPAPMVFWKVP RSGIENSTVTLSHPNGTTSVTSILHIKDPKNQVGKEVICQVLHLGTVTDF KQTVNKGYWFSVPLLLSIVSLVILLVLISILLYWKRHRNQDREP |

TABLE 12-continued

Summary Table of Sequences

| SEQ ID | Description | Sequence |
|---|---|---|
| 3 | Full-length, mature human CD200 | VIRMPFSHLSTYSLVWVMAAVVLCTAQVQVVTQDEREQLYTTASLKCSLQ NAQEALIVTWQKKKAVSPENMVTFSENHGVVIQPAYKDKINITQLGLQNS TITFWNITLEDEGCYMCLFNTFGFGKISGTACLTVYVQPIVSLHYKFSED HLNITCSATARPAPMVFWKVPRSGIENSTVTLSHPNGTTSVTSILHIKDP KNQVGKEVICQVLHLGTVTDFKQTVNKGYWFSVPLLLSIVSLVILLVLIS ILLYWKRHRNQDRGELSQGVQKMT |
| 4 | IgG2/G4 hybrid constant region | ASTKGPSVFPLAPCSRSTSESTAALGCLVKDYFPEPVTVSWNSGALTSGVHTF PAVLQSSGLYSLSSVVTVPSSNFGTQTYTCNVDHKPSNTKVDKTVERKCCVEC PPCPAPPVAGPSVFLFPPKPKDTLMISRTPEVTCVVVDVSQEDPEVQFNWYVD GVEVHNAKTKPREEQFNSTYRVVSVLTVLHQDWLNGKEYKCKVSNKGLPSSIE KTISKAKGQPREPQVYTLPPSQEEMTKNQVSLTCLVKGFYPSDIAVEWESNGQ PENNYKTTPPVLDSDGSFFLYSRLTVDKSRWQEGNVFSCSVMHEALHNHYTQ KSLSLSLGK |
| 5 | Samalizumab/ C2aB7 heavy chain CDR1 | DYIIL |
| 6 | Samalizumab/ C2aB7 heavy chain CDR2 | HIDPYYGSSNYNLKFKG |
| 7 | Samalizumab/ C2aB7 heavy chain CDR3 | SKRDYFDY |
| 8 | Samalizumab/ C2aB7 light chain CDR1 | KASQDINSYLS |
| 9 | Samalizumab/ C2aB7 light chain CDR2 | RANRLVD |
| 10 | Samalizumab/ C2aB7 light chain CDR3 | LQYDEFPYT |
| 11 | Samalizumab VH | QVQLQQSGSELKKPGASVKISCKASGYSFTDYIILWVRQNPGKGLEWIGHIDP YYGSSNYNLKFKGRVTITADQSTTTAYMELSSLRSEDTAVYYCGRSKRDYFDY WGQGTTLTVSS |
| 12 | Samalizumab VL | DIQMTQSPSSLSASIGDRVTITCKASQDINSYLSWFQQKPGKAPKLLIYRANR LVDGVPSRFSGSGSGTDYTLTISSLQPEDFAVYYCLQYDEFPYTFGGGTKLEI K |
| 13 | Samalizumab HC | QVQLQQSGSELKKPGASVKISCKASGYSFTDYIILWVRQNPGKGLEWIGHIDP YYGSSNYNLKFKGRVTITADQSTTTAYMELSSLRSEDTAVYYCGRSKRDYFDY WGQGTTLTVSSASTKGPSVFPLAPCSRSTSESTAALGCLVKDYFPEPVTVSWN SGALTSGVHTFPAVLQSSGLYSLSSVVTVPSSNFGTQTYTCNVDHKPSNTKVD KTVERKCCVECPPCPAPPVAGPSVFLFPPKPKDTLMISRTPEVTCVVVDVSQE DPEVQFNWYVDGVEVHNAKTKPREE QFNSTYRVVSVLTVLHQDWLNGKEYKCKVSNKGLPSSIEKTISKAKGQPREPQ VYTLPPSQEEMTKNQVSLTCLVKGFYPSDIAVEWESNGQPENNYKTTPPVLDS DGSFFLYSRLTVDKSRWQEGNVFSCSVMHEALHNHYTQKSLSLSLGK |
| 14 | Samalizumab LC | DIQMTQSPSSLSASIGDRVTITCKASQDINSYLSWFQQKPGKAPKLLIYRANR LVDGVPSRFSGSGSGTDYTLTISSLQPEDFAVYYCLQYDEFPYTFGGGTKLEI KRTVAAPSVFIFPPSDEQLKSGTASVVCLLNNFYPREAKVQWKVDNALQSGNS QESVTEQDSKDSTYSLSSTLTLSKADYEKHKVYACEVTHQGLSSPVTKSFN RGEC |
| 15 | Fab with samalizumab VH and VL (aka TPP-101) | DIQMTQSPSSLSASIGDRVTITCKASQDINSYLSWFQQKPGKAPKLLIYR ANRLVDGVPSRFSGSGSGTDYTLTISSLQPEDFAVYYCLQYDEFPYTFGG GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLQQSGSELKKPGASVKISCKASGYSFTDYIILW VRQNPGKGLEWIGHIDPYYGSSNYNLKFKGRVTITADQSTTTAYMELSSL RSEDTAVYYCGRSKRDYFDYWGQGTTLTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |

TABLE 12-continued

| Summary Table of Sequences | | |
|---|---|---|
| SEQ ID | Description | Sequence |
| 16 | C2aB7 VH | EVQLQQSGPELVKPGASLKMSCKASGYSFTDYIILWVKQNHGKSLEWIGH<br>IDPYYGSSNYNLKFKGKATLTVDKSSSTAYMQLNSLTSEDSAVYYCGRSK<br>RDYFDYWGQGTTLTVSS |
| 17 | C2aB7 VL | DIQMTQSPSSMYASLGERVTITCKASQDINSYLSWFQQKPGKSPKTLIYR<br>ANRLVDGVPSRFSGSGSGQDYSLTISSLEYEDMGIYYCLQYDEFPYTFGG<br>GTKLEIK |
| 18 | Fab with C2aB7 VH and VL (aka TPP-100) | DIQMTQSPSSMYASLGERVTITCKASQDINSYLSWFQQKPGKSPKTLIYR<br>ANRLVDGVPSRFSGSGSGQDYSLTISSLEYEDMGIYYCLQYDEFPYTFGG<br>GTKLEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGECEVQLQQSGPELVKPGASLKMSCKASGYSFTDYIILW<br>VKQNHGKSLEWIGHIDPYYGSSNYNLKFKGKATLTVDKSSSTAYMQLNSL<br>TSEDSAVYYCGRSKRDYFDYWGQGTTLTVSSASTKGPSVFPLAPSSKSTS<br>GGTAALGCLVKDYFPEPVTVSWNSGALTSGVHTFPAVLQSSGLYSLSSVV<br>TVPSSSLGTQTYICNVNHKPSNTKVDKRVEPKSC |
| 19 | TPP-119 Fab | QMTQSPSSLSASVGDRVTITCKASQDINSYLSWFQQKPGKAPKSLIYRAN<br>RLVDGVPSRFSGSGSGTDFTLTISSLQPEDFATYYCLQYDEFPYTFGQGT<br>KLEIKRTVAAPSVFIFPPSDEQLKSGTASVVCLLNNFYPREAKVQWKVDN<br>ALQSGNSQESVTEQDSKDSTYSLSSTLTLSKADYEKHKVYACEVTHQGLS<br>SPVTKSFNRGECQVQLVQSGAEVKKPGASVKVSCKASGYSFTDYIILWVR<br>QAPGQRLEWMGHIDPYYGSSNYNLKFKGRVTITRDTSASTAYMELSSLRS<br>EDTAVYYCARSKRDYFDYWGQGTLVTVSSASTKGPSVFPLAPSSKSTSGG<br>TAALGCLVKDYFPEPVTVSWNSGALTSGVHTFPAVLQSSGLYSLSSVVTV<br>PSSSLGTQTYICNVNHKPSNTKVDKRVEPKSC |
| 20 | TPP-119 VH | QVQLVQSGAEVKKPGASVKVSCKASGYSFTDYTILWVRQAPGQRLEWMGH<br>IDPYYGSSNYNLKFKGRVTITRDTSASTAYMELSSLRSEDTAVYYCARSK<br>RDYFDYWGQGTLVTVSS |
| 21 | TPP-119 VL | QMTQSPSSLSASVGDRVTITCKASQDINSYLSWFQQKPGKAPKSLIYRAN<br>RLVDGVPSRFSGSGSGTDFTLTISSLQPEDFATYYCLQYDEFPYTFGQGT<br>KLEIK |
| 22 | TPP-542 | DIQMTQSPSSLYASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGECQVQLVQSGPEVKKPGASVKVSCKASGYSFTDYIILW<br>VRQAPGQRLEWMGHIDPYYGSSNYNLKFKGRVTITRDTSASTAYMELSSL<br>RSEDTAVYYCARSKRDYFDYWGQGTLVTVSSASTKGPSVFPLAPSSKSTS<br>GGTAALGCLVKDYFPEPVTVSWNSGALTSGVHTFPAVLQSSGLYSLSSVV<br>TVPSSSLGTQTYICNVNHKPSNTKVDKRVEPKSC |
| 23 | TPP-542 VH | QVQLVQSGPEVKKPGASVKVSCKASGYSFTDYIILWVRQAPGQRLEWMGH<br>IDPYYGSSNYNLKFKGRVTITRDTSASTAYMELSSLRSEDTAVYYCARSK<br>RDYFDYWGQGTLVTVSS |
| 24 | TPP-542 VL | DIQMTQSPSSLYASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIK |
| 25 | TPP-545 | DIQMTQSPSSLYASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGECQVQLVQSGAEVKKPGASLKVSCKASGYSFTDYIILW<br>VRQAPGQRLEWMGHIDPYYGSSNYNLKFKGRVTITRDTSASTAYMELSSL<br>RSEDTAVYYCARSKRDYFDYWGQGTLVTVSSASTKGPSVFPLAPSSKSTS<br>GGTAALGCLVKDYFPEPVTVSWNSGALTSGVHTFPAVLQSSGLYSLSSVV<br>TVPSSSLGTQTYICNVNHKPSNTKVDKRVEPKSC |
| 26 | TPP-545 VH | QVQLVQSGAEVKKPGASLKVSCKASGYSFTDYIILWVRQAPGQRLEWMGH<br>IDPYYGSSNYNLKFKGRVTITRDTSASTAYMELSSLRSEDTAVYYCARSK<br>RDYFDYWGQGTLVTVSS |
| 27 | TPP-545 VL | DIQMTQSPSSLYASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIK |
| 28 | TPP-548 | DIQMTQSPSSLYASVGDRVTITCKASQDINSYLSWFQQKPGKAPKSLIYR<br>ANRLVDGVPSRFSGSGSGTDFTLTISSLQPEDFATYYCLQYDEFPYTFGQ |

TABLE 12-continued

Summary Table of Sequences

| SEQ ID | Description | Sequence |
|---|---|---|
| | | GTKLEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGECQVQLVQSGAEVKKPGASVKVSCKASGYSFTDYIILW<br>VRQNPGQRLEWMGHIDPYYGSSNYNLKFKGRVTITRDTSASTAYMELSSL<br>RSEDTAVYYCARSKRDYFDYWGQGTLVTVSSASTKGPSVFPLAPSSKSTS<br>GGTAALGCLVKDYFPEPVTVSWNSGALTSGVHTFPAVLQSSGLYSLSSVV<br>TVPSSSLGTQTYICNVNHKPSNTKVDKRVEPKSC |
| 29 | TPP-548 VH | QVQLVQSGAEVKKPGASVKVSCKASGYSFTDYIILWVRQNPGQRLEWMGH<br>IDPYYGSSNYNLKFKGRVTITRDTSASTAYMELSSLRSEDTAVYYCARSK<br>RDYFDYWGQGTLVTVSS |
| 30 | TPP-548 VL | DIQMTQSPSSLYASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIK |
| 31 | TPP-550 | DIQMTQSPSSLYASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGECQVQLVQSGAEVKKPGASVKVSCKASGYSFTDYIILW<br>VRQAPGKRLEWMGHIDPYYGSSNYNLKFKGRVTITRDTSASTAYMELSSL<br>RSEDTAVYYCARSKRDYFDYWGQGTLVTVSSASTKGPSVFPLAPSSKSTS<br>GGTAALGCLVKDYFPEPVTVSWNSGALTSGVHTFPAVLQSSGLYSLSSVV<br>TVPSSSLGTQTYICNVNHKPSNTKVDKRVEPKSC |
| 32 | TPP-550 VH | QVQLVQSGAEVKKPGASVKVSCKASGYSFTDYIILWVRQAPGKRLEWMGH<br>IDPYYGSSNYNLKFKGRVTITRDTSASTAYMELSSLRSEDTAVYYCARSK<br>RDYFDYWGQGTLVTVSS |
| 33 | TPP-550 VL | DIQMTQSPSSLYASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIK |
| 34 | TPP-552 | DIQMTQSPSSLYASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGECQVQLVQSGAEVKKPGASVKVSCKASGYSFTDYIILW<br>VRQAPGQRLEWIGHIDPYYGSSNYNLKFKGRVTITRDTSASTAYMELSSL<br>RSEDTAVYYCARSKRDYFDYWGQGTLVTVSSASTKGPSVFPLAPSSKSTS<br>GGTAALGCLVKDYFPEPVTVSWNSGALTSGVHTFPAVLQSSGLYSLSSVV<br>TVPSSSLGTQTYICNVNHKPSNTKVDKRVEPKSC |
| 35 | TPP-552 VH | QVQLVQSGAEVKKPGASVKVSCKASGYSFTDYIILWVRQAPGQRLEWIGH<br>IDPYYGSSNYNLKFKGRVTITRDTSASTAYMELSSLRSEDTAVYYCARSK<br>RDYFDYWGQGTLVTVSS |
| 36 | TPP-552 VL | DIQMTQSPSSLYASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIK |
| 37 | TPP-556 | DIQMTQSPSSLYASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGECQVQLVQSGAEVKKPGASVKVSCKASGYSFTDYIILW<br>VRQAPGQRLEWMGHIDPYYGSSNYNLKFKGRVTITVDTSASTAYMELSSL<br>RSEDTAVYYCARSKRDYFDYWGQGTLVTVSSASTKGPSVFPLAPSSKSTS<br>GGTAALGCLVKDYFPEPVTVSWNSGALTSGVHTFPAVLQSSGLYSLSSVV<br>TVPSSSLGTQTYICNVNHKPSNTKVDKRVEPKSC |
| 38 | TPP-556 VH | QVQLVQSGAEVKKPGASVKVSCKASGYSFTDYTILWVRQAPGQRLEWMGH<br>IDPYYGSSNYNLKFKGRVTITVDTSASTAYMELSSLRSEDTAVYYCARSK<br>RDYFDYWGQGTLVTVSS |
| 39 | TPP-556 VL | DIQMTQSPSSLYASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIK |
| 40 | TPP-557 | DIQMTQSPSSLYASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>VRQAPGQRLEWMGHIDPYYGSSNYNLKFKGRVTITRDKSASTAYMELSSL |

TABLE 12-continued

Summary Table of Sequences

| SEQ ID | Description | Sequence |
|---|---|---|
| | | RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 41 | TPP-557 VH | QVQLVQSGAEVKKPGASVKVSCKASGYSFTDYIILWVRQAPGQRLEWMGH IDPYYGSSNYNLKFKGRVTITRDKSASTAYMELSSLRSEDTAVYYCARSK RDYFDYWGQGTLVTVSS |
| 42 | TPP-557 VL | DIQMTQSPSSLYASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 43 | TPP-559 | DIQMTQSPSSLYASVGDRVTITCKASQDINSYLSWFQQKPGKAPKSLIYR ANRLVDGVPSRFSGSGSGTDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITRDTSASTAYMQLSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 44 | TPP-559 VH | QVQLVQSGAEVKKPGASVKVSCKASGYSFTDYIILWVRQAPGQRLEWMGH IDPYYGSSNYNLKFKGRVTITRDTSASTAYMQLSSLRSEDTAVYYCARSK RDYFDYWGQGTLVTVSS |
| 45 | TPP-559 VL | DIQMTQSPSSLYASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 46 | TPP-560 | DIQMTQSPSSLYASVGDRVTITCKASQDINSYLSWFQQKPGKAPKSLIYR ANRLVDGVPSRFSGSGSGTDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITRDTSASTAYMELNSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 47 | TPP-560 VH | QVQLVQSGAEVKKPGASVKVSCKASGYSFTDYIILWVRQAPGQRLEWMGH IDPYYGSSNYNLKFKGRVTITRDTSASTAYMELNSLRSEDTAVYYCARSK RDYFDYWGQGTLVTVSS |
| 48 | TPP-560 VL | DIQMTQSPSSLYASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 49 | TPP-561 | DIQMTQSPSSLYASVGDRVTITCKASQDINSYLSWFQQKPGKAPKSLIYR ANRLVDGVPSRFSGSGSGTDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITRDTSASTAYMELSSL TSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 50 | TPP-561 VH | QVQLVQSGAEVKKPGASVKVSCKASGYSFTDYIILWVRQAPGQRLEWMGH IDPYYGSSNYNLKFKGRVTITRDTSASTAYMELSSLTSEDTAVYYCARSK RDYFDYWGQGTLVTVSS |
| 51 | TPP-561 VL | DIQMTQSPSSLYASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 52 | TPP-562 | DIQMTQSPSSLYASVGDRVTITCKASQDINSYLSWFQQKPGKAPKSLIYR ANRLVDGVPSRFSGSGSGTDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITRDTSASTAYMELSSL RSEDTAVYYCGRSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |

TABLE 12-continued

Summary Table of Sequences

| SEQ ID | Description | Sequence |
|---|---|---|
| 53 | TPP-562 VH | QVQLVQSGAEVKKPGASVKVSCKASGYSFTDYIILWVRQAPGQRLEWMGH IDPYYGSSNYNLKFKGRVTITRDTSASTAYMELSSLRSEDTAVYYCGRSK RDYFDYWGQGTLVTVSS |
| 54 | TPP-562 VL | DIQMTQSPSSLYASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 55 | TPP-563 | DIQMTQSPSSLSASVGDRVTITCKASQDINSYLSWFQQKPGKAPKSLIYR ANRLVDGVPSRFSGSGSGQDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGPEVKKPGASVKVSCKASGYSFTDYIILW VRQAPGQRLEWMGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 56 | TPP-563 VH | QVQLVQSGPEVKKPGASVKVSCKASGYSFTDYIILWVRQAPGQRLEWMGH IDPYYGSSNYNLKFKGRVTITRDTSASTAYMELSSLRSEDTAVYYCARSK RDYFDYWGQGTLVTVSS |
| 57 | TPP-563 VL | DIQMTQSPSSLSASVGDRVTITCKASQDINSYLSWFQQKPGKAPKSLIYR ANRLVDGVPSRFSGSGSGQDFTLTISSLQPEDFATYYCLQYDEFPYTFGQ GTKLEIK |
| 58 | TPP-564 | DIQMTQSPSSLSASVGDRVTITCKASQDINSYLSWFQQKPGKAPKSLIYR ANRLVDGVPSRFSGSGSGQDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAELKKPGASVKVSCKASGYSFTDYIILW VRQAPGQRLEWMGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 59 | TPP-564 VH | QVQLVQSGAELKKPGASVKVSCKASGYSFTDYIILWVRQAPGQRLEWMGH IDPYYGSSNYNLKFKGRVTITRDTSASTAYMELSSLRSEDTAVYYCARSK RDYFDYWGQGTLVTVSS |
| 60 | TPP-564 VL | DIQMTQSPSSLSASVGDRVTITCKASQDINSYLSWFQQKPGKAPKSLIYR ANRLVDGVPSRFSGSGSGQDFTLTISSLQPEDFATYYCLQYDEFPYTFGQ GTKLEIK |
| 61 | TPP-571 | DIQMTQSPSSLSASVGDRVTITCKASQDINSYLSWFQQKPGKAPKSLIYR ANRLVDGVPSRFSGSGSGQDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGKRLEWMGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 62 | TPP-571 VH | QVQLVQSGAEVKKPGASVKVSCKASGYSFTDYIILWVRQAPGKRLEWMGH IDPYYGSSNYNLKFKGRVTITRDTSASTAYMELSSLRSEDTAVYYCARSK RDYFDYWGQGTLVTVSS |
| 63 | TPP-571 VL | DIQMTQSPSSLSASVGDRVTITCKASQDINSYLSWFQQKPGKAPKSLIYR ANRLVDGVPSRFSGSGSGQDFTLTISSLQPEDFATYYCLQYDEFPYTFGQ GTKLEIK |
| 64 | TPP-572 | DIQMTQSPSSLSASVGDRVTITCKASQDINSYLSWFQQKPGKAPKSLIYR ANRLVDGVPSRFSGSGSGQDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQSLEWMGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |

TABLE 12-continued

Summary Table of Sequences

| SEQ ID | Description | Sequence |
|---|---|---|
| 65 | TPP-572 VH | QVQLVQSGAEVKKPGASVKVSCKASGYSFTDYIILWVRQAPGQSLEWMGH IDPYYGSSNYNLKFKGRVTITRDTSASTAYMELSSLRSEDTAVYYCARSK RDYFDYWGQGTLVTVSS |
| 66 | TPP-572 VL | DIQMTQSPSSLSASVGDRVTITCKASQDINSYLSWFQQKPGKAPKSLIYR ANRLVDGVPSRFSGSGSGQDFTLTISSLQPEDFATYYCLQYDEFPYTFGQ GTKLEIK |
| 67 | TPP-573 | DIQMTQSPSSLSASVGDRVTITCKASQDINSYLSWFQQKPGKAPKSLIYR ANRLVDGVPSRFSGSGSGQDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWIGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 68 | TPP-573 VH | QVQLVQSGAEVKKPGASVKVSCKASGYSFTDYIILWVRQAPGQRLEWIGH IDPYYGSSNYNLKFKGRVTITRDTSASTAYMELSSLRSEDTAVYYCARSK RDYFDYWGQGTLVTVSS |
| 69 | TPP-573 VL | DIQMTQSPSSLSASVGDRVTITCKASQDINSYLSWFQQKPGKAPKSLIYR ANRLVDGVPSRFSGSGSGQDFTLTISSLQPEDFATYYCLQYDEFPYTFGQ GTKLEIK |
| 70 | TPP-575 | DIQMTQSPSSLSASVGDRVTITCKASQDINSYLSWFQQKPGKAPKSLIYR ANRLVDGVPSRFSGSGSGQDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRATITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 71 | TPP-575 VH | QVQLVQSGAEVKKPGASVKVSCKASGYSFTDYIILWVRQAPGQRLEWMGH IDPYYGSSNYNLKFKGRATITRDTSASTAYMELSSLRSEDTAVYYCARSK RDYFDYWGQGTLVTVSS |
| 72 | TPP-575 VL | DIQMTQSPSSLSASVGDRVTITCKASQDINSYLSWFQQKPGKAPKSLIYR ANRLVDGVPSRFSGSGSGQDFTLTISSLQPEDFATYYCLQYDEFPYTFGQ GTKLEIK |
| 73 | TPP-578 | DIQMTQSPSSLSASVGDRVTITCKASQDINSYLSWFQQKPGKAPKSLIYR ANRLVDGVPSRFSGSGSGQDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITRDKSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 74 | TPP-578 VH | QVQLVQSGAEVKKPGASVKVSCKASGYSFTDYIILWVRQAPGQRLEWMGH IDPYYGSSNYNLKFKGRVTITRDKSASTAYMELSSLRSEDTAVYYCARSK RDYFDYWGQGTLVTVSS |
| 75 | TPP-578 VL | DIQMTQSPSSLSASVGDRVTITCKASQDINSYLSWFQQKPGKAPKSLIYR ANRLVDGVPSRFSGSGSGQDFTLTISSLQPEDFATYYCLQYDEFPYTFGQ GTKLEIK |
| 76 | TPP-579 | DIQMTQSPSSLSASVGDRVTITCKASQDINSYLSWFQQKPGKAPKSLIYR ANRLVDGVPSRFSGSGSGQDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITRDTSSSTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |

TABLE 12-continued

Summary Table of Sequences

| SEQ ID | Description | Sequence |
|---|---|---|
| 77 | TPP-579 VH | QVQLVQSGAEVKKPGASVKVSCKASGYSFTDYIILWVRQAPGQRLEWMGH IDPYYGSSNYNLKFKGRVTITRDTSSSTAYMELSSLRSEDTAVYYCARSK RDYFDYWGQGTLVTVSS |
| 78 | TPP-579 VL | DIQMTQSPSSLSASVGDRVTITCKASQDINSYLSWFQQKPGKAPKSLIYR ANRLVDGVPSRFSGSGSGQDFTLTISSLQPEDFATYYCLQYDEFPYTFGQ GTKLEIK |
| 79 | TPP-583 | DIQMTQSPSSLSASVGDRVTITCKASQDINSYLSWFQQKPGKAPKSLIYR ANRLVDGVPSRFSGSGSGQDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITRDTSASTAYMELSSL RSEDTAVYYCGRSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 80 | TPP-583 VH | QVQLVQSGAEVKKPGASVKVSCKASGYSFTDYIILWVRQAPGQRLEWMGH IDPYYGSSNYNLKFKGRVTITRDTSASTAYMELSSLRSEDTAVYYCGRSK RDYFDYWGQGTLVTVSS |
| 81 | TPP-583 VL | DIQMTQSPSSLSASVGDRVTITCKASQDINSYLSWFQQKPGKAPKSLIYR ANRLVDGVPSRFSGSGSGQDFTLTISSLQPEDFATYYCLQYDEFPYTFGQ GTKLEIK |
| 82 | TPP-604 | DIQMTQSPSSLSASVGDRVTITCKASQDINSYLSWFQQKPGKAPKSLIYR ANRLVDGVPSRFSGSGSGTDYTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITRDTSASTAYMELSSL RSEDTAVYYCGRSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 83 | TPP-604 VH | QVQLVQSGAEVKKPGASVKVSCKASGYSFTDYIILWVRQAPGQRLEWMGH IDPYYGSSNYNLKFKGRVTITRDTSASTAYMELSSLRSEDTAVYYCGRSK RDYFDYWGQGTLVTVSS |
| 84 | TPP-604 VL | DIQMTQSPSSLSASVGDRVTITCKASQDINSYLSWFQQKPGKAPKSLIYR ANRLVDGVPSRFSGSGSGTDYTLTISSLQPEDFATYYCLQYDEFPYTFGQ GTKLEIK |
| 85 | TPP-669 | DIQMTQSPSSLSASVGDRVTITCKASQDINSYLSWFQQKPGKAPKSLIYR ANRLVDGVPSRFSGSGSGTDFTLTISSLQPEDMATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAELKKPGASVKVSCKASGYSFTDYIILW VRQAPGQRLEWMGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 86 | TPP-669 VH | QVQLVQSGAELKKPGASVKVSCKASGYSFTDYIILWVRQAPGQRLEWMGH IDPYYGSSNYNLKFKGRVTITRDTSASTAYMELSSLRSEDTAVYYCARSK RDYFDYWGQGTLVTVSS |
| 87 | TPP-669 VL | DIQMTQSPSSLSASVGDRVTITCKASQDINSYLSWFQQKPGKAPKSLIYR ANRLVDGVPSRFSGSGSGTDFTLTISSLQPEDMATYYCLQYDEFPYTFGQ GTKLEIK |
| 88 | TPP-671 | DIQMTQSPSSLSASVGDRVTITCKASQDINSYLSWFQQKPGKAPKSLIYR ANRLVDGVPSRFSGSGSGTDFTLTISSLQPEDMATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG VRQAPGQRLEWMGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 89 | TPP-671 VH | QVQLVQSGAEVKKPGASLKVSCKASGYSFTDYIILWVRQAPGQRLEWMGH IDPYYGSSNYNLKFKGRVTITRDTSASTAYMELSSLRSEDTAVYYCARSK RDYFDYWGQGTLVTVSS |

TABLE 12-continued

| Summary Table of Sequences | | |
|---|---|---|
| SEQ ID | Description | Sequence |
| 90 | TPP-671 VL | DIQMTQSPSSLSASVGDRVTITCKASQDINSYLSWFQQKPGKAPKSLIYR ANRLVDGVPSRFSGSGSGTDFTLTISSLQPEDMATYYCLQYDEFPYTFGQ GTKLEIK |
| 91 | TPP-678 | DIQMTQSPSSLSASVGDRVTITCKASQDINSYLSWFQQKPGKAPKSLIYR ANRLVDGVPSRFSGSGSGTDFTLTISSLQPEDMATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWIGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 92 | TPP-678 VH | QVQLVQSGAEVKKPGASVKVSCKASGYSFTDYIILWVRQAPGQRLEWIGH IDPYYGSSNYNLKFKGRVTITRDTSASTAYMELSSLRSEDTAVYYCARSK RDYFDYWGQGTLVTVSS |
| 93 | TPP-678 VL | DIQMTQSPSSLSASVGDRVTITCKASQDINSYLSWFQQKPGKAPKSLIYR ANRLVDGVPSRFSGSGSGTDFTLTISSLQPEDMATYYCLQYDEFPYTFGQ GTKLEIK |
| 94 | TPP-686 | DIQMTQSPSSLSASVGDRVTITCKASQDINSYLSWFQQKPGKAPKSLIYR ANRLVDGVPSRFSGSGSGTDFTLTISSLQPEDMATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITRDTSASTAYMELNSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 95 | TPP-686 VH | QVQLVQSGAEVKKPGASVKVSCKASGYSFTDYIILWVRQAPGQRLEWMGH IDPYYGSSNYNLKFKGRVTITRDTSASTAYMELNSLRSEDTAVYYCARSK RDYFDYWGQGTLVTVSS |
| 96 | TPP-686 VL | DIQMTQSPSSLSASVGDRVTITCKASQDINSYLSWFQQKPGKAPKSLIYR ANRLVDGVPSRFSGSGSGTDFTLTISSLQPEDMATYYCLQYDEFPYTFGQ GTKLEIK |
| 97 | TPP-688 | DIQMTQSPSSLSASVGDRVTITCKASQDINSYLSWFQQKPGKAPKSLIYR ANRLVDGVPSRFSGSGSGTDFTLTISSLQPEDMATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITRDTSASTAYMELSSL RSEDTAVYYCGRSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 98 | TPP-688 VH | QLVQSGAEVKKPGASVKVSCKASGYSFTDYIILWVRQAPGQRLEWMGHID PYYGSSNYNLKFKGRVTITRDTSASTAYMELSSLRSEDTAVYYCGRSKRD YFDYWGQGTLVTVSS |
| 99 | TPP-688 VL | DIQMTQSPSSLSASVGDRVTITCKASQDINSYLSWFQQKPGKAPKSLIYR ANRLVDGVPSRFSGSGSGTDFTLTISSLQPEDMATYYCLQYDEFPYTFGQ GTKLEIK |
| 100 | TPP-690 | DIQMTQSPSSLSASVGDRVTITCKASQDINSYLSWFQQKPGKAPKSLIYR ANRLVDGVPSRFSGSGSGTDFTLTISSLQPEDFGTYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAELKKPGASVKVSCKASGYSFTDYIILW VRQAPGQRLEWMGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 101 | TPP-690 VH | QVQLVQSGAELKKPGASVKVSCKASGYSFTDYIILWVRQAPGQRLEWMGH IDPYYGSSNYNLKFKGRVTITRDTSASTAYMELSSLRSEDTAVYYCARSK RDYFDYWGQGTLVTVSS |

TABLE 12-continued

| Summary Table of Sequences | | |
|---|---|---|
| SEQ ID | Description | Sequence |
| 102 | TPP-690 VL | DIQMTQSPSSLSASVGDRVTITCKASQDINSYLSWFQQKPGKAPKSLIYR<br>ANRLVDGVPSRFSGSGSGTDFTLTISSLQPEDFGTYYCLQYDEFPYTFGQ<br>GTKLEIK |
| 103 | TPP-697 | DIQMTQSPSSLSASVGDRVTITCKASQDINSYLSWFQQKPGKAPKSLIYR<br>ANRLVDGVPSRFSGSGSGTDFTLTISSLQPEDFGTYYCLQYDEFPYTFGQ<br>GTKLEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGECQVQLVQSGAEVKKPGASVKVSCKASGYSFTDYIILW<br>VRQAPGKRLEWMGHIDPYYGSSNYNLKFKGRVTITRDTSASTAYMELSSL<br>RSEDTAVYYCARSKRDYFDYWGQGTLVTVSSASTKGPSVFPLAPSSKSTS<br>GGTAALGCLVKDYFPEPVTVSWNSGALTSGVHTFPAVLQSSGLYSLSSVV<br>TVPSSSLGTQTYICNVNHKPSNTKVDKRVEPKSC |
| 104 | TPP-697 VH | QVQLVQSGAEVKKPGASVKVSCKASGYSFTDYIILWVRQAPGKRLEWMGH<br>IDPYYGSSNYNLKFKGRVTITRDTSASTAYMELSSLRSEDTAVYYCARSK<br>RDYFDYWGQGTLVTVSS |
| 105 | TPP-697 VL | DIQMTQSPSSLSASVGDRVTITCKASQDINSYLSWFQQKPGKAPKSLIYR<br>ANRLVDGVPSRFSGSGSGTDFTLTISSLQPEDFGTYYCLQYDEFPYTFGQ<br>GTKLEIK |
| 106 | TPP-709 | DIQMTQSPSSLSASVGDRVTITCKASQDINSYLSWFQQKPGKAPKSLIYR<br>ANRLVDGVPSRFSGSGSGTDFTLTISSLQPEDFGTYYCLQYDEFPYTFGQ<br>GTKLEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGECQVQLVQSGAEVKKPGASVKVSCKASGYSFTDYIILW<br>VRQAPGQRLEWMGHIDPYYGSSNYNLKFKGRVTITRDTSASTAYMELSSL<br>RSEDTAVYYCGRSKRDYFDYWGQGTLVTVSSASTKGPSVFPLAPSSKSTS<br>GGTAALGCLVKDYFPEPVTVSWNSGALTSGVHTFPAVLQSSGLYSLSSVV<br>TVPSSSLGTQTYICNVNHKPSNTKVDKRVEPKSC |
| 107 | TPP-709 VH | QVQLVQSGAEVKKPGASVKVSCKASGYSFTDYIILWVRQAPGQRLEWMGH<br>IDPYYGSSNYNLKFKGRVTITRDTSASTAYMELSSLRSEDTAVYYCGRSK<br>RDYFDYWGQGTLVTVSS |
| 108 | TPP-709 VL | DIQMTQSPSSLSASVGDRVTITCKASQDINSYLSWFQQKPGKAPKSLIYR<br>ANRLVDGVPSRFSGSGSGTDFTLTISSLQPEDFGTYYCLQYDEFPYTFGQ<br>GTKLEIK |
| 109 | TPP-712 | DIQMTQSPSSLSASVGDRVTITCKASQDINSYLSWFQQKPGKAPKSLIYR<br>ANRLVDGVPSRFSGSGSGTDFTLTISSLQPEDFAIYYCLQYDEFPYTFGQ<br>GTKLEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>VRQAPGQRLEWMGHIDPYYGSSNYNLKFKGRVTITRDTSASTAYMELSSL<br>RSEDTAVYYCARSKRDYFDYWGQGTLVTVSSASTKGPSVFPLAPSSKSTS<br>GGTAALGCLVKDYFPEPVTVSWNSGALTSGVHTFPAVLQSSGLYSLSSVV<br>TVPSSSLGTQTYICNVNHKPSNTKVDKRVEPKSC |
| 110 | TPP-712 VH | QVQLVQSGAEVVKPGASVKVSCKASGYSFTDYIILWVRQAPGQRLEWMGH<br>IDPYYGSSNYNLKFKGRVTITRDTSASTAYMELSSLRSEDTAVYYCARSK<br>RDYFDYWGQGTLVTVSS |
| 111 | TPP-712 VL | DIQMTQSPSSLSASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIK |
| 112 | TPP-714 | DIQMTQSPSSLSASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGECQVQLVQSGAEVKKPGASVKMSCKASGYSFTDYIILW<br>VRQAPGQRLEWMGHIDPYYGSSNYNLKFKGRVTITRDTSASTAYMELSSL<br>RSEDTAVYYCARSKRDYFDYWGQGTLVTVSSASTKGPSVFPLAPSSKSTS<br>GGTAALGCLVKDYFPEPVTVSWNSGALTSGVHTFPAVLQSSGLYSLSSVV<br>TVPSSSLGTQTYICNVNHKPSNTKVDKRVEPKSC |
| 113 | TPP-714 VH | QVQLVQSGAEVKKPGASVKMSCKASGYSFTDYIILWVRQAPGQRLEWMGH<br>IDPYYGSSNYNLKFKGRVTITRDTSASTAYMELSSLRSEDTAVYYCARSK<br>RDYFDYWGQGTLVTVSS |
| 114 | TPP-714 VL | DIQMTQSPSSLSASVGDRVTITCKASQDINSYLSWFQQKPGKAPKSLIYR<br>ANRLVDGVPSRFSGSGSGTDFTLTISSLQPEDFAIYYCLQYDEFPYTFGQ<br>GTKLEIK |

TABLE 12-continued

Summary Table of Sequences

| SEQ ID | Description | Sequence |
| --- | --- | --- |
| 115 | TPP-718 | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGKRLEWMGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 116 | TPP-718 VH | QVQLVQSGAEVKKPGASVKVSCKASGYSFTDYIILWVRQAPGKRLEWMGH IDPYYGSSNYNLKFKGRVTITRDTSASTAYMELSSLRSEDTAVYYCARSK RDYFDYWGQGTLVTVSS |
| 117 | TPP-718 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 118 | TPP-719 | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQSLEWMGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 119 | TPP-719 VH | QVQLVQSGAEVKKPGASVKVSCKASGYSFTDYIILWVRQAPGQSLEWMGH IDPYYGSSNYNLKFKGRVTITRDTSASTAYMELSSLRSEDTAVYYCARSK RDYFDYWGQGTLVTVSS |
| 120 | TPP-719 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 121 | TPP-720 | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGKVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 122 | TPP-720 VH | QVQLVQSGAEVKKPGASVKVSCKASGYSFTDYIILWVRQAPGQRLEWMGH IDPYYGSSNYNLKFKGKVTITRDTSASTAYMELSSLRSEDTAVYYCARSK RDYFDYWGQGTLVTVSS |
| 123 | TPP-720 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 124 | TPP-721 | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWIGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 125 | TPP-721 VH | QVQLVQSGAEVKKPGASVKVSCKASGYSFTDYIILWVRQAPGQRLEWIGH IDPYYGSSNYNLKFKGRVTITRDTSASTAYMELSSLRSEDTAVYYCARSK RDYFDYWGQGTLVTVSS |
| 126 | TPP-721 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 127 | TPP-722 | DIQMTQSPSSLSASVGDRVTITCKASQDINSYLSWFQQKPGKAPKSLIYR ANRLVDGVPSRFSGSGSGTDFTLTISSLQPEDFAIYYCLQYDEFPYTFGQ |

TABLE 12-continued

Summary Table of Sequences

| SEQ ID | Description | Sequence |
|---|---|---|
| | | GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRATITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 128 | TPP-722 VH | QVQLVQSGAEVKKPGASVKVSCKASGYSFTDYIILWVRQAPGQRLEWMGH IDPYYGSSNYNLKFKGRATITRDTSASTAYMELSSLRSEDTAVYYCARSK RDYFDYWGQGTLVTVSS |
| 129 | TPP-722 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 130 | TPP-724 | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITVDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 131 | TPP-724 VH | QVQLVQSGAEVKKPGASVKVSCKASGYSFTDYIILWVRQAPGQRLEWMGH IDPYYGSSNYNLKFKGRVTITVDTSASTAYMELSSLRSEDTAVYYCARSK RDYFDYWGQGTLVTVSS |
| 132 | TPP-724 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 133 | TPP-727 | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITRDTSASTAYMQLSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 134 | TPP-727 VH | QVQLVQSGAEVKKPGASVKVSCKASGYSFTDYIILWVRQAPGQRLEWMGH IDPYYGSSNYNLKFKGRVTITRDTSASTAYMQLSSLRSEDTAVYYCARSK RDYFDYWGQGTLVTVSS |
| 135 | TPP-727 VL | DIQMTQSPSSLSASVGDRVTITCKASQDINSYLSWFQQKPGKAPKSLIYR ANRLVDGVPSRFSGSGSGTDFTLTISSLQPEDFAIYYCLQYDEFPYTFGQ GTKLEIK |
| 136 | TPP-730 | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITRDTSASTAYMELSSL RSEDTAVYYCGRSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 137 | TPP-730 VH | QVQLVQSGAEVKKPGASVKVSCKASGYSFTDYIILWVRQAPGQRLEWMGH IDPYYGSSNYNLKFKGRVTITRDTSASTAYMELSSLRSEDTAVYYCGRSK RDYFDYWGQGTLVTVSS |
| 138 | TPP-730 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 139 | TPP-733 | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVVKPGASVKVSCKASGYSFTDYIILW |

TABLE 12-continued

Summary Table of Sequences

| SEQ ID | Description | Sequence |
|---|---|---|
| | | VRQAPGQRLEWMGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 140 | TPP-733 VH | QVQLVQSGAEVVKPGASVKVSCKASGYSFTDYIILWVRQAPGQRLEWMGH IDPYYGSSNYNLKFKGRVTITRDTSASTAYMELSSLRSEDTAVYYCARSK RDYFDYWGQGTLVTVSS |
| 141 | TPP-733 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 142 | TPP-735 | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKMSCKASGYSFTDYIILW VRQAPGQRLEWMGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 143 | TPP-735 VH | QVQLVQSGAEVKKPGASVKMSCKASGYSFTDYIILWVRQAPGQRLEWMGH IDPYYGSSNYNLKFKGRVTITRDTSASTAYMELSSLRSEDTAVYYCARSK RDYFDYWGQGTLVTVSS |
| 144 | TPP-735 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 145 | TPP-738 | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAHGQRLEWMGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 146 | TPP-738 VH | QVQLVQSGAEVKKPGASVKVSCKASGYSFTDYIILWVRQAHGQRLEWMGH IDPYYGSSNYNLKFKGRVTITRDTSASTAYMELSSLRSEDTAVYYCARSK RDYFDYWGQGTLVTVSS |
| 147 | TPP-738 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 148 | TPP-741 | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWIGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 149 | TPP-741 VH | QVQLVQSGAEVKKPGASVKVSCKASGYSFTDYIILWVRQAPGQRLEWIGH IDPYYGSSNYNLKFKGRVTITRDTSASTAYMELSSLRSEDTAVYYCARSK RDYFDYWGQGTLVTVSS |
| 150 | TPP-741 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 151 | TPP-749 | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITRDTSASTAYMELNSL |

TABLE 12-continued

Summary Table of Sequences

| SEQ ID | Description | Sequence |
|---|---|---|
| | | RSEDTAVYYCARSKRDYFDYWGQGTLVTVSSASTKGPSVFPLAPSSKSTS<br>GGTAALGCLVKDYFPEPVTVSWNSGALTSGVHTFPAVLQSSGLYSLSSVV<br>TVPSSSLGTQTYICNVNHKPSNTKVDKRVEPKSC |
| 152 | TPP-749 VH | QVQLVQSGAEVKKPGASVKVSCKASGYSFTDYIILWVRQAPGQRLEWMGH<br>IDPYYGSSNYNLKFKGRVTITRDTSASTAYMELNSLRSEDTAVYYCARSK<br>RDYFDYWGQGTLVTVSS |
| 153 | TPP-749 VL | DIQMTQSPSSLSASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIK |
| 154 | TPP-750 | DIQMTQSPSSLSASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGECQVQLVQSGAEVKKPGASVKVSCKASGYSFTDYIILW<br>VRQAPGQRLEWMGHIDPYYGSSNYNLKFKGRVTITRDTSASTAYMELSSL<br>TSEDTAVYYCARSKRDYFDYWGQGTLVTVSSASTKGPSVFPLAPSSKSTS<br>GGTAALGCLVKDYFPEPVTVSWNSGALTSGVHTFPAVLQSSGLYSLSSVV<br>TVPSSSLGTQTYICNVNHKPSNTKVDKRVEPKSC |
| 155 | TPP-750 VH | QVQLVQSGAEVKKPGASVKVSCKASGYSFTDYIILWVRQAPGQRLEWMGH<br>IDPYYGSSNYNLKFKGRVTITRDTSASTAYMELSSLTSEDTAVYYCARSK<br>RDYFDYWGQGTLVTVSS |
| 156 | TPP-750 VL | DIQMTQSPSSLSASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIK |
| 157 | TPP-751 | DIQMTQSPSSLSASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGECQVQLVQSGAEVKKPGASVKVSCKASGYSFTDYIILW<br>VRQAPGQRLEWMGHIDPYYGSSNYNLKFKGRVTITRDTSASTAYMELSSL<br>RSEDTAVYYCGRSKRDYFDYWGQGTLVTVSSASTKGPSVFPLAPSSKSTS<br>GGTAALGCLVKDYFPEPVTVSWNSGALTSGVHTFPAVLQSSGLYSLSSVV<br>TVPSSSLGTQTYICNVNHKPSNTKVDKRVEPKSC |
| 158 | TPP-751 VH | QVQLVQSGAEVKKPGASVKVSCKASGYSFTDYIILWVRQAPGQRLEWMGH<br>IDPYYGSSNYNLKFKGRVTITRDTSASTAYMELSSLRSEDTAVYYCGRSK<br>RDYFDYWGQGTLVTVSS |
| 159 | TPP-751 VL | DIQMTQSPSSLSASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIK |
| 160 | TPP-752 | DIQMTQSPSSLSASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGECQVQLVQSGAEVKKPGASVKVSCKASGYSFTDYIILW<br>VRQAPGQRLEWMGHIDPYYGSSNYNLKFKGRVTITRDTSASTAYMELSSL<br>RSEDTAVYYCARSKRDYFDYWGQGTLVTVSSASTKGPSVFPLAPSSKSTS<br>GGTAALGCLVKDYFPEPVTVSWNSGALTSGVHTFPAVLQSSGLYSLSSVV<br>TVPSSSLGTQTYICNVNHKPSNTKVDKRVEPKSC |
| 161 | TPP-752 VH | QVQLVQSGAEVKKPGASVKVSCKASGYSFTDYIILWVRQAPGQRLEWMGH<br>IDPYYGSSNYNLKFKGRVTITRDTSASTAYMELSSLRSEDTAVYYCARSK<br>RDYFDYWGQGTLVTVSS |
| 162 | TPP-752 VL | DIQMTQSPSSLSASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIK |
| 163 | TPP-753 | DIQMTQSPSSLYASVGDRVTITCKASQDINSYLSWFQQKPGKAPKSLIYR<br>ANRLVDGVPSRFSGSGSGTDFTLTISSLQPEDFATYYCLQYDEFPYTFGQ<br>GTKLEIKRTVAAPSVFIFPPSDEQLKSGTASVVCLLNNFYPREAKVQWKV<br>DNALQSGNSQESVTEQDSKDSTYSLSSTLTLSKADYEKHKVYACEVTHQG<br>LSSPVTKSFNRGECQVQLVQSGAEVKKPGASVKVSCKASGYSFTDYIILW<br>VRQAPGQRLEWMGHIDPYYGSSNYNLKFKGRVTITRDTSASTAYMELSSL<br>RSEDTAVYYCARSKRDYFDYWGQGTLVTVSSASTKGPSVFPLAPSSKSTS<br>GGTAALGCLVKDYFPEPVTVSWNSGALTSGVHTFPAVLQSSGLYSLSSVV<br>TVPSSSLGTQTYICNVNHKPSNTKVDKRVEPKSC |

TABLE 12-continued

Summary Table of Sequences

| SEQ ID | Description | Sequence |
|---|---|---|
| 164 | TPP-753 VH | QVQLVQSGAEVKKPGASVKVSCKASGYSFTDYIILWVRQAPGQRLEWMGH IDPYYGSSNYNLKFKGRVTITRDTSASTAYMELSSLRSEDTAVYYCARSK RDYFDYWGQGTLVTVSS |
| 165 | TPP-753 VL | DIQMTQSPSSLYASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 166 | TPP-756 | DIQMTQSPSSLSASVGDRVTITCKASQDINSYLSWFQQKPGKAPKSLIYR ANRLVDGVPSRFSGSGSGTDFSLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 167 | TPP-756 VH | QVQLVQSGAEVKKPGASVKVSCKASGYSFTDYTILWVRQAPGQRLEWMGH IDPYYGSSNYNLKFKGRVTITRDTSASTAYMELSSLRSEDTAVYYCARSK RDYFDYWGQGTLVTVSS |
| 168 | TPP-756 VL | DIQMTQSPSSLSASVGDRVTITCKASQDINSYLSWFQQKPGKAPKSLIYR ANRLVDGVPSRFSGSGSGTDFSLTISSLQPEDFATYYCLQYDEFPYTFGQ GTKLEIK |
| 169 | TPP-757 | DIQMTQSPSSLSASVGDRVTITCKASQDINSYLSWFQQKPGKAPKSLIYR ANRLVDGVPSRFSGSGSGTDFTLTISSLEPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 170 | TPP-757 VH | QVQLVQSGAEVKKPGASVKVSCKASGYSFTDYIILWVRQAPGQRLEWMGH IDPYYGSSNYNLKFKGRVTITRDTSASTAYMELSSLRSEDTAVYYCARSK RDYFDYWGQGTLVTVSS |
| 171 | TPP-757 VL | DIQMTQSPSSLSASVGDRVTITCKASQDINSYLSWFQQKPGKAPKSLIYR ANRLVDGVPSRFSGSGSGTDFTLTISSLEPEDFATYYCLQYDEFPYTFGQ GTKLEIK |
| 172 | TPP-758 | DIQMTQSPSSLSASVGDRVTITCKASQDINSYLSWFQQKPGKAPKSLIYR ANRLVDGVPSRFSGSGSGTDFTLTISSLQYEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 173 | TPP-758 VH | QVQLVQSGAEVKKPGASVKVSCKASGYSFTDYIILWVRQAPGQRLEWMGH IDPYYGSSNYNLKFKGRVTITRDTSASTAYMELSSLRSEDTAVYYCARSK RDYFDYWGQGTLVTVSS |
| 174 | TPP-758 VL | DIQMTQSPSSLSASVGDRVTITCKASQDINSYLSWFQQKPGKAPKSLIYR ANRLVDGVPSRFSGSGSGTDFTLTISSLQYEDFATYYCLQYDEFPYTFGQ GTKLEIK |
| 175 | TPP-759 | DIQMTQSPSSLSASVGDRVTITCKASQDINSYLSWFQQKPGKAPKSLIYR ANRLVDGVPSRFSGSGSGTDFTLTISSLQPEDMATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |

TABLE 12-continued

Summary Table of Sequences

| SEQ ID | Description | Sequence |
| --- | --- | --- |
| 176 | TPP-759 VH | QVQLVQSGAEVKKPGASVKVSCKASGYSFTDYIILWVRQAPGQRLEWMGH IDPYYGSSNYNLKFKGRVTITRDTSASTAYMELSSLRSEDTAVYYCARSK RDYFDYWGQGTLVTVSS |
| 177 | TPP-759 VL | DIQMTQSPSSLSASVGDRVTITCKASQDINSYLSWFQQKPGKAPKSLIYR ANRLVDGVPSRFSGSGSGTDFTLTISSLQPEDMATYYCLQYDEFPYTFGQ GTKLEIK |
| 178 | TPP-760 | DIQMTQSPSSLSASVGDRVTITCKASQDINSYLSWFQQKPGKAPKSLIYR ANRLVDGVPSRFSGSGSGTDFTLTISSLQPEDFGTYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGECQVQLVQSGAEVKKPGASVKVSCKASGYSFTDYIILW VRQAPGQRLEWMGHIDPYYGSSNYNLKFKGRVTITRDTSASTAYMELSSL RSEDTAVYYCARSKRDYFDYWGQGTLVTVSSASTKGPSVFPLAPSSKSTS GGTAALGCLVKDYFPEPVTVSWNSGALTSGVHTFPAVLQSSGLYSLSSVV TVPSSSLGTQTYICNVNHKPSNTKVDKRVEPKSC |
| 179 | TPP-760 VH | QVQLVQSGAEVKKPGASVKVSCKASGYSFTDYIILWVRQAPGQRLEWMGH IDPYYGSSNYNLKFKGRVTITRDTSASTAYMELSSLRSEDTAVYYCARSK RDYFDYWGQGTLVTVSS |
| 180 | TPP-760 VL | DIQMTQSPSSLSASVGDRVTITCKASQDINSYLSWFQQKPGKAPKSLIYR ANRLVDGVPSRFSGSGSGTDFTLTISSLQPEDFGTYYCLQYDEFPYTFGQ GTKLEIK |
| 181 | TPP-1141 HC | QVQLVQSGAEVKKPGASVKVSCKASGYSFTDYIILWVRQAPGQRLEWIGH IDPYYGSSNYNLKFKGRVTITRDTSASTAYMELSSLRSEDTAVYYCARSK RDYFDYWGQGTLVTVSSASTKGPSVFPLAPCSRSTSESTAALGCLVKDYF PEPVTVSWNSGALTSGVHTFPAVLQSSGLYSLSSVVTVPSSNFGTQTYTC NVDHKPSNTKVDKTVERKCCVECPPCPAPPVAGPSVFLFPPKPKDTLMIS RTPEVTCVVVDVSQEDPEVQFNWYVDGVEVHNAKTKPREEQFNSTYRVVS VLTVLHQDWLNGKEYKCKVSNKGLPSSIEKTISKAKGQPREPQVYTLPPS QEEMTKNQVSLTCLVKGFYPSDIAVEWESNGQPENNYKTTPPVLDSDGSF FLYSRLTVDKSRWQEGNVFSCSVMHEALHNHYTQKSLSLSLGK |
| 182 | TPP-1141 LC | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC |
| 183 | TPP-1142 HC | QVQLVQSGAEVKKPGASVKVSCKASGYSFTDYTILWVRQAPGQRLEWMGH IDPYYGSSNYNLKFKGRVTITRDTSASTAYMELSSLRSEDTAVYYCGRSK RDYFDYWGQGTLVTVSSASTKGPSVFPLAPCSRSTSESTAALGCLVKDYF PEPVTVSWNSGALTSGVHTFPAVLQSSGLYSLSSVVTVPSSNFGTQTYTC NVDHKPSNTKVDKTVERKCCVECPPCPAPPVAGPSVFLFPPKPKDTLMIS RTPEVTCVVVDVSQEDPEVQFNWYVDGVEVHNAKTKPREEQFNSTYRVVS VLTVLHQDWLNGKEYKCKVSNKGLPSSIEKTISKAKGQPREPQVYTLPPS QEEMTKNQVSLTCLVKGFYPSDIAVEWESNGQPENNYKTTPPVLDSDGSF FLYSRLTVDKSRWQEGNVFSCSVMHEALHNHYTQKSLSLSLGK |
| 184 | TPP-1142 LC | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC |
| 185 | TPP-1143 HC | QVQLVQSGAEVKKPGASVKVSCKASGYSFTDYIILWVRQAPGQRLEWMGH IDPYYGSSNYNLKFKGRVTITRDTSASTAYMELSSLRSEDTAVYYCGRSK RDYFDYWGQGTLVTVSSASTKGPSVFPLAPCSRSTSESTAALGCLVKDYF PEPVTVSWNSGALTSGVHTFPAVLQSSGLYSLSSVVTVPSSNFGTQTYTC NVDHKPSNTKVDKTVERKCCVECPPCPAPPVAGPSVFLFPPKPKDTLMIS RTPEVTCVVVDVSQEDPEVQFNWYVDGVEVHNAKTKPREEQFNSTYRVVS VLTVLHQDWLNGKEYKCKVSNKGLPSSIEKTISKAKGQPREPQVYTLPPS QEEMTKNQVSLTCLVKGFYPSDIAVEWESNGQPENNYKTTPPVLDSDGS FFLYSRLTVDKSRWQEGNVFSCSVMHEALHNHYTQKSLSLSLGK |
| 186 | TPP-1143 LC | DIQMTQSPSSLSASVGDRVTITCKASQDINSYLSWFQQKPGKAPKSLIYR ANRLVDGVPSRFSGSGSGTDFTLTISSLQPEDFGTYYCLQYDEFPYTFGQ GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC |

TABLE 12-continued

Summary Table of Sequences

| SEQ ID | Description | Sequence |
|---|---|---|
| 187 | TPP-542 HC nucleotide | CAAGTGCAACTGGTGCAGAGCGGCCCTGAAGTGAAGAAACCAGGCGCCAG<br>CGTGAAGGTGTCCTGCAAGGCCAGCGGCTACAGCTTCACCGACTACATCA<br>TCCTGTGGGTCCGACAGGCCCCTGGCCAGAGACTGGAATGGATGGGCCAC<br>ATCGACCCCTACTACGGCAGCAGCAACTACAACCTGAAGTTCAAGGGCAG<br>AGTGACCATCACCCGGGACACCAGCGCCAGCACCGCCTACATGGAACTGA<br>GCAGCCTGAGAAGCGAGGACACCGCCGTGTACTACTGCGCCAGAAGCAAG<br>CGGGACTACTTCGACTACTGGGGCCAGGGCACCCTGGTCACCGTTAGCTC<br>TGCCTCCACCAAGGGCCCATCGGTCTTCCCCCTGGCACCCTCCTCCAAGA<br>GCACCTCTGGGGGCACAGCGGCCCTGGGCTGCCTGGTCAAGGACTACTTC<br>CCCGAACCGGTGACGGTGTCGTGGAACTCAGGCGCCCTGACCAGCGGCGT<br>GCACACCTTCCCGGCTGTCCTACAGTCCTCAGGACTCTACTCCCTCAGCA<br>GCGTGGTGACCGTGCCCTCCAGCAGCTTGGGCACCCAGACCTACATCTGC<br>AACGTGAATCACAAGCCCAGCAACACCAAGGTGGACAAGAGAGTTGAGCC<br>CAAATCTTGT |
| 188 | TPP-542 LC nucleotide | GACATCCAAATGACCCAGAGCCCCAGCAGCCTGTACGCCAGCGTGGGCGA<br>CAGAGTGACCATCACATGCAAGGCCAGCCAGGACATCAACAGCTACCTGA<br>GCTGGTTCCAGCAGAAGCCCGGCAAGGCCCCTAAGAGCCTGATCTACCGG<br>GCCAACAGACTGGTGGACGGCGTGCCAAGCAGATTCAGCGGCAGCGGCTC<br>TGGCACCGACTTCACCCTGACCATCAGCTCCCTGCAGCCCGAGGACTTCG<br>CCACCTACTACTGCCTGCAGTACGACGAGTTCCCCTACACCTTCGGCCAG<br>GGCACCAAGCTGGAAATCAAGCGGACCGTGGCTGCACCATCTGTCTTCAT<br>CTTCCCGCCATCTGATGAGCAGTTGAAATCTGGAACTGCCTCTGTTGTGT<br>GCCTGCTGAATAACTTCTATCCCAGAGAGGCCAAAGTACAGTGGAAGGTG<br>GATAACGCCCTCCAATCGGGTAACTCCCAGGAGAGTGTCACAGAGCAGGA<br>CAGCAAGGACAGCACCTACAGCCTCAGCAGCACCCTGACGCTGAGCAAAG<br>CAGACTACGAGAAACACAAAGTCTACGCCTGCGAAGTCACCCATCAGGGC<br>CTGAGCTCGCCCGTCACAAAGAGCTTCAACAGGGGAGAGTGT |
| 189 | TPP-545 HC nucleotide | CAGGTGCAGCTGGTGCAGTCTGGCGCCGAAGTGAAGAAGCCAGGCGCCAG<br>CCTGAAGGTGTCCTGCAAGGCCAGCGGCTACAGCTTCACCGACTACATCA<br>TCCTGTGGGTCCGACAGGCCCCTGGCCAGAGACTGGAATGGATGGGCCAC<br>ATCGACCCCTACTACGGCAGCAGCAACTACAACCTGAAGTTCAAGGGCAG<br>AGTGACCATCACCCGGGACACCAGCGCCAGCACCGCCTACATGGAACTGA<br>GCAGCCTGAGAAGCGAGGACACCGCCGTGTACTACTGCGCCAGAAGCAAG<br>CGGGACTACTTCGACTACTGGGGCCAGGGCACCCTGGTCACCGTTAGCTC<br>TGCCTCCACCAAGGGCCCATCGGTCTTCCCCCTGGCACCCTCCTCCAAGA<br>GCACCTCTGGGGGCACAGCGGCCCTGGGCTGCCTGGTCAAGGACTACTTC<br>CCCGAACCGGTGACGGTGTCGTGGAACTCAGGCGCCCTGACCAGCGGCGT<br>GCACACCTTCCCGGCTGTCCTACAGTCCTCAGGACTCTACTCCCTCAGCA<br>GCGTGGTGACCGTGCCCTCCAGCAGCTTGGGCACCCAGACCTACATCTGC<br>AACGTGAATCACAAGCCCAGCAACACCAAGGTGGACAAGAGAGTTGAGCC<br>CAAATCTTGT |
| 190 | TPP-545 LC nucleotide | GACATCCAAATGACCCAGAGCCCCAGCAGCCTGTACGCCAGCGTGGGCGA<br>CAGAGTGACCATCACATGCAAGGCCAGCCAGGACATCAACAGCTACCTGA<br>GCTGGTTCCAGCAGAAGCCCGGCAAGGCCCCTAAGAGCCTGATCTACCGG<br>GCCAACAGACTGGTGGACGGCGTGCCAAGCAGATTCAGCGGCAGCGGCTC<br>TGGCACCGACTTCACCCTGACCATCAGCTCCCTGCAGCCCGAGGACTTCG<br>CCACCTACTACTGCCTGCAGTACGACGAGTTCCCCTACACCTTCGGCCAG<br>GGCACCAAGCTGGAAATCAAGCGGACCGTGGCTGCACCATCTGTCTTCAT<br>CTTCCCGCCATCTGATGAGCAGTTGAAATCTGGAACTGCCTCTGTTGTGT<br>GCCTGCTGAATAACTTCTATCCCAGAGAGGCCAAAGTACAGTGGAAGGTG<br>GATAACGCCCTCCAATCGGGTAACTCCCAGGAGAGTGTCACAGAGCAGGA<br>CAGCAAGGACAGCACCTACAGCCTCAGCAGCACCCTGACGCTGAGCAAAG<br>CAGACTACGAGAAACACAAAGTCTACGCCTGCGAAGTCACCCATCAGGGC<br>CTGAGCTCGCCCGTCACAAAGAGCTTCAACAGGGGAGAGTGT |
| 191 | TPP-550 HC nucleotide | CAGGTGCAGCTGGTGCAGTCTGGCGCCGAAGTGAAGAAACCAGGCGCCAG<br>CGTGAAGGTGTCCTGCAAGGCCAGCGGCTACAGCTTCACCGACTACATCA<br>TCCTGTGGGTCCGACAGGCCCCTGGCAAGAGACTGGAATGGATGGGCCAC<br>ATCGACCCCTACTACGGCAGCAGCAACTACAACCTGAAGTTCAAGGGCAG<br>AGTGACCATCACCCGGGACACCAGCGCCAGCACCGCCTACATGGAACTGA<br>GCAGCCTGAGAAGCGAGGACACCGCCGTGTACTACTGCGCCAGAAGCAAG<br>CGGGACTACTTCGACTACTGGGGCCAGGGCACCCTGGTCACCGTTAGCTC<br>TGCCTCCACCAAGGGCCCATCGGTCTTCCCCCTGGCACCCTCCTCCAAGA<br>GCACCTCTGGGGGCACAGCGGCCCTGGGCTGCCTGGTCAAGGACTACTTC<br>CCCGAACCGGTGACGGTGTCGTGGAACTCAGGCGCCCTGACCAGCGGCGT<br>GCACACCTTCCCGGCTGTCCTACAGTCCTCAGGACTCTACTCCCTCAGCA<br>GCGTGGTGACCGTGCCCTCCAGCAGCTTGGGCACCCAGACCTACATCTGC<br>AACGTGAATCACAAGCCCAGCAACACCAAGGTGGACAAGAGAGTTGAGCC<br>CAAATCTTGT |
| 192 | TPP-550 LC nucleotide | GACATCCAAATGACCCAGAGCCCCAGCAGCCTGTACGCCAGCGTGGGCGA<br>CAGAGTGACCATCACATGCAAGGCCAGCCAGGACATCAACAGCTACCTGA |

TABLE 12-continued

Summary Table of Sequences

| SEQ ID | Description | Sequence |
|---|---|---|
| | | GCTGGTTCCAGCAGAAGCCCGGCAAGGCCCCTAAGAGCCTGATCTACCGG GCCAACAGACTGGTGGACGGCGTGCCAAGCAGATTCAGCGGCAGCGGCTC TGGCACCGACTTCACCCTGACCATCAGCTCCCTGCAGCCCGAGGACTTCG CCACCTACTACTGCCTGCAGTACGACGAGTTCCCCTACACCTTCGGCCAG GGCACCAAGCTGGAAATCAAGCGGACCGTGGCTGCACCATCTGTCTTCAT CTTCCCGCCATCTGATGAGCAGTTGAAATCTGGAACTGCCTCTGTTGTGT GCCTGCTGAATAACTTCTATCCCAGAGAGGCCAAAGTACAGTGGAAGGTG GATAACGCCCTCCAATCGGGTAACTCCCAGGAGAGTGTCACAGAGCAGGA CAGCAAGGACAGCACCTACAGCCTCAGCAGCACCCTGACGCTGAGCAAAG CAGACTACGAGAAACACAAAGTCTACGCCTGCGAAGTCACCCATCAGGGC CTGAGCTCGCCCGTCACAAAGAGCTTCAACAGGGGAGAGTGT |
| 193 | TPP-552 HC nucleotide | CAGGTGCAGCTGGTGCAGTCTGGCGCCGAAGTGAAGAAACCAGGCGCCAG CGTGAAGGTGTCCTGCAAGGCCAGCGGCTACAGCTTCACCGACTACATCA TCCTGTGGGTCCGACAGGCCCCTGGCCAGAGACTGGAATGGATTGGCCAC ATCGACCCCTACTACGGCAGCAGCAACTACAACCTGAAGTTCAAGGGCAG AGTGACCATCACCCGGGACACCAGCGCCAGCACCGCCTACATGGAACTGA GCAGCCTGAGAAGCGAGGACACCGCCGTGTACTACTGCGCCAGAAGCAAG CGGGACTACTTCGACTACTGGGGCCAGGGCACCCTGGTCACCGTTAGCTC TGCCTCCACCAAGGGCCCATCGGTCTTCCCCCTGGCACCCTCCTCCAAGA GCACCTCTGGGGGCACAGCGGCCCTGGGCTGCCTGGTCAAGGACTACTTC CCCGAACCGGTGACGGTGTCGTGGAACTCAGGCGCCCTGACCAGCGGCGT GCACACCTTCCCGGCTGTCCTACAGTCCTCAGGACTCTACTCCCTCAGCA GCGTGGTGACCGTGCCCTCCAGCAGCTTGGGCACCCAGACCTACATCTGC AACGTGAATCACAAGCCCAGCAACACCAAGGTGGACAAGAGAGTTGAGCC CAAATCTTGT |
| 194 | TPP-552 LC nucleotide | GACATCCAAATGACCCAGAGCCCCAGCAGCCTGTACGCCAGCGTGGGCGA CAGAGTGACCATCACATGCAAGGCCAGCCAGGACATCAACAGCTACCTGA GCTGGTTCCAGCAGAAGCCCGGCAAGGCCCCTAAGAGCCTGATCTACCGG GCCAACAGACTGGTGGACGGCGTGCCAAGCAGATTCAGCGGCAGCGGCTC TGGCACCGACTTCACCCTGACCATCAGCTCCCTGCAGCCCGAGGACTTCG CCACCTACTACTGCCTGCAGTACGACGAGTTCCCCTACACCTTCGGCCAG GGCACCAAGCTGGAAATCAAGCGGACCGTGGCTGCACCATCTGTCTTCAT CTTCCCGCCATCTGATGAGCAGTTGAAATCTGGAACTGCCTCTGTTGTGT GCCTGCTGAATAACTTCTATCCCAGAGAGGCCAAAGTACAGTGGAAGGTG GATAACGCCCTCCAATCGGGTAACTCCCAGGAGAGTGTCACAGAGCAGGA CAGCAAGGACAGCACCTACAGCCTCAGCAGCACCCTGACGCTGAGCAAAG CAGACTACGAGAAACACAAAGTCTACGCCTGCGAAGTCACCCATCAGGGC CTGAGCTCGCCCGTCACAAAGAGCTTCAACAGGGGAGAGTGT |
| 195 | TPP-556 HC nucleotide | CAGGTGCAGCTGGTGCAGTCTGGCGCCGAAGTGAAGAAACCAGGCGCCAG CGTGAAGGTGTCCTGCAAGGCCAGCGGCTACAGCTTCACCGACTACATCA TCCTGTGGGTCCGACAGGCCCCTGGCCAGAGACTGGAATGGATGGGCCAC ATCGACCCCTACTACGGCAGCAGCAACTACAACCTGAAGTTCAAGGGCAG AGTGACCATCACCGTGGACACCAGCGCCAGCACCGCCTACATGGAACTGA GCAGCCTGAGAAGCGAGGACACCGCCGTGTACTACTGCGCCAGAAGCAAG CGGGACTACTTCGACTACTGGGGCCAGGGCACCCTGGTCACCGTTAGCTC TGCCTCCACCAAGGGCCCATCGGTCTTCCCCCTGGCACCCTCCTCCAAGA GCACCTCTGGGGGCACAGCGGCCCTGGGCTGCCTGGTCAAGGACTACTTC CCCGAACCGGTGACGGTGTCGTGGAACTCAGGCGCCCTGACCAGCGGCGT GCACACCTTCCCGGCTGTCCTACAGTCCTCAGGACTCTACTCCCTCAGCA GCGTGGTGACCGTGCCCTCCAGCAGCTTGGGCACCCAGACCTACATCTGC AACGTGAATCACAAGCCCAGCAACACCAAGGTGGACAAGAGAGTTGAGCC CAAATCTTGT |
| 196 | TPP-556 LC nucleotide | GACATCCAAATGACCCAGAGCCCCAGCAGCCTGTACGCCAGCGTGGGCGA CAGAGTGACCATCACATGCAAGGCCAGCCAGGACATCAACAGCTACCTGA GCTGGTTCCAGCAGAAGCCCGGCAAGGCCCCTAAGAGCCTGATCTACCGG GCCAACAGACTGGTGGACGGCGTGCCAAGCAGATTCAGCGGCAGCGGCTC TGGCACCGACTTCACCCTGACCATCAGCTCCCTGCAGCCCGAGGACTTCG CCACCTACTACTGCCTGCAGTACGACGAGTTCCCCTACACCTTCGGCCAG GGCACCAAGCTGGAAATCAAGCGGACCGTGGCTGCACCATCTGTCTTCAT CTTCCCGCCATCTGATGAGCAGTTGAAATCTGGAACTGCCTCTGTTGTGT GCCTGCTGAATAACTTCTATCCCAGAGAGGCCAAAGTACAGTGGAAGGTG GATAACGCCCTCCAATCGGGTAACTCCCAGGAGAGTGTCACAGAGCAGGA CAGCAAGGACAGCACCTACAGCCTCAGCAGCACCCTGACGCTGAGCAAAG CAGACTACGAGAAACACAAAGTCTACGCCTGCGAAGTCACCCATCAGGGC CTGAGCTCGCCCGTCACAAAGAGCTTCAACAGGGGAGAGTGT |
| 197 | TPP-557 HC nucleotide | CAGGTGCAGCTGGTGCAGTCTGGCGCCGAAGTGAAGAAACCAGGCGCCAG CGTGAAGGTGTCCTGCAAGGCCAGCGGCTACAGCTTCACCGACTACATCA TCCTGTGGGTCCGACAGGCCCCTGGCCAGAGACTGGAATGGATGGGCCAC ATCGACCCCTACTACGGCAGCAGCAACTACAACCTGAAGTTCAAGGGCAG AGTGACCATCACCCGGGACAAGAGCGCCAGCACCGCCTACATGGAACTGA |

TABLE 12-continued

Summary Table of Sequences

| SEQ ID | Description | Sequence |
|---|---|---|
| | | GCAGCCTGAGAAGCGAGGACACCGCCGTGTACTACTGCGCCAGAAGCAAG<br>CGGGACTACTTCGACTACTGGGGCCAGGGCACCCTGGTCACCGTTAGCTC<br>TGCCTCCACCAAGGGCCCATCGGTCTTCCCCCTGGCACCCTCCTCCAAGA<br>GCACCTCTGGGGGCACAGCGGCCCTGGGCTGCCTGGTCAAGGACTACTTC<br>CCCGAACCGGTGACGGTGTCGTGGAACTCAGGCGCCCTGACCAGCGGCGT<br>GCACACCTTCCCGGCTGTCCTACAGTCCTCAGGACTCTACTCCCTCAGCA<br>GCGTGGTGACCGTGCCCTCCAGCAGCTTGGGCACCCAGACCTACATCTGC<br>AACGTGAATCACAAGCCCAGCAACACCAAGGTGGACAAGAGAGTTGAGCC<br>CAAATCTTGT |
| 198 | TPP-557 LC<br>nucleotide | GACATCCAAATGACCCAGAGCCCCAGCAGCCTGTACGCCAGCGTGGGCGA<br>CAGAGTGACCATCACATGCAAGGCCAGCCAGGACATCAACAGCTACCTGA<br>GCTGGTTCCAGCAGAAGCCCGGCAAGGCCCCTAAGAGCCTGATCTACCGG<br>GCCAACAGACTGGTGGACGGCGTGCCAAGCAGATTCAGCGGCAGCGGCTC<br>TGGCACCGACTTCACCCTGACCATCAGCTCCCTGCAGCCCGAGGACTTCG<br>CCACCTACTACTGCCTGCAGTACGACGAGTTCCCCTACACCTTCGGCCAG<br>GGCACCAAGCTGGAAATCAAGCGGACCGTGGCTGCACCATCTGTCTTCAT<br>CTTCCCGCCATCTGATGAGCAGTTGAAATCTGGAACTGCCTCTGTTGTGT<br>GCCTGCTGAATAACTTCTATCCCAGAGAGGCCAAAGTACAGTGGAAGGTG<br>GATAACGCCCTCCAATCGGGTAACTCCCAGGAGAGTGTCACAGAGCAGGA<br>CAGCAAGGACAGCACCTACAGCCTCAGCAGCACCCTGACGCTGAGCAAAG<br>CAGACTACGAGAAACACAAAGTCTACGCCTGCGAAGTCACCCATCAGGGC<br>CTGAGCTCGCCCGTCACAAAGAGCTTCAACAGGGGAGAGTGT |
| 199 | TPP-559 HC<br>nucleotide | CAGGTGCAGCTGGTGCAGTCTGGCGCCGAAGTGAAGAAACCAGGCGCCAG<br>CGTGAAGGTGTCCTGCAAGGCCAGCGGCTACAGCTTCACCGACTACATCA<br>TCCTGTGGGTCCGACAGGCCCCTGGCCAGAGACTGGAATGGATGGGCCAC<br>ATCGACCCCTACTACGGCAGCAGCAACTACAACCTGAAGTTCAAGGGCAG<br>AGTGACCATCACCCGGGACACCAGCGCCAGCACCGCCTACATGCAACTGA<br>GCAGCCTGAGAAGCGAGGACACCGCCGTGTACTACTGCGCCAGAAGCAAG<br>CGGGACTACTTCGACTACTGGGGCCAGGGCACCCTGGTCACCGTTAGCTC<br>TGCCTCCACCAAGGGCCCATCGGTCTTCCCCCTGGCACCCTCCTCCAAGA<br>GCACCTCTGGGGGCACAGCGGCCCTGGGCTGCCTGGTCAAGGACTACTTC<br>CCCGAACCGGTGACGGTGTCGTGGAACTCAGGCGCCCTGACCAGCGGCGT<br>GCACACCTTCCCGGCTGTCCTACAGTCCTCAGGACTCTACTCCCTCAGCA<br>GCGTGGTGACCGTGCCCTCCAGCAGCTTGGGCACCCAGACCTACATCTGC<br>AACGTGAATCACAAGCCCAGCAACACCAAGGTGGACAAGAGAGTTGAGCC<br>CAAATCTTGT |
| 200 | TPP-559 LC<br>nucleotide | GACATCCAAATGACCCAGAGCCCCAGCAGCCTGTACGCCAGCGTGGGCGA<br>CAGAGTGACCATCACATGCAAGGCCAGCCAGGACATCAACAGCTACCTGA<br>GCTGGTTCCAGCAGAAGCCCGGCAAGGCCCCTAAGAGCCTGATCTACCGG<br>GCCAACAGACTGGTGGACGGCGTGCCAAGCAGATTCAGCGGCAGCGGCTC<br>TGGCACCGACTTCACCCTGACCATCAGCTCCCTGCAGCCCGAGGACTTCG<br>CCACCTACTACTGCCTGCAGTACGACGAGTTCCCCTACACCTTCGGCCAG<br>GGCACCAAGCTGGAAATCAAGCGGACCGTGGCTGCACCATCTGTCTTCAT<br>CTTCCCGCCATCTGATGAGCAGTTGAAATCTGGAACTGCCTCTGTTGTGT<br>GCCTGCTGAATAACTTCTATCCCAGAGAGGCCAAAGTACAGTGGAAGGTG<br>GATAACGCCCTCCAATCGGGTAACTCCCAGGAGAGTGTCACAGAGCAGGA<br>CAGCAAGGACAGCACCTACAGCCTCAGCAGCACCCTGACGCTGAGCAAAG<br>CAGACTACGAGAAACACAAAGTCTACGCCTGCGAAGTCACCCATCAGGGC<br>CTGAGCTCGCCCGTCACAAAGAGCTTCAACAGGGGAGAGTGT |
| 201 | TPP-562 HC<br>nucleotide | CAGGTGCAGCTGGTGCAGTCTGGCGCCGAAGTGAAGAAACCAGGCGCCAG<br>CGTGAAGGTGTCCTGCAAGGCCAGCGGCTACAGCTTCACCGACTACATCA<br>TCCTGTGGGTCCGACAGGCCCCTGGCCAGAGACTGGAATGGATGGGCCAC<br>ATCGACCCCTACTACGGCAGCAGCAACTACAACCTGAAGTTCAAGGGCAG<br>AGTGACCATCACCCGGGACACCAGCGCCAGCACCGCCTACATGGAACTGA<br>GCAGCCTGAGAAGCGAGGACACCGCCGTGTACTACTGCGGAAGAAGCAAG<br>CGGGACTACTTCGACTACTGGGGCCAGGGCACCCTGGTCACCGTTAGCTC<br>TGCCTCCACCAAGGGCCCATCGGTCTTCCCCCTGGCACCCTCCTCCAAGA<br>GCACCTCTGGGGGCACAGCGGCCCTGGGCTGCCTGGTCAAGGACTACTTC<br>CCCGAACCGGTGACGGTGTCGTGGAACTCAGGCGCCCTGACCAGCGGCGT<br>GCACACCTTCCCGGCTGTCCTACAGTCCTCAGGACTCTACTCCCTCAGCA<br>GCGTGGTGACCGTGCCCTCCAGCAGCTTGGGCACCCAGACCTACATCTGC<br>AACGTGAATCACAAGCCCAGCAACACCAAGGTGGACAAGAGAGTTGAGCC<br>CAAATCTTGT |
| 202 | TPP-562 LC<br>nucleotide | GACATCCAAATGACCCAGAGCCCCAGCAGCCTGTACGCCAGCGTGGGCGA<br>CAGAGTGACCATCACATGCAAGGCCAGCCAGGACATCAACAGCTACCTGA<br>GCTGGTTCCAGCAGAAGCCCGGCAAGGCCCCTAAGAGCCTGATCTACCGG<br>GCCAACAGACTGGTGGACGGCGTGCCAAGCAGATTCAGCGGCAGCGGCTC<br>TGGCACCGACTTCACCCTGACCATCAGCTCCCTGCAGCCCGAGGACTTCG<br>CCACCTACTACTGCCTGCAGTACGACGAGTTCCCCTACACCTTCGGCCAG<br>GGCACCAAGCTGGAAATCAAGCGGACCGTGGCTGCACCATCTGTCTTCAT |

TABLE 12-continued

Summary Table of Sequences

| SEQ ID | Description | Sequence |
|---|---|---|
| | | CTTCCCGCCATCTGATGAGCAGTTGAAATCTGGAACTGCCTCTGTTGTGT GCCTGCTGAATAACTTCTATCCCAGAGAGGCCAAAGTACAGTGGAAGGTG GATAACGCCCTCCAATCGGGTAACTCCCAGGAGAGTGTCACAGAGCAGGA CAGCAAGGACAGCACCTACAGCCTCAGCAGCACCCTGACGCTGAGCAAAG CAGACTACGAGAAACACAAAGTCTACGCCTGCGAAGTCACCCATCAGGGC CTGAGCTCGCCCGTCACAAAGAGCTTCAACAGGGGAGAGTGT |
| 203 | TPP-563 HC nucleotide | CAAGTGCAACTGGTGCAGAGCGGCCCTGAAGTGAAGAAACCAGGCGCCAG CGTGAAGGTGTCCTGCAAGGCCAGCGGCTACAGCTTCACCGACTACATCA TCCTGTGGGTCCGACAGGCCCCTGGCCAGAGACTGGAATGGATGGGCCAC ATCGACCCCTACTACGGCAGCAGCAACTACAACCTGAAGTTCAAGGGCAG AGTGACCATCACCCGGGACACCAGCGCCAGCACCGCCTACATGGAACTGA GCAGCCTGAGAAGCGAGGACACCGCCGTGTACTACTGCGCCAGAAGCAAG CGGGACTACTTCGACTACTGGGGCCAGGGCACCCTGGTCACCGTTAGCTC TGCCTCCACCAAGGGCCCATCGGTCTTCCCCCTGGCACCCTCCTCCAAGA GCACCTCTGGGGGCACAGCGGCCCTGGGCTGCCTGGTCAAGGACTACTTC CCCGAACCGGTGACGGTGTCGTGGAACTCAGGCGCCCTGACCAGCGGCGT GCACACCTTCCCGGCTGTCCTACAGTCCTCAGGACTCTACTCCCTCAGCA GCGTGGTGACCGTGCCCTCCAGCAGCTTGGGCACCCAGACCTACATCTGC AACGTGAATCACAAGCCCAGCAACACCAAGGTGGACAAGAGAGTTGAGCC CAAATCTTGT |
| 204 | TPP-563 LC nucleotide | GACATCCAAATGACCCAGAGCCCCAGCAGCCTGTCTGCCAGCGTGGGCGA CAGAGTGACCATCACATGCAAGGCCAGCCAGGACATCAACAGCTACCTGA GCTGGTTCCAGCAGAAGCCCGGCAAGGCCCCTAAGAGCCTGATCTACCGG GCCAACAGACTGGTGGACGGCGTGCCAAGCAGATTCAGCGGCAGCGGCTC TGGCCAGGACTTCACCCTGACCATCAGCTCCCTGCAGCCCGAGGACTTCG CCACCTACTACTGCCTGCAGTACGACGAGTTCCCCTACACCTTCGGCCAG GGCACCAAGCTGGAAATCAAGCGGACCGTGGCTGCACCATCTGTCTTCAT CTTCCCGCCATCTGATGAGCAGTTGAAATCTGGAACTGCCTCTGTTGTGT GCCTGCTGAATAACTTCTATCCCAGAGAGGCCAAAGTACAGTGGAAGGTG GATAACGCCCTCCAATCGGGTAACTCCCAGGAGAGTGTCACAGAGCAGGA CAGCAAGGACAGCACCTACAGCCTCAGCAGCACCCTGACGCTGAGCAAAG CAGACTACGAGAAACACAAAGTCTACGCCTGCGAAGTCACCCATCAGGGC CTGAGCTCGCCCGTCACAAAGAGCTTCAACAGGGGAGAGTGT |
| 205 | TPP-571 HC nucleotide | CAGGTGCAGCTGGTGCAGTCTGGCGCCGAAGTGAAGAAACCAGGCGCCAG CGTGAAGGTGTCCTGCAAGGCCAGCGGCTACAGCTTCACCGACTACATCA TCCTGTGGGTCCGACAGGCCCCTGGCAAGAGACTGGAATGGATGGGCCAC ATCGACCCCTACTACGGCAGCAGCAACTACAACCTGAAGTTCAAGGGCAG AGTGACCATCACCCGGGACACCAGCGCCAGCACCGCCTACATGGAACTGA GCAGCCTGAGAAGCGAGGACACCGCCGTGTACTACTGCGCCAGAAGCAAG CGGGACTACTTCGACTACTGGGGCCAGGGCACCCTGGTCACCGTTAGCTC TGCCTCCACCAAGGGCCCATCGGTCTTCCCCCTGGCACCCTCCTCCAAGA GCACCTCTGGGGGCACAGCGGCCCTGGGCTGCCTGGTCAAGGACTACTTC CCCGAACCGGTGACGGTGTCGTGGAACTCAGGCGCCCTGACCAGCGGCGT GCACACCTTCCCGGCTGTCCTACAGTCCTCAGGACTCTACTCCCTCAGCA GCGTGGTGACCGTGCCCTCCAGCAGCTTGGGCACCCAGACCTACATCTGC AACGTGAATCACAAGCCCAGCAACACCAAGGTGGACAAGAGAGTTGAGCC CAAATCTTGT |
| 206 | TPP-571 LC nucleotide | GACATCCAAATGACCCAGAGCCCCAGCAGCCTGTCTGCCAGCGTGGGCGA CAGAGTGACCATCACATGCAAGGCCAGCCAGGACATCAACAGCTACCTGA GCTGGTTCCAGCAGAAGCCCGGCAAGGCCCCTAAGAGCCTGATCTACCGG GCCAACAGACTGGTGGACGGCGTGCCAAGCAGATTCAGCGGCAGCGGCTC TGGCCAGGACTTCACCCTGACCATCAGCTCCCTGCAGCCCGAGGACTTCG CCACCTACTACTGCCTGCAGTACGACGAGTTCCCCTACACCTTCGGCCAG GGCACCAAGCTGGAAATCAAGCGGACCGTGGCTGCACCATCTGTCTTCAT CTTCCCGCCATCTGATGAGCAGTTGAAATCTGGAACTGCCTCTGTTGTGT GCCTGCTGAATAACTTCTATCCCAGAGAGGCCAAAGTACAGTGGAAGGTG GATAACGCCCTCCAATCGGGTAACTCCCAGGAGAGTGTCACAGAGCAGGA CAGCAAGGACAGCACCTACAGCCTCAGCAGCACCCTGACGCTGAGCAAAG CAGACTACGAGAAACACAAAGTCTACGCCTGCGAAGTCACCCATCAGGGC CTGAGCTCGCCCGTCACAAAGAGCTTCAACAGGGGAGAGTGT |
| 207 | TPP-572 HC nucleotide | CAGGTGCAGCTGGTGCAGTCTGGCGCCGAAGTGAAGAAACCAGGCGCCAG CGTGAAGGTGTCCTGCAAGGCCAGCGGCTACAGCTTCACCGACTACATCA TCCTGTGGGTCCGACAGGCCCCTGGCCAGTCTCTGGAATGGATGGGCCAC ATCGACCCCTACTACGGCAGCAGCAACTACAACCTGAAGTTCAAGGGCAG AGTGACCATCACCCGGGACACCAGCGCCAGCACCGCCTACATGGAACTGA GCAGCCTGAGAAGCGAGGACACCGCCGTGTACTACTGCGCCAGAAGCAAG CGGGACTACTTCGACTACTGGGGCCAGGGCACCCTGGTCACCGTTAGCTC TGCCTCCACCAAGGGCCCATCGGTCTTCCCCCTGGCACCCTCCTCCAAGA GCACCTCTGGGGGCACAGCGGCCCTGGGCTGCCTGGTCAAGGACTACTTC CCCGAACCGGTGACGGTGTCGTGGAACTCAGGCGCCCTGACCAGCGGCGT |

TABLE 12-continued

| Summary Table of Sequences | | |
|---|---|---|
| SEQ ID | Description | Sequence |
| | | GCACACCTTCCCGGCTGTCCTACAGTCCTCAGGACTCTACTCCCTCAGCA GCGTGGTGACCGTGCCCTCCAGCAGCTTGGGCACCCAGACCTACATCTGC AACGTGAATCACAAGCCCAGCAACACCAAGGTGGACAAGAGAGTTGAGCC CAAATCTTGTCACCATCACCATCACCAT |
| 208 | TPP-572 LC nucleotide | GACATCCAAATGACCCAGAGCCCCAGCAGCCTGTCTGCCAGCGTGGGCGA CAGAGTGACCATCACATGCAAGGCCAGCCAGGACATCAACAGCTACCTGA GCTGGTTCCAGCAGAAGCCCGGCAAGGCCCCTAAGAGCCTGATCTACCGG GCCAACAGACTGGTGGACGGCGTGCCAAGCAGATTCAGCGGCAGCGGCTC TGGCCAGGACTTCACCCTGACCATCAGCTCCCTGCAGCCCGAGGACTTCG CCACCTACTACTGCCTGCAGTACGACGAGTTCCCCTACACCTTCGGCCAG GGCACCAAGCTGGAAATCAAGCGGACCGTGGCTGCACCATCTGTCTTCAT CTTCCCGCCATCTGATGAGCAGTTGAAATCTGGAACTGCCTCTGTTGTGT GCCTGCTGAATAACTTCTATCCCAGAGAGGCCAAAGTACAGTGGAAGGTG GATAACGCCCTCCAATCGGGTAACTCCCAGGAGAGTGTCACAGAGCAGGA CAGCAAGGACAGCACCTACAGCCTCAGCAGCACCCTGACGCTGAGCAAAG CAGACTACGAGAAACACAAAGTCTACGCCTGCGAAGTCACCCATCAGGGC CTGAGCTCGCCCGTCACAAAGAGCTTCAACAGGGGAGAGTGT |
| 209 | TPP-573 HC nucleotide | CAGGTGCAGCTGGTGCAGTCTGGCGCCGAAGTGAAGAAACCAGGCGCCAG CGTGAAGGTGTCCTGCAAGGCCAGCGGCTACAGCTTCACCGACTACATCA TCCTGTGGGTCCGACAGGCCCCTGGCCAGAGACTGGAATGGATTGGCCAC ATCGACCCCTACTACGGCAGCAGCAACTACAACCTGAAGTTCAAGGGCAG AGTGACCATCACCCGGGACACCAGCGCCAGCACCGCCTACATGGAACTGA GCAGCCTGAGAAGCGAGGACACCGCCGTGTACTACTGCGCCAGAAGCAAG CGGGACTACTTCGACTACTGGGGCCAGGGCACCCTGGTCACCGTTAGCTC TGCCTCCACCAAGGGCCCATCGGTCTTCCCCCTGGCACCCTCCTCCAAGA GCACCTCTGGGGGCACAGCGGCCCTGGGCTGCCTGGTCAAGGACTACTTC CCCGAACCGGTGACGGTGTCGTGGAACTCAGGCGCCCTGACCAGCGGCGT GCACACCTTCCCGGCTGTCCTACAGTCCTCAGGACTCTACTCCCTCAGCA GCGTGGTGACCGTGCCCTCCAGCAGCTTGGGCACCCAGACCTACATCTGC AACGTGAATCACAAGCCCAGCAACACCAAGGTGGACAAGAGAGTTGAGCC CAAATCTTGT |
| 210 | TPP-573 LC nucleotide | GACATCCAAATGACCCAGAGCCCCAGCAGCCTGTCTGCCAGCGTGGGCGA CAGAGTGACCATCACATGCAAGGCCAGCCAGGACATCAACAGCTACCTGA GCTGGTTCCAGCAGAAGCCCGGCAAGGCCCCTAAGAGCCTGATCTACCGG GCCAACAGACTGGTGGACGGCGTGCCAAGCAGATTCAGCGGCAGCGGCTC TGGCCAGGACTTCACCCTGACCATCAGCTCCCTGCAGCCCGAGGACTTCG CCACCTACTACTGCCTGCAGTACGACGAGTTCCCCTACACCTTCGGCCAG GGCACCAAGCTGGAAATCAAGCGGACCGTGGCTGCACCATCTGTCTTCAT CTTCCCGCCATCTGATGAGCAGTTGAAATCTGGAACTGCCTCTGTTGTGT GCCTGCTGAATAACTTCTATCCCAGAGAGGCCAAAGTACAGTGGAAGGTG GATAACGCCCTCCAATCGGGTAACTCCCAGGAGAGTGTCACAGAGCAGGA CAGCAAGGACAGCACCTACAGCCTCAGCAGCACCCTGACGCTGAGCAAAG CAGACTACGAGAAACACAAAGTCTACGCCTGCGAAGTCACCCATCAGGGC CTGAGCTCGCCCGTCACAAAGAGCTTCAACAGGGGAGAGTGT |
| 211 | TPP-578 HC nucleotide | CAGGTGCAGCTGGTGCAGTCTGGCGCCGAAGTGAAGAAACCAGGCGCCAG CGTGAAGGTGTCCTGCAAGGCCAGCGGCTACAGCTTCACCGACTACATCA TCCTGTGGGTCCGACAGGCCCCTGGCCAGAGACTGGAATGGATGGGCCAC ATCGACCCCTACTACGGCAGCAGCAACTACAACCTGAAGTTCAAGGGCAG AGTGACCATCACCCGGGACAAGAGCGCCAGCACCGCCTACATGGAACTGA GCAGCCTGAGAAGCGAGGACACCGCCGTGTACTACTGCGCCAGAAGCAAG CGGGACTACTTCGACTACTGGGGCCAGGGCACCCTGGTCACCGTTAGCTC TGCCTCCACCAAGGGCCCATCGGTCTTCCCCCTGGCACCCTCCTCCAAGA GCACCTCTGGGGGCACAGCGGCCCTGGGCTGCCTGGTCAAGGACTACTTC CCCGAACCGGTGACGGTGTCGTGGAACTCAGGCGCCCTGACCAGCGGCGT GCACACCTTCCCGGCTGTCCTACAGTCCTCAGGACTCTACTCCCTCAGCA GCGTGGTGACCGTGCCCTCCAGCAGCTTGGGCACCCAGACCTACATCTGC AACGTGAATCACAAGCCCAGCAACACCAAGGTGGACAAGAGAGTTGAGCC CAAATCTTGT |
| 212 | TPP-578 LC nucleotide | GACATCCAAATGACCCAGAGCCCCAGCAGCCTGTCTGCCAGCGTGGGCGA CAGAGTGACCATCACATGCAAGGCCAGCCAGGACATCAACAGCTACCTGA GCTGGTTCCAGCAGAAGCCCGGCAAGGCCCCTAAGAGCCTGATCTACCGG GCCAACAGACTGGTGGACGGCGTGCCAAGCAGATTCAGCGGCAGCGGCTC TGGCCAGGACTTCACCCTGACCATCAGCTCCCTGCAGCCCGAGGACTTCG CCACCTACTACTGCCTGCAGTACGACGAGTTCCCCTACACCTTCGGCCAG GGCACCAAGCTGGAAATCAAGCGGACCGTGGCTGCACCATCTGTCTTCAT CTTCCCGCCATCTGATGAGCAGTTGAAATCTGGAACTGCCTCTGTTGTGT GCCTGCTGAATAACTTCTATCCCAGAGAGGCCAAAGTACAGTGGAAGGTG GATAACGCCCTCCAATCGGGTAACTCCCAGGAGAGTGTCACAGAGCAGGA CAGCAAGGACAGCACCTACAGCCTCAGCAGCACCCTGACGCTGAGCAAAG |

TABLE 12-continued

| Summary Table of Sequences | | |
|---|---|---|
| SEQ ID | Description | Sequence |
| | | CAGACTACGAGAAACACAAAGTCTACGCCTGCGAAGTCACCCATCAGGGC<br>CTGAGCTCGCCCGTCACAAAGAGCTTCAACAGGGGAGAGTGT |
| 213 | TPP-583 HC nucleotide | CAGGTGCAGCTGGTGCAGTCTGGCGCCGAAGTGAAGAAACCAGGCGCCAG<br>CGTGAAGGTGTCCTGCAAGGCCAGCGGCTACAGCTTCACCGACTACATCA<br>TCCTGTGGGTCCGACAGGCCCCTGGCCAGAGACTGGAATGGATGGGCCAC<br>ATCGACCCCTACTACGGCAGCAGCAACTACAACCTGAAGTTCAAGGGCAG<br>AGTGACCATCACCCGGGACACCAGCGCCAGCACCGCCTACATGGAACTGA<br>GCAGCCTGAGAAGCGAGGACACCGCCGTGTACTACTGCGGAAGAAGCAAG<br>CGGGACTACTTCGACTACTGGGGCCAGGGCACCCTGGTCACCGTTAGCTC<br>TGCCTCCACCAAGGGCCCATCGGTCTTCCCCCTGGCACCCTCCTCCAAGA<br>GCACCTCTGGGGGCACAGCGGCCCTGGGCTGCCTGGTCAAGGACTACTTC<br>CCCGAACCGGTGACGGTGTCGTGGAACTCAGGCGCCCTGACCAGCGGCGT<br>GCACACCTTCCCGGCTGTCCTACAGTCCTCAGGACTCTACTCCCTCAGCA<br>GCGTGGTGACCGTGCCCTCCAGCAGCTTGGGCACCCAGACCTACATCTGC<br>AACGTGAATCACAAGCCCAGCAACACCAAGGTGGACAAGAGAGTTGAGCC<br>CAAATCTTGT |
| 214 | TPP-583 LC nucleotide | GACATCCAAATGACCCAGAGCCCCAGCAGCCTGTCTGCCAGCGTGGGCGA<br>CAGAGTGACCATCACATGCAAGGCCAGCCAGGACATCAACAGCTACCTGA<br>GCTGGTTCCAGCAGAAGCCCGGCAAGGCCCCTAAGAGCCTGATCTACCGG<br>GCCAACAGACTGGTGGACGGCGTGCCAAGCAGATTCAGCGGCAGCGGCTC<br>TGGCCAGGACTTCACCCTGACCATCAGCTCCCTGCAGCCCGAGGACTTCG<br>CCACCTACTACTGCCTGCAGTACGACGAGTTCCCCTACACCTTCGGCCAG<br>GGCACCAAGCTGGAAATCAAGCGGACCGTGGCTGCACCATCTGTCTTCAT<br>CTTCCCGCCATCTGATGAGCAGTTGAAATCTGGAACTGCCTCTGTTGTGT<br>GCCTGCTGAATAACTTCTATCCCAGAGAGGCCAAAGTACAGTGGAAGGTG<br>GATAACGCCCTCCAATCGGGTAACTCCCAGGAGAGTGTCACAGAGCAGGA<br>CAGCAAGGACAGCACCTACAGCCTCAGCAGCACCCTGACGCTGAGCAAAG<br>CAGACTACGAGAAACACAAAGTCTACGCCTGCGAAGTCACCCATCAGGGC<br>CTGAGCTCGCCCGTCACAAAGAGCTTCAACAGGGGAGAGTGT |
| 215 | TPP-604 HC nucleotide | CAGGTGCAGCTGGTGCAGTCTGGCGCCGAAGTGAAGAAACCAGGCGCCAG<br>CGTGAAGGTGTCCTGCAAGGCCAGCGGCTACAGCTTCACCGACTACATCA<br>TCCTGTGGGTCCGACAGGCCCCTGGCCAGAGACTGGAATGGATGGGCCAC<br>ATCGACCCCTACTACGGCAGCAGCAACTACAACCTGAAGTTCAAGGGCAG<br>AGTGACCATCACCCGGGACACCAGCGCCAGCACCGCCTACATGGAACTGA<br>GCAGCCTGAGAAGCGAGGACACCGCCGTGTACTACTGCGGAAGAAGCAAG<br>CGGGACTACTTCGACTACTGGGGCCAGGGCACCCTGGTCACCGTTAGCTC<br>TGCCTCCACCAAGGGCCCATCGGTCTTCCCCCTGGCACCCTCCTCCAAGA<br>GCACCTCTGGGGGCACAGCGGCCCTGGGCTGCCTGGTCAAGGACTACTTC<br>CCCGAACCGGTGACGGTGTCGTGGAACTCAGGCGCCCTGACCAGCGGCGT<br>GCACACCTTCCCGGCTGTCCTACAGTCCTCAGGACTCTACTCCCTCAGCA<br>GCGTGGTGACCGTGCCCTCCAGCAGCTTGGGCACCCAGACCTACATCTGC<br>AACGTGAATCACAAGCCCAGCAACACCAAGGTGGACAAGAGAGTTGAGCC<br>CAAATCTTGT |
| 216 | TPP-604 LC nucleotide | GACATCCAAATGACCCAGAGCCCCAGCAGCCTGTCTGCCAGCGTGGGCGA<br>CAGAGTGACCATCACATGCAAGGCCAGCCAGGACATCAACAGCTACCTGA<br>GCTGGTTCCAGCAGAAGCCCGGCAAGGCCCCTAAGAGCCTGATCTACCGG<br>GCCAACAGACTGGTGGACGGCGTGCCAAGCAGATTCAGCGGCAGCGGCTC<br>TGGCACCGACTACACCCTGACCATCAGCTCCCTGCAGCCCGAGGACTTCG<br>CCACCTACTACTGCCTGCAGTACGACGAGTTCCCCTACACCTTCGGCCAG<br>GGCACCAAGCTGGAAATCAAGCGGACCGTGGCTGCACCATCTGTCTTCAT<br>CTTCCCGCCATCTGATGAGCAGTTGAAATCTGGAACTGCCTCTGTTGTGT<br>GCCTGCTGAATAACTTCTATCCCAGAGAGGCCAAAGTACAGTGGAAGGTG<br>GATAACGCCCTCCAATCGGGTAACTCCCAGGAGAGTGTCACAGAGCAGGA<br>CAGCAAGGACAGCACCTACAGCCTCAGCAGCACCCTGACGCTGAGCAAAG<br>CAGACTACGAGAAACACAAAGTCTACGCCTGCGAAGTCACCCATCAGGGC<br>CTGAGCTCGCCCGTCACAAAGAGCTTCAACAGGGGAGAGTGT |
| 217 | TPP-678 HC nucleotide | CAGGTGCAGCTGGTGCAGTCTGGCGCCGAAGTGAAGAAACCAGGCGCCAG<br>CGTGAAGGTGTCCTGCAAGGCCAGCGGCTACAGCTTCACCGACTACATCA<br>TCCTGTGGGTCCGACAGGCCCCTGGCCAGAGACTGGAATGGATTGGCCAC<br>ATCGACCCCTACTACGGCAGCAGCAACTACAACCTGAAGTTCAAGGGCAG<br>AGTGACCATCACCCGGGACACCAGCGCCAGCACCGCCTACATGGAACTGA<br>GCAGCCTGAGAAGCGAGGACACCGCCGTGTACTACTGCGCCAGAAGCAAG<br>CGGGACTACTTCGACTACTGGGGCCAGGGCACCCTGGTCACCGTTAGCTC<br>TGCCTCCACCAAGGGCCCATCGGTCTTCCCCCTGGCACCCTCCTCCAAGA<br>GCACCTCTGGGGGCACAGCGGCCCTGGGCTGCCTGGTCAAGGACTACTTC<br>CCCGAACCGGTGACGGTGTCGTGGAACTCAGGCGCCCTGACCAGCGGCGT<br>GCACACCTTCCCGGCTGTCCTACAGTCCTCAGGACTCTACTCCCTCAGCA<br>GCGTGGTGACCGTGCCCTCCAGCAGCTTGGGCACCCAGACCTACATCTGC<br>AACGTGAATCACAAGCCCAGCAACACCAAGGTGGACAAGAGAGTTGAGCC<br>CAAATCTTGT |

TABLE 12-continued

Summary Table of Sequences

| SEQ ID | Description | Sequence |
|---|---|---|
| 218 | TPP-678 LC nucleotide | GACATCCAAATGACCCAGAGCCCCAGCAGCCTGTCTGCCAGCGTGGGCGA<br>CAGAGTGACCATCACATGCAAGGCCAGCCAGGACATCAACAGCTACCTGA<br>GCTGGTTCCAGCAGAAGCCCGGCAAGGCCCCTAAGAGCCTGATCTACCGG<br>GCCAACAGACTGGTGGACGGCGTGCCAAGCAGATTCAGCGGCAGCGGCTC<br>TGGCACCGACTTCACCCTGACCATCAGCTCCCTGCAGCCCGAGGACATGG<br>CCACCTACTACTGCCTGCAGTACGACGAGTTCCCCTACACCTTCGGCCAG<br>GGCACCAAGCTGGAAATCAAGCGGACCGTGGCTGCACCATCTGTCTTCAT<br>CTTCCCGCCATCTGATGAGCAGTTGAAATCTGGAACTGCCTCTGTTGTGT<br>GCCTGCTGAATAACTTCTATCCCAGAGAGGCCAAAGTACAGTGGAAGGTG<br>GATAACGCCCTCCAATCGGGTAACTCCCAGGAGAGTGTCACAGAGCAGGA<br>CAGCAAGGACAGCACCIACAGCCTCAGCAGCACCCTGACGCTGAGCAAAG<br>CAGACTACGAGAAACACAAAGTCTACGCCTGCGAAGTCACCCATCAGGGC<br>CTGAGCTCGCCCGTCACAAAGAGCTTCAACAGGGGAGAGTGT |
| 219 | TPP-688 HC nucleotide | CAGGTGCAGCTGGTGCAGTCTGGCGCCGAAGTGAAGAAACCAGGCGCCAG<br>CGTGAAGGTGTCCTGCAAGGCCAGCGGCTACAGCTTCACCGACTACATCA<br>TCCTGTGGGTCCGACAGGCCCCTGGCCAGAGACTGGAATGGATGGGCCAC<br>ATCGACCCCTACTACGGCAGCAGCAACTACAACCTGAAGTTCAAGGGCAG<br>AGTGACCATCACCCGGGACACCAGCGCCAGCACCGCCTACATGGAACTGA<br>GCAGCCTGAGAAGCGAGGACACCGCCGTGTACTACTGCGGAAGAAGCAAG<br>CGGGACTACTTCGACTACTGGGGCCAGGGCACCCTGGTCACCGTTAGCTC<br>TGCCTCCACCAAGGGCCCATCGGTCTTCCCCCTGGCACCCTCCTCCAAGA<br>GCACCTCTGGGGGCACAGCGGCCCTGGGCTGCCTGGTCAAGGACTACTTC<br>CCCGAACCGGTGACGGTGTCGTGGAACTCAGGCGCCCTGACCAGCGGCGT<br>GCACACCTTCCCGGCTGTCCTACAGTCCTCAGGACTCTACTCCCTCAGCA<br>GCGTGGTGACCGTGCCCTCCAGCAGCTTGGGCACCCAGACCTACATCTGC<br>AACGTGAATCACAAGCCCAGCAACACCAAGGTGGACAAGAGAGTTGAGCC<br>CAAATCTTGT |
| 220 | TPP-688 LC nucleotide | GACATCCAAATGACCCAGAGCCCCAGCAGCCTGTCTGCCAGCGTGGGCGA<br>CAGAGTGACCATCACATGCAAGGCCAGCCAGGACATCAACAGCTACCTGA<br>GCTGGTTCCAGCAGAAGCCCGGCAAGGCCCCTAAGAGCCTGATCTACCGG<br>GCCAACAGACTGGTGGACGGCGTGCCAAGCAGATTCAGCGGCAGCGGCTC<br>TGGCACCGACTTCACCCTGACCATCAGCTCCCTGCAGCCCGAGGACATGG<br>CCACCTACTACTGCCTGCAGTACGACGAGTTCCCCTACACCTTCGGCCAG<br>GGCACCAAGCTGGAAATCAAGCGGACCGTGGCTGCACCATCTGTCTTCAT<br>CTTCCCGCCATCTGATGAGCAGTTGAAATCTGGAACTGCCTCTGTTGTGT<br>GCCTGCTGAATAACTTCTATCCCAGAGAGGCCAAAGTACAGTGGAAGGTG<br>GATAACGCCCTCCAATCGGGTAACTCCCAGGAGAGTGTCACAGAGCAGGA<br>CAGCAAGGACAGCACCTACAGCCTCAGCAGCACCCTGACGCTGAGCAAAG<br>CAGACTACGAGAAACACAAAGTCTACGCCTGCGAAGTCACCCATCAGGGC<br>CTGAGCTCGCCCGTCACAAAGAGCTTCAACAGGGGAGAGTGT |
| 221 | TPP-709 HC nucleotide | CAGGTGCAGCTGGTGCAGTCTGGCGCCGAAGTGAAGAAACCAGGCGCCAG<br>CGTGAAGGTGTCCTGCAAGGCCAGCGGCTACAGCTTCACCGACTACATCA<br>TCCTGTGGGTCCGACAGGCCCCTGGCCAGAGACTGGAATGGATGGGCCAC<br>ATCGACCCCTACTACGGCAGCAGCAACTACAACCTGAAGTTCAAGGGCAG<br>AGTGACCATCACCCGGGACACCAGCGCCAGCACCGCCTACATGGAACTGA<br>GCAGCCTGAGAAGCGAGGACACCGCCGTGTACTACTGCGGAAGAAGCAAG<br>CGGGACTACTTCGACTACTGGGGCCAGGGCACCCTGGTCACCGTTAGCTC<br>TGCCTCCACCAAGGGCCCATCGGTCTTCCCCCTGGCACCCTCCTCCAAGA<br>GCACCTCTGGGGGCACAGCGGCCCTGGGCTGCCTGGTCAAGGACTACTTC<br>CCCGAACCGGTGACGGTGTCGTGGAACTCAGGCGCCCTGACCAGCGGCGT<br>GCACACCTTCCCGGCTGTCCTACAGTCCTCAGGACTCTACTCCCTCAGCA<br>GCGTGGTGACCGTGCCCTCCAGCAGCTTGGGCACCCAGACCTACATCTGC<br>AACGTGAATCACAAGCCCAGCAACACCAAGGTGGACAAGAGAGTTGAGCC<br>CAAATCTTGT |
| 222 | TPP-709 LC nucleotide | GACATCCAAATGACCCAGAGCCCCAGCAGCCTGTCTGCCAGCGTGGGCGA<br>CAGAGTGACCATCACATGCAAGGCCAGCCAGGACATCAACAGCTACCTGA<br>GCTGGTTCCAGCAGAAGCCCGGCAAGGCCCCTAAGAGCCTGATCTACCGG<br>GCCAACAGACTGGTGGACGGCGTGCCAAGCAGATTCAGCGGCAGCGGCTC<br>TGGCACCGACTTCACCCTGACCATCAGCTCCCTGCAGCCCGAGGACTTCG<br>GCACCTACTACTGCCTGCAGTACGACGAGTTCCCCTACACCTTCGGCCAG<br>GGCACCAAGCTGGAAATCAAGCGGACCGTGGCTGCACCATCTGTCTTCAT<br>CTTCCCGCCATCTGATGAGCAGTTGAAATCTGGAACTGCCTCTGTTGTGT<br>GCCTGCTGAATAACTTCTATCCCAGAGAGGCCAAAGTACAGTGGAAGGTG<br>GATAACGCCCTCCAATCGGGTAACTCCCAGGAGAGTGTCACAGAGCAGGA<br>CAGCAAGGACAGCACCTACAGCCTCAGCAGCACCCTGACGCTGAGCAAAG<br>CAGACTACGAGAAACACAAAGTCTACGCCTGCGAAGTCACCCATCAGGGC<br>CTGAGCTCGCCCGTCACAAAGAGCTTCAACAGGGGAGAGTGT |
| 223 | TPP-720 HC nucleotide | CAGGTGCAGCTGGTGCAGTCTGGCGCCGAAGTGAAGAAACCAGGCGCCAG<br>CGTGAAGGTGTCCTGCAAGGCCAGCGGCTACAGCTTCACCGACTACATCA |

TABLE 12-continued

Summary Table of Sequences

| SEQ ID | Description | Sequence |
|---|---|---|
| | | TCCTGTGGGTCCGACAGGCCCCTGGCCAGAGACTGGAATGGATTGGCCAC<br>ATCGACCCCTACTACGGCAGCAGCAACTACAACCTGAAGTTCAAGGGCAG<br>AGTGACCATCACCCGGGACACCAGCGCCAGCACCGCCTACATGGAACTGA<br>GCAGCCTGAGAAGCGAGGACACCGCCGTGTACTACTGCGCCAGAAGCAAG<br>CGGGACTACTTCGACTACTGGGGCCAGGGCACCCTGGTCACCGTTAGCTC<br>TGCCTCCACCAAGGGCCCATCGGTCTTCCCCCTGGCACCCTCCTCCAAGA<br>GCACCTCTGGGGGCACAGCGGCCCTGGGCTGCCTGGTCAAGGACTACTTC<br>CCCGAACCGGTGACGGTGTCGTGGAACTCAGGCGCCCTGACCAGCGGCGT<br>GCACACCTTCCCGGCTGTCCTACAGTCCTCAGGACTCTACTCCCTCAGCA<br>GCGTGGTGACCGTGCCCTCCAGCAGCTTGGGCACCCAGACCTACATCTGC<br>AACGTGAATCACAAGCCCAGCAACACCAAGGTGGACAAGAGAGTTGAGCC<br>CAAATCTTGT |
| 224 | TPP-720 LC nucleotide | GACATCCAAATGACCCAGAGCCCCAGCAGCCTGTCTGCCAGCGTGGGCGA<br>CAGAGTGACCATCACATGCAAGGCCAGCCAGGACATCAACAGCTACCTGA<br>GCTGGTTCCAGCAGAAGCCCGGCAAGGCCCCTAAGAGCCTGATCTACCGG<br>GCCAACAGACTGGTGGACGGCGTGCCAAGCAGATTCAGCGGCAGCGGCTC<br>TGGCACCGACTTCACCCTGACCATCAGCTCCCTGCAGCCCGAGGACTTCG<br>CCATCTACTACTGCCTGCAGTACGACGAGTTCCCCTACACCTTCGGCCAG<br>GGCACCAAGCTGGAAATCAAG |
| 225 | TPP-730 HC nucleotide | CAGGTGCAGCTGGTGCAGTCTGGCGCCGAAGTGAAGAAACCAGGCGCCAG<br>CGTGAAGGTGTCCTGCAAGGCCAGCGGCTACAGCTTCACCGACTACATCA<br>TCCTGTGGGTCCGACAGGCCCCTGGCCAGAGACTGGAATGGATGGGCCAC<br>ATCGACCCCTACTACGGCAGCAGCAACTACAACCTGAAGTTCAAGGGCAG<br>AGTGACCATCACCCGGGACACCAGCGCCAGCACCGCCTACATGGAACTGA<br>GCAGCCTGAGAAGCGAGGACACCGCCGTGTACTACTGCGGAAGAAGCAAG<br>CGGGACTACTTCGACTACTGGGGCCAGGGCACCCTGGTCACCGTTAGCTC<br>TGCCTCCACCAAGGGCCCATCGGTCTTCCCCCTGGCACCCTCCTCCAAGA<br>GCACCTCTGGGGGCACAGCGGCCCTGGGCTGCCTGGTCAAGGACTACTTC<br>CCCGAACCGGTGACGGTGTCGTGGAACTCAGGCGCCCTGACCAGCGGCGT<br>GCACACCTTCCCGGCTGTCCTACAGTCCTCAGGACTCTACTCCCTCAGCA<br>GCGTGGTGACCGTGCCCTCCAGCAGCTTGGGCACCCAGACCTACATCTGC<br>AACGTGAATCACAAGCCCAGCAACACCAAGGTGGACAAGAGAGTTGAGCC<br>CAAATCTTGT |
| 226 | TPP-730 LC nucleotide | GACATCCAAATGACCCAGAGCCCCAGCAGCCTGTCTGCCAGCGTGGGCGA<br>CAGAGTGACCATCACATGCAAGGCCAGCCAGGACATCAACAGCTACCTGA<br>GCTGGTTCCAGCAGAAGCCCGGCAAGGCCCCTAAGAGCCTGATCTACCGG<br>GCCAACAGACTGGTGGACGGCGTGCCAAGCAGATTCAGCGGCAGCGGCTC<br>TGGCACCGACTTCACCCTGACCATCAGCTCCCTGCAGCCCGAGGACTTCG<br>CCATCTACTACTGCCTGCAGTACGACGAGTTCCCCTACACCTTCGGCCAG<br>GGCACCAAGCTGGAAATCAAGCGGACCGTGGCTGCACCATCTGTCTTCAT<br>CTTCCCGCCATCTGATGAGCAGTTGAAATCTGGAACTGCCTCTGTTGTGT<br>GCCTGCTGAATAACTTCTATCCCAGAGAGGCCAAAGTACAGTGGAAGGTG<br>GATAACGCCCTCCAATCGGGTAACTCCCAGGAGAGTGTCACAGAGCAGGA<br>CAGCAAGGACAGCACCTACAGCCTCAGCAGCACCCTGACGCTGAGCAAAG<br>CAGACTACGAGAAACACAAAGTCTACGCCTGCGAAGTCACCCATCAGGGC<br>CTGAGCTCGCCCGTCACAAAGAGCTTCAACAGGGGAGAGTGT |
| 227 | TPP-741 HC nucleotide | CAGGTGCAGCTGGTGCAGTCTGGCGCCGAAGTGAAGAAACCAGGCGCCAG<br>CGTGAAGGTGTCCTGCAAGGCCAGCGGCTACAGCTTCACCGACTACATCA<br>TCCTGTGGGTCCGACAGGCCCCTGGCCAGAGACTGGAATGGATTGGCCAC<br>ATCGACCCCTACTACGGCAGCAGCAACTACAACCTGAAGTTCAAGGGCAG<br>AGTGACCATCACCCGGGACACCAGCGCCAGCACCGCCTACATGGAACTGA<br>GCAGCCTGAGAAGCGAGGACACCGCCGTGTACTACTGCGCCAGAAGCAAG<br>CGGGACTACTTCGACTACTGGGGCCAGGGCACCCTGGTCACCGTTAGCTC<br>TGCCTCCACCAAGGGCCCATCGGTCTTCCCCCTGGCACCCTCCTCCAAGA<br>GCACCTCTGGGGGCACAGCGGCCCTGGGCTGCCTGGTCAAGGACTACTTC<br>CCCGAACCGGTGACGGTGTCGTGGAACTCAGGCGCCCTGACCAGCGGCGT<br>GCACACCTTCCCGGCTGTCCTACAGTCCTCAGGACTCTACTCCCTCAGCA<br>GCGTGGTGACCGTGCCCTCCAGCAGCTTGGGCACCCAGACCTACATCTGC<br>AACGTGAATCACAAGCCCAGCAACACCAAGGTGGACAAGAGAGTTGAGCC<br>CAAATCTTGT |
| 228 | TPP-741 LC nucleotide | GACATCCAGATGACCCAGAGCCCCAGCAGCCTGAGCGCCAGCGTGGGCGA<br>CAGAGTGACCATCACATGCAAGGCCAGCCAGGACATCAACAGCTACCTGA<br>GCTGGTTCCAGCAGAAGCCCGGCAAGGCCCCCAAGAGCCTGATCTACCGG<br>GCCAACAGACTGGTGGACGGCGTGCCCAGCAGATTCAGCGGCAGCGGCTC<br>CGGCACCGACTTCACCCTGACCATCAGCAGCCTGCAGCCCGAGGACTTCG<br>CCACCTACTACTGCCTGCAGTACGACGAGTTCCCCTACACCTTCGGCCAG<br>GGCACCAAGCTGGAAATCAAGCGGACCGTGGCTGCACCATCTGTCTTCAT<br>CTTCCCGCCATCTGATGAGCAGTTGAAATCTGGAACTGCCTCTGTTGTGT<br>GCCTGCTGAATAACTTCTATCCCAGAGAGGCCAAAGTACAGTGGAAGGTG<br>GATAACGCCCTCCAATCGGGTAACTCCCAGGAGAGTGTCACAGAGCAGGA |

TABLE 12-continued

| SEQ ID | Description | Sequence |
|---|---|---|
| | Summary Table of Sequences | |
| | | CAGCAAGGACAGCACCTACAGCCTCAGCAGCACCCTGACGCTGAGCAAAG CAGACTACGAGAAACACAAAGTCTACGCCTGCGAAGTCACCCATCAGGGC CTGAGCTCGCCCGTCACAAAGAGCTTCAACAGGGGAGAGTGT |
| 229 | TPP-751 HC nucleotide | CAGGTGCAGCTGGTGCAGTCTGGCGCCGAAGTGAAGAAACCAGGCGCCAG CGTGAAGGTGTCCTGCAAGGCCAGCGGCTACAGCTTCACCGACTACATCA TCCTGTGGGTCCGACAGGCCCCTGGCCAGAGACTGGAATGGATGGGCCAC ATCGACCCCTACTACGGCAGCAGCAACTACAACCTGAAGTTCAAGGGCAG AGTGACCATCACCCGGGACACCAGCGCCAGCACCGCCTACATGGAACTGA GCAGCCTGAGAAGCGAGGACACCGCCGTGTACTACTGCGGAAGAAGCAAG CGGGACTACTTCGACTACTGGGGCCAGGGCACCCTGGTCACCGTTAGCTC TGCCTCCACCAAGGGCCCATCGGTCTTCCCCCTGGCACCCTCCTCCAAGA GCACCTCTGGGGGCACAGCGGCCCTGGGCTGCCTGGTCAAGGACTACTTC CCCGAACCGGTGACGGTGTCGTGGAACTCAGGCGCCCTGACCAGCGGCGT GCACACCTTCCCGGCTGTCCTACAGTCCTCAGGACTCTACTCCCTCAGCA GCGTGGTGACCGTGCCCTCCAGCAGCTTGGGCACCCAGACCTACATCTGC AACGTGAATCACAAGCCCAGCAACACCAAGGTGGACAAGAGAGTTGAGCC CAAATCTTGT |
| 230 | TPP-751 LC nucleotide | GACATCCAGATGACCCAGAGCCCCAGCAGCCTGAGCGCCAGCGTGGGCGA CAGAGTGACCATCACATGCAAGGCCAGCCAGGACATCAACAGCTACCTGA GCTGGTTCCAGCAGAAGCCCGGCAAGGCCCCCAAGAGCCTGATCTACCGG GCCAACAGACTGGTGGACGGCGTGCCCAGCAGATTCAGCGGCAGCGGCTC CGGCACCGACTTCACCCTGACCATCAGCAGCCTGCAGCCCGAGGACTTCG CCACCTACTACTGCCTGCAGTACGACGAGTTCCCCTACACCTTCGGCCAG GGCACCAAGCTGGAAATCAAGCGGACCGTGGCTGCACCATCTGTCTTCAT CTTCCCGCCATCTGATGAGCAGTTGAAATCTGGAACTGCCTCTGTTGTGT GCCTGCTGAATAACTTCTATCCCAGAGAGGCCAAAGTACAGTGGAAGGTG GATAACGCCCTCCAATCGGGTAACTCCCAGGAGAGTGTCACAGAGCAGGA CAGCAAGGACAGCACCTACAGCCTCAGCAGCACCCTGACGCTGAGCAAAG CAGACTACGAGAAACACAAAGTCTACGCCTGCGAAGTCACCCATCAGGGC CTGAGCTCGCCCGTCACAAAGAGCTTCAACAGGGGAGAGTGT |
| 231 | TPP-753 HC nucleotide | CAAGTGCAGCTGGTGCAGTCTGGCGCCGAAGTGAAGAAACCTGGCGCCAG CGTGAAGGTGTCCTGCAAGGCCAGCGGCTACAGCTTCACCGACTACATCA TCCTGTGGGTGCGCCAGGCCCCTGGCCAGAGACTGGAATGGATGGGCCAC ATCGACCCCTACTACGGCAGCAGCAACTACAACCTGAAGTTCAAGGGCAG AGTGACCATCACCCGGGACACCAGCGCCAGCACCGCCTACATGGAACTGA GCAGCCTGCGGAGCGAGGACACCGCCGTGTACTACTGCGCCAGAAGCAAG CGGGACTACTTCGACTACTGGGGCCAGGGCACCCTGGTGACAGTGTCCAG CGCCTCCACCAAGGGCCCATCGGTCTTCCCCCTGGCACCCTCCTCCAAGA GCACCTCTGGGGGCACAGCGGCCCTGGGCTGCCTGGTCAAGGACTACTTC CCCGAACCGGTGACGGTGTCGTGGAACTCAGGCGCCCTGACCAGCGGCGT GCACACCTTCCCGGCTGTCCTACAGTCCTCAGGACTCTACTCCCTCAGCA GCGTGGTGACCGTGCCCTCCAGCAGCTTGGGCACCCAGACCTACATCTGC AACGTGAATCACAAGCCCAGCAACACCAAGGTGGACAAGAGAGTTGAGCC CAAATCTTGT |
| 232 | TPP-753 LC nucleotide | GACATCCAAATGACCCAGAGCCCCAGCAGCCTGTACGCCAGCGTGGGCGA CAGAGTGACCATCACATGCAAGGCCAGCCAGGACATCAACAGCTACCTGA GCTGGTTCCAGCAGAAGCCCGGCAAGGCCCCTAAGAGCCTGATCTACCGG GCCAACAGACTGGTGGACGGCGTGCCAAGCAGATTCAGCGGCAGCGGCTC TGGCACCGACTTCACCCTGACCATCAGCTCCCTGCAGCCCGAGGACTTCG CCACCTACTACTGCCTGCAGTACGACGAGTTCCCCTACACCTTCGGCCAG GGCACCAAGCTGGAAATCAAGCGGACCGTGGCTGCACCATCTGTCTTCAT CTTCCCGCCATCTGATGAGCAGTTGAAATCTGGAACTGCCTCTGTTGTGT GCCTGCTGAATAACTTCTATCCCAGAGAGGCCAAAGTACAGTGGAAGGTG GATAACGCCCTCCAATCGGGTAACTCCCAGGAGAGTGTCACAGAGCAGGA CAGCAAGGACAGCACCTACAGCCTCAGCAGCACCCTGACGCTGAGCAAAG CAGACTACGAGAAACACAAAGTCTACGCCTGCGAAGTCACCCATCAGGGC CTGAGCTCGCCCGTCACAAAGAGCTTCAACAGGGGAGAGTGT |
| 233 | TPP-759 HC nucleotide | CAAGTGCAGCTGGTGCAGTCTGGCGCCGAAGTGAAGAAACCTGGCGCCAG CGTGAAGGTGTCCTGCAAGGCCAGCGGCTACAGCTTCACCGACTACATCA TCCTGTGGGTGCGCCAGGCCCCTGGCCAGAGACTGGAATGGATGGGCCAC ATCGACCCCTACTACGGCAGCAGCAACTACAACCTGAAGTTCAAGGGCAG AGTGACCATCACCCGGGACACCAGCGCCAGCACCGCCTACATGGAACTGA GCAGCCTGCGGAGCGAGGACACCGCCGTGTACTACTGCGCCAGAAGCAAG CGGGACTACTTCGACTACTGGGGCCAGGGCACCCTGGTGACAGTGTCCAG CGCCTCCACCAAGGGCCCATCGGTCTTCCCCCTGGCACCCTCCTCCAAGA GCACCTCTGGGGGCACAGCGGCCCTGGGCTGCCTGGTCAAGGACTACTTC CCCGAACCGGTGACGGTGTCGTGGAACTCAGGCGCCCTGACCAGCGGCGT GCACACCTTCCCGGCTGTCCTACAGTCCTCAGGACTCTACTCCCTCAGCA GCGTGGTGACCGTGCCCTCCAGCAGCTTGGGCACCCAGACCTACATCTGC |

TABLE 12-continued

| Summary Table of Sequences | | |
|---|---|---|
| SEQ ID | Description | Sequence |
| | | AACGTGAATCACAAGCCCAGCAACACCAAGGTGGACAAGAGAGTTGAGCC CAAATCTTGT |
| 234 | TPP-759 LC nucleotide | GACATCCAAATGACCCAGAGCCCCAGCAGCCTGTCTGCCAGCGTGGGCGA CAGAGTGACCATCACATGCAAGGCCAGCCAGGACATCAACAGCTACCTGA GCTGGTTCCAGCAGAAGCCCGGCAAGGCCCCTAAGAGCCTGATCTACCGG GCCAACAGACTGGTGGACGGCGTGCCAAGCAGATTCAGCGGCAGCGGCTC TGGCACCGACTTCACCCTGACCATCAGCTCCCTGCAGCCCGAGGACATGG CCACCTACTACTGCCTGCAGTACGACGAGTTCCCCTACACCTTCGGCCAG GGCACCAAGCTGGAAATCAAGCGGACCGTGGCTGCACCATCTGTCTTCAT CTTCCCGCCATCTGATGAGCAGTTGAAATCTGGAACTGCCTCTGTTGTGT GCCTGCTGAATAACTTCTATCCCAGAGAGGCCAAAGTACAGTGGAAGGTG GATAACGCCCTCCAATCGGGTAACTCCCAGGAGAGTGTCACAGAGCAGGA CAGCAAGGACAGCACCTACAGCCTCAGCAGCACCCTGACGCTGAGCAAAG CAGACTACGAGAAACACAAAGTCTACGCCTGCGAAGTCACCCATCAGGGC CTGAGCTCGCCCGTCACAAAGAGCTTCAACAGGGGAGAGTGT |
| 235 | Ec (1-46) | QVQLVQSGAEVKKPGASVKVSCKASGYSFTDYTILWVRQAPGQGLEWMGH IDPYYGSSNYNLKFKGRVTMTRDTSTSTVYMELSSLRSEDTAVYYCARSK RDYFDYWGQGTLVTVSS |
| 236 | IGHV1-69 | QVQLVQSGAEVKKPGSSVKVSCKASGYSFTDYIILWVRQAPGQGLEWMGH IDPYYGSSNYNLKFKGRVTITADESTSTAYMELSSLRSEDTAVYYCARSK RDYFDYWGQGTLVTVSS |
| 237 | IGHV1-18 | QVQLVQSGAEVKKPGASVKVSCKASGYSFTDYIILWVRQAPGQGLEWMGH IDPYYGSSNYNLKFKGRVTMTTDTSTSTAYMELRSLRSDDTAVYYCARSK RDYFDYWGQGTLVTVSS |
| 238 | IGHV1-2 | QVQLVQSGAEVKKPGASVKVSCKASGYSFTDYIILWVRQAPGQGLEWMGH IDPYYGSSNYNLKFKGRVTMTRDTSISTAYMELSRLRSDDTAVYYCARSK RDYFDYWGQGTLVTVSS |
| 239 | IGHV1-3 | QVQLVQSGAEVKKPGASVKVSCKASGYSFTDYIILWVRQAPGQRLEWMGH IDPYYGSSNYNLKFKGRVTITRDTSASTAYMELSSLRSEDTAVYYCARSK RDYFDYWGQGTLVTVSS |
| 240 | IGHV1-8 | QVQLVQSGAEVKKPGASVKVSCKASGYSFTDYIILWVRQATGQGLEWMGH IDPYYGSSNYNLKFKGRVTMTRNTSISTAYMELSSLRSEDTAVYYCARSK RDYFDYWGQGTLVTVSS |
| 241 | IGHV5-10-1 | EVQLVQSGAEVKKPGESLRISCKGSGYSFTDYIILWVRQMPGKGLEWMGH IDPYYGSSNYNLKFKGHVTISADKSISTAYLQWSSLKARTPPCITVRDSK RDYFDYWGQGTLVTVSS |
| 242 | IGHV1-45 | QMQLVQSGAEVKKTGSSVKVSCKASGYSFTDYIILWVRQAPGQALEWMGH IDPYYGSSNYNLKFKGRVTITRDRSMSTAYMELSSLRSEDTAMYYCARSK RDYFDYWGQGTLVTVSS |
| 243 | IGHV1-58 | QMQLVQSGPEVKKPGTSVKVSCKASGYSFTDYIILWVRQARGQRLEWIGH IDPYYGSSNYNLKFKGRVTITRDMSTSTAYMELSSLRSEDTAVYYCAASK RDYFDYWGQGTLVTVSS |
| 244 | IGHV7-4-1 | QVQLVQSGSELKKPGASVKVSCKASGYSFTDYTILWVRQAPGQGLEWMGH IDPYYGSSNYNLKFKGRFVFSLDTSVSTAYLQISSLKAEDTAVYYCARSK RDYFDYWGQGTLVTVSS |
| 245 | Ec (1-39) | DIQMTQSPSSLSASVGDRVTITCKASQDINSYLSWYQRKPGKAPKLLIYR ANRLVDGVPSRFSGSGSGTDFTLTISSLQPEDFATYYCLQYDEFPYTFGQ GTKVEIK |
| 246 | IGKV1-16 | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 247 | IGKV1D-33 | DIQMTQSPSSLSASVGDRVTITCKASQDINSYLSWYQQKPGKAPKLLIYR ANRLVDGVPSRFSGSGSGTDFTFTISSLQPEDIATYYCLQYDEFPYTFGQ GTKLEIK |
| 248 | IGKV1-12 | DIQMTQSPSSVSASVGDRVTITCKASQDINSYLSWYQQKPGKAPKLLIYR ANRLVDGVPSRFSGSGSGTDFTLTISSLQPEDFATYYCLQYDEFPYTFGQ GTKLEIK |

TABLE 12-continued

| Summary Table of Sequences | | |
|---|---|---|
| SEQ ID | Description | Sequence |
| 249 | TPP-102 VH | QVQLVQSGAEVKKPGASVKVSCKASGYSFTDYIILWVRQAPGQGLEWMGH IDPYYGSSNYNLKFKGRVTMTRDTSTSTVYMELSSLRSEDTAVYYCARSK RDYFDYWGQGTLVTVSS |
| 250 | TPP-102 VL | DIQMTQSPSSLSASVGDRVTITCKASQDINSYLSWYQRKPGKAPKLLIYR ANRLVDGVPSRFSGSGSGTDFTLTISSLQPEDFATYYCLQYDEFPYTFGQ GTKVEIK |
| 251 | TPP-103 VH | QVQLVQSGAEVKKPGASVKVSCKASGYSFTDYTILWVRQAPGQGLEWMGH IDPYYGSSNYNLKFKGRVTMTRDTSTSTVYMELSSLRSEDTAVYYCARSK RDYFDYWGQGTLVTVSS |
| 252 | TPP-103 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 253 | TPP-104 VH | QVQLVQSGAEVKKPGASVKVSCKASGYSFTDYIILWVRQAPGQGLEWMGH IDPYYGSSNYNLKFKGRVTMTRDTSTSTVYMELSSLRSEDTAVYYCARSK RDYFDYWGQGTLVTVSS |
| 254 | TPP-104 VL | DIQMTQSPSSLSASVGDRVTITCKASQDINSYLSWYQQKPGKAPKLLIYR ANRLVDGVPSRFSGSGSGTDFTFTISSLQPEDIATYYCLQYDEFPYTFGQ GTKLEIK |
| 255 | TPP-105 VH | QVQLVQSGAEVKKPGASVKVSCKASGYSFTDYTILWVRQAPGQGLEWMGH IDPYYGSSNYNLKFKGRVTMTRDTSTSTVYMELSSLRSEDTAVYYCARSK RDYFDYWGQGTLVTVSS |
| 256 | TPP-105 VL | DIQMTQSPSSVSASVGDRVTITCKASQDINSYLSWYQQKPGKAPKLLIYR ANRLVDGVPSRFSGSGSGTDFTLTISSLQPEDFATYYCLQYDEFPYTFGQ GTKLEIK |
| 257 | TPP-106 VH | QVQLVQSGAEVKKPGSSVKVSCKASGYSFTDYIILWVRQAPGQGLEWMGH IDPYYGSSNYNLKFKGRVTITADESTSTAYMELSSLRSEDTAVYYCARSK RDYFDYWGQGTLVTVSS |
| 258 | TPP-106 VL | DIQMTQSPSSLSASVGDRVTITCKASQDINSYLSWYQRKPGKAPKLLIYR ANRLVDGVPSRFSGSGSGTDFTLTISSLQPEDFATYYCLQYDEFPYTFGQ GTKVEIK |
| 259 | TPP-107 VH | QVQLVQSGAEVKKPGSSVKVSCKASGYSFTDYTILWVRQAPGQGLEWMGH IDPYYGSSNYNLKFKGRVTITADESTSTAYMELSSLRSEDTAVYYCARSK RDYFDYWGQGTLVTVSS |
| 260 | TPP-107 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 261 | TPP-108 VH | QVQLVQSGAEVKKPGSSVKVSCKASGYSFTDYIILWVRQAPGQGLEWMGH IDPYYGSSNYNLKFKGRVTITADESTSTAYMELSSLRSEDTAVYYCARSK RDYFDYWGQGTLVTVSS |
| 262 | TPP-108 VL | DIQMTQSPSSLSASVGDRVTITCKASQDINSYLSWYQQKPGKAPKLLIYR ANRLVDGVPSRFSGSGSGTDFTFTISSLQPEDIATYYCLQYDEFPYTFGQ GTKLEIK |
| 263 | TPP-109 VH | QVQLVQSGAEVKKPGSSVKVSCKASGYSFTDYIILWVRQAPGQGLEWMGH IDPYYGSSNYNLKFKGRVTITADESTSTAYMELSSLRSEDTAVYYCARSK RDYFDYWGQGTLVTVSS |
| 264 | TPP-109 VL | DIQMTQSPSSVSASVGDRVTITCKASQDINSYLSWYQQKPGKAPKLLIYR ANRLVDGVPSRFSGSGSGTDFTLTISSLQPEDFATYYCLQYDEFPYTFGQ GTKLEIK |
| 265 | TPP-110 VH | QVQLVQSGAEVKKPGASVKVSCKASGYSFTDYIILWVRQAPGQGLEWMGH IDPYYGSSNYNLKFKGRVTMTTDTSTSTAYMELRSLRSDDTAVYYCARSK RDYFDYWGQGTLVTVSS |
| 266 | TPP-110 VL | DIQMTQSPSSLSASVGDRVTITCKASQDINSYLSWYQRKPGKAPKLLIYR ANRLVDGVPSRFSGSGSGTDFTLTISSLQPEDFATYYCLQYDEFPYTFGQ GTKVEIK |

TABLE 12-continued

Summary Table of Sequences

| SEQ ID | Description | Sequence |
|---|---|---|
| 267 | TPP-111 VH | QVQLVQSGAEVKKPGASVKVSCKASGYSFTDYTILWVRQAPGQGLEWMGH IDPYYGSSNYNLKFKGRVTMTTDTSTSTAYMELRSLRSDDTAVYYCARSK RDYFDYWGQGTLVTVSS |
| 268 | TPP-111 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 269 | TPP-112 VH | QVQLVQSGAEVKKPGASVKVSCKASGYSFTDYIILWVRQAPGQGLEWMGH IDPYYGSSNYNLKFKGRVTMTTDTSTSTAYMELRSLRSDDTAVYYCARSK RDYFDYWGQGTLVTVSS |
| 270 | TPP-112 VL | DIQMTQSPSSLSASVGDRVTITCKASQDINSYLSWYQQKPGKAPKLLIYR ANRLVDGVPSRFSGSGSGTDFTFTISSLQPEDIATYYCLQYDEFPYTFGQ GTKLEIK |
| 271 | TPP-113 VH | QVQLVQSGAEVKKPGASVKVSCKASGYSFTDYIILWVRQAPGQGLEWMGH IDPYYGSSNYNLKFKGRVTMTTDTSTSTAYMELRSLRSDDTAVYYCARSK RDYFDYWGQGTLVTVSS |
| 272 | TPP-113 VL | DIQMTQSPSSVSASVGDRVTITCKASQDINSYLSWYQQKPGKAPKLLIYR ANRLVDGVPSRFSGSGSGTDFTLTISSLQPEDFATYYCLQYDEFPYTFGQ GTKLEIK |
| 273 | TPP-114 VH | QVQLVQSGAEVKKPGASVKVSCKASGYSFTDYIILWVRQAPGQGLEWMGH IDPYYGSSNYNLKFKGRVTMTRDTSISTAYMELSRLRSDDTAVYYCARSK RDYFDYWGQGTLVTVSS |
| 274 | TPP-114 VL | DIQMTQSPSSLSASVGDRVTITCKASQDINSYLSWYQRKPGKAPKLLIYR ANRLVDGVPSRFSGSGSGTDFTLTISSLQPEDFATYYCLQYDEFPYTFGQ GTKVEIK |
| 275 | TPP-115 VH | QVQLVQSGAEVKKPGASVKVSCKASGYSFTDYIILWVRQAPGQGLEWMGH IDPYYGSSNYNLKFKGRVTMTRDTSISTAYMELSRLRSDDTAVYYCARSK RDYFDYWGQGTLVTVSS |
| 276 | TPP-115 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 277 | TPP-116 VH | QVQLVQSGAEVKKPGASVKVSCKASGYSFTDYTILWVRQAPGQGLEWMGH IDPYYGSSNYNLKFKGRVTMTRDTSISTAYMELSRLRSDDTAVYYCARSK RDYFDYWGQGTLVTVSS |
| 278 | TPP-116 VL | DIQMTQSPSSLSASVGDRVTITCKASQDINSYLSWYQQKPGKAPKLLIYR ANRLVDGVPSRFSGSGSGTDFTFTISSLQPEDIATYYCLQYDEFPYTFGQ GTKLEIK |
| 279 | TPP-117 VH | QVQLVQSGAEVKKPGASVKVSCKASGYSFTDYIILWVRQAPGQGLEWMGH IDPYYGSSNYNLKFKGRVTMTRDTSISTAYMELSRLRSDDTAVYYCARSK RDYFDYWGQGTLVTVSS |
| 280 | TPP-117 VL | DIQMTQSPSSVSASVGDRVTITCKASQDINSYLSWYQQKPGKAPKLLIYR ANRLVDGVPSRFSGSGSGTDFTLTISSLQPEDFATYYCLQYDEFPYTFGQ GTKLEIK |
| 281 | TPP-118 VH | QVQLVQSGAEVKKPGASVKVSCKASGYSFTDYIILWVRQAPGQRLEWMGH IDPYYGSSNYNLKFKGRVTITRDTSASTAYMELSSLRSEDTAVYYCARSK RDYFDYWGQGTLVTVSS |
| 282 | TPP-118 VL | DIQMTQSPSSLSASVGDRVTITCKASQDINSYLSWYQRKPGKAPKLLIYR ANRLVDGVPSRFSGSGSGTDFTLTISSLQPEDFATYYCLQYDEFPYTFGQ GTKVEIK |
| | TPP-119 VH | SEQ ID NO: 20 |
| | TPP-119 VL | SEQ ID NO: 21 |
| 283 | TPP-120 VH | QVQLVQSGAEVKKPGASVKVSCKASGYSFTDYIILWVRQAPGQRLEWMGH IDPYYGSSNYNLKFKGRVTITRDTSASTAYMELSSLRSEDTAVYYCARSK RDYFDYWGQGTLVTVSS |

TABLE 12-continued

Summary Table of Sequences

| SEQ ID | Description | Sequence |
|---|---|---|
| 284 | TPP-120 VL | DIQMTQSPSSLSASVGDRVTITCKASQDINSYLSWYQQKPGKAPKLLIYR ANRLVDGVPSRFSGSGSGTDFTFTISSLQPEDIATYYCLQYDEFPYTFGQ GTKLEIK |
| 285 | TPP-121 VH | QVQLVQSGAEVKKPGASVKVSCKASGYSFTDYIILWVRQAPGQRLEWMGH IDPYYGSSNYNLKFKGRVTITRDTSASTAYMELSSLRSEDTAVYYCARSK RDYFDYWGQGTLVTVSS |
| 286 | TPP-121 VL | DIQMTQSPSSVSASVGDRVTITCKASQDINSYLSWYQQKPGKAPKLLIYR ANRLVDGVPSRFSGSGSGTDFTLTISSLQPEDFATYYCLQYDEFPYTFGQ GTKLEIK |
| 287 | TPP-122 VH | QVQLVQSGAEVKKPGASVKVSCKASGYSFTDYIILWVRQATGQGLEWMGH IDPYYGSSNYNLKFKGRVTMTRNTSISTAYMELSSLRSEDTAVYYCARSK RDYFDYWGQGTLVTVSS |
| 288 | TPP-122 VL | DIQMTQSPSSLSASVGDRVTITCKASQDINSYLSWYQRKPGKAPKLLIYR ANRLVDGVPSRFSGSGSGTDFTLTISSLQPEDFATYYCLQYDEFPYTFGQ GTKVEIK |
| 289 | TPP-123 VH | QVQLVQSGAEVKKPGASVKVSCKASGYSFTDYIILWVRQATGQGLEWMGH IDPYYGSSNYNLKFKGRVTMTRNTSISTAYMELSSLRSEDTAVYYCARSK RDYFDYWGQGTLVTVSS |
| 290 | TPP-123 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 291 | TPP-124 VH | QVQLVQSGAEVKKPGASVKVSCKASGYSFTDYTILWVRQATGQGLEWMGH IDPYYGSSNYNLKFKGRVTMTRNTSISTAYMELSSLRSEDTAVYYCARSK RDYFDYWGQGTLVTVSS |
| 292 | TPP-124 VL | DIQMTQSPSSLSASVGDRVTITCKASQDINSYLSWYQQKPGKAPKLLIYR ANRLVDGVPSRFSGSGSGTDFTFTISSLQPEDIATYYCLQYDEFPYTFGQ GTKLEIK |
| 293 | TPP-125 VH | QVQLVQSGAEVKKPGASVKVSCKASGYSFTDYIILWVRQATGQGLEWMGH IDPYYGSSNYNLKFKGRVTMTRNTSISTAYMELSSLRSEDTAVYYCARSK RDYFDYWGQGTLVTVSS |
| 294 | TPP-125 VL | DIQMTQSPSSVSASVGDRVTITCKASQDINSYLSWYQQKPGKAPKLLIYR ANRLVDGVPSRFSGSGSGTDFTLTISSLQPEDFATYYCLQYDEFPYTFGQ GTKLEIK |
| 295 | TPP-126 VH | EVQLVQSGAEVKKPGESLRISCKGSGYSFTDYIILWVRQMPGKGLEWMGH IDPYYGSSNYNLKFKGHVTISADKSISTAYLQWSSLKARTPPCITVRDSK RDYFDYWGQGTLVTVSS |
| 296 | TPP-126 VL | DIQMTQSPSSLSASVGDRVTITCKASQDINSYLSWYQRKPGKAPKLLIYR ANRLVDGVPSRFSGSGSGTDFTLTISSLQPEDFATYYCLQYDEFPYTFGQ GTKVEIK |
| 297 | TPP-127 VH | EVQLVQSGAEVKKPGESLRISCKGSGYSFTDYIILWVRQMPGKGLEWMGH IDPYYGSSNYNLKFKGHVTISADKSISTAYLQWSSLKARTPPCITVRDSK RDYFDYWGQGTLVTVSS |
| 298 | TPP-127 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 299 | TPP-128 VH | EVQLVQSGAEVKKPGESLRISCKGSGYSFTDYIILWVRQMPGKGLEWMGH IDPYYGSSNYNLKFKGHVTISADKSISTAYLQWSSLKARTPPCITVRDSK RDYFDYWGQGTLVTVSS |
| 300 | TPP-128 VL | DIQMTQSPSSLSASVGDRVTITCKASQDINSYLSWYQQKPGKAPKLLIYR ANRLVDGVPSRFSGSGSGTDFTFTISSLQPEDIATYYCLQYDEFPYTFGQ GTKLEIK |
| 301 | TPP-129 VH | EVQLVQSGAEVKKPGESLRISCKGSGYSFTDYIILWVRQMPGKGLEWMGH IDPYYGSSNYNLKFKGHVTISADKSISTAYLQWSSLKARTPPCITVRDSK RDYFDYWGQGTLVTVSS |

TABLE 12-continued

| Summary Table of Sequences | | |
|---|---|---|
| SEQ ID | Description | Sequence |
| 302 | TPP-129 VL | DIQMTQSPSSVSASVGDRVTITCKASQDINSYLSWYQQKPGKAPKLLIYR ANRLVDGVPSRFSGSGSGTDFTLTISSLQPEDFATYYCLQYDEFPYTFGQ GTKLEIK |
| 303 | TPP-130 VH | QMQLVQSGAEVKKTGSSVKVSCKASGYSFTDYIILWVRQAPGQALEWMGH IDPYYGSSNYNLKFKGRVTITRDRSMSTAYMELSSLRSEDTAMYYCARSK RDYFDYWGQGTLVTVSS |
| 304 | TPP-130 VL | DIQMTQSPSSLSASVGDRVTITCKASQDINSYLSWYQRKPGKAPKLLIYR ANRLVDGVPSRFSGSGSGTDFTLTISSLQPEDFATYYCLQYDEFPYTFGQ GTKVEIK |
| 305 | TPP-131 VH | QMQLVQSGAEVKKTGSSVKVSCKASGYSFTDYTILWVRQAPGQALEWMGH IDPYYGSSNYNLKFKGRVTITRDRSMSTAYMELSSLRSEDTAMYYCARSK RDYFDYWGQGTLVTVSS |
| 306 | TPP-131 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 307 | TPP-132 VH | QMQLVQSGAEVKKTGSSVKVSCKASGYSFTDYIILWVRQAPGQALEWMGH IDPYYGSSNYNLKFKGRVTITRDRSMSTAYMELSSLRSEDTAMYYCARSK RDYFDYWGQGTLVTVSS |
| 308 | TPP-132 VL | DIQMTQSPSSLSASVGDRVTITCKASQDINSYLSWYQQKPGKAPKLLIYR ANRLVDGVPSRFSGSGSGTDFTFTISSLQPEDIATYYCLQYDEFPYTFGQ GTKLEIK |
| 309 | TPP-133 VH | QMQLVQSGAEVKKTGSSVKVSCKASGYSFTDYIILWVRQAPGQALEWMGH IDPYYGSSNYNLKFKGRVTITRDRSMSTAYMELSSLRSEDTAMYYCARSK RDYFDYWGQGTLVTVSS |
| 310 | TPP-133 VL | DIQMTQSPSSVSASVGDRVTITCKASQDINSYLSWYQQKPGKAPKLLIYR ANRLVDGVPSRFSGSGSGTDFTLTISSLQPEDFATYYCLQYDEFPYTFGQ GTKLEIK |
| 311 | TPP-134 VH | QMQLVQSGPEVKKPGTSVKVSCKASGYSFTDYIILWVRQARGQRLEWIGH IDPYYGSSNYNLKFKGRVTITRDMSTSTAYMELSSLRSEDTAVYYCAASK RDYFDYWGQGTLVTVSS |
| 312 | TPP-134 VL | DIQMTQSPSSLSASVGDRVTITCKASQDINSYLSWYQRKPGKAPKLLIYR ANRLVDGVPSRFSGSGSGTDFTLTISSLQPEDFATYYCLQYDEFPYTFGQ GTKVEIK |
| 313 | TPP-135 VH | QMQLVQSGPEVKKPGTSVKVSCKASGYSFTDYIILWVRQARGQRLEWIGH IDPYYGSSNYNLKFKGRVTITRDMSTSTAYMELSSLRSEDTAVYYCAASK RDYFDYWGQGTLVTVSS |
| 314 | TPP-135 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 315 | TPP-136 VH | QMQLVQSGPEVKKPGTSVKVSCKASGYSFTDYIILWVRQARGQRLEWIGH IDPYYGSSNYNLKFKGRVTITRDMSTSTAYMELSSLRSEDTAVYYCAASK RDYFDYWGQGTLVTVSS |
| 316 | TPP-136 VL | DIQMTQSPSSLSASVGDRVTITCKASQDINSYLSWYQQKPGKAPKLLIYR ANRLVDGVPSRFSGSGSGTDFTFTISSLQPEDIATYYCLQYDEFPYTFGQ GTKLEIK |
| 317 | TPP-137 VH | QMQLVQSGPEVKKPGTSVKVSCKASGYSFTDYIILWVRQARGQRLEWIGH IDPYYGSSNYNLKFKGRVTITRDMSTSTAYMELSSLRSEDTAVYYCAASK RDYFDYWGQGTLVTVSS |
| 318 | TPP-137 VL | DIQMTQSPSSVSASVGDRVTITCKASQDINSYLSWYQQKPGKAPKLLIYR ANRLVDGVPSRFSGSGSGTDFTLTISSLQPEDFATYYCLQYDEFPYTFGQ GTKLEIK |
| 319 | TPP-138 VH | QVQLVQSGSELKKPGASVKVSCKASGYSFTDYIILWVRQAPGQGLEWMGH IDPYYGSSNYNLKFKGRFVFSLDTSVSTAYLQISSLKAEDTAVYYCARSK RDYFDYWGQGTLVTVSS |

TABLE 12-continued

| Summary Table of Sequences | | |
|---|---|---|
| SEQ ID | Description | Sequence |
| 320 | TPP-138 VL | DIQMTQSPSSLSASVGDRVTITCKASQDINSYLSWYQRKPGKAPKLLIYR ANRLVDGVPSRFSGSGSGTDFTLTISSLQPEDFATYYCLQYDEFPYTFGQ GTKVEIK |
| 321 | TPP-139 VH | QVQLVQSGSELKKPGASVKVSCKASGYSFTDYIILWVRQAPGQGLEWMGH IDPYYGSSNYNLKFKGRFVFSLDTSVSTAYLQISSLKAEDTAVYYCARSK RDYFDYWGQGTLVTVSS |
| 322 | TPP-139 VL | DIQMTQSPSSLSASVGDRVTITCKASQDINSYLSWFQQKPGKAPKSLIYR ANRLVDGVPSRFSGSGSGTDFTLTISSLQPEDFATYYCLQYDEFPYTFGQ GTKLEIK |
| 323 | TPP-140 VH | QVQLVQSGSELKKPGASVKVSCKASGYSFTDYIILWVRQAPGQGLEWMGH IDPYYGSSNYNLKFKGRFVFSLDTSVSTAYLQISSLKAEDTAVYYCARSK RDYFDYWGQGTLVTVSS |
| 324 | TPP-140 VL | DIQMTQSPSSLSASVGDRVTITCKASQDINSYLSWYQQKPGKAPKLLIYR ANRLVDGVPSRFSGSGSGTDFTFTISSLQPEDIATYYCLQYDEFPYTFGQ GTKLEIK |
| 325 | TPP-141 VH | QVQLVQSGSELKKPGASVKVSCKASGYSFTDYIILWVRQAPGQGLEWMGH IDPYYGSSNYNLKFKGRFVFSLDTSVSTAYLQISSLKAEDTAVYYCARSK RDYFDYWGQGTLVTVSS |
| 326 | TPP-141 VL | DIQMTQSPSSVSASVGDRVTITCKASQDINSYLSWYQQKPGKAPKLLIYR ANRLVDGVPSRFSGSGSGTDFTLTISSLQPEDFATYYCLQYDEFPYTFGQ GTKLEIK |

EQUIVALENTS

Those skilled in the art will recognize, or be able to ascertain using no more than routine experimentation, many equivalents of the specific embodiments disclosed herein. Such equivalents are intended to be encompassed by the following claims.

We claim:

1. An isolated humanized antibody which binds to human CD200 and comprises heavy and light chain variable regions, wherein the heavy chain variable region comprises the amino acid sequence set forth in SEQ ID NO: 20, and the light chain variable region comprises the amino acid sequence set forth in SEQ ID NO: 21, wherein (a) alanine at position 97 of the heavy chain variable region is substituted with glycine, (b) alanine at position 84 of the light chain variable region is substituted with glycine, or (c) alanine at position 97 of the heavy chain variable region is substituted with glycine, and alanine at position 84 of the light chain variable region is substituted with glycine and wherein the numbering is according to the amino acid sequence in SEQ ID NO: 20 for the heavy chain variable region and SEQ ID NO: 21 for the light chain variable region.

2. The isolated antibody of claim 1, wherein the antibody comprises a modified Fc constant region which exhibits decreased effector function relative to the effector function of the corresponding unmodified Fc constant region.

3. The isolated antibody of claim 1, wherein the antibody is selected from the group consisting of a Fab fragment, a F(ab')2 fragment, a Fab' fragment, an scFv fragment, a minibody, a diabody, or a triabody.

4. The isolated antibody of claim 1, further comprising a detectable or therapeutic moiety.

5. A bispecific antibody comprising the antibody of claim 1, linked to a molecule having a second binding specificity.

6. A composition comprising the antibody of claim 1, and a pharmaceutically acceptable carrier.

7. A kit comprising the antibody of claim 1, and instructions for use.

8. An isolated antibody which binds to human CD200 and comprises heavy and light chain variable region sequences selected from the group consisting of:

a) SEQ ID NOs: 107 and 108, respectively;
b) SEQ ID NOs: 158 and 159, respectively;
c) SEQ ID NOs: 149 and 150, respectively;
d) SEQ ID NOs: 26 and 27, respectively;
e) SEQ ID NOs: 29 and 30, respectively;
f) SEQ ID NOs: 32 and 33, respectively;
g) SEQ ID NOs: 35 and 36, respectively;
h) SEQ ID NOs: 38 and 39, respectively;
i) SEQ ID NOs: 41 and 42, respectively;
j) SEQ ID NOs: 44 and 45, respectively;
k) SEQ ID NOs: 47 and 48, respectively;
l) SEQ ID NOs: 50 and 51, respectively;
m) SEQ ID NOs: 53 and 54, respectively;
n) SEQ ID NOs: 56 and 57, respectively;
o) SEQ ID NOs: 59 and 60, respectively;
p) SEQ ID NOs: 62 and 63, respectively;
q) SEQ ID NOs: 65 and 66, respectively;
r) SEQ ID NOs: 68 and 69, respectively;
s) SEQ ID NOs: 71 and 72, respectively;
t) SEQ ID NOs: 74 and 75, respectively;
u) SEQ ID NOs: 77 and 78, respectively;
v) SEQ ID NOs: 80 and 81, respectively;
w) SEQ ID NOs: 83 and 84, respectively;
x) SEQ ID NOs: 86 and 87, respectively;
y) SEQ ID NOs: 89 and 90, respectively;
z) SEQ ID NOs: 92 and 93, respectively;
aa) SEQ ID NOs: 95 and 96, respectively;
bb) SEQ ID NOs: 98 and 99, respectively;
cc) SEQ ID NOs: 101 and 102, respectively;
dd) SEQ ID NOs: 104 and 105, respectively;
ee) SEQ ID NOs: 110 and 111, respectively;
ff) SEQ ID NOs: 113 and 114, respectively;
gg) SEQ ID NOs: 116 and 117, respectively;
hh) SEQ ID NOs: 119 and 120, respectively;
ii) SEQ ID NOs: 122 and 123, respectively;
jj) SEQ ID NOs: 125 and 126, respectively;
kk) SEQ ID NOs: 128 and 129, respectively;
ll) SEQ ID NOs: 131 and 132, respectively;
mm) SEQ ID NOs: 134 and 135, respectively;
nn) SEQ ID NOs: 137 and 138, respectively;
oo) SEQ ID NOs: 140 and 141, respectively;
pp) SEQ ID NOs: 143 and 144, respectively;
qq) SEQ ID NOs: 146 and 147, respectively;
rr) SEQ ID NOs: 152 and 153, respectively;
ss) SEQ ID NOs: 155 and 156, respectively;
tt) SEQ ID NOs: 161 and 162, respectively;
uu) SEQ ID NOs: 164 and 165, respectively;
vv) SEQ ID NOs: 167 and 168, respectively;
ww) SEQ ID NOs: 170 and 171, respectively;
xx) SEQ ID NOs: 173 and 174, respectively;
yy) SEQ ID NOs: 176 and 177, respectively; and
zz) SEQ ID NOs: 179 and 180, respectively.

9. An isolated antibody which binds to human CD200 and comprises heavy and light chain sequences selected from the group consisting of:

a. SEQ ID NOs: 185 and 186, respectively,
b. SEQ ID NOs: 183 and 184, respectively, and
c. SEQ ID NOs: 181 and 182, respectively.

10. A nucleic acid sequence encoding the heavy and/or light chain variable region, or antigen-binding portion thereof, of the antibody of claim 1.

11. The nucleic acid of claim 10, which comprises a nucleotide sequence selected from the group consisting of SEQ ID NOs: 187-234.

12. One or more expression vectors comprising the nucleic acid of claim 10.

13. A host cell comprising the nucleic acid of claim 10, or an expression vector comprising the nucleic acid.

14. A method of detecting CD200 in a sample comprising contacting the sample with the antibody of claim 1, under conditions that allow for formation of a complex between the antibody, or antigen binding portion thereof, and CD200, and detecting the formation of the complex.

15. A method of treating cancer comprising administering to a subject in need thereof a therapeutically effective amount of the antibody of claim 1.

16. A method of treating an autoimmune disease comprising administering to a subject in need thereof a therapeutically effective amount of the antibody of claim 1.

17. A method of inhibiting an immune response in a subject in need thereof who has received or will receive a cell, tissue, or organ transplant, wherein said method comprises administering to the subject an effective amount of the antibody of claim 1.

18. A method for prolonging the survival of an allograft, the method comprising administering to a recipient mammal in need thereof the antibody of claim 1 in an amount and with a frequency effective to prolong the survival of the allograft in the recipient mammal, wherein the recipient mammal is presensitized to the allograft.

19. A method for transplanting an allograft organ into a recipient mammal in need thereof, the method comprising:

(a) prior to transplantation of an allograft organ into a recipient mammal, administering the antibody of claim 1 as a single agent to the recipient mammal, wherein the recipient mammal is presensitized to the allograft organ;
(b) transplanting the allograft organ into the recipient mammal; and
(c) administering the antibody as a single agent to the recipient mammal following transplantation of the allograft organ.

* * * * *

UNITED STATES PATENT AND TRADEMARK OFFICE

CERTIFICATE OF CORRECTION

PATENT NO. : 11,802,154 B2
APPLICATION NO. : 16/954562
DATED : October 31, 2023
INVENTOR(S) : Mack et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 455 days.

Signed and Sealed this
Twelfth Day of November, 2024

Katherine Kelly Vidal

Katherine Kelly Vidal
*Director of the United States Patent and Trademark Office*

SEQUENCE LISTING

<160> NUMBER OF SEQ ID NOS: 326

<210> SEQ ID NO 1
<211> LENGTH: 269
<212> TYPE: PRT
<213> ORGANISM: Homo sapiens
<220> FEATURE:
<221> NAME/KEY: misc_feature
<223> OTHER INFORMATION: Precursor human CD200 isoform A

<400> SEQUENCE: 1

Met Glu Arg Leu Val Ile Arg Met Pro Phe Ser His Leu Ser Thr Tyr
1 5 10 15

Ser Leu Val Trp Val Met Ala Ala Val Val Leu Cys Thr Ala Gln Val
20 25 30

Gln Val Val Thr Gln Asp Glu Arg Glu Gln Leu Tyr Thr Pro Ala Ser
35 40 45

Leu Lys Cys Ser Leu Gln Asn Ala Gln Glu Ala Leu Ile Val Thr Trp
50 55 60

Gln Lys Lys Lys Ala Val Ser Pro Glu Asn Met Val Thr Phe Ser Glu
65 70 75 80

Asn His Gly Val Val Ile Gln Pro Ala Tyr Lys Asp Lys Ile Asn Ile
85 90 95

Thr Gln Leu Gly Leu Gln Asn Ser Thr Ile Thr Phe Trp Asn Ile Thr
100 105 110

Leu Glu Asp Glu Gly Cys Tyr Met Cys Leu Phe Asn Thr Phe Gly Phe
115 120 125

Gly Lys Ile Ser Gly Thr Ala Cys Leu Thr Val Tyr Val Gln Pro Ile
130 135 140

Val Ser Leu His Tyr Lys Phe Ser Glu Asp His Leu Asn Ile Thr Cys
145 150 155 160

Ser Ala Thr Ala Arg Pro Ala Pro Met Val Phe Trp Lys Val Pro Arg
165 170 175

Ser Gly Ile Glu Asn Ser Thr Val Thr Leu Ser His Pro Asn Gly Thr
180 185 190

Thr Ser Val Thr Ser Ile Leu His Ile Lys Asp Pro Lys Asn Gln Val
195 200 205

Gly Lys Glu Val Ile Cys Gln Val Leu His Leu Gly Thr Val Thr Asp
210 215 220

Phe Lys Gln Thr Val Asn Lys Gly Tyr Trp Phe Ser Val Pro Leu Leu
225 230 235 240

Leu Ser Ile Val Ser Leu Val Ile Leu Leu Val Leu Ile Ser Ile Leu
245 250 255

Leu Tyr Trp Lys Arg His Arg Asn Gln Asp Arg Glu Pro
260 265

<210> SEQ ID NO 2
<211> LENGTH: 294
<212> TYPE: PRT
<213> ORGANISM: Homo sapiens
<220> FEATURE:
<221> NAME/KEY: misc_feature
<223> OTHER INFORMATION: Human CD200 isoform B

<400> SEQUENCE: 2

Met Glu Arg Leu Thr Leu Thr Arg Thr Ile Gly Gly Pro Leu Leu Thr
1 5 10 15

Ala Thr Leu Leu Gly Lys Thr Thr Ile Asn Asp Tyr Gln Val Ile Arg
20 25 30

Met Pro Phe Ser His Leu Ser Thr Tyr Ser Leu Val Trp Val Met Ala
35 40 45

Ala Val Val Leu Cys Thr Ala Gln Val Gln Val Val Thr Gln Asp Glu
50 55 60

Arg Glu Gln Leu Tyr Thr Pro Ala Ser Leu Lys Cys Ser Leu Gln Asn
65 70 75 80

Ala Gln Glu Ala Leu Ile Val Thr Trp Gln Lys Lys Lys Ala Val Ser
85 90 95

Pro Glu Asn Met Val Thr Phe Ser Glu Asn His Gly Val Val Ile Gln
100 105 110

Pro Ala Tyr Lys Asp Lys Ile Asn Ile Thr Gln Leu Gly Leu Gln Asn
115 120 125

Ser Thr Ile Thr Phe Trp Asn Ile Thr Leu Glu Asp Glu Gly Cys Tyr
130 135 140

Met Cys Leu Phe Asn Thr Phe Gly Phe Gly Lys Ile Ser Gly Thr Ala
145 150 155 160

Cys Leu Thr Val Tyr Val Gln Pro Ile Val Ser Leu His Tyr Lys Phe
165 170 175

Ser Glu Asp His Leu Asn Ile Thr Cys Ser Ala Thr Ala Arg Pro Ala
180 185 190

```
Pro Met Val Phe Trp Lys Val Pro Arg Ser Gly Ile Glu Asn Ser Thr
        195                 200                 205

Val Thr Leu Ser His Pro Asn Gly Thr Thr Ser Val Thr Ser Ile Leu
    210                 215                 220

His Ile Lys Asp Pro Lys Asn Gln Val Gly Lys Glu Val Ile Cys Gln
225                 230                 235                 240

Val Leu His Leu Gly Thr Val Thr Asp Phe Lys Gln Thr Val Asn Lys
                245                 250                 255

Gly Tyr Trp Phe Ser Val Pro Leu Leu Leu Ser Ile Val Ser Leu Val
            260                 265                 270

Ile Leu Leu Val Leu Ile Ser Ile Leu Leu Tyr Trp Lys Arg His Arg
        275                 280                 285

Asn Gln Asp Arg Glu Pro
    290


<210> SEQ ID NO 3
<211> LENGTH: 274
<212> TYPE: PRT
<213> ORGANISM: Homo sapiens
<220> FEATURE:
<221> NAME/KEY: misc_feature
<223> OTHER INFORMATION: Full-length, mature human CD200

<400> SEQUENCE: 3

Val Ile Arg Met Pro Phe Ser His Leu Ser Thr Tyr Ser Leu Val Trp
1               5                   10                  15

Val Met Ala Ala Val Val Leu Cys Thr Ala Gln Val Gln Val Val Thr
            20                  25                  30

Gln Asp Glu Arg Glu Gln Leu Tyr Thr Thr Ala Ser Leu Lys Cys Ser
        35                  40                  45

Leu Gln Asn Ala Gln Glu Ala Leu Ile Val Thr Trp Gln Lys Lys Lys
    50                  55                  60

Ala Val Ser Pro Glu Asn Met Val Thr Phe Ser Glu Asn His Gly Val
65                  70                  75                  80

Val Ile Gln Pro Ala Tyr Lys Asp Lys Ile Asn Ile Thr Gln Leu Gly
                85                  90                  95

Leu Gln Asn Ser Thr Ile Thr Phe Trp Asn Ile Thr Leu Glu Asp Glu
            100                 105                 110

Gly Cys Tyr Met Cys Leu Phe Asn Thr Phe Gly Phe Gly Lys Ile Ser
        115                 120                 125

Gly Thr Ala Cys Leu Thr Val Tyr Val Gln Pro Ile Val Ser Leu His
    130                 135                 140

Tyr Lys Phe Ser Glu Asp His Leu Asn Ile Thr Cys Ser Ala Thr Ala
145                 150                 155                 160

Arg Pro Ala Pro Met Val Phe Trp Lys Val Pro Arg Ser Gly Ile Glu
                165                 170                 175

Asn Ser Thr Val Thr Leu Ser His Pro Asn Gly Thr Thr Ser Val Thr
            180                 185                 190

Ser Ile Leu His Ile Lys Asp Pro Lys Asn Gln Val Gly Lys Glu Val
        195                 200                 205

Ile Cys Gln Val Leu His Leu Gly Thr Val Thr Asp Phe Lys Gln Thr
    210                 215                 220

Val Asn Lys Gly Tyr Trp Phe Ser Val Pro Leu Leu Leu Ser Ile Val
225                 230                 235                 240

Ser Leu Val Ile Leu Leu Val Leu Ile Ser Ile Leu Leu Tyr Trp Lys
```

```
                245                 250                 255

Arg His Arg Asn Gln Asp Arg Gly Glu Leu Ser Gln Gly Val Gln Lys
            260                 265                 270

Met Thr


<210> SEQ ID NO 4
<211> LENGTH: 326
<212> TYPE: PRT
<213> ORGANISM: Artificial Sequence
<220> FEATURE:
<223> OTHER INFORMATION: Synthetic: IgG2/G4 hybrid constant region

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325
```

<210> SEQ ID NO 5
<211> LENGTH: 5
<212> TYPE: PRT
<213> ORGANISM: Artificial Sequence
<220> FEATURE:
<223> OTHER INFORMATION: Synthetic: Samalizumab/C2aB7 heavy chain CDR1

<400> SEQUENCE: 5

Asp Tyr Ile Ile Leu
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic: Samalizumab/C2aB7 heavy chain CDR2

<400> SEQUENCE: 6

His Ile Asp Pro Tyr Tyr Gly Ser Ser Asn Tyr Asn Leu Lys Phe Lys
1               5                   10                  15

Gly

<210> SEQ ID NO 7
<211> LENGTH: 8
<212> TYPE: PRT
<213> ORGANISM: Artificial Sequence
<220> FEATURE:
<223> OTHER INFORMATION: Synthetic: Samalizumab/C2aB7 heavy chain CDR3

<400> SEQUENCE: 7

Ser Lys Arg Asp Tyr Phe Asp Tyr
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic: Samalizumab/C2aB7 light chain CDR1

<400> SEQUENCE: 8

Lys Ala Ser Gln Asp Ile Asn Ser Tyr Leu Ser
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic: Samalizumab/C2aB7 light chain CDR2

<400> SEQUENCE: 9

Arg Ala Asn Arg Leu Val Asp
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic: Samalizumab/C2aB7 light chain CDR3

<400> SEQUENCE: 10

Leu Gln Tyr Asp Glu Phe Pro Tyr Thr 1 5

<210> SEQ ID NO 11
<211> LENGTH: 117
<212> TYPE: PRT
<213> ORGANISM: Artificial Sequence
<220> FEATURE:
<223> OTHER INFORMATION: Synthetic: Samalizumab VH

<400> SEQUENCE: 11

Gln Val Gln Leu Gln Gln Ser Gly Ser Glu Leu Lys Lys Pro Gly Ala
1 5 10 15

Ser Val Lys Ile Ser Cys Lys Ala Ser Gly Tyr Ser Phe Thr Asp Tyr
20 25 30

Ile Ile Leu Trp Val Arg Gln Asn Pro Gly Lys Gly Leu Glu Trp Ile
35 40 45

Gly His Ile Asp Pro Tyr Tyr Gly Ser Ser Asn Tyr Asn Leu Lys Phe
50 55 60

Lys Gly Arg Val Thr Ile Thr Ala Asp Gln Ser Thr Thr Thr Ala Tyr
65 70 75 80

Met Glu Leu Ser Ser Leu Arg Ser Glu Asp Thr Ala Val Tyr Tyr Cys
85 90 95

Gly Arg Ser Lys Arg Asp Tyr Phe Asp Tyr Trp Gly Gln Gly Thr Thr
100 105 110

Leu Thr Val Ser Ser
115

<210> SEQ ID NO 12
<211> LENGTH: 107
<212> TYPE: PRT
<213> ORGANISM: Artificial Sequence
<220> FEATURE:
<223> OTHER INFORMATION: Synthetic: Samalizumab VL

<400> SEQUENCE: 12

Asp Ile Gln Met Thr Gln Ser Pro Ser Ser Leu Ser Ala Ser Ile Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Val Tyr Tyr Cys Leu Gln Tyr Asp Glu Phe Pro Tyr
85 90 95

Thr Phe Gly Gly Gly Thr Lys Leu Glu Ile Lys
100 105

<210> SEQ ID NO 13
<211> LENGTH: 443
<212> TYPE: PRT
<213> ORGANISM: Artificial Sequence
<220> FEATURE:
<223> OTHER INFORMATION: Synthetic: Samalizumab HC

<400> SEQUENCE: 13

Gln Val Gln Leu Gln Gln Ser Gly Ser Glu Leu Lys Lys Pro Gly Ala
1 5 10 15

-continued

```
Ser Val Lys Ile Ser Cys Lys Ala Ser Gly Tyr Ser Phe Thr Asp Tyr
            20                  25                  30

Ile Ile Leu Trp Val Arg Gln Asn Pro Gly Lys Gly Leu Glu Trp Ile
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Ala Asp Gln Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Gly Arg Ser Lys Arg Asp Tyr Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430
```

Thr Gln Lys Ser Leu Ser Leu Ser Leu Gly Lys
435 440

<210> SEQ ID NO 14
<211> LENGTH: 214
<212> TYPE: PRT
<213> ORGANISM: Artificial Sequence
<220> FEATURE:
<223> OTHER INFORMATION: Synthetic: Samalizumab LC

<400> SEQUENCE: 14

Asp Ile Gln Met Thr Gln Ser Pro Ser Ser Leu Ser Ala Ser Ile Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Val Tyr Tyr Cys Leu Gln Tyr Asp Glu Phe Pro Tyr
85 90 95

Thr Phe Gly Gly Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 15
<211> LENGTH: 434
<212> TYPE: PRT
<213> ORGANISM: Artificial Sequence
<220> FEATURE:
<223> OTHER INFORMATION: Synthetic: Fab with samalizumab VH and VL (aka TPP-101)

<400> SEQUENCE: 15

Asp Ile Gln Met Thr Gln Ser Pro Ser Ser Leu Ser Ala Ser Ile Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Tyr Thr Leu Thr Ile Ser Ser Leu Gln Pro

```
65                  70                  75                  80

Glu Asp Phe Ala Val Tyr Tyr Cys Leu Gln Tyr Asp Glu Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Gln Gln Ser Gly Ser Glu
    210                 215                 220

Leu Lys Lys Pro Gly Ala Ser Val Lys Ile Ser Cys Lys Ala Ser Gly
225                 230                 235                 240

Tyr Ser Phe Thr Asp Tyr Ile Ile Leu Trp Val Arg Gln Asn Pro Gly
                245                 250                 255

Lys Gly Leu Glu Trp Ile Gly His Ile Asp Pro Tyr Tyr Gly Ser Ser
            260                 265                 270

Asn Tyr Asn Leu Lys Phe Lys Gly Arg Val Thr Ile Thr Ala Asp Gln
        275                 280                 285

Ser Thr Thr Thr Ala Tyr Met Glu Leu Ser Ser Leu Arg Ser Glu Asp
    290                 295                 300

Thr Ala Val Tyr Tyr Cys Gly Arg Ser Lys Arg Asp Tyr Phe Asp Tyr
305                 310                 315                 320

Trp Gly Gln Gly Thr Thr Leu Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
            420                 425                 430

Ser Cys
```

<210> SEQ ID NO 16
<211> LENGTH: 117
<212> TYPE: PRT
<213> ORGANISM: Artificial Sequence
<220> FEATURE:
<223> OTHER INFORMATION: Synthetic: C2aB7 VH

<400> SEQUENCE: 16

```
Glu Val Gln Leu Gln Gln Ser Gly Pro Glu Leu Val Lys Pro Gly Ala
1               5                   10                  15

Ser Leu Lys Met Ser Cys Lys Ala Ser Gly Tyr Ser Phe Thr Asp Tyr
            20                  25                  30

Ile Ile Leu Trp Val Lys Gln Asn His Gly Lys Ser Leu Glu Trp Ile
        35                  40                  45

Gly His Ile Asp Pro Tyr Tyr Gly Ser Ser Asn Tyr Asn Leu Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Gly Arg Ser Lys Arg Asp Tyr Phe Asp Tyr Trp Gly Gln Gly Thr Thr
            100                 105                 110

Leu Thr Val Ser Ser
        115


<210> SEQ ID NO 17
<211> LENGTH: 107
<212> TYPE: PRT
<213> ORGANISM: Artificial Sequence
<220> FEATURE:
<223> OTHER INFORMATION: Synthetic: C2aB7 VL

<400> SEQUENCE: 17

Asp Ile Gln Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105


<210> SEQ ID NO 18
<211> LENGTH: 434
<212> TYPE: PRT
<213> ORGANISM: Artificial Sequence
<220> FEATURE:
<223> OTHER INFORMATION: Synthetic: Fab with C2aB7 VH and VL (aka TPP-
      100)

<400> SEQUENCE: 18

Asp Ile Gln Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60
```

```
Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Val Gln Leu Gln Gln Ser Gly Pro Glu
    210                 215                 220

Leu Val Lys Pro Gly Ala Ser Leu Lys Met Ser Cys Lys Ala Ser Gly
225                 230                 235                 240

Tyr Ser Phe Thr Asp Tyr Ile Ile Leu Trp Val Lys Gln Asn His Gly
                245                 250                 255

Lys Ser Leu Glu Trp Ile Gly His Ile Asp Pro Tyr Tyr Gly Ser Ser
            260                 265                 270

Asn Tyr Asn Leu Lys Phe Lys Gly Lys Ala Thr Leu Thr Val Asp Lys
        275                 280                 285

Ser Ser Ser Thr Ala Tyr Met Gln Leu Asn Ser Leu Thr Ser Glu Asp
    290                 295                 300

Ser Ala Val Tyr Tyr Cys Gly Arg Ser Lys Arg Asp Tyr Phe Asp Tyr
305                 310                 315                 320

Trp Gly Gln Gly Thr Thr Leu Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
            420                 425                 430

Ser Cys
```

<210> SEQ ID NO 19
<211> LENGTH: 432
<212> TYPE: PRT
<213> ORGANISM: Artificial Sequence
<220> FEATURE:
<223> OTHER INFORMATION: Synthetic: TPP-119 Fab

<400> SEQUENCE: 19

Gln Met Thr Gln Ser Pro Ser Ser Leu Ser Ala Ser Val Gly Asp Arg
1 5 10 15

Val Thr Ile Thr Cys Lys Ala Ser Gln Asp Ile Asn Ser Tyr Leu Ser
20 25 30

Trp Phe Gln Gln Lys Pro Gly Lys Ala Pro Lys Ser Leu Ile Tyr Arg
35 40 45

Ala Asn Arg Leu Val Asp Gly Val Pro Ser Arg Phe Ser Gly Ser Gly
50 55 60

Ser Gly Thr Asp Phe Thr Leu Thr Ile Ser Ser Leu Gln Pro Glu Asp
65 70 75 80

Phe Ala Thr Tyr Tyr Cys Leu Gln Tyr Asp Glu Phe Pro Tyr Thr Phe
85 90 95

Gly Gln Gly Thr Lys Leu Glu Ile Lys Arg Thr Val Ala Ala Pro Ser
100 105 110

Val Phe Ile Phe Pro Pro Ser Asp Glu Gln Leu Lys Ser Gly Thr Ala
115 120 125

Ser Val Val Cys Leu Leu Asn Asn Phe Tyr Pro Arg Glu Ala Lys Val
130 135 140

Gln Trp Lys Val Asp Asn Ala Leu Gln Ser Gly Asn Ser Gln Glu Ser
145 150 155 160

Val Thr Glu Gln Asp Ser Lys Asp Ser Thr Tyr Ser Leu Ser Ser Thr
165 170 175

Leu Thr Leu Ser Lys Ala Asp Tyr Glu Lys His Lys Val Tyr Ala Cys
180 185 190

Glu Val Thr His Gln Gly Leu Ser Ser Pro Val Thr Lys Ser Phe Asn
195 200 205

Arg Gly Glu Cys Gln Val Gln Leu Val Gln Ser Gly Ala Glu Val Lys
210 215 220

Lys Pro Gly Ala Ser Val Lys Val Ser Cys Lys Ala Ser Gly Tyr Ser
225 230 235 240

Phe Thr Asp Tyr Ile Ile Leu Trp Val Arg Gln Ala Pro Gly Gln Arg
245 250 255

Leu Glu Trp Met Gly His Ile Asp Pro Tyr Tyr Gly Ser Ser Asn Tyr
260 265 270

Asn Leu Lys Phe Lys Gly Arg Val Thr Ile Thr Arg Asp Thr Ser Ala
275 280 285

Ser Thr Ala Tyr Met Glu Leu Ser Ser Leu Arg Ser Glu Asp Thr Ala
290 295 300

Val Tyr Tyr Cys Ala Arg Ser Lys Arg Asp Tyr Phe Asp Tyr Trp Gly
305 310 315 320

Gln Gly Thr Leu Val Thr Val Ser Ser Ala Ser Thr Lys Gly Pro Ser
325 330 335

Val Phe Pro Leu Ala Pro Ser Ser Lys Ser Thr Ser Gly Gly Thr Ala
340 345 350

Ala Leu Gly Cys Leu Val Lys Asp Tyr Phe Pro Glu Pro Val Thr Val
355 360 365

Ser Trp Asn Ser Gly Ala Leu Thr Ser Gly Val His Thr Phe Pro Ala
370 375 380

Val Leu Gln Ser Ser Gly Leu Tyr Ser Leu Ser Ser Val Val Thr Val
385 390 395 400

Pro Ser Ser Ser Leu Gly Thr Gln Thr Tyr Ile Cys Asn Val Asn His
405 410 415

-continued

Lys Pro Ser Asn Thr Lys Val Asp Lys Arg Val Glu Pro Lys Ser Cys
420 425 430

<210> SEQ ID NO 20
<211> LENGTH: 117
<212> TYPE: PRT
<213> ORGANISM: Artificial Sequence
<220> FEATURE:
<223> OTHER INFORMATION: Synthetic: TPP-119 VH

<400> SEQUENCE: 20

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 21
<211> LENGTH: 105
<212> TYPE: PRT
<213> ORGANISM: Artificial Sequence
<220> FEATURE:
<223> OTHER INFORMATION: Synthetic: TPP-119 VL

<400> SEQUENCE: 21

Gln Met Thr Gln Ser Pro Ser Ser Leu Ser Ala Ser Val Gly Asp Arg
1 5 10 15

Val Thr Ile Thr Cys Lys Ala Ser Gln Asp Ile Asn Ser Tyr Leu Ser
20 25 30

Trp Phe Gln Gln Lys Pro Gly Lys Ala Pro Lys Ser Leu Ile Tyr Arg
35 40 45

Ala Asn Arg Leu Val Asp Gly Val Pro Ser Arg Phe Ser Gly Ser Gly
50 55 60

Ser Gly Thr Asp Phe Thr Leu Thr Ile Ser Ser Leu Gln Pro Glu Asp
65 70 75 80

Phe Ala Thr Tyr Tyr Cys Leu Gln Tyr Asp Glu Phe Pro Tyr Thr Phe
85 90 95

Gly Gln Gly Thr Lys Leu Glu Ile Lys
100 105

<210> SEQ ID NO 22
<211> LENGTH: 434
<212> TYPE: PRT
<213> ORGANISM: Artificial Sequence
<220> FEATURE:
<223> OTHER INFORMATION: Synthetic: TPP-542

<400> SEQUENCE: 22

-continued

```
Asp Ile Gln Met Thr Gln Ser Pro Ser Ser Leu Tyr Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Pro Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 23
<211> LENGTH: 117
<212> TYPE: PRT
<213> ORGANISM: Artificial Sequence
<220> FEATURE:
<223> OTHER INFORMATION: Synthetic: TPP-542 VH

<400> SEQUENCE: 23

Gln Val Gln Leu Val Gln Ser Gly Pro Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 24
<211> LENGTH: 107
<212> TYPE: PRT
<213> ORGANISM: Artificial Sequence
<220> FEATURE:
<223> OTHER INFORMATION: Synthetic: TPP-542 VL

<400> SEQUENCE: 24

Asp Ile Gln Met Thr Gln Ser Pro Ser Ser Leu Tyr Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 25
<211> LENGTH: 434
<212> TYPE: PRT
<213> ORGANISM: Artificial Sequence
<220> FEATURE:
<223> OTHER INFORMATION: Synthetic: TPP-545

<400> SEQUENCE: 25

-continued

```
Asp Ile Gln Met Thr Gln Ser Pro Ser Ser Leu Tyr Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Leu Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 26
<211> LENGTH: 117
<212> TYPE: PRT
<213> ORGANISM: Artificial Sequence
<220> FEATURE:
<223> OTHER INFORMATION: Synthetic: TPP-545 VH

<400> SEQUENCE: 26

Gln Val Gln Leu Val Gln Ser Gly Ala Glu Val Lys Lys Pro Gly Ala
1 5 10 15

Ser Leu Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 27
<211> LENGTH: 107
<212> TYPE: PRT
<213> ORGANISM: Artificial Sequence
<220> FEATURE:
<223> OTHER INFORMATION: Synthetic: TPP-545 VL

<400> SEQUENCE: 27

Asp Ile Gln Met Thr Gln Ser Pro Ser Ser Leu Tyr Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 28
<211> LENGTH: 434
<212> TYPE: PRT
<213> ORGANISM: Artificial Sequence
<220> FEATURE:
<223> OTHER INFORMATION: Synthetic: TPP-548

<400> SEQUENCE: 28

-continued

```
Asp Ile Gln Met Thr Gln Ser Pro Ser Ser Leu Tyr Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Asn Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

```
        420                 425                 430

Ser Cys


<210> SEQ ID NO 29
<211> LENGTH: 117
<212> TYPE: PRT
<213> ORGANISM: Artificial Sequence
<220> FEATURE:
<223> OTHER INFORMATION: Synthetic: TPP-548 VH

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Asn Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 30
<211> LENGTH: 107
<212> TYPE: PRT
<213> ORGANISM: Artificial Sequence
<220> FEATURE:
<223> OTHER INFORMATION: Synthetic: TPP-548 VL

<400> SEQUENCE: 30

Asp Ile Gln Met Thr Gln Ser Pro Ser Ser Leu Tyr Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 31
<211> LENGTH: 434
<212> TYPE: PRT
<213> ORGANISM: Artificial Sequence
<220> FEATURE:
<223> OTHER INFORMATION: Synthetic: TPP-550

<400> SEQUENCE: 31
```

-continued

```
Asp Ile Gln Met Thr Gln Ser Pro Ser Ser Leu Tyr Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Lys Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

```
        420                 425                 430

Ser Cys


<210> SEQ ID NO 32
<211> LENGTH: 117
<212> TYPE: PRT
<213> ORGANISM: Artificial Sequence
<220> FEATURE:
<223> OTHER INFORMATION: Synthetic: TPP-550 VH

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Lys Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 33
<211> LENGTH: 107
<212> TYPE: PRT
<213> ORGANISM: Artificial Sequence
<220> FEATURE:
<223> OTHER INFORMATION: Synthetic: TPP-550 VL

<400> SEQUENCE: 33

Asp Ile Gln Met Thr Gln Ser Pro Ser Ser Leu Tyr Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 34
<211> LENGTH: 434
<212> TYPE: PRT
<213> ORGANISM: Artificial Sequence
<220> FEATURE:
<223> OTHER INFORMATION: Synthetic: TPP-552

<400> SEQUENCE: 34
```

-continued

```
Asp Ile Gln Met Thr Gln Ser Pro Ser Ser Leu Tyr Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Ile Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

```
        420                 425                 430

Ser Cys


<210> SEQ ID NO 35
<211> LENGTH: 117
<212> TYPE: PRT
<213> ORGANISM: Artificial Sequence
<220> FEATURE:
<223> OTHER INFORMATION: Synthetic: TPP-552 VH

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Ile
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 36
<211> LENGTH: 107
<212> TYPE: PRT
<213> ORGANISM: Artificial Sequence
<220> FEATURE:
<223> OTHER INFORMATION: Synthetic: TPP-552 VL

<400> SEQUENCE: 36

Asp Ile Gln Met Thr Gln Ser Pro Ser Ser Leu Tyr Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 37
<211> LENGTH: 434
<212> TYPE: PRT
<213> ORGANISM: Artificial Sequence
<220> FEATURE:
<223> OTHER INFORMATION: Synthetic: TPP-556

<400> SEQUENCE: 37
```

-continued

```
Asp Ile Gln Met Thr Gln Ser Pro Ser Ser Leu Tyr Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Val Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

```
        420                 425                 430

Ser Cys


<210> SEQ ID NO 38
<211> LENGTH: 117
<212> TYPE: PRT
<213> ORGANISM: Artificial Sequence
<220> FEATURE:
<223> OTHER INFORMATION: Synthetic: TPP-556 VH

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 39
<211> LENGTH: 107
<212> TYPE: PRT
<213> ORGANISM: Artificial Sequence
<220> FEATURE:
<223> OTHER INFORMATION: Synthetic: TPP-556 VL

<400> SEQUENCE: 39

Asp Ile Gln Met Thr Gln Ser Pro Ser Ser Leu Tyr Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 40
<211> LENGTH: 434
<212> TYPE: PRT
<213> ORGANISM: Artificial Sequence
<220> FEATURE:
<223> OTHER INFORMATION: Synthetic: TPP-557

<400> SEQUENCE: 40
```

-continued

```
Asp Ile Gln Met Thr Gln Ser Pro Ser Ser Leu Tyr Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Lys
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 41
<211> LENGTH: 117
<212> TYPE: PRT
<213> ORGANISM: Artificial Sequence
<220> FEATURE:
<223> OTHER INFORMATION: Synthetic: TPP-557 VH

<400> SEQUENCE: 41

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Lys Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 42
<211> LENGTH: 107
<212> TYPE: PRT
<213> ORGANISM: Artificial Sequence
<220> FEATURE:
<223> OTHER INFORMATION: Synthetic: TPP-557 VL

<400> SEQUENCE: 42

Asp Ile Gln Met Thr Gln Ser Pro Ser Ser Leu Tyr Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 43
<211> LENGTH: 434
<212> TYPE: PRT
<213> ORGANISM: Artificial Sequence
<220> FEATURE:
<223> OTHER INFORMATION: Synthetic: TPP-559

<400> SEQUENCE: 43

-continued

Asp Ile Gln Met Thr Gln Ser Pro Ser Ser Leu Tyr Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gln Val Gln Leu Val Gln Ser Gly Ala Glu
210 215 220

Val Lys Lys Pro Gly Ala Ser Val Lys Val Ser Cys Lys Ala Ser Gly
225 230 235 240

Tyr Ser Phe Thr Asp Tyr Ile Ile Leu Trp Val Arg Gln Ala Pro Gly
245 250 255

Gln Arg Leu Glu Trp Met Gly His Ile Asp Pro Tyr Tyr Gly Ser Ser
260 265 270

Asn Tyr Asn Leu Lys Phe Lys Gly Arg Val Thr Ile Thr Arg Asp Thr
275 280 285

Ser Ala Ser Thr Ala Tyr Met Gln Leu Ser Ser Leu Arg Ser Glu Asp
290 295 300

Thr Ala Val Tyr Tyr Cys Ala Arg Ser Lys Arg Asp Tyr Phe Asp Tyr
305 310 315 320

Trp Gly Gln Gly Thr Leu Val Thr Val Ser Ser Ala Ser Thr Lys Gly
325 330 335

Pro Ser Val Phe Pro Leu Ala Pro Ser Ser Lys Ser Thr Ser Gly Gly
340 345 350

Thr Ala Ala Leu Gly Cys Leu Val Lys Asp Tyr Phe Pro Glu Pro Val
355 360 365

Thr Val Ser Trp Asn Ser Gly Ala Leu Thr Ser Gly Val His Thr Phe
370 375 380

Pro Ala Val Leu Gln Ser Ser Gly Leu Tyr Ser Leu Ser Ser Val Val
385 390 395 400

Thr Val Pro Ser Ser Ser Leu Gly Thr Gln Thr Tyr Ile Cys Asn Val
405 410 415

Asn His Lys Pro Ser Asn Thr Lys Val Asp Lys Arg Val Glu Pro Lys

```
            420                 425                 430

Ser Cys


<210> SEQ ID NO 44
<211> LENGTH: 117
<212> TYPE: PRT
<213> ORGANISM: Artificial Sequence
<220> FEATURE:
<223> OTHER INFORMATION: Synthetic: TPP-559 VH

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Gln Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 45
<211> LENGTH: 107
<212> TYPE: PRT
<213> ORGANISM: Artificial Sequence
<220> FEATURE:
<223> OTHER INFORMATION: Synthetic: TPP-559 VL

<400> SEQUENCE: 45

Asp Ile Gln Met Thr Gln Ser Pro Ser Ser Leu Tyr Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 46
<211> LENGTH: 434
<212> TYPE: PRT
<213> ORGANISM: Artificial Sequence
<220> FEATURE:
<223> OTHER INFORMATION: Synthetic: TPP-560

<400> SEQUENCE: 46
```

-continued

Asp Ile Gln Met Thr Gln Ser Pro Ser Ser Leu Tyr Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gln Val Gln Leu Val Gln Ser Gly Ala Glu
210 215 220

Val Lys Lys Pro Gly Ala Ser Val Lys Val Ser Cys Lys Ala Ser Gly
225 230 235 240

Tyr Ser Phe Thr Asp Tyr Ile Ile Leu Trp Val Arg Gln Ala Pro Gly
245 250 255

Gln Arg Leu Glu Trp Met Gly His Ile Asp Pro Tyr Tyr Gly Ser Ser
260 265 270

Asn Tyr Asn Leu Lys Phe Lys Gly Arg Val Thr Ile Thr Arg Asp Thr
275 280 285

Ser Ala Ser Thr Ala Tyr Met Glu Leu Asn Ser Leu Arg Ser Glu Asp
290 295 300

Thr Ala Val Tyr Tyr Cys Ala Arg Ser Lys Arg Asp Tyr Phe Asp Tyr
305 310 315 320

Trp Gly Gln Gly Thr Leu Val Thr Val Ser Ser Ala Ser Thr Lys Gly
325 330 335

Pro Ser Val Phe Pro Leu Ala Pro Ser Ser Lys Ser Thr Ser Gly Gly
340 345 350

Thr Ala Ala Leu Gly Cys Leu Val Lys Asp Tyr Phe Pro Glu Pro Val
355 360 365

Thr Val Ser Trp Asn Ser Gly Ala Leu Thr Ser Gly Val His Thr Phe
370 375 380

Pro Ala Val Leu Gln Ser Ser Gly Leu Tyr Ser Leu Ser Ser Val Val
385 390 395 400

Thr Val Pro Ser Ser Ser Leu Gly Thr Gln Thr Tyr Ile Cys Asn Val
405 410 415

Asn His Lys Pro Ser Asn Thr Lys Val Asp Lys Arg Val Glu Pro Lys

```
            420                 425                 430

Ser Cys


<210> SEQ ID NO 47
<211> LENGTH: 117
<212> TYPE: PRT
<213> ORGANISM: Artificial Sequence
<220> FEATURE:
<223> OTHER INFORMATION: Synthetic: TPP-560 VH

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Asn Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 48
<211> LENGTH: 107
<212> TYPE: PRT
<213> ORGANISM: Artificial Sequence
<220> FEATURE:
<223> OTHER INFORMATION: Synthetic: TPP-560 VL

<400> SEQUENCE: 48

Asp Ile Gln Met Thr Gln Ser Pro Ser Ser Leu Tyr Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 49
<211> LENGTH: 434
<212> TYPE: PRT
<213> ORGANISM: Artificial Sequence
<220> FEATURE:
<223> OTHER INFORMATION: Synthetic: TPP-561

<400> SEQUENCE: 49
```

-continued

```
Asp Ile Gln Met Thr Gln Ser Pro Ser Ser Leu Tyr Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Thr Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 50
<211> LENGTH: 117
<212> TYPE: PRT
<213> ORGANISM: Artificial Sequence
<220> FEATURE:
<223> OTHER INFORMATION: Synthetic: TPP-561 VH

<400> SEQUENCE: 50

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Thr Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 51
<211> LENGTH: 107
<212> TYPE: PRT
<213> ORGANISM: Artificial Sequence
<220> FEATURE:
<223> OTHER INFORMATION: Synthetic: TPP-561 VL

<400> SEQUENCE: 51

Asp Ile Gln Met Thr Gln Ser Pro Ser Ser Leu Tyr Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 52
<211> LENGTH: 434
<212> TYPE: PRT
<213> ORGANISM: Artificial Sequence
<220> FEATURE:
<223> OTHER INFORMATION: Synthetic: TPP-562

<400> SEQUENCE: 52

-continued

```
Asp Ile Gln Met Thr Gln Ser Pro Ser Ser Leu Tyr Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Gly Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

```
            420                 425                 430

Ser Cys


<210> SEQ ID NO 53
<211> LENGTH: 117
<212> TYPE: PRT
<213> ORGANISM: Artificial Sequence
<220> FEATURE:
<223> OTHER INFORMATION: Synthetic: TPP-562 VH

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Ser Lys Arg Asp Tyr Phe Asp Tyr Trp Gly Gln Gly Thr Leu
            100                 105                 110

Val Thr Val Ser Ser
        115


<210> SEQ ID NO 54
<211> LENGTH: 107
<212> TYPE: PRT
<213> ORGANISM: Artificial Sequence
<220> FEATURE:
<223> OTHER INFORMATION: Synthetic: TPP-562 VL

<400> SEQUENCE: 54

Asp Ile Gln Met Thr Gln Ser Pro Ser Ser Leu Tyr Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 55
<211> LENGTH: 434
<212> TYPE: PRT
<213> ORGANISM: Artificial Sequence
<220> FEATURE:
<223> OTHER INFORMATION: Synthetic: TPP-563

<400> SEQUENCE: 55
```

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Pro Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 56
<211> LENGTH: 117
<212> TYPE: PRT
<213> ORGANISM: Artificial Sequence
<220> FEATURE:
<223> OTHER INFORMATION: Synthetic: TPP-563 VH

<400> SEQUENCE: 56

Gln Val Gln Leu Val Gln Ser Gly Pro Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 57
<211> LENGTH: 107
<212> TYPE: PRT
<213> ORGANISM: Artificial Sequence
<220> FEATURE:
<223> OTHER INFORMATION: Synthetic: TPP-563 VL

<400> SEQUENCE: 57

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Gln Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 58
<211> LENGTH: 434
<212> TYPE: PRT
<213> ORGANISM: Artificial Sequence
<220> FEATURE:
<223> OTHER INFORMATION: Synthetic: TPP-564

<400> SEQUENCE: 58

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Leu Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 59
<211> LENGTH: 117
<212> TYPE: PRT
<213> ORGANISM: Artificial Sequence
<220> FEATURE:
<223> OTHER INFORMATION: Synthetic: TPP-564 VH

<400> SEQUENCE: 59

Gln Val Gln Leu Val Gln Ser Gly Ala Glu Leu Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 60
<211> LENGTH: 107
<212> TYPE: PRT
<213> ORGANISM: Artificial Sequence
<220> FEATURE:
<223> OTHER INFORMATION: Synthetic: TPP-564 VL

<400> SEQUENCE: 60

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Gln Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 61
<211> LENGTH: 434
<212> TYPE: PRT
<213> ORGANISM: Artificial Sequence
<220> FEATURE:
<223> OTHER INFORMATION: Synthetic: TPP-571

<400> SEQUENCE: 61

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Lys Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 62
<211> LENGTH: 117
<212> TYPE: PRT
<213> ORGANISM: Artificial Sequence
<220> FEATURE:
<223> OTHER INFORMATION: Synthetic: TPP-571 VH

<400> SEQUENCE: 62

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Lys Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 63
<211> LENGTH: 107
<212> TYPE: PRT
<213> ORGANISM: Artificial Sequence
<220> FEATURE:
<223> OTHER INFORMATION: Synthetic: TPP-571 VL

<400> SEQUENCE: 63

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Gln Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 64
<211> LENGTH: 434
<212> TYPE: PRT
<213> ORGANISM: Artificial Sequence
<220> FEATURE:
<223> OTHER INFORMATION: Synthetic: TPP-572

<400> SEQUENCE: 64

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Ser Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 65
<211> LENGTH: 117
<212> TYPE: PRT
<213> ORGANISM: Artificial Sequence
<220> FEATURE:
<223> OTHER INFORMATION: Synthetic: TPP-572 VH

<400> SEQUENCE: 65

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Ser Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 66
<211> LENGTH: 107
<212> TYPE: PRT
<213> ORGANISM: Artificial Sequence
<220> FEATURE:
<223> OTHER INFORMATION: Synthetic: TPP-572 VL

<400> SEQUENCE: 66

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Gln Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 67
<211> LENGTH: 434
<212> TYPE: PRT
<213> ORGANISM: Artificial Sequence
<220> FEATURE:
<223> OTHER INFORMATION: Synthetic: TPP-573

<400> SEQUENCE: 67

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Ile Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 68
<211> LENGTH: 117
<212> TYPE: PRT
<213> ORGANISM: Artificial Sequence
<220> FEATURE:
<223> OTHER INFORMATION: Synthetic: TPP-573 VH

<400> SEQUENCE: 68

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Ile
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 69
<211> LENGTH: 107
<212> TYPE: PRT
<213> ORGANISM: Artificial Sequence
<220> FEATURE:
<223> OTHER INFORMATION: Synthetic: TPP-573 VL

<400> SEQUENCE: 69

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Gln Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 70
<211> LENGTH: 434
<212> TYPE: PRT
<213> ORGANISM: Artificial Sequence
<220> FEATURE:
<223> OTHER INFORMATION: Synthetic: TPP-575

<400> SEQUENCE: 70

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Ala Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 71
<211> LENGTH: 117
<212> TYPE: PRT
<213> ORGANISM: Artificial Sequence
<220> FEATURE:
<223> OTHER INFORMATION: Synthetic: TPP-575 VH

<400> SEQUENCE: 71

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Ala Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 72
<211> LENGTH: 107
<212> TYPE: PRT
<213> ORGANISM: Artificial Sequence
<220> FEATURE:
<223> OTHER INFORMATION: Synthetic: TPP-575 VL

<400> SEQUENCE: 72

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Gln Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 73
<211> LENGTH: 434
<212> TYPE: PRT
<213> ORGANISM: Artificial Sequence
<220> FEATURE:
<223> OTHER INFORMATION: Synthetic: TPP-578

<400> SEQUENCE: 73

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Lys
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 74
<211> LENGTH: 117
<212> TYPE: PRT
<213> ORGANISM: Artificial Sequence
<220> FEATURE:
<223> OTHER INFORMATION: Synthetic: TPP-578 VH

<400> SEQUENCE: 74

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Lys Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 75
<211> LENGTH: 107
<212> TYPE: PRT
<213> ORGANISM: Artificial Sequence
<220> FEATURE:
<223> OTHER INFORMATION: Synthetic: TPP-578 VL

<400> SEQUENCE: 75

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Gln Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 76
<211> LENGTH: 434
<212> TYPE: PRT
<213> ORGANISM: Artificial Sequence
<220> FEATURE:
<223> OTHER INFORMATION: Synthetic: TPP-579

<400> SEQUENCE: 76

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ser Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 77
<211> LENGTH: 117
<212> TYPE: PRT
<213> ORGANISM: Artificial Sequence
<220> FEATURE:
<223> OTHER INFORMATION: Synthetic: TPP-579 VH

<400> SEQUENCE: 77

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115
```

<210> SEQ ID NO 78
<211> LENGTH: 107
<212> TYPE: PRT
<213> ORGANISM: Artificial Sequence
<220> FEATURE:
<223> OTHER INFORMATION: Synthetic: TPP-579 VL

<400> SEQUENCE: 78

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105
```

<210> SEQ ID NO 79
<211> LENGTH: 434
<212> TYPE: PRT
<213> ORGANISM: Artificial Sequence
<220> FEATURE:
<223> OTHER INFORMATION: Synthetic: TPP-583

<400> SEQUENCE: 79

-continued

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Gln Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gln Val Gln Leu Val Gln Ser Gly Ala Glu
210 215 220

Val Lys Lys Pro Gly Ala Ser Val Lys Val Ser Cys Lys Ala Ser Gly
225 230 235 240

Tyr Ser Phe Thr Asp Tyr Ile Ile Leu Trp Val Arg Gln Ala Pro Gly
245 250 255

Gln Arg Leu Glu Trp Met Gly His Ile Asp Pro Tyr Tyr Gly Ser Ser
260 265 270

Asn Tyr Asn Leu Lys Phe Lys Gly Arg Val Thr Ile Thr Arg Asp Thr
275 280 285

Ser Ala Ser Thr Ala Tyr Met Glu Leu Ser Ser Leu Arg Ser Glu Asp
290 295 300

Thr Ala Val Tyr Tyr Cys Gly Arg Ser Lys Arg Asp Tyr Phe Asp Tyr
305 310 315 320

Trp Gly Gln Gly Thr Leu Val Thr Val Ser Ser Ala Ser Thr Lys Gly
325 330 335

Pro Ser Val Phe Pro Leu Ala Pro Ser Ser Lys Ser Thr Ser Gly Gly
340 345 350

Thr Ala Ala Leu Gly Cys Leu Val Lys Asp Tyr Phe Pro Glu Pro Val
355 360 365

Thr Val Ser Trp Asn Ser Gly Ala Leu Thr Ser Gly Val His Thr Phe
370 375 380

Pro Ala Val Leu Gln Ser Ser Gly Leu Tyr Ser Leu Ser Ser Val Val
385 390 395 400

Thr Val Pro Ser Ser Ser Leu Gly Thr Gln Thr Tyr Ile Cys Asn Val
405 410 415

Asn His Lys Pro Ser Asn Thr Lys Val Asp Lys Arg Val Glu Pro Lys

```
            420                 425                 430

Ser Cys


<210> SEQ ID NO 80
<211> LENGTH: 117
<212> TYPE: PRT
<213> ORGANISM: Artificial Sequence
<220> FEATURE:
<223> OTHER INFORMATION: Synthetic: TPP-583 VH

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Ser Lys Arg Asp Tyr Phe Asp Tyr Trp Gly Gln Gly Thr Leu
            100                 105                 110

Val Thr Val Ser Ser
        115


<210> SEQ ID NO 81
<211> LENGTH: 107
<212> TYPE: PRT
<213> ORGANISM: Artificial Sequence
<220> FEATURE:
<223> OTHER INFORMATION: Synthetic: TPP-583 VL

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 82
<211> LENGTH: 434
<212> TYPE: PRT
<213> ORGANISM: Artificial Sequence
<220> FEATURE:
<223> OTHER INFORMATION: Synthetic: TPP-604

<400> SEQUENCE: 82
```

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Gly Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 83
<211> LENGTH: 117
<212> TYPE: PRT
<213> ORGANISM: Artificial Sequence
<220> FEATURE:
<223> OTHER INFORMATION: Synthetic: TPP-604 VH

<400> SEQUENCE: 83

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Gly Arg Ser Lys Arg Asp Tyr Phe Asp Tyr Trp Gly Gln Gly Thr Leu
100 105 110

Val Thr Val Ser Ser
115

<210> SEQ ID NO 84
<211> LENGTH: 107
<212> TYPE: PRT
<213> ORGANISM: Artificial Sequence
<220> FEATURE:
<223> OTHER INFORMATION: Synthetic: TPP-604 VL

<400> SEQUENCE: 84

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 85
<211> LENGTH: 434
<212> TYPE: PRT
<213> ORGANISM: Artificial Sequence
<220> FEATURE:
<223> OTHER INFORMATION: Synthetic: TPP-669

<400> SEQUENCE: 85

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Met Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Leu Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 86
<211> LENGTH: 117
<212> TYPE: PRT
<213> ORGANISM: Artificial Sequence
<220> FEATURE:
<223> OTHER INFORMATION: Synthetic: TPP-669 VH

<400> SEQUENCE: 86

Gln Val Gln Leu Val Gln Ser Gly Ala Glu Leu Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 87
<211> LENGTH: 107
<212> TYPE: PRT
<213> ORGANISM: Artificial Sequence
<220> FEATURE:
<223> OTHER INFORMATION: Synthetic: TPP-669 VL

<400> SEQUENCE: 87

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Met Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 88
<211> LENGTH: 434
<212> TYPE: PRT
<213> ORGANISM: Artificial Sequence
<220> FEATURE:
<223> OTHER INFORMATION: Synthetic: TPP-671

<400> SEQUENCE: 88

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Met Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Leu Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

```
            420                 425                 430

Ser Cys


<210> SEQ ID NO 89
<211> LENGTH: 117
<212> TYPE: PRT
<213> ORGANISM: Artificial Sequence
<220> FEATURE:
<223> OTHER INFORMATION: Synthetic: TPP-671 VH

<400> SEQUENCE: 89

Gln Val Gln Leu Val Gln Ser Gly Ala Glu Val Lys Lys Pro Gly Ala
1               5                   10                  15

Ser Leu Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 90
<211> LENGTH: 107
<212> TYPE: PRT
<213> ORGANISM: Artificial Sequence
<220> FEATURE:
<223> OTHER INFORMATION: Synthetic: TPP-671 VL

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Met Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 91
<211> LENGTH: 434
<212> TYPE: PRT
<213> ORGANISM: Artificial Sequence
<220> FEATURE:
<223> OTHER INFORMATION: Synthetic: TPP-678

<400> SEQUENCE: 91
```

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Met Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Ile Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 92
<211> LENGTH: 117
<212> TYPE: PRT
<213> ORGANISM: Artificial Sequence
<220> FEATURE:
<223> OTHER INFORMATION: Synthetic: TPP-678 VH

<400> SEQUENCE: 92

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Ile
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 93
<211> LENGTH: 107
<212> TYPE: PRT
<213> ORGANISM: Artificial Sequence
<220> FEATURE:
<223> OTHER INFORMATION: Synthetic: TPP-678 VL

<400> SEQUENCE: 93

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Met Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 94
<211> LENGTH: 434
<212> TYPE: PRT
<213> ORGANISM: Artificial Sequence
<220> FEATURE:
<223> OTHER INFORMATION: Synthetic: TPP-686

<400> SEQUENCE: 94

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Met Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Asn Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

```
            420                 425                 430

Ser Cys


<210> SEQ ID NO 95
<211> LENGTH: 117
<212> TYPE: PRT
<213> ORGANISM: Artificial Sequence
<220> FEATURE:
<223> OTHER INFORMATION: Synthetic: TPP-686 VH

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Asn Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 96
<211> LENGTH: 107
<212> TYPE: PRT
<213> ORGANISM: Artificial Sequence
<220> FEATURE:
<223> OTHER INFORMATION: Synthetic: TPP-686 VL

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Met Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 97
<211> LENGTH: 434
<212> TYPE: PRT
<213> ORGANISM: Artificial Sequence
<220> FEATURE:
<223> OTHER INFORMATION: Synthetic: TPP-688

<400> SEQUENCE: 97
```

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Met Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Gly Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 98
<211> LENGTH: 115
<212> TYPE: PRT
<213> ORGANISM: Artificial Sequence
<220> FEATURE:
<223> OTHER INFORMATION: Synthetic: TPP-688 VH

<400> SEQUENCE: 98

Gln Leu Val Gln Ser Gly Ala Glu Val Lys Lys Pro Gly Ala Ser Val
1 5 10 15

Lys Val Ser Cys Lys Ala Ser Gly Tyr Ser Phe Thr Asp Tyr Ile Ile
20 25 30

Leu Trp Val Arg Gln Ala Pro Gly Gln Arg Leu Glu Trp Met Gly His
35 40 45

Ile Asp Pro Tyr Tyr Gly Ser Ser Asn Tyr Asn Leu Lys Phe Lys Gly
50 55 60

Arg Val Thr Ile Thr Arg Asp Thr Ser Ala Ser Thr Ala Tyr Met Glu
65 70 75 80

Leu Ser Ser Leu Arg Ser Glu Asp Thr Ala Val Tyr Tyr Cys Gly Arg
85 90 95

Ser Lys Arg Asp Tyr Phe Asp Tyr Trp Gly Gln Gly Thr Leu Val Thr
100 105 110

Val Ser Ser
115

<210> SEQ ID NO 99
<211> LENGTH: 107
<212> TYPE: PRT
<213> ORGANISM: Artificial Sequence
<220> FEATURE:
<223> OTHER INFORMATION: Synthetic: TPP-688 VL

<400> SEQUENCE: 99

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Met Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 100
<211> LENGTH: 434
<212> TYPE: PRT
<213> ORGANISM: Artificial Sequence
<220> FEATURE:
<223> OTHER INFORMATION: Synthetic: TPP-690

<400> SEQUENCE: 100

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Leu Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 101
<211> LENGTH: 117
<212> TYPE: PRT
<213> ORGANISM: Artificial Sequence
<220> FEATURE:
<223> OTHER INFORMATION: Synthetic: TPP-690 VH

<400> SEQUENCE: 101

Gln Val Gln Leu Val Gln Ser Gly Ala Glu Leu Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 102
<211> LENGTH: 107
<212> TYPE: PRT
<213> ORGANISM: Artificial Sequence
<220> FEATURE:
<223> OTHER INFORMATION: Synthetic: TPP-690 VL

<400> SEQUENCE: 102

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Gly Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 103
<211> LENGTH: 434
<212> TYPE: PRT
<213> ORGANISM: Artificial Sequence
<220> FEATURE:
<223> OTHER INFORMATION: Synthetic: TPP-697

<400> SEQUENCE: 103

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Lys Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 104
<211> LENGTH: 117
<212> TYPE: PRT
<213> ORGANISM: Artificial Sequence
<220> FEATURE:
<223> OTHER INFORMATION: Synthetic: TPP-697 VH

<400> SEQUENCE: 104

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Lys Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 105
<211> LENGTH: 107
<212> TYPE: PRT
<213> ORGANISM: Artificial Sequence
<220> FEATURE:
<223> OTHER INFORMATION: Synthetic: TPP-697 VL

<400> SEQUENCE: 105

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Gly Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 106
<211> LENGTH: 434
<212> TYPE: PRT
<213> ORGANISM: Artificial Sequence
<220> FEATURE:
<223> OTHER INFORMATION: Synthetic: TPP-709

<400> SEQUENCE: 106

-continued

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Gly Thr Tyr Tyr Cys Leu Gln Tyr Asp Glu Phe Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gln Val Gln Leu Val Gln Ser Gly Ala Glu
210 215 220

Val Lys Lys Pro Gly Ala Ser Val Lys Val Ser Cys Lys Ala Ser Gly
225 230 235 240

Tyr Ser Phe Thr Asp Tyr Ile Ile Leu Trp Val Arg Gln Ala Pro Gly
245 250 255

Gln Arg Leu Glu Trp Met Gly His Ile Asp Pro Tyr Tyr Gly Ser Ser
260 265 270

Asn Tyr Asn Leu Lys Phe Lys Gly Arg Val Thr Ile Thr Arg Asp Thr
275 280 285

Ser Ala Ser Thr Ala Tyr Met Glu Leu Ser Ser Leu Arg Ser Glu Asp
290 295 300

Thr Ala Val Tyr Tyr Cys Gly Arg Ser Lys Arg Asp Tyr Phe Asp Tyr
305 310 315 320

Trp Gly Gln Gly Thr Leu Val Thr Val Ser Ser Ala Ser Thr Lys Gly
325 330 335

Pro Ser Val Phe Pro Leu Ala Pro Ser Ser Lys Ser Thr Ser Gly Gly
340 345 350

Thr Ala Ala Leu Gly Cys Leu Val Lys Asp Tyr Phe Pro Glu Pro Val
355 360 365

Thr Val Ser Trp Asn Ser Gly Ala Leu Thr Ser Gly Val His Thr Phe
370 375 380

Pro Ala Val Leu Gln Ser Ser Gly Leu Tyr Ser Leu Ser Ser Val Val
385 390 395 400

Thr Val Pro Ser Ser Ser Leu Gly Thr Gln Thr Tyr Ile Cys Asn Val
405 410 415

Asn His Lys Pro Ser Asn Thr Lys Val Asp Lys Arg Val Glu Pro Lys 420 425 430

Ser Cys

<210> SEQ ID NO 107
<211> LENGTH: 117
<212> TYPE: PRT
<213> ORGANISM: Artificial Sequence
<220> FEATURE:
<223> OTHER INFORMATION: Synthetic: TPP-709 VH

<400> SEQUENCE: 107

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Gly Arg Ser Lys Arg Asp Tyr Phe Asp Tyr Trp Gly Gln Gly Thr Leu
100 105 110

Val Thr Val Ser Ser
115

<210> SEQ ID NO 108
<211> LENGTH: 107
<212> TYPE: PRT
<213> ORGANISM: Artificial Sequence
<220> FEATURE:
<223> OTHER INFORMATION: Synthetic: TPP-709 VL

<400> SEQUENCE: 108

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Gly Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 109
<211> LENGTH: 434
<212> TYPE: PRT
<213> ORGANISM: Artificial Sequence
<220> FEATURE:
<223> OTHER INFORMATION: Synthetic: TPP-712

<400> SEQUENCE: 109

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Val Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

```
            420                 425                 430

Ser Cys


<210> SEQ ID NO 110
<211> LENGTH: 117
<212> TYPE: PRT
<213> ORGANISM: Artificial Sequence
<220> FEATURE:
<223> OTHER INFORMATION: Synthetic: TPP-712 VH

<400> SEQUENCE: 110

Gln Val Gln Leu Val Gln Ser Gly Ala Glu Val Val Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 111
<211> LENGTH: 107
<212> TYPE: PRT
<213> ORGANISM: Artificial Sequence
<220> FEATURE:
<223> OTHER INFORMATION: Synthetic: TPP-712 VL

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 112
<211> LENGTH: 434
<212> TYPE: PRT
<213> ORGANISM: Artificial Sequence
<220> FEATURE:
<223> OTHER INFORMATION: Synthetic: TPP-714

<400> SEQUENCE: 112
```

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Ile Tyr Tyr Cys Leu Gln Tyr Asp Glu Phe Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gln Val Gln Leu Val Gln Ser Gly Ala Glu
210 215 220

Val Lys Lys Pro Gly Ala Ser Val Lys Met Ser Cys Lys Ala Ser Gly
225 230 235 240

Tyr Ser Phe Thr Asp Tyr Ile Ile Leu Trp Val Arg Gln Ala Pro Gly
245 250 255

Gln Arg Leu Glu Trp Met Gly His Ile Asp Pro Tyr Tyr Gly Ser Ser
260 265 270

Asn Tyr Asn Leu Lys Phe Lys Gly Arg Val Thr Ile Thr Arg Asp Thr
275 280 285

Ser Ala Ser Thr Ala Tyr Met Glu Leu Ser Ser Leu Arg Ser Glu Asp
290 295 300

Thr Ala Val Tyr Tyr Cys Ala Arg Ser Lys Arg Asp Tyr Phe Asp Tyr
305 310 315 320

Trp Gly Gln Gly Thr Leu Val Thr Val Ser Ser Ala Ser Thr Lys Gly
325 330 335

Pro Ser Val Phe Pro Leu Ala Pro Ser Ser Lys Ser Thr Ser Gly Gly
340 345 350

Thr Ala Ala Leu Gly Cys Leu Val Lys Asp Tyr Phe Pro Glu Pro Val
355 360 365

Thr Val Ser Trp Asn Ser Gly Ala Leu Thr Ser Gly Val His Thr Phe
370 375 380

Pro Ala Val Leu Gln Ser Ser Gly Leu Tyr Ser Leu Ser Ser Val Val
385 390 395 400

Thr Val Pro Ser Ser Ser Leu Gly Thr Gln Thr Tyr Ile Cys Asn Val
405 410 415

Asn His Lys Pro Ser Asn Thr Lys Val Asp Lys Arg Val Glu Pro Lys 420 425 430

Ser Cys

<210> SEQ ID NO 113
<211> LENGTH: 117
<212> TYPE: PRT
<213> ORGANISM: Artificial Sequence
<220> FEATURE:
<223> OTHER INFORMATION: Synthetic: TPP-714 VH

<400> SEQUENCE: 113

Gln Val Gln Leu Val Gln Ser Gly Ala Glu Val Lys Lys Pro Gly Ala
1 5 10 15

Ser Val Lys Met Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 114
<211> LENGTH: 107
<212> TYPE: PRT
<213> ORGANISM: Artificial Sequence
<220> FEATURE:
<223> OTHER INFORMATION: Synthetic: TPP-714 VL

<400> SEQUENCE: 114

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Ile Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 115
<211> LENGTH: 434
<212> TYPE: PRT
<213> ORGANISM: Artificial Sequence
<220> FEATURE:
<223> OTHER INFORMATION: Synthetic: TPP-718

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Lys Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys

```
            420                 425                 430

Ser Cys


<210> SEQ ID NO 116
<211> LENGTH: 117
<212> TYPE: PRT
<213> ORGANISM: Artificial Sequence
<220> FEATURE:
<223> OTHER INFORMATION: Synthetic: TPP-718 VH

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Lys Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 117
<211> LENGTH: 107
<212> TYPE: PRT
<213> ORGANISM: Artificial Sequence
<220> FEATURE:
<223> OTHER INFORMATION: Synthetic: TPP-718 VL

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 118
<211> LENGTH: 434
<212> TYPE: PRT
<213> ORGANISM: Artificial Sequence
<220> FEATURE:
<223> OTHER INFORMATION: Synthetic: TPP-719

<400> SEQUENCE: 118
```

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Ser Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 119
<211> LENGTH: 117
<212> TYPE: PRT
<213> ORGANISM: Artificial Sequence
<220> FEATURE:
<223> OTHER INFORMATION: Synthetic: TPP-719 VH

<400> SEQUENCE: 119

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Ser Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 120
<211> LENGTH: 107
<212> TYPE: PRT
<213> ORGANISM: Artificial Sequence
<220> FEATURE:
<223> OTHER INFORMATION: Synthetic: TPP-719 VL

<400> SEQUENCE: 120

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Ile Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 121
<211> LENGTH: 434
<212> TYPE: PRT
<213> ORGANISM: Artificial Sequence
<220> FEATURE:
<223> OTHER INFORMATION: Synthetic: TPP-720

<400> SEQUENCE: 121

-continued

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Ile Tyr Tyr Cys Leu Gln Tyr Asp Glu Phe Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gln Val Gln Leu Val Gln Ser Gly Ala Glu
210 215 220

Val Lys Lys Pro Gly Ala Ser Val Lys Val Ser Cys Lys Ala Ser Gly
225 230 235 240

Tyr Ser Phe Thr Asp Tyr Ile Ile Leu Trp Val Arg Gln Ala Pro Gly
245 250 255

Gln Arg Leu Glu Trp Met Gly His Ile Asp Pro Tyr Tyr Gly Ser Ser
260 265 270

Asn Tyr Asn Leu Lys Phe Lys Gly Lys Val Thr Ile Thr Arg Asp Thr
275 280 285

Ser Ala Ser Thr Ala Tyr Met Glu Leu Ser Ser Leu Arg Ser Glu Asp
290 295 300

Thr Ala Val Tyr Tyr Cys Ala Arg Ser Lys Arg Asp Tyr Phe Asp Tyr
305 310 315 320

Trp Gly Gln Gly Thr Leu Val Thr Val Ser Ser Ala Ser Thr Lys Gly
325 330 335

Pro Ser Val Phe Pro Leu Ala Pro Ser Ser Lys Ser Thr Ser Gly Gly
340 345 350

Thr Ala Ala Leu Gly Cys Leu Val Lys Asp Tyr Phe Pro Glu Pro Val
355 360 365

Thr Val Ser Trp Asn Ser Gly Ala Leu Thr Ser Gly Val His Thr Phe
370 375 380

Pro Ala Val Leu Gln Ser Ser Gly Leu Tyr Ser Leu Ser Ser Val Val
385 390 395 400

Thr Val Pro Ser Ser Ser Leu Gly Thr Gln Thr Tyr Ile Cys Asn Val
405 410 415

Asn His Lys Pro Ser Asn Thr Lys Val Asp Lys Arg Val Glu Pro Lys

```
            420                 425                 430

Ser Cys


<210> SEQ ID NO 122
<211> LENGTH: 117
<212> TYPE: PRT
<213> ORGANISM: Artificial Sequence
<220> FEATURE:
<223> OTHER INFORMATION: Synthetic: TPP-720 VH

<400> SEQUENCE: 122

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Lys Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 123
<211> LENGTH: 107
<212> TYPE: PRT
<213> ORGANISM: Artificial Sequence
<220> FEATURE:
<223> OTHER INFORMATION: Synthetic: TPP-720 VL

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 124
<211> LENGTH: 434
<212> TYPE: PRT
<213> ORGANISM: Artificial Sequence
<220> FEATURE:
<223> OTHER INFORMATION: Synthetic: TPP-721

<400> SEQUENCE: 124
```

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Ile Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

```
        420                 425                 430

Ser Cys


<210> SEQ ID NO 125
<211> LENGTH: 117
<212> TYPE: PRT
<213> ORGANISM: Artificial Sequence
<220> FEATURE:
<223> OTHER INFORMATION: Synthetic: TPP-721 VH

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Ile
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 126
<211> LENGTH: 107
<212> TYPE: PRT
<213> ORGANISM: Artificial Sequence
<220> FEATURE:
<223> OTHER INFORMATION: Synthetic: TPP-721 VL

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 127
<211> LENGTH: 434
<212> TYPE: PRT
<213> ORGANISM: Artificial Sequence
<220> FEATURE:
<223> OTHER INFORMATION: Synthetic: TPP-722

<400> SEQUENCE: 127
```

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Ala Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

```
            420                 425                 430

Ser Cys


<210> SEQ ID NO 128
<211> LENGTH: 117
<212> TYPE: PRT
<213> ORGANISM: Artificial Sequence
<220> FEATURE:
<223> OTHER INFORMATION: Synthetic: TPP-722 VH

<400> SEQUENCE: 128

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 129
<211> LENGTH: 107
<212> TYPE: PRT
<213> ORGANISM: Artificial Sequence
<220> FEATURE:
<223> OTHER INFORMATION: Synthetic: TPP-722 VL

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 130
<211> LENGTH: 434
<212> TYPE: PRT
<213> ORGANISM: Artificial Sequence
<220> FEATURE:
<223> OTHER INFORMATION: Synthetic: TPP-724

<400> SEQUENCE: 130
```

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Val Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 131
<211> LENGTH: 117
<212> TYPE: PRT
<213> ORGANISM: Artificial Sequence
<220> FEATURE:
<223> OTHER INFORMATION: Synthetic: TPP-724 VH

<400> SEQUENCE: 131

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Val Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 132
<211> LENGTH: 107
<212> TYPE: PRT
<213> ORGANISM: Artificial Sequence
<220> FEATURE:
<223> OTHER INFORMATION: Synthetic: TPP-724 VL

<400> SEQUENCE: 132

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Ile Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 133
<211> LENGTH: 434
<212> TYPE: PRT
<213> ORGANISM: Artificial Sequence
<220> FEATURE:
<223> OTHER INFORMATION: Synthetic: TPP-727

<400> SEQUENCE: 133

-continued

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Ile Tyr Tyr Cys Leu Gln Tyr Asp Glu Phe Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gln Val Gln Leu Val Gln Ser Gly Ala Glu
210 215 220

Val Lys Lys Pro Gly Ala Ser Val Lys Val Ser Cys Lys Ala Ser Gly
225 230 235 240

Tyr Ser Phe Thr Asp Tyr Ile Ile Leu Trp Val Arg Gln Ala Pro Gly
245 250 255

Gln Arg Leu Glu Trp Met Gly His Ile Asp Pro Tyr Tyr Gly Ser Ser
260 265 270

Asn Tyr Asn Leu Lys Phe Lys Gly Arg Val Thr Ile Thr Arg Asp Thr
275 280 285

Ser Ala Ser Thr Ala Tyr Met Gln Leu Ser Ser Leu Arg Ser Glu Asp
290 295 300

Thr Ala Val Tyr Tyr Cys Ala Arg Ser Lys Arg Asp Tyr Phe Asp Tyr
305 310 315 320

Trp Gly Gln Gly Thr Leu Val Thr Val Ser Ser Ala Ser Thr Lys Gly
325 330 335

Pro Ser Val Phe Pro Leu Ala Pro Ser Ser Lys Ser Thr Ser Gly Gly
340 345 350

Thr Ala Ala Leu Gly Cys Leu Val Lys Asp Tyr Phe Pro Glu Pro Val
355 360 365

Thr Val Ser Trp Asn Ser Gly Ala Leu Thr Ser Gly Val His Thr Phe
370 375 380

Pro Ala Val Leu Gln Ser Ser Gly Leu Tyr Ser Leu Ser Ser Val Val
385 390 395 400

Thr Val Pro Ser Ser Ser Leu Gly Thr Gln Thr Tyr Ile Cys Asn Val
405 410 415

Asn His Lys Pro Ser Asn Thr Lys Val Asp Lys Arg Val Glu Pro Lys

```
            420                 425                 430

Ser Cys


<210> SEQ ID NO 134
<211> LENGTH: 117
<212> TYPE: PRT
<213> ORGANISM: Artificial Sequence
<220> FEATURE:
<223> OTHER INFORMATION: Synthetic: TPP-727 VH

<400> SEQUENCE: 134

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Gln Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 135
<211> LENGTH: 107
<212> TYPE: PRT
<213> ORGANISM: Artificial Sequence
<220> FEATURE:
<223> OTHER INFORMATION: Synthetic: TPP-727 VL

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 136
<211> LENGTH: 434
<212> TYPE: PRT
<213> ORGANISM: Artificial Sequence
<220> FEATURE:
<223> OTHER INFORMATION: Synthetic: TPP-730

<400> SEQUENCE: 136
```

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Gly Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 137
<211> LENGTH: 117
<212> TYPE: PRT
<213> ORGANISM: Artificial Sequence
<220> FEATURE:
<223> OTHER INFORMATION: Synthetic: TPP-730 VH

<400> SEQUENCE: 137

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Gly Arg Ser Lys Arg Asp Tyr Phe Asp Tyr Trp Gly Gln Gly Thr Leu
100 105 110

Val Thr Val Ser Ser
115

<210> SEQ ID NO 138
<211> LENGTH: 107
<212> TYPE: PRT
<213> ORGANISM: Artificial Sequence
<220> FEATURE:
<223> OTHER INFORMATION: Synthetic: TPP-730 VL

<400> SEQUENCE: 138

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Ile Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 139
<211> LENGTH: 434
<212> TYPE: PRT
<213> ORGANISM: Artificial Sequence
<220> FEATURE:
<223> OTHER INFORMATION: Synthetic: TPP-733

<400> SEQUENCE: 139

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gln Val Gln Leu Val Gln Ser Gly Ala Glu
210 215 220

Val Val Lys Pro Gly Ala Ser Val Lys Val Ser Cys Lys Ala Ser Gly
225 230 235 240

Tyr Ser Phe Thr Asp Tyr Ile Ile Leu Trp Val Arg Gln Ala Pro Gly
245 250 255

Gln Arg Leu Glu Trp Met Gly His Ile Asp Pro Tyr Tyr Gly Ser Ser
260 265 270

Asn Tyr Asn Leu Lys Phe Lys Gly Arg Val Thr Ile Thr Arg Asp Thr
275 280 285

Ser Ala Ser Thr Ala Tyr Met Glu Leu Ser Ser Leu Arg Ser Glu Asp
290 295 300

Thr Ala Val Tyr Tyr Cys Ala Arg Ser Lys Arg Asp Tyr Phe Asp Tyr
305 310 315 320

Trp Gly Gln Gly Thr Leu Val Thr Val Ser Ser Ala Ser Thr Lys Gly
325 330 335

Pro Ser Val Phe Pro Leu Ala Pro Ser Ser Lys Ser Thr Ser Gly Gly
340 345 350

Thr Ala Ala Leu Gly Cys Leu Val Lys Asp Tyr Phe Pro Glu Pro Val
355 360 365

Thr Val Ser Trp Asn Ser Gly Ala Leu Thr Ser Gly Val His Thr Phe
370 375 380

Pro Ala Val Leu Gln Ser Ser Gly Leu Tyr Ser Leu Ser Ser Val Val
385 390 395 400

Thr Val Pro Ser Ser Ser Leu Gly Thr Gln Thr Tyr Ile Cys Asn Val
405 410 415

Asn His Lys Pro Ser Asn Thr Lys Val Asp Lys Arg Val Glu Pro Lys

```
          420                 425                 430

Ser Cys


<210> SEQ ID NO 140
<211> LENGTH: 117
<212> TYPE: PRT
<213> ORGANISM: Artificial Sequence
<220> FEATURE:
<223> OTHER INFORMATION: Synthetic: TPP-733 VH

<400> SEQUENCE: 140

Gln Val Gln Leu Val Gln Ser Gly Ala Glu Val Val Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 141
<211> LENGTH: 107
<212> TYPE: PRT
<213> ORGANISM: Artificial Sequence
<220> FEATURE:
<223> OTHER INFORMATION: Synthetic: TPP-733 VL

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 142
<211> LENGTH: 434
<212> TYPE: PRT
<213> ORGANISM: Artificial Sequence
<220> FEATURE:
<223> OTHER INFORMATION: Synthetic: TPP-735

<400> SEQUENCE: 142
```

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Met Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

```
            420                 425                 430

Ser Cys


<210> SEQ ID NO 143
<211> LENGTH: 117
<212> TYPE: PRT
<213> ORGANISM: Artificial Sequence
<220> FEATURE:
<223> OTHER INFORMATION: Synthetic: TPP-735 VH

<400> SEQUENCE: 143

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 144
<211> LENGTH: 107
<212> TYPE: PRT
<213> ORGANISM: Artificial Sequence
<220> FEATURE:
<223> OTHER INFORMATION: Synthetic: TPP-735 VL

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 145
<211> LENGTH: 434
<212> TYPE: PRT
<213> ORGANISM: Artificial Sequence
<220> FEATURE:
<223> OTHER INFORMATION: Synthetic: TPP-738

<400> SEQUENCE: 145
```

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala His Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 146
<211> LENGTH: 117
<212> TYPE: PRT
<213> ORGANISM: Artificial Sequence
<220> FEATURE:
<223> OTHER INFORMATION: Synthetic: TPP-738 VH

<400> SEQUENCE: 146

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala His Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 147
<211> LENGTH: 107
<212> TYPE: PRT
<213> ORGANISM: Artificial Sequence
<220> FEATURE:
<223> OTHER INFORMATION: Synthetic: TPP-738 VL

<400> SEQUENCE: 147

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 148
<211> LENGTH: 434
<212> TYPE: PRT
<213> ORGANISM: Artificial Sequence
<220> FEATURE:
<223> OTHER INFORMATION: Synthetic: TPP-741

<400> SEQUENCE: 148

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Ile Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 149
<211> LENGTH: 117
<212> TYPE: PRT
<213> ORGANISM: Artificial Sequence
<220> FEATURE:
<223> OTHER INFORMATION: Synthetic: TPP-741 VH

<400> SEQUENCE: 149

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Ile
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 150
<211> LENGTH: 107
<212> TYPE: PRT
<213> ORGANISM: Artificial Sequence
<220> FEATURE:
<223> OTHER INFORMATION: Synthetic: TPP-741 VL

<400> SEQUENCE: 150

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 151
<211> LENGTH: 434
<212> TYPE: PRT
<213> ORGANISM: Artificial Sequence
<220> FEATURE:
<223> OTHER INFORMATION: Synthetic: TPP-749

<400> SEQUENCE: 151

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Asn Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 152
<211> LENGTH: 117
<212> TYPE: PRT
<213> ORGANISM: Artificial Sequence
<220> FEATURE:
<223> OTHER INFORMATION: Synthetic: TPP-749 VH

<400> SEQUENCE: 152

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Asn Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 153
<211> LENGTH: 107
<212> TYPE: PRT
<213> ORGANISM: Artificial Sequence
<220> FEATURE:
<223> OTHER INFORMATION: Synthetic: TPP-749 VL

<400> SEQUENCE: 153

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 154
<211> LENGTH: 434
<212> TYPE: PRT
<213> ORGANISM: Artificial Sequence
<220> FEATURE:
<223> OTHER INFORMATION: Synthetic: TPP-750

<400> SEQUENCE: 154

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Thr Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

```
            420                 425                 430

Ser Cys


<210> SEQ ID NO 155
<211> LENGTH: 117
<212> TYPE: PRT
<213> ORGANISM: Artificial Sequence
<220> FEATURE:
<223> OTHER INFORMATION: Synthetic: TPP-750 VH

<400> SEQUENCE: 155

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Thr Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 156
<211> LENGTH: 107
<212> TYPE: PRT
<213> ORGANISM: Artificial Sequence
<220> FEATURE:
<223> OTHER INFORMATION: Synthetic: TPP-750 VL

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 157
<211> LENGTH: 434
<212> TYPE: PRT
<213> ORGANISM: Artificial Sequence
<220> FEATURE:
<223> OTHER INFORMATION: Synthetic: TPP-751

<400> SEQUENCE: 157
```

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gln Val Gln Leu Val Gln Ser Gly Ala Glu
210 215 220

Val Lys Lys Pro Gly Ala Ser Val Lys Val Ser Cys Lys Ala Ser Gly
225 230 235 240

Tyr Ser Phe Thr Asp Tyr Ile Ile Leu Trp Val Arg Gln Ala Pro Gly
245 250 255

Gln Arg Leu Glu Trp Met Gly His Ile Asp Pro Tyr Tyr Gly Ser Ser
260 265 270

Asn Tyr Asn Leu Lys Phe Lys Gly Arg Val Thr Ile Thr Arg Asp Thr
275 280 285

Ser Ala Ser Thr Ala Tyr Met Glu Leu Ser Ser Leu Arg Ser Glu Asp
290 295 300

Thr Ala Val Tyr Tyr Cys Gly Arg Ser Lys Arg Asp Tyr Phe Asp Tyr
305 310 315 320

Trp Gly Gln Gly Thr Leu Val Thr Val Ser Ser Ala Ser Thr Lys Gly
325 330 335

Pro Ser Val Phe Pro Leu Ala Pro Ser Ser Lys Ser Thr Ser Gly Gly
340 345 350

Thr Ala Ala Leu Gly Cys Leu Val Lys Asp Tyr Phe Pro Glu Pro Val
355 360 365

Thr Val Ser Trp Asn Ser Gly Ala Leu Thr Ser Gly Val His Thr Phe
370 375 380

Pro Ala Val Leu Gln Ser Ser Gly Leu Tyr Ser Leu Ser Ser Val Val
385 390 395 400

Thr Val Pro Ser Ser Ser Leu Gly Thr Gln Thr Tyr Ile Cys Asn Val
405 410 415

Asn His Lys Pro Ser Asn Thr Lys Val Asp Lys Arg Val Glu Pro Lys 420 425 430

Ser Cys

<210> SEQ ID NO 158
<211> LENGTH: 117
<212> TYPE: PRT
<213> ORGANISM: Artificial Sequence
<220> FEATURE:
<223> OTHER INFORMATION: Synthetic: TPP-751 VH

<400> SEQUENCE: 158

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Gly Arg Ser Lys Arg Asp Tyr Phe Asp Tyr Trp Gly Gln Gly Thr Leu
100 105 110

Val Thr Val Ser Ser
115

<210> SEQ ID NO 159
<211> LENGTH: 107
<212> TYPE: PRT
<213> ORGANISM: Artificial Sequence
<220> FEATURE:
<223> OTHER INFORMATION: Synthetic: TPP-751 VL

<400> SEQUENCE: 159

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 160
<211> LENGTH: 434
<212> TYPE: PRT
<213> ORGANISM: Artificial Sequence
<220> FEATURE:
<223> OTHER INFORMATION: Synthetic: TPP-752

<400> SEQUENCE: 160

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

420 425 430

Ser Cys

<210> SEQ ID NO 161
<211> LENGTH: 117
<212> TYPE: PRT
<213> ORGANISM: Artificial Sequence
<220> FEATURE:
<223> OTHER INFORMATION: Synthetic: TPP-752 VH

<400> SEQUENCE: 161

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 162
<211> LENGTH: 107
<212> TYPE: PRT
<213> ORGANISM: Artificial Sequence
<220> FEATURE:
<223> OTHER INFORMATION: Synthetic: TPP-752 VL

<400> SEQUENCE: 162

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 163
<211> LENGTH: 434
<212> TYPE: PRT
<213> ORGANISM: Artificial Sequence
<220> FEATURE:
<223> OTHER INFORMATION: Synthetic: TPP-753

<400> SEQUENCE: 163

-continued

```
Asp Ile Gln Met Thr Gln Ser Pro Ser Ser Leu Tyr Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

```
            420                 425                 430

Ser Cys


<210> SEQ ID NO 164
<211> LENGTH: 117
<212> TYPE: PRT
<213> ORGANISM: Artificial Sequence
<220> FEATURE:
<223> OTHER INFORMATION: Synthetic: TPP-753 VH

<400> SEQUENCE: 164

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 165
<211> LENGTH: 107
<212> TYPE: PRT
<213> ORGANISM: Artificial Sequence
<220> FEATURE:
<223> OTHER INFORMATION: Synthetic: TPP-753 VL

<400> SEQUENCE: 165

Asp Ile Gln Met Thr Gln Ser Pro Ser Ser Leu Tyr Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 166
<211> LENGTH: 434
<212> TYPE: PRT
<213> ORGANISM: Artificial Sequence
<220> FEATURE:
<223> OTHER INFORMATION: Synthetic: TPP-756

<400> SEQUENCE: 166
```

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

```
            420                 425                 430

Ser Cys


<210> SEQ ID NO 167
<211> LENGTH: 117
<212> TYPE: PRT
<213> ORGANISM: Artificial Sequence
<220> FEATURE:
<223> OTHER INFORMATION: Synthetic: TPP-756 VH

<400> SEQUENCE: 167

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 168
<211> LENGTH: 107
<212> TYPE: PRT
<213> ORGANISM: Artificial Sequence
<220> FEATURE:
<223> OTHER INFORMATION: Synthetic: TPP-756 VL

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 169
<211> LENGTH: 434
<212> TYPE: PRT
<213> ORGANISM: Artificial Sequence
<220> FEATURE:
<223> OTHER INFORMATION: Synthetic: TPP-757

<400> SEQUENCE: 169
```

-continued

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

```
        420                 425                 430

Ser Cys


<210> SEQ ID NO 170
<211> LENGTH: 117
<212> TYPE: PRT
<213> ORGANISM: Artificial Sequence
<220> FEATURE:
<223> OTHER INFORMATION: Synthetic: TPP-757 VH

<400> SEQUENCE: 170

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 171
<211> LENGTH: 107
<212> TYPE: PRT
<213> ORGANISM: Artificial Sequence
<220> FEATURE:
<223> OTHER INFORMATION: Synthetic: TPP-757 VL

<400> SEQUENCE: 171

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 172
<211> LENGTH: 434
<212> TYPE: PRT
<213> ORGANISM: Artificial Sequence
<220> FEATURE:
<223> OTHER INFORMATION: Synthetic: TPP-758

<400> SEQUENCE: 172
```

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Tyr
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys Gln Val Gln Leu Val Gln Ser Gly Ala Glu
210 215 220

Val Lys Lys Pro Gly Ala Ser Val Lys Val Ser Cys Lys Ala Ser Gly
225 230 235 240

Tyr Ser Phe Thr Asp Tyr Ile Ile Leu Trp Val Arg Gln Ala Pro Gly
245 250 255

Gln Arg Leu Glu Trp Met Gly His Ile Asp Pro Tyr Tyr Gly Ser Ser
260 265 270

Asn Tyr Asn Leu Lys Phe Lys Gly Arg Val Thr Ile Thr Arg Asp Thr
275 280 285

Ser Ala Ser Thr Ala Tyr Met Glu Leu Ser Ser Leu Arg Ser Glu Asp
290 295 300

Thr Ala Val Tyr Tyr Cys Ala Arg Ser Lys Arg Asp Tyr Phe Asp Tyr
305 310 315 320

Trp Gly Gln Gly Thr Leu Val Thr Val Ser Ser Ala Ser Thr Lys Gly
325 330 335

Pro Ser Val Phe Pro Leu Ala Pro Ser Ser Lys Ser Thr Ser Gly Gly
340 345 350

Thr Ala Ala Leu Gly Cys Leu Val Lys Asp Tyr Phe Pro Glu Pro Val
355 360 365

Thr Val Ser Trp Asn Ser Gly Ala Leu Thr Ser Gly Val His Thr Phe
370 375 380

Pro Ala Val Leu Gln Ser Ser Gly Leu Tyr Ser Leu Ser Ser Val Val
385 390 395 400

Thr Val Pro Ser Ser Ser Leu Gly Thr Gln Thr Tyr Ile Cys Asn Val
405 410 415

Asn His Lys Pro Ser Asn Thr Lys Val Asp Lys Arg Val Glu Pro Lys

```
            420                 425                 430

Ser Cys


<210> SEQ ID NO 173
<211> LENGTH: 117
<212> TYPE: PRT
<213> ORGANISM: Artificial Sequence
<220> FEATURE:
<223> OTHER INFORMATION: Synthetic: TPP-758 VH

<400> SEQUENCE: 173

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 174
<211> LENGTH: 107
<212> TYPE: PRT
<213> ORGANISM: Artificial Sequence
<220> FEATURE:
<223> OTHER INFORMATION: Synthetic: TPP-758 VL

<400> SEQUENCE: 174

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Tyr
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 175
<211> LENGTH: 434
<212> TYPE: PRT
<213> ORGANISM: Artificial Sequence
<220> FEATURE:
<223> OTHER INFORMATION: Synthetic: TPP-759

<400> SEQUENCE: 175
```

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Met Ala Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

```
            420                 425                 430

Ser Cys


<210> SEQ ID NO 176
<211> LENGTH: 117
<212> TYPE: PRT
<213> ORGANISM: Artificial Sequence
<220> FEATURE:
<223> OTHER INFORMATION: Synthetic: TPP-759 VH

<400> SEQUENCE: 176

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 177
<211> LENGTH: 107
<212> TYPE: PRT
<213> ORGANISM: Artificial Sequence
<220> FEATURE:
<223> OTHER INFORMATION: Synthetic: TPP-759 VL

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Met Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 178
<211> LENGTH: 434
<212> TYPE: PRT
<213> ORGANISM: Artificial Sequence
<220> FEATURE:
<223> OTHER INFORMATION: Synthetic: TPP-760

<400> SEQUENCE: 178
```

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240

Tyr Ser Phe Thr Asp Tyr Ile Ile Leu Trp Val Arg Gln Ala Pro Gly
                245                 250                 255

Gln Arg Leu Glu Trp Met Gly His Ile Asp Pro Tyr Tyr Gly Ser Ser
            260                 265                 270

Asn Tyr Asn Leu Lys Phe Lys Gly Arg Val Thr Ile Thr Arg Asp Thr
        275                 280                 285

Ser Ala Ser Thr Ala Tyr Met Glu Leu Ser Ser Leu Arg Ser Glu Asp
    290                 295                 300

Thr Ala Val Tyr Tyr Cys Ala Arg Ser Lys Arg Asp Tyr Phe Asp Tyr
305                 310                 315                 320

Trp Gly Gln Gly Thr Leu Val Thr Val Ser Ser Ala Ser Thr Lys Gly
                325                 330                 335

Pro Ser Val Phe Pro Leu Ala Pro Ser Ser Lys Ser Thr Ser Gly Gly
            340                 345                 350

Thr Ala Ala Leu Gly Cys Leu Val Lys Asp Tyr Phe Pro Glu Pro Val
        355                 360                 365

Thr Val Ser Trp Asn Ser Gly Ala Leu Thr Ser Gly Val His Thr Phe
    370                 375                 380

Pro Ala Val Leu Gln Ser Ser Gly Leu Tyr Ser Leu Ser Ser Val Val
385                 390                 395                 400

Thr Val Pro Ser Ser Ser Leu Gly Thr Gln Thr Tyr Ile Cys Asn Val
                405                 410                 415

Asn His Lys Pro Ser Asn Thr Lys Val Asp Lys Arg Val Glu Pro Lys
```

```
            420                 425                 430

Ser Cys


<210> SEQ ID NO 179
<211> LENGTH: 117
<212> TYPE: PRT
<213> ORGANISM: Artificial Sequence
<220> FEATURE:
<223> OTHER INFORMATION: Synthetic: TPP-760 VH

<400> SEQUENCE: 179

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 180
<211> LENGTH: 107
<212> TYPE: PRT
<213> ORGANISM: Artificial Sequence
<220> FEATURE:
<223> OTHER INFORMATION: Synthetic: TPP-760 VL

<400> SEQUENCE: 180

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 181
<211> LENGTH: 443
<212> TYPE: PRT
<213> ORGANISM: Artificial Sequence
<220> FEATURE:
<223> OTHER INFORMATION: Synthetic: TPP-1141 HC

<400> SEQUENCE: 181
```

-continued

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Ile
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
```

420 425 430

Thr Gln Lys Ser Leu Ser Leu Ser Leu Gly Lys
435 440

<210> SEQ ID NO 182
<211> LENGTH: 214
<212> TYPE: PRT
<213> ORGANISM: Artificial Sequence
<220> FEATURE:
<223> OTHER INFORMATION: Synthetic: TPP-1141 LC

<400> SEQUENCE: 182

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 183
<211> LENGTH: 443
<212> TYPE: PRT
<213> ORGANISM: Artificial Sequence
<220> FEATURE:
<223> OTHER INFORMATION: Synthetic: TPP-1142 HC

<400> SEQUENCE: 183

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

-continued

```
Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Gly Arg Ser Lys Arg Asp Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440
```

<210> SEQ ID NO 184
<211> LENGTH: 214
<212> TYPE: PRT
<213> ORGANISM: Artificial Sequence
<220> FEATURE:
<223> OTHER INFORMATION: Synthetic: TPP-1142 LC

<400> SEQUENCE: 184

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 185
<211> LENGTH: 443
<212> TYPE: PRT
<213> ORGANISM: Artificial Sequence
<220> FEATURE:
<223> OTHER INFORMATION: Synthetic: TPP-1143 HC

<400> SEQUENCE: 185

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Arg Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Gly Arg Ser Lys Arg Asp Tyr Phe Asp Tyr Trp Gly Gln Gly Thr Leu
100 105 110

Val Thr Val Ser Ser Ala Ser Thr Lys Gly Pro Ser Val Phe Pro Leu
115 120 125

-continued

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly Lys
        435                 440

<210> SEQ ID NO 186
<211> LENGTH: 214
<212> TYPE: PRT
<213> ORGANISM: Artificial Sequence
<220> FEATURE:
<223> OTHER INFORMATION: Synthetic: TPP-1143 LC

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

```
Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Thr Tyr Tyr Cys Leu Gln Tyr Asp Glu Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 187
<211> LENGTH: 660
<212> TYPE: DNA
<213> ORGANISM: Artificial Sequence
<220> FEATURE:
<223> OTHER INFORMATION: Synthetic: TPP-542 HC nucleotide

<400> SEQUENCE: 187

```
caagtgcaac tggtgcagag cggccctgaa gtgaagaaac caggcgccag cgtgaaggtg     60

tcctgcaagg ccagcggcta cagcttcacc gactacatca tcctgtgggt ccgacaggcc    120

cctggccaga gactggaatg gatgggccac atcgacccct actacggcag cagcaactac    180

aacctgaagt tcaagggcag agtgaccatc acccgggaca ccagcgccag caccgcctac    240

atggaactga gcagcctgag aagcgaggac accgccgtgt actactgcgc cagaagcaag    300

cgggactact tcgactactg gggccagggc accctggtca ccgttagctc tgcctccacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga gagttgagcc caaatcttgt    660
```

<210> SEQ ID NO 188
<211> LENGTH: 642
<212> TYPE: DNA
<213> ORGANISM: Artificial Sequence
<220> FEATURE:
<223> OTHER INFORMATION: Synthetic: TPP-542 LC nucleotide

<400> SEQUENCE: 188

```
gacatccaaa tgacccagag ccccagcagc ctgtacgcca gcgtgggcga cagagtgacc     60

atcacatgca aggccagcca ggacatcaac agctacctga gctggttcca gcagaagccc    120
```

-continued

```
ggcaaggccc ctaagagcct gatctaccgg gccaacagac tggtggacgg cgtgccaagc    180

agattcagcg gcagcggctc tggcaccgac ttcaccctga ccatcagctc cctgcagccc    240

gaggacttcg ccacctacta ctgcctgcag tacgacgagt tcccctacac cttcggccag    300

ggcaccaagc tggaaatcaa gcggaccgtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 189
<211> LENGTH: 660
<212> TYPE: DNA
<213> ORGANISM: Artificial Sequence
<220> FEATURE:
<223> OTHER INFORMATION: Synthetic: TPP-545 HC nucleotide

<400> SEQUENCE: 189

```
caggtgcagc tggtgcagtc tggcgccgaa gtgaagaagc caggcgccag cctgaaggtg     60

tcctgcaagg ccagcggcta cagcttcacc gactacatca tcctgtgggt ccgacaggcc    120

cctggccaga gactggaatg gatgggccac atcgacccct actacggcag cagcaactac    180

aacctgaagt tcaagggcag agtgaccatc acccgggaca ccagcgccag caccgcctac    240

atggaactga gcagcctgag aagcgaggac accgccgtgt actactgcgc cagaagcaag    300

cgggactact tcgactactg gggccagggc accctggtca ccgttagctc tgcctccacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga gagttgagcc caaatcttgt    660
```

<210> SEQ ID NO 190
<211> LENGTH: 642
<212> TYPE: DNA
<213> ORGANISM: Artificial Sequence
<220> FEATURE:
<223> OTHER INFORMATION: Synthetic: TPP-545 LC nucleotide

<400> SEQUENCE: 190

```
gacatccaaa tgacccagag ccccagcagc ctgtacgcca gcgtgggcga cagagtgacc     60

atcacatgca aggccagcca ggacatcaac agctacctga gctggttcca gcagaagccc    120

ggcaaggccc ctaagagcct gatctaccgg gccaacagac tggtggacgg cgtgccaagc    180

agattcagcg gcagcggctc tggcaccgac ttcaccctga ccatcagctc cctgcagccc    240

gaggacttcg ccacctacta ctgcctgcag tacgacgagt tcccctacac cttcggccag    300

ggcaccaagc tggaaatcaa gcggaccgtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600
```

ctgagctcgc ccgtcacaaa gagcttcaac aggggagagt gt 642

<210> SEQ ID NO 191
<211> LENGTH: 660
<212> TYPE: DNA
<213> ORGANISM: Artificial Sequence
<220> FEATURE:
<223> OTHER INFORMATION: Synthetic: TPP-550 HC nucleotide

<400> SEQUENCE: 191
caggtgcagc tggtgcagtc tggcgccgaa gtgaagaaac caggcgccag cgtgaaggtg 60
tcctgcaagg ccagcggcta cagcttcacc gactacatca tcctgtgggt ccgacaggcc 120
cctggcaaga gactggaatg gatgggccac atcgacccct actacggcag cagcaactac 180
aacctgaagt tcaagggcag agtgaccatc acccgggaca ccagcgccag caccgcctac 240
atggaactga gcagcctgag aagcgaggac accgccgtgt actactgcgc cagaagcaag 300
cgggactact tcgactactg gggccagggc accctggtca ccgttagctc tgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660

<210> SEQ ID NO 192
<211> LENGTH: 642
<212> TYPE: DNA
<213> ORGANISM: Artificial Sequence
<220> FEATURE:
<223> OTHER INFORMATION: Synthetic: TPP-550 LC nucleotide

<400> SEQUENCE: 192
gacatccaaa tgacccagag ccccagcagc ctgtacgcca gcgtgggcga cagagtgacc 60
atcacatgca aggccagcca ggacatcaac agctacctga gctggttcca gcagaagccc 120
ggcaaggccc ctaagagcct gatctaccgg gccaacagac tggtggacgg cgtgccaagc 180
agattcagcg gcagcggctc tggcaccgac ttcaccctga ccatcagctc cctgcagccc 240
gaggacttcg ccacctacta ctgcctgcag tacgacgagt tcccctacac cttcggccag 300
ggcaccaagc tggaaatcaa gcggaccgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 193
<211> LENGTH: 660
<212> TYPE: DNA
<213> ORGANISM: Artificial Sequence
<220> FEATURE:
<223> OTHER INFORMATION: Synthetic: TPP-552 HC nucleotide

<400> SEQUENCE: 193
caggtgcagc tggtgcagtc tggcgccgaa gtgaagaaac caggcgccag cgtgaaggtg 60
tcctgcaagg ccagcggcta cagcttcacc gactacatca tcctgtgggt ccgacaggcc 120
cctggccaga gactggaatg gattggccac atcgacccct actacggcag cagcaactac 180
aacctgaagt tcaagggcag agtgaccatc acccgggaca ccagcgccag caccgcctac 240
atggaactga gcagcctgag aagcgaggac accgccgtgt actactgcgc cagaagcaag 300
cgggactact tcgactactg gggccagggc accctggtca ccgttagctc tgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660

<210> SEQ ID NO 194
<211> LENGTH: 642
<212> TYPE: DNA
<213> ORGANISM: Artificial Sequence
<220> FEATURE:
<223> OTHER INFORMATION: Synthetic: TPP-552 LC nucleotide

<400> SEQUENCE: 194
gacatccaaa tgacccagag ccccagcagc ctgtacgcca gcgtgggcga cagagtgacc 60
atcacatgca aggccagcca ggacatcaac agctacctga gctggttcca gcagaagccc 120
ggcaaggccc ctaagagcct gatctaccgg gccaacagac tggtggacgg cgtgccaagc 180
agattcagcg gcagcggctc tggcaccgac ttcaccctga ccatcagctc cctgcagccc 240
gaggacttcg ccacctacta ctgcctgcag tacgacgagt tcccctacac cttcggccag 300
ggcaccaagc tggaaatcaa gcggaccgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 195
<211> LENGTH: 660
<212> TYPE: DNA
<213> ORGANISM: Artificial Sequence
<220> FEATURE:
<223> OTHER INFORMATION: Synthetic: TPP-556 HC nucleotide

<400> SEQUENCE: 195
caggtgcagc tggtgcagtc tggcgccgaa gtgaagaaac caggcgccag cgtgaaggtg 60
tcctgcaagg ccagcggcta cagcttcacc gactacatca tcctgtgggt ccgacaggcc 120
cctggccaga gactggaatg gatgggccac atcgacccct actacggcag cagcaactac 180
aacctgaagt tcaagggcag agtgaccatc accgtggaca ccagcgccag caccgcctac 240
atggaactga gcagcctgag aagcgaggac accgccgtgt actactgcgc cagaagcaag 300
cgggactact tcgactactg gggccagggc accctggtca ccgttagctc tgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660

<210> SEQ ID NO 196
<211> LENGTH: 642
<212> TYPE: DNA
<213> ORGANISM: Artificial Sequence
<220> FEATURE:
<223> OTHER INFORMATION: Synthetic: TPP-556 LC nucleotide

<400> SEQUENCE: 196
gacatccaaa tgacccagag ccccagcagc ctgtacgcca gcgtgggcga cagagtgacc 60
atcacatgca aggccagcca ggacatcaac agctacctga gctggttcca gcagaagccc 120
ggcaaggccc ctaagagcct gatctaccgg gccaacagac tggtggacgg cgtgccaagc 180
agattcagcg gcagcggctc tggcaccgac ttcaccctga ccatcagctc cctgcagccc 240
gaggacttcg ccacctacta ctgcctgcag tacgacgagt tcccctacac cttcggccag 300
ggcaccaagc tggaaatcaa gcggaccgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 197
<211> LENGTH: 660
<212> TYPE: DNA
<213> ORGANISM: Artificial Sequence
<220> FEATURE:
<223> OTHER INFORMATION: Synthetic: TPP-557 HC nucleotide

<400> SEQUENCE: 197
caggtgcagc tggtgcagtc tggcgccgaa gtgaagaaac caggcgccag cgtgaaggtg 60
tcctgcaagg ccagcggcta cagcttcacc gactacatca tcctgtgggt ccgacaggcc 120
cctggccaga gactggaatg gatgggccac atcgacccct actacggcag cagcaactac 180
aacctgaagt tcaagggcag agtgaccatc acccgggaca agagcgccag caccgcctac 240
atggaactga gcagcctgag aagcgaggac accgccgtgt actactgcgc cagaagcaag 300
cgggactact tcgactactg gggccagggc accctggtca ccgttagctc tgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660

<210> SEQ ID NO 198
<211> LENGTH: 642
<212> TYPE: DNA
<213> ORGANISM: Artificial Sequence
<220> FEATURE:
<223> OTHER INFORMATION: Synthetic: TPP-557 LC nucleotide

<400> SEQUENCE: 198

```
gacatccaaa tgacccagag ccccagcagc ctgtacgcca gcgtgggcga cagagtgacc     60

atcacatgca aggccagcca ggacatcaac agctacctga gctggttcca gcagaagccc    120

ggcaaggccc ctaagagcct gatctaccgg gccaacagac tggtggacgg cgtgccaagc    180

agattcagcg gcagcggctc tggcaccgac ttcaccctga ccatcagctc cctgcagccc    240

gaggacttcg ccacctacta ctgcctgcag tacgacgagt tcccctacac cttcggccag    300

ggcaccaagc tggaaatcaa gcggaccgtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 199
<211> LENGTH: 660
<212> TYPE: DNA
<213> ORGANISM: Artificial Sequence
<220> FEATURE:
<223> OTHER INFORMATION: Synthetic: TPP-559 HC nucleotide

<400> SEQUENCE: 199

```
caggtgcagc tggtgcagtc tggcgccgaa gtgaagaaac caggcgccag cgtgaaggtg     60

tcctgcaagg ccagcggcta cagcttcacc gactacatca tcctgtgggt ccgacaggcc    120

cctggccaga gactggaatg gatgggccac atcgacccct actacggcag cagcaactac    180

aacctgaagt tcaagggcag agtgaccatc acccgggaca ccagcgccag caccgcctac    240

atgcaactga gcagcctgag aagcgaggac accgccgtgt actactgcgc cagaagcaag    300

cgggactact tcgactactg gggccagggc accctggtca ccgttagctc tgcctccacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga gagttgagcc caaatcttgt    660
```

<210> SEQ ID NO 200
<211> LENGTH: 642
<212> TYPE: DNA
<213> ORGANISM: Artificial Sequence
<220> FEATURE:
<223> OTHER INFORMATION: Synthetic: TPP-559 LC nucleotide

<400> SEQUENCE: 200

```
gacatccaaa tgacccagag ccccagcagc ctgtacgcca gcgtgggcga cagagtgacc     60

atcacatgca aggccagcca ggacatcaac agctacctga gctggttcca gcagaagccc    120

ggcaaggccc ctaagagcct gatctaccgg gccaacagac tggtggacgg cgtgccaagc    180

agattcagcg gcagcggctc tggcaccgac ttcaccctga ccatcagctc cctgcagccc    240

gaggacttcg ccacctacta ctgcctgcag tacgacgagt tcccctacac cttcggccag    300

ggcaccaagc tggaaatcaa gcggaccgtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480
```

gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 201
<211> LENGTH: 660
<212> TYPE: DNA
<213> ORGANISM: Artificial Sequence
<220> FEATURE:
<223> OTHER INFORMATION: Synthetic: TPP-562 HC nucleotide

<400> SEQUENCE: 201
caggtgcagc tggtgcagtc tggcgccgaa gtgaagaaac caggcgccag cgtgaaggtg 60
tcctgcaagg ccagcggcta cagcttcacc gactacatca tcctgtgggt ccgacaggcc 120
cctggccaga gactggaatg gatgggccac atcgacccct actacggcag cagcaactac 180
aacctgaagt tcaagggcag agtgaccatc acccgggaca ccagcgccag caccgcctac 240
atggaactga gcagcctgag aagcgaggac accgccgtgt actactgcgg aagaagcaag 300
cgggactact tcgactactg gggccagggc accctggtca ccgttagctc tgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660

<210> SEQ ID NO 202
<211> LENGTH: 642
<212> TYPE: DNA
<213> ORGANISM: Artificial Sequence
<220> FEATURE:
<223> OTHER INFORMATION: Synthetic: TPP-562 LC nucleotide

<400> SEQUENCE: 202
gacatccaaa tgacccagag ccccagcagc ctgtacgcca gcgtgggcga cagagtgacc 60
atcacatgca aggccagcca ggacatcaac agctacctga gctggttcca gcagaagccc 120
ggcaaggccc ctaagagcct gatctaccgg gccaacagac tggtggacgg cgtgccaagc 180
agattcagcg gcagcggctc tggcaccgac ttcaccctga ccatcagctc cctgcagccc 240
gaggacttcg ccacctacta ctgcctgcag tacgacgagt tcccctacac cttcggccag 300
ggcaccaagc tggaaatcaa gcggaccgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 203
<211> LENGTH: 660
<212> TYPE: DNA
<213> ORGANISM: Artificial Sequence
<220> FEATURE:
<223> OTHER INFORMATION: Synthetic: TPP-563 HC nucleotide

<400> SEQUENCE: 203
caagtgcaac tggtgcagag cggccctgaa gtgaagaaac caggcgccag cgtgaaggtg 60
tcctgcaagg ccagcggcta cagcttcacc gactacatca tcctgtgggt ccgacaggcc 120
cctggccaga gactggaatg gatgggccac atcgacccct actacggcag cagcaactac 180
aacctgaagt tcaagggcag agtgaccatc acccgggaca ccagcgccag caccgcctac 240
atggaactga gcagcctgag aagcgaggac accgccgtgt actactgcgc cagaagcaag 300
cgggactact tcgactactg gggccagggc accctggtca ccgttagctc tgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660

<210> SEQ ID NO 204
<211> LENGTH: 642
<212> TYPE: DNA
<213> ORGANISM: Artificial Sequence
<220> FEATURE:
<223> OTHER INFORMATION: Synthetic: TPP-563 LC nucleotide

<400> SEQUENCE: 204
gacatccaaa tgacccagag ccccagcagc ctgtctgcca gcgtgggcga cagagtgacc 60
atcacatgca aggccagcca ggacatcaac agctacctga gctggttcca gcagaagccc 120
ggcaaggccc ctaagagcct gatctaccgg gccaacagac tggtggacgg cgtgccaagc 180
agattcagcg gcagcggctc tggccaggac ttcaccctga ccatcagctc cctgcagccc 240
gaggacttcg ccacctacta ctgcctgcag tacgacgagt tcccctacac cttcggccag 300
ggcaccaagc tggaaatcaa gcggaccgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 205
<211> LENGTH: 660
<212> TYPE: DNA
<213> ORGANISM: Artificial Sequence
<220> FEATURE:
<223> OTHER INFORMATION: Synthetic: TPP-571 HC nucleotide

<400> SEQUENCE: 205
caggtgcagc tggtgcagtc tggcgccgaa gtgaagaaac caggcgccag cgtgaaggtg 60
tcctgcaagg ccagcggcta cagcttcacc gactacatca tcctgtgggt ccgacaggcc 120
cctggcaaga gactggaatg gatgggccac atcgacccct actacggcag cagcaactac 180
aacctgaagt tcaagggcag agtgaccatc acccgggaca ccagcgccag caccgcctac 240
atggaactga gcagcctgag aagcgaggac accgccgtgt actactgcgc cagaagcaag 300
cgggactact tcgactactg gggccagggc accctggtca ccgttagctc tgcctccacc 360
aagggcccat cggtcttccc cctggcaccc tcctccaaga gcacctctgg gggcacagcg 420

```
gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga gagttgagcc caaatcttgt    660
```

<210> SEQ ID NO 206
<211> LENGTH: 642
<212> TYPE: DNA
<213> ORGANISM: Artificial Sequence
<220> FEATURE:
<223> OTHER INFORMATION: Synthetic: TPP-571 LC nucleotide

<400> SEQUENCE: 206

```
gacatccaaa tgacccagag ccccagcagc ctgtctgcca gcgtgggcga cagagtgacc     60

atcacatgca aggccagcca ggacatcaac agctacctga gctggttcca gcagaagccc    120

ggcaaggccc ctaagagcct gatctaccgg gccaacagac tggtggacgg cgtgccaagc    180

agattcagcg gcagcggctc tggccaggac ttcaccctga ccatcagctc cctgcagccc    240

gaggacttcg ccacctacta ctgcctgcag tacgacgagt tcccctacac cttcggccag    300

ggcaccaagc tggaaatcaa gcggaccgtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 207
<211> LENGTH: 678
<212> TYPE: DNA
<213> ORGANISM: Artificial Sequence
<220> FEATURE:
<223> OTHER INFORMATION: Synthetic: TPP-572 HC nucleotide

<400> SEQUENCE: 207

```
caggtgcagc tggtgcagtc tggcgccgaa gtgaagaaac caggcgccag cgtgaaggtg     60

tcctgcaagg ccagcggcta cagcttcacc gactacatca tcctgtgggt ccgacaggcc    120

cctggccagt ctctggaatg gatgggccac atcgacccct actacggcag cagcaactac    180

aacctgaagt tcaagggcag agtgaccatc acccgggaca ccagcgccag caccgcctac    240

atggaactga gcagcctgag aagcgaggac accgccgtgt actactgcgc cagaagcaag    300

cgggactact tcgactactg gggccagggc accctggtca ccgttagctc tgcctccacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga gagttgagcc caaatcttgt    660

caccatcacc atcaccat                                                  678
```

<210> SEQ ID NO 208
<211> LENGTH: 642
<212> TYPE: DNA

<213> ORGANISM: Artificial Sequence
<220> FEATURE:
<223> OTHER INFORMATION: Synthetic: TPP-572 LC nucleotide

<400> SEQUENCE: 208
gacatccaaa tgacccagag ccccagcagc ctgtctgcca gcgtgggcga cagagtgacc 60
atcacatgca aggccagcca ggacatcaac agctacctga gctggttcca gcagaagccc 120
ggcaaggccc ctaagagcct gatctaccgg gccaacagac tggtggacgg cgtgccaagc 180
agattcagcg gcagcggctc tggccaggac ttcaccctga ccatcagctc cctgcagccc 240
gaggacttcg ccacctacta ctgcctgcag tacgacgagt tcccctacac cttcggccag 300
ggcaccaagc tggaaatcaa gcggaccgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 209
<211> LENGTH: 660
<212> TYPE: DNA
<213> ORGANISM: Artificial Sequence
<220> FEATURE:
<223> OTHER INFORMATION: Synthetic: TPP-573 HC nucleotide

<400> SEQUENCE: 209
caggtgcagc tggtgcagtc tggcgccgaa gtgaagaaac caggcgccag cgtgaaggtg 60
tcctgcaagg ccagcggcta cagcttcacc gactacatca tcctgtgggt ccgacaggcc 120
cctggccaga gactggaatg gattggccac atcgacccct actacggcag cagcaactac 180
aacctgaagt tcaagggcag agtgaccatc acccgggaca ccagcgccag caccgcctac 240
atggaactga gcagcctgag aagcgaggac accgccgtgt actactgcgc cagaagcaag 300
cgggactact tcgactactg gggccagggc accctggtca ccgttagctc tgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660

<210> SEQ ID NO 210
<211> LENGTH: 642
<212> TYPE: DNA
<213> ORGANISM: Artificial Sequence
<220> FEATURE:
<223> OTHER INFORMATION: Synthetic: TPP-573 LC nucleotide

<400> SEQUENCE: 210
gacatccaaa tgacccagag ccccagcagc ctgtctgcca gcgtgggcga cagagtgacc 60
atcacatgca aggccagcca ggacatcaac agctacctga gctggttcca gcagaagccc 120
ggcaaggccc ctaagagcct gatctaccgg gccaacagac tggtggacgg cgtgccaagc 180
agattcagcg gcagcggctc tggccaggac ttcaccctga ccatcagctc cctgcagccc 240
gaggacttcg ccacctacta ctgcctgcag tacgacgagt tcccctacac cttcggccag 300

```
ggcaccaagc tggaaatcaa gcggaccgtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                        642
```

<210> SEQ ID NO 211
<211> LENGTH: 660
<212> TYPE: DNA
<213> ORGANISM: Artificial Sequence
<220> FEATURE:
<223> OTHER INFORMATION: Synthetic: TPP-578 HC nucleotide

<400> SEQUENCE: 211

```
caggtgcagc tggtgcagtc tggcgccgaa gtgaagaaac caggcgccag cgtgaaggtg     60

tcctgcaagg ccagcggcta cagcttcacc gactacatca tcctgtgggt ccgacaggcc    120

cctggccaga gactggaatg gatgggccac atcgacccct actacggcag cagcaactac    180

aacctgaagt tcaagggcag agtgaccatc acccgggaca agagcgccag caccgcctac    240

atggaactga gcagcctgag aagcgaggac accgccgtgt actactgcgc cagaagcaag    300

cgggactact tcgactactg gggccagggc accctggtca ccgttagctc tgcctccacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga gagttgagcc caaatcttgt    660
```

<210> SEQ ID NO 212
<211> LENGTH: 642
<212> TYPE: DNA
<213> ORGANISM: Artificial Sequence
<220> FEATURE:
<223> OTHER INFORMATION: Synthetic: TPP-578 LC nucleotide

<400> SEQUENCE: 212

```
gacatccaaa tgacccagag ccccagcagc ctgtctgcca gcgtgggcga cagagtgacc     60

atcacatgca aggccagcca ggacatcaac agctacctga gctggttcca gcagaagccc    120

ggcaaggccc ctaagagcct gatctaccgg gccaacagac tggtggacgg cgtgccaagc    180

agattcagcg gcagcggctc tggccaggac ttcaccctga ccatcagctc cctgcagccc    240

gaggacttcg ccacctacta ctgcctgcag tacgacgagt tcccctacac cttcggccag    300

ggcaccaagc tggaaatcaa gcggaccgtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                        642
```

<210> SEQ ID NO 213

<211> LENGTH: 660
<212> TYPE: DNA
<213> ORGANISM: Artificial Sequence
<220> FEATURE:
<223> OTHER INFORMATION: Synthetic: TPP-583 HC nucleotide

<400> SEQUENCE: 213
caggtgcagc tggtgcagtc tggcgccgaa gtgaagaaac caggcgccag cgtgaaggtg 60
tcctgcaagg ccagcggcta cagcttcacc gactacatca tcctgtgggt ccgacaggcc 120
cctggccaga gactggaatg gatgggccac atcgacccct actacggcag cagcaactac 180
aacctgaagt tcaagggcag agtgaccatc acccgggaca ccagcgccag caccgcctac 240
atggaactga gcagcctgag aagcgaggac accgccgtgt actactgcgg aagaagcaag 300
cgggactact tcgactactg gggccagggc accctggtca ccgttagctc tgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660

<210> SEQ ID NO 214
<211> LENGTH: 642
<212> TYPE: DNA
<213> ORGANISM: Artificial Sequence
<220> FEATURE:
<223> OTHER INFORMATION: Synthetic: TPP-583 LC nucleotide

<400> SEQUENCE: 214
gacatccaaa tgacccagag ccccagcagc ctgtctgcca gcgtgggcga cagagtgacc 60
atcacatgca aggccagcca ggacatcaac agctacctga gctggttcca gcagaagccc 120
ggcaaggccc ctaagagcct gatctaccgg gccaacagac tggtggacgg cgtgccaagc 180
agattcagcg gcagcggctc tggccaggac ttcaccctga ccatcagctc cctgcagccc 240
gaggacttcg ccacctacta ctgcctgcag tacgacgagt tcccctacac cttcggccag 300
ggcaccaagc tggaaatcaa gcggaccgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 215
<211> LENGTH: 660
<212> TYPE: DNA
<213> ORGANISM: Artificial Sequence
<220> FEATURE:
<223> OTHER INFORMATION: Synthetic: TPP-604 HC nucleotide

<400> SEQUENCE: 215
caggtgcagc tggtgcagtc tggcgccgaa gtgaagaaac caggcgccag cgtgaaggtg 60
tcctgcaagg ccagcggcta cagcttcacc gactacatca tcctgtgggt ccgacaggcc 120
cctggccaga gactggaatg gatgggccac atcgacccct actacggcag cagcaactac 180
aacctgaagt tcaagggcag agtgaccatc acccgggaca ccagcgccag caccgcctac 240
atggaactga gcagcctgag aagcgaggac accgccgtgt actactgcgg aagaagcaag 300
cgggactact tcgactactg gggccagggc accctggtca ccgttagctc tgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660

<210> SEQ ID NO 216
<211> LENGTH: 642
<212> TYPE: DNA
<213> ORGANISM: Artificial Sequence
<220> FEATURE:
<223> OTHER INFORMATION: Synthetic: TPP-604 LC nucleotide

<400> SEQUENCE: 216
gacatccaaa tgacccagag ccccagcagc ctgtctgcca gcgtgggcga cagagtgacc 60
atcacatgca aggccagcca ggacatcaac agctacctga gctggttcca gcagaagccc 120
ggcaaggccc ctaagagcct gatctaccgg gccaacagac tggtggacgg cgtgccaagc 180
agattcagcg gcagcggctc tggcaccgac tacaccctga ccatcagctc cctgcagccc 240
gaggacttcg ccacctacta ctgcctgcag tacgacgagt tcccctacac cttcggccag 300
ggcaccaagc tggaaatcaa gcggaccgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 217
<211> LENGTH: 660
<212> TYPE: DNA
<213> ORGANISM: Artificial Sequence
<220> FEATURE:
<223> OTHER INFORMATION: Synthetic: TPP-678 HC nucleotide

<400> SEQUENCE: 217
caggtgcagc tggtgcagtc tggcgccgaa gtgaagaaac caggcgccag cgtgaaggtg 60
tcctgcaagg ccagcggcta cagcttcacc gactacatca tcctgtgggt ccgacaggcc 120
cctggccaga gactggaatg gattggccac atcgacccct actacggcag cagcaactac 180
aacctgaagt tcaagggcag agtgaccatc acccgggaca ccagcgccag caccgcctac 240
atggaactga gcagcctgag aagcgaggac accgccgtgt actactgcgc cagaagcaag 300
cgggactact tcgactactg gggccagggc accctggtca ccgttagctc tgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660

<210> SEQ ID NO 218
<211> LENGTH: 642
<212> TYPE: DNA
<213> ORGANISM: Artificial Sequence
<220> FEATURE:
<223> OTHER INFORMATION: Synthetic: TPP-678 LC nucleotide

<400> SEQUENCE: 218
gacatccaaa tgacccagag ccccagcagc ctgtctgcca gcgtgggcga cagagtgacc 60
atcacatgca aggccagcca ggacatcaac agctacctga gctggttcca gcagaagccc 120
ggcaaggccc ctaagagcct gatctaccgg gccaacagac tggtggacgg cgtgccaagc 180
agattcagcg gcagcggctc tggcaccgac ttcaccctga ccatcagctc cctgcagccc 240
gaggacatgg ccacctacta ctgcctgcag tacgacgagt tcccctacac cttcggccag 300
ggcaccaagc tggaaatcaa gcggaccgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 219
<211> LENGTH: 660
<212> TYPE: DNA
<213> ORGANISM: Artificial Sequence
<220> FEATURE:
<223> OTHER INFORMATION: Synthetic: TPP-688 HC nucleotide

<400> SEQUENCE: 219
caggtgcagc tggtgcagtc tggcgccgaa gtgaagaaac caggcgccag cgtgaaggtg 60
tcctgcaagg ccagcggcta cagcttcacc gactacatca tcctgtgggt ccgacaggcc 120
cctggccaga gactggaatg gatgggccac atcgacccct actacggcag cagcaactac 180
aacctgaagt tcaagggcag agtgaccatc acccgggaca ccagcgccag caccgcctac 240
atggaactga gcagcctgag aagcgaggac accgccgtgt actactgcgg aagaagcaag 300
cgggactact tcgactactg gggccagggc accctggtca ccgttagctc tgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660

<210> SEQ ID NO 220
<211> LENGTH: 642
<212> TYPE: DNA
<213> ORGANISM: Artificial Sequence
<220> FEATURE:
<223> OTHER INFORMATION: Synthetic: TPP-688 LC nucleotide

<400> SEQUENCE: 220
gacatccaaa tgacccagag ccccagcagc ctgtctgcca gcgtgggcga cagagtgacc 60
atcacatgca aggccagcca ggacatcaac agctacctga gctggttcca gcagaagccc 120
ggcaaggccc ctaagagcct gatctaccgg gccaacagac tggtggacgg cgtgccaagc 180

```
agattcagcg gcagcggctc tggcaccgac ttcaccctga ccatcagctc cctgcagccc    240

gaggacatgg ccacctacta ctgcctgcag tacgacgagt tcccctacac cttcggccag    300

ggcaccaagc tggaaatcaa gcggaccgtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                        642
```

<210> SEQ ID NO 221
<211> LENGTH: 660
<212> TYPE: DNA
<213> ORGANISM: Artificial Sequence
<220> FEATURE:
<223> OTHER INFORMATION: Synthetic: TPP-709 HC nucleotide

<400> SEQUENCE: 221

```
caggtgcagc tggtgcagtc tggcgccgaa gtgaagaaac caggcgccag cgtgaaggtg     60

tcctgcaagg ccagcggcta cagcttcacc gactacatca tcctgtgggt ccgacaggcc    120

cctggccaga gactggaatg gatgggccac atcgacccct actacggcag cagcaactac    180

aacctgaagt tcaagggcag agtgaccatc acccgggaca ccagcgccag caccgcctac    240

atggaactga gcagcctgag aagcgaggac accgccgtgt actactgcgg aagaagcaag    300

cgggactact tcgactactg gggccagggc accctggtca ccgttagctc tgcctccacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga gagttgagcc caaatcttgt    660
```

<210> SEQ ID NO 222
<211> LENGTH: 642
<212> TYPE: DNA
<213> ORGANISM: Artificial Sequence
<220> FEATURE:
<223> OTHER INFORMATION: Synthetic: TPP-709 LC nucleotide

<400> SEQUENCE: 222

```
gacatccaaa tgacccagag ccccagcagc ctgtctgcca gcgtgggcga cagagtgacc     60

atcacatgca aggccagcca ggacatcaac agctacctga gctggttcca gcagaagccc    120

ggcaaggccc ctaagagcct gatctaccgg gccaacagac tggtggacgg cgtgccaagc    180

agattcagcg gcagcggctc tggcaccgac ttcaccctga ccatcagctc cctgcagccc    240

gaggacttcg gcacctacta ctgcctgcag tacgacgagt tcccctacac cttcggccag    300

ggcaccaagc tggaaatcaa gcggaccgtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600
```

ctgagctcgc ccgtcacaaa gagcttcaac aggggagagt gt 642

<210> SEQ ID NO 223
<211> LENGTH: 660
<212> TYPE: DNA
<213> ORGANISM: Artificial Sequence
<220> FEATURE:
<223> OTHER INFORMATION: Synthetic: TPP-720 HC nucleotide

<400> SEQUENCE: 223
caggtgcagc tggtgcagtc tggcgccgaa gtgaagaaac caggcgccag cgtgaaggtg 60
tcctgcaagg ccagcggcta cagcttcacc gactacatca tcctgtgggt ccgacaggcc 120
cctggccaga gactggaatg gattggccac atcgacccct actacggcag cagcaactac 180
aacctgaagt tcaagggcag agtgaccatc acccgggaca ccagcgccag caccgcctac 240
atggaactga gcagcctgag aagcgaggac accgccgtgt actactgcgc cagaagcaag 300
cgggactact tcgactactg gggccagggc accctggtca ccgttagctc tgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660

<210> SEQ ID NO 224
<211> LENGTH: 321
<212> TYPE: DNA
<213> ORGANISM: Artificial Sequence
<220> FEATURE:
<223> OTHER INFORMATION: Synthetic: TPP-720 LC nucleotide

<400> SEQUENCE: 224
gacatccaaa tgacccagag ccccagcagc ctgtctgcca gcgtgggcga cagagtgacc 60
atcacatgca aggccagcca ggacatcaac agctacctga gctggttcca gcagaagccc 120
ggcaaggccc ctaagagcct gatctaccgg gccaacagac tggtggacgg cgtgccaagc 180
agattcagcg gcagcggctc tggcaccgac ttcaccctga ccatcagctc cctgcagccc 240
gaggacttcg ccatctacta ctgcctgcag tacgacgagt tccccctacac cttcggccag 300 ggcaccaagc tggaaatcaa g 321

<210> SEQ ID NO 225
<211> LENGTH: 660
<212> TYPE: DNA
<213> ORGANISM: Artificial Sequence
<220> FEATURE:
<223> OTHER INFORMATION: Synthetic: TPP-730 HC nucleotide

<400> SEQUENCE: 225
caggtgcagc tggtgcagtc tggcgccgaa gtgaagaaac caggcgccag cgtgaaggtg 60
tcctgcaagg ccagcggcta cagcttcacc gactacatca tcctgtgggt ccgacaggcc 120
cctggccaga gactggaatg gatgggccac atcgacccct actacggcag cagcaactac 180
aacctgaagt tcaagggcag agtgaccatc acccgggaca ccagcgccag caccgcctac 240
atggaactga gcagcctgag aagcgaggac accgccgtgt actactgcgg aagaagcaag 300
cgggactact tcgactactg gggccagggc accctggtca ccgttagctc tgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660

<210> SEQ ID NO 226
<211> LENGTH: 642
<212> TYPE: DNA
<213> ORGANISM: Artificial Sequence
<220> FEATURE:
<223> OTHER INFORMATION: Synthetic: TPP-730 LC nucleotide

<400> SEQUENCE: 226
gacatccaaa tgacccagag ccccagcagc ctgtctgcca gcgtgggcga cagagtgacc 60
atcacatgca aggccagcca ggacatcaac agctacctga gctggttcca gcagaagccc 120
ggcaaggccc ctaagagcct gatctaccgg gccaacagac tggtggacgg cgtgccaagc 180
agattcagcg gcagcggctc tggcaccgac ttcaccctga ccatcagctc cctgcagccc 240
gaggacttcg ccatctacta ctgcctgcag tacgacgagt tcccctacac cttcggccag 300
ggcaccaagc tggaaatcaa gcggaccgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 227
<211> LENGTH: 660
<212> TYPE: DNA
<213> ORGANISM: Artificial Sequence
<220> FEATURE:
<223> OTHER INFORMATION: Synthetic: TPP-741 HC nucleotide

<400> SEQUENCE: 227
caggtgcagc tggtgcagtc tggcgccgaa gtgaagaaac caggcgccag cgtgaaggtg 60
tcctgcaagg ccagcggcta cagcttcacc gactacatca tcctgtgggt ccgacaggcc 120
cctggccaga gactggaatg gattggccac atcgacccct actacggcag cagcaactac 180
aacctgaagt tcaagggcag agtgaccatc acccgggaca ccagcgccag caccgcctac 240
atggaactga gcagcctgag aagcgaggac accgccgtgt actactgcgc cagaagcaag 300
cgggactact tcgactactg gggccagggc accctggtca ccgttagctc tgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660

<210> SEQ ID NO 228
<211> LENGTH: 642
<212> TYPE: DNA
<213> ORGANISM: Artificial Sequence
<220> FEATURE:

<223> OTHER INFORMATION: Synthetic: TPP-741 LC nucleotide

<400> SEQUENCE: 228
gacatccaga tgacccagag ccccagcagc ctgagcgcca gcgtgggcga cagagtgacc 60
atcacatgca aggccagcca ggacatcaac agctacctga gctggttcca gcagaagccc 120
ggcaaggccc ccaagagcct gatctaccgg gccaacagac tggtggacgg cgtgcccagc 180
agattcagcg gcagcggctc cggcaccgac ttcaccctga ccatcagcag cctgcagccc 240
gaggacttcg ccacctacta ctgcctgcag tacgacgagt tcccctacac cttcggccag 300
ggcaccaagc tggaaatcaa gcggaccgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 229
<211> LENGTH: 660
<212> TYPE: DNA
<213> ORGANISM: Artificial Sequence
<220> FEATURE:
<223> OTHER INFORMATION: Synthetic: TPP-751 HC nucleotide

<400> SEQUENCE: 229
caggtgcagc tggtgcagtc tggcgccgaa gtgaagaaac caggcgccag cgtgaaggtg 60
tcctgcaagg ccagcggcta cagcttcacc gactacatca tcctgtgggt ccgacaggcc 120
cctggccaga gactggaatg gatgggccac atcgacccct actacggcag cagcaactac 180
aacctgaagt tcaagggcag agtgaccatc acccgggaca ccagcgccag caccgcctac 240
atggaactga gcagcctgag aagcgaggac accgccgtgt actactgcgg aagaagcaag 300
cgggactact tcgactactg gggccagggc accctggtca ccgttagctc tgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660

<210> SEQ ID NO 230
<211> LENGTH: 642
<212> TYPE: DNA
<213> ORGANISM: Artificial Sequence
<220> FEATURE:
<223> OTHER INFORMATION: Synthetic: TPP-751 LC nucleotide

<400> SEQUENCE: 230
gacatccaga tgacccagag ccccagcagc ctgagcgcca gcgtgggcga cagagtgacc 60
atcacatgca aggccagcca ggacatcaac agctacctga gctggttcca gcagaagccc 120
ggcaaggccc ccaagagcct gatctaccgg gccaacagac tggtggacgg cgtgcccagc 180
agattcagcg gcagcggctc cggcaccgac ttcaccctga ccatcagcag cctgcagccc 240
gaggacttcg ccacctacta ctgcctgcag tacgacgagt tcccctacac cttcggccag 300
ggcaccaagc tggaaatcaa gcggaccgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 231
<211> LENGTH: 660
<212> TYPE: DNA
<213> ORGANISM: Artificial Sequence
<220> FEATURE:
<223> OTHER INFORMATION: Synthetic: TPP-753 HC nucleotide

<400> SEQUENCE: 231
caagtgcagc tggtgcagtc tggcgccgaa gtgaagaaac ctggcgccag cgtgaaggtg 60
tcctgcaagg ccagcggcta cagcttcacc gactacatca tcctgtgggt gcgccaggcc 120
cctggccaga gactggaatg gatgggccac atcgacccct actacggcag cagcaactac 180
aacctgaagt tcaagggcag agtgaccatc acccgggaca ccagcgccag caccgcctac 240
atggaactga gcagcctgcg gagcgaggac accgccgtgt actactgcgc cagaagcaag 300
cgggactact tcgactactg gggccagggc accctggtga cagtgtccag cgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660

<210> SEQ ID NO 232
<211> LENGTH: 642
<212> TYPE: DNA
<213> ORGANISM: Artificial Sequence
<220> FEATURE:
<223> OTHER INFORMATION: Synthetic: TPP-753 LC nucleotide

<400> SEQUENCE: 232
gacatccaaa tgacccagag ccccagcagc ctgtacgcca gcgtgggcga cagagtgacc 60
atcacatgca aggccagcca ggacatcaac agctacctga gctggttcca gcagaagccc 120
ggcaaggccc ctaagagcct gatctaccgg gccaacagac tggtggacgg cgtgccaagc 180
agattcagcg gcagcggctc tggcaccgac ttcaccctga ccatcagctc cctgcagccc 240
gaggacttcg ccacctacta ctgcctgcag tacgacgagt tcccctacac cttcggccag 300
ggcaccaagc tggaaatcaa gcggaccgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 233
<211> LENGTH: 660
<212> TYPE: DNA

<213> ORGANISM: Artificial Sequence
<220> FEATURE:
<223> OTHER INFORMATION: Synthetic: TPP-759 HC nucleotide

<400> SEQUENCE: 233
caagtgcagc tggtgcagtc tggcgccgaa gtgaagaaac ctggcgccag cgtgaaggtg 60
tcctgcaagg ccagcggcta cagcttcacc gactacatca tcctgtgggt gcgccaggcc 120
cctggccaga gactggaatg gatgggccac atcgacccct actacggcag cagcaactac 180
aacctgaagt tcaagggcag agtgaccatc acccgggaca ccagcgccag caccgcctac 240
atggaactga gcagcctgcg gagcgaggac accgccgtgt actactgcgc cagaagcaag 300
cgggactact tcgactactg gggccagggc accctggtga cagtgtccag cgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacaaga gagttgagcc caaatcttgt 660

<210> SEQ ID NO 234
<211> LENGTH: 642
<212> TYPE: DNA
<213> ORGANISM: Artificial Sequence
<220> FEATURE:
<223> OTHER INFORMATION: Synthetic: TPP-759 LC nucleotide

<400> SEQUENCE: 234
gacatccaaa tgacccagag ccccagcagc ctgtctgcca gcgtgggcga cagagtgacc 60
atcacatgca aggccagcca ggacatcaac agctacctga gctggttcca gcagaagccc 120
ggcaaggccc ctaagagcct gatctaccgg gccaacagac tggtggacgg cgtgccaagc 180
agattcagcg gcagcggctc tggcaccgac ttcaccctga ccatcagctc cctgcagccc 240
gaggacatgg ccacctacta ctgcctgcag tacgacgagt tcccctacac cttcggccag 300
ggcaccaagc tggaaatcaa gcggaccgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 235
<211> LENGTH: 117
<212> TYPE: PRT
<213> ORGANISM: Artificial Sequence
<220> FEATURE:
<223> OTHER INFORMATION: Synthetic: Ec (1-46)

<400> SEQUENCE: 235

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Gly Leu Glu Trp Met
35 40 45

```
Gly His Ile Asp Pro Tyr Tyr Gly Ser Ser Asn Tyr Asn Leu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115
```

<210> SEQ ID NO 236
<211> LENGTH: 117
<212> TYPE: PRT
<213> ORGANISM: Artificial Sequence
<220> FEATURE:
<223> OTHER INFORMATION: Synthetic: IGHV1-69

<400> SEQUENCE: 236

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115
```

<210> SEQ ID NO 237
<211> LENGTH: 117
<212> TYPE: PRT
<213> ORGANISM: Artificial Sequence
<220> FEATURE:
<223> OTHER INFORMATION: Synthetic: IGHV1-18

<400> SEQUENCE: 237

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110
```

```
Val Thr Val Ser Ser
        115


<210> SEQ ID NO 238
<211> LENGTH: 117
<212> TYPE: PRT
<213> ORGANISM: Artificial Sequence
<220> FEATURE:
<223> OTHER INFORMATION: Synthetic: IGHV1-2

<400> SEQUENCE: 238

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 239
<211> LENGTH: 117
<212> TYPE: PRT
<213> ORGANISM: Artificial Sequence
<220> FEATURE:
<223> OTHER INFORMATION: Synthetic: IGHV1-3

<400> SEQUENCE: 239

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 240
<211> LENGTH: 117
<212> TYPE: PRT
<213> ORGANISM: Artificial Sequence
<220> FEATURE:
<223> OTHER INFORMATION: Synthetic: IGHV1-8
```

<400> SEQUENCE: 240

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Thr Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115

<210> SEQ ID NO 241
<211> LENGTH: 117
<212> TYPE: PRT
<213> ORGANISM: Artificial Sequence
<220> FEATURE:
<223> OTHER INFORMATION: Synthetic: IGHV5-10-1

<400> SEQUENCE: 241

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Asp Tyr
            20                  25                  30

Ile Ile Leu Trp Val Arg Gln Met Pro Gly Lys Gly Leu Glu Trp Met
        35                  40                  45

Gly His Ile Asp Pro Tyr Tyr Gly Ser Ser Asn Tyr Asn Leu Lys Phe
    50                  55                  60

Lys Gly His Val Thr Ile Ser Ala Asp Lys Ser Ile Ser Thr Ala Tyr
65                  70                  75                  80

Leu Gln Trp Ser Ser Leu Lys Ala Arg Thr Pro Pro Cys Ile Thr Val
                85                  90                  95

Arg Asp Ser Lys Arg Asp Tyr Phe Asp Tyr Trp Gly Gln Gly Thr Leu
            100                 105                 110

Val Thr Val Ser Ser
        115

<210> SEQ ID NO 242
<211> LENGTH: 117
<212> TYPE: PRT
<213> ORGANISM: Artificial Sequence
<220> FEATURE:
<223> OTHER INFORMATION: Synthetic: IGHV1-45

<400> SEQUENCE: 242

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Ala Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115

<210> SEQ ID NO 243
<211> LENGTH: 117
<212> TYPE: PRT
<213> ORGANISM: Artificial Sequence
<220> FEATURE:
<223> OTHER INFORMATION: Synthetic: IGHV1-58

<400> SEQUENCE: 243

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Arg Gly Gln Arg Leu Glu Trp Ile
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Ser Lys Arg Asp Tyr Phe Asp Tyr Trp Gly Gln Gly Thr Leu
            100                 105                 110

Val Thr Val Ser Ser
        115

<210> SEQ ID NO 244
<211> LENGTH: 117
<212> TYPE: PRT
<213> ORGANISM: Artificial Sequence
<220> FEATURE:
<223> OTHER INFORMATION: Synthetic: IGHV7-4-1

<400> SEQUENCE: 244

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ser Lys Arg Asp Tyr Phe Asp Tyr Trp Gly Gln Gly Thr Leu

```
            100                 105                 110

Val Thr Val Ser Ser
        115


<210> SEQ ID NO 245
<211> LENGTH: 107
<212> TYPE: PRT
<213> ORGANISM: Artificial Sequence
<220> FEATURE:
<223> OTHER INFORMATION: Synthetic: Ec (1-39)

<400> SEQUENCE: 245

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Arg Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Val Glu Ile Lys
            100                 105


<210> SEQ ID NO 246
<211> LENGTH: 107
<212> TYPE: PRT
<213> ORGANISM: Artificial Sequence
<220> FEATURE:
<223> OTHER INFORMATION: Synthetic: IGKV1-16

<400> SEQUENCE: 246

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 247
<211> LENGTH: 107
<212> TYPE: PRT
<213> ORGANISM: Artificial Sequence
<220> FEATURE:
<223> OTHER INFORMATION: Synthetic: IGKV1D-33

<400> SEQUENCE: 247

Asp Ile Gln Met Thr Gln Ser Pro Ser Ser Leu Ser Ala Ser Val Gly
1               5                   10                  15
```

```
Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 248
<211> LENGTH: 107
<212> TYPE: PRT
<213> ORGANISM: Artificial Sequence
<220> FEATURE:
<223> OTHER INFORMATION: Synthetic: IGKV1-12

<400> SEQUENCE: 248

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 249
<211> LENGTH: 117
<212> TYPE: PRT
<213> ORGANISM: Artificial Sequence
<220> FEATURE:
<223> OTHER INFORMATION: Synthetic: TPP-102 VH

<400> SEQUENCE: 249

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
```

```
            100                 105                 110

Val Thr Val Ser Ser
        115


<210> SEQ ID NO 250
<211> LENGTH: 107
<212> TYPE: PRT
<213> ORGANISM: Artificial Sequence
<220> FEATURE:
<223> OTHER INFORMATION: Synthetic: TPP-102 VL

<400> SEQUENCE: 250

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Arg Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Val Glu Ile Lys
            100                 105


<210> SEQ ID NO 251
<211> LENGTH: 117
<212> TYPE: PRT
<213> ORGANISM: Artificial Sequence
<220> FEATURE:
<223> OTHER INFORMATION: Synthetic: TPP-103 VH

<400> SEQUENCE: 251

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 252
<211> LENGTH: 107
<212> TYPE: PRT
<213> ORGANISM: Artificial Sequence
<220> FEATURE:
<223> OTHER INFORMATION: Synthetic: TPP-103 VL

<400> SEQUENCE: 252
```

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105
```

<210> SEQ ID NO 253
<211> LENGTH: 117
<212> TYPE: PRT
<213> ORGANISM: Artificial Sequence
<220> FEATURE:
<223> OTHER INFORMATION: Synthetic: TPP-104 VH

<400> SEQUENCE: 253

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115
```

<210> SEQ ID NO 254
<211> LENGTH: 107
<212> TYPE: PRT
<213> ORGANISM: Artificial Sequence
<220> FEATURE:
<223> OTHER INFORMATION: Synthetic: TPP-104 VL

<400> SEQUENCE: 254

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Phe Thr Ile Ser Ser Leu Gln Pro
```

```
65                  70                  75                  80

Glu Asp Ile Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 255
<211> LENGTH: 117
<212> TYPE: PRT
<213> ORGANISM: Artificial Sequence
<220> FEATURE:
<223> OTHER INFORMATION: Synthetic: TPP-105 VH

<400> SEQUENCE: 255

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 256
<211> LENGTH: 107
<212> TYPE: PRT
<213> ORGANISM: Artificial Sequence
<220> FEATURE:
<223> OTHER INFORMATION: Synthetic: TPP-105 VL

<400> SEQUENCE: 256

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 257
<211> LENGTH: 117
<212> TYPE: PRT
<213> ORGANISM: Artificial Sequence
<220> FEATURE:
```

<223> OTHER INFORMATION: Synthetic: TPP-106 VH

<400> SEQUENCE: 257

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115
```

<210> SEQ ID NO 258
<211> LENGTH: 107
<212> TYPE: PRT
<213> ORGANISM: Artificial Sequence
<220> FEATURE:
<223> OTHER INFORMATION: Synthetic: TPP-106 VL

<400> SEQUENCE: 258

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Arg Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Val Glu Ile Lys
            100                 105
```

<210> SEQ ID NO 259
<211> LENGTH: 117
<212> TYPE: PRT
<213> ORGANISM: Artificial Sequence
<220> FEATURE:
<223> OTHER INFORMATION: Synthetic: TPP-107 VH

<400> SEQUENCE: 259

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
```

```
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 260
<211> LENGTH: 107
<212> TYPE: PRT
<213> ORGANISM: Artificial Sequence
<220> FEATURE:
<223> OTHER INFORMATION: Synthetic: TPP-107 VL

<400> SEQUENCE: 260

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 261
<211> LENGTH: 117
<212> TYPE: PRT
<213> ORGANISM: Artificial Sequence
<220> FEATURE:
<223> OTHER INFORMATION: Synthetic: TPP-108 VH

<400> SEQUENCE: 261

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115
```

<210> SEQ ID NO 262
<211> LENGTH: 107
<212> TYPE: PRT
<213> ORGANISM: Artificial Sequence
<220> FEATURE:
<223> OTHER INFORMATION: Synthetic: TPP-108 VL

<400> SEQUENCE: 262

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105
```

<210> SEQ ID NO 263
<211> LENGTH: 117
<212> TYPE: PRT
<213> ORGANISM: Artificial Sequence
<220> FEATURE:
<223> OTHER INFORMATION: Synthetic: TPP-109 VH

<400> SEQUENCE: 263

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115
```

<210> SEQ ID NO 264
<211> LENGTH: 107
<212> TYPE: PRT
<213> ORGANISM: Artificial Sequence
<220> FEATURE:
<223> OTHER INFORMATION: Synthetic: TPP-109 VL

<400> SEQUENCE: 264

```
Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Ile Asn Ser Tyr
```

```
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 265
<211> LENGTH: 117
<212> TYPE: PRT
<213> ORGANISM: Artificial Sequence
<220> FEATURE:
<223> OTHER INFORMATION: Synthetic: TPP-110 VH

<400> SEQUENCE: 265

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 266
<211> LENGTH: 107
<212> TYPE: PRT
<213> ORGANISM: Artificial Sequence
<220> FEATURE:
<223> OTHER INFORMATION: Synthetic: TPP-110 VL

<400> SEQUENCE: 266

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Arg Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95
```

```
Thr Phe Gly Gln Gly Thr Lys Val Glu Ile Lys
            100                 105


<210> SEQ ID NO 267
<211> LENGTH: 117
<212> TYPE: PRT
<213> ORGANISM: Artificial Sequence
<220> FEATURE:
<223> OTHER INFORMATION: Synthetic: TPP-111 VH

<400> SEQUENCE: 267

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 268
<211> LENGTH: 107
<212> TYPE: PRT
<213> ORGANISM: Artificial Sequence
<220> FEATURE:
<223> OTHER INFORMATION: Synthetic: TPP-111 VL

<400> SEQUENCE: 268

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 269
<211> LENGTH: 117
<212> TYPE: PRT
<213> ORGANISM: Artificial Sequence
<220> FEATURE:
<223> OTHER INFORMATION: Synthetic: TPP-112 VH

<400> SEQUENCE: 269

Gln Val Gln Leu Val Gln Ser Gly Ala Glu Val Lys Lys Pro Gly Ala
```

```
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 270
<211> LENGTH: 107
<212> TYPE: PRT
<213> ORGANISM: Artificial Sequence
<220> FEATURE:
<223> OTHER INFORMATION: Synthetic: TPP-112 VL

<400> SEQUENCE: 270

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 271
<211> LENGTH: 117
<212> TYPE: PRT
<213> ORGANISM: Artificial Sequence
<220> FEATURE:
<223> OTHER INFORMATION: Synthetic: TPP-113 VH

<400> SEQUENCE: 271

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Met Thr Thr Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 272
<211> LENGTH: 107
<212> TYPE: PRT
<213> ORGANISM: Artificial Sequence
<220> FEATURE:
<223> OTHER INFORMATION: Synthetic: TPP-113 VL

<400> SEQUENCE: 272

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 273
<211> LENGTH: 117
<212> TYPE: PRT
<213> ORGANISM: Artificial Sequence
<220> FEATURE:
<223> OTHER INFORMATION: Synthetic: TPP-114 VH

<400> SEQUENCE: 273

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 274
<211> LENGTH: 107
<212> TYPE: PRT
<213> ORGANISM: Artificial Sequence
```

<220> FEATURE:
<223> OTHER INFORMATION: Synthetic: TPP-114 VL

<400> SEQUENCE: 274

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Tyr Gln Arg Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Val Glu Ile Lys
100 105

<210> SEQ ID NO 275
<211> LENGTH: 117
<212> TYPE: PRT
<213> ORGANISM: Artificial Sequence
<220> FEATURE:
<223> OTHER INFORMATION: Synthetic: TPP-115 VH

<400> SEQUENCE: 275

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Gly Leu Glu Trp Met
35 40 45

Gly His Ile Asp Pro Tyr Tyr Gly Ser Ser Asn Tyr Asn Leu Lys Phe
50 55 60

Lys Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 276
<211> LENGTH: 107
<212> TYPE: PRT
<213> ORGANISM: Artificial Sequence
<220> FEATURE:
<223> OTHER INFORMATION: Synthetic: TPP-115 VL

<400> SEQUENCE: 276

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

```
Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 277
<211> LENGTH: 117
<212> TYPE: PRT
<213> ORGANISM: Artificial Sequence
<220> FEATURE:
<223> OTHER INFORMATION: Synthetic: TPP-116 VH

<400> SEQUENCE: 277

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 278
<211> LENGTH: 107
<212> TYPE: PRT
<213> ORGANISM: Artificial Sequence
<220> FEATURE:
<223> OTHER INFORMATION: Synthetic: TPP-116 VL

<400> SEQUENCE: 278

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 279
```

<211> LENGTH: 117
<212> TYPE: PRT
<213> ORGANISM: Artificial Sequence
<220> FEATURE:
<223> OTHER INFORMATION: Synthetic: TPP-117 VH

<400> SEQUENCE: 279

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Gly Leu Glu Trp Met
35 40 45

Gly His Ile Asp Pro Tyr Tyr Gly Ser Ser Asn Tyr Asn Leu Lys Phe
50 55 60

Lys Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 280
<211> LENGTH: 107
<212> TYPE: PRT
<213> ORGANISM: Artificial Sequence
<220> FEATURE:
<223> OTHER INFORMATION: Synthetic: TPP-117 VL

<400> SEQUENCE: 280

Asp Ile Gln Met Thr Gln Ser Pro Ser Ser Val Ser Ala Ser Val Gly
1 5 10 15

Asp Arg Val Thr Ile Thr Cys Lys Ala Ser Gln Asp Ile Asn Ser Tyr
20 25 30

Leu Ser Trp Tyr Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 281
<211> LENGTH: 117
<212> TYPE: PRT
<213> ORGANISM: Artificial Sequence
<220> FEATURE:
<223> OTHER INFORMATION: Synthetic: TPP-118 VH

<400> SEQUENCE: 281

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

```
Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115
```

<210> SEQ ID NO 282
<211> LENGTH: 107
<212> TYPE: PRT
<213> ORGANISM: Artificial Sequence
<220> FEATURE:
<223> OTHER INFORMATION: Synthetic: TPP-118 VL

<400> SEQUENCE: 282

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Arg Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Val Glu Ile Lys
            100                 105
```

<210> SEQ ID NO 283
<211> LENGTH: 117
<212> TYPE: PRT
<213> ORGANISM: Artificial Sequence
<220> FEATURE:
<223> OTHER INFORMATION: Synthetic: TPP-120 VH

<400> SEQUENCE: 283

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110
```

```
Val Thr Val Ser Ser
        115


<210> SEQ ID NO 284
<211> LENGTH: 107
<212> TYPE: PRT
<213> ORGANISM: Artificial Sequence
<220> FEATURE:
<223> OTHER INFORMATION: Synthetic: TPP-120 VL

<400> SEQUENCE: 284

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 285
<211> LENGTH: 117
<212> TYPE: PRT
<213> ORGANISM: Artificial Sequence
<220> FEATURE:
<223> OTHER INFORMATION: Synthetic: TPP-121 VH

<400> SEQUENCE: 285

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Arg Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 286
<211> LENGTH: 107
<212> TYPE: PRT
<213> ORGANISM: Artificial Sequence
<220> FEATURE:
<223> OTHER INFORMATION: Synthetic: TPP-121 VL

<400> SEQUENCE: 286
```

-continued

```
Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 287
<211> LENGTH: 117
<212> TYPE: PRT
<213> ORGANISM: Artificial Sequence
<220> FEATURE:
<223> OTHER INFORMATION: Synthetic: TPP-122 VH

<400> SEQUENCE: 287

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Thr Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 288
<211> LENGTH: 107
<212> TYPE: PRT
<213> ORGANISM: Artificial Sequence
<220> FEATURE:
<223> OTHER INFORMATION: Synthetic: TPP-122 VL

<400> SEQUENCE: 288

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Arg Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Leu Gln Tyr Asp Glu Phe Pro Tyr
85 90 95

Thr Phe Gly Gln Gly Thr Lys Val Glu Ile Lys
100 105

<210> SEQ ID NO 289
<211> LENGTH: 117
<212> TYPE: PRT
<213> ORGANISM: Artificial Sequence
<220> FEATURE:
<223> OTHER INFORMATION: Synthetic: TPP-123 VH

<400> SEQUENCE: 289

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Thr Gly Gln Gly Leu Glu Trp Met
35 40 45

Gly His Ile Asp Pro Tyr Tyr Gly Ser Ser Asn Tyr Asn Leu Lys Phe
50 55 60

Lys Gly Arg Val Thr Met Thr Arg Asn Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 290
<211> LENGTH: 107
<212> TYPE: PRT
<213> ORGANISM: Artificial Sequence
<220> FEATURE:
<223> OTHER INFORMATION: Synthetic: TPP-123 VL

<400> SEQUENCE: 290

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 291
<211> LENGTH: 117
<212> TYPE: PRT
<213> ORGANISM: Artificial Sequence
<220> FEATURE:
<223> OTHER INFORMATION: Synthetic: TPP-124 VH

<400> SEQUENCE: 291

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Thr Gly Gln Gly Leu Glu Trp Met
35 40 45

Gly His Ile Asp Pro Tyr Tyr Gly Ser Ser Asn Tyr Asn Leu Lys Phe
50 55 60

Lys Gly Arg Val Thr Met Thr Arg Asn Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 292
<211> LENGTH: 107
<212> TYPE: PRT
<213> ORGANISM: Artificial Sequence
<220> FEATURE:
<223> OTHER INFORMATION: Synthetic: TPP-124 VL

<400> SEQUENCE: 292

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Tyr Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 293
<211> LENGTH: 117
<212> TYPE: PRT
<213> ORGANISM: Artificial Sequence
<220> FEATURE:
<223> OTHER INFORMATION: Synthetic: TPP-125 VH

<400> SEQUENCE: 293

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Asp Tyr
20 25 30

Ile Ile Leu Trp Val Arg Gln Ala Thr Gly Gln Gly Leu Glu Trp Met
35 40 45

Gly His Ile Asp Pro Tyr Tyr Gly Ser Ser Asn Tyr Asn Leu Lys Phe
50 55 60

Lys Gly Arg Val Thr Met Thr Arg Asn Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 294
<211> LENGTH: 107
<212> TYPE: PRT
<213> ORGANISM: Artificial Sequence
<220> FEATURE:
<223> OTHER INFORMATION: Synthetic: TPP-125 VL

<400> SEQUENCE: 294

Asp Ile Gln Met Thr Gln Ser Pro Ser Ser Val Ser Ala Ser Val Gly
1 5 10 15

Asp Arg Val Thr Ile Thr Cys Lys Ala Ser Gln Asp Ile Asn Ser Tyr
20 25 30

Leu Ser Trp Tyr Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 295
<211> LENGTH: 117
<212> TYPE: PRT
<213> ORGANISM: Artificial Sequence
<220> FEATURE:
<223> OTHER INFORMATION: Synthetic: TPP-126 VH

<400> SEQUENCE: 295

Glu Val Gln Leu Val Gln Ser Gly Ala Glu Val Lys Lys Pro Gly Glu
1 5 10 15

Ser Leu Arg Ile Ser Cys Lys Gly Ser Gly Tyr Ser Phe Thr Asp Tyr
20 25 30

Ile Ile Leu Trp Val Arg Gln Met Pro Gly Lys Gly Leu Glu Trp Met
35 40 45

Gly His Ile Asp Pro Tyr Tyr Gly Ser Ser Asn Tyr Asn Leu Lys Phe
50 55 60

Lys Gly His Val Thr Ile Ser Ala Asp Lys Ser Ile Ser Thr Ala Tyr
65 70 75 80

Leu Gln Trp Ser Ser Leu Lys Ala Arg Thr Pro Pro Cys Ile Thr Val
85 90 95

Arg Asp Ser Lys Arg Asp Tyr Phe Asp Tyr Trp Gly Gln Gly Thr Leu
100 105 110

Val Thr Val Ser Ser
115

<210> SEQ ID NO 296
<211> LENGTH: 107
<212> TYPE: PRT
<213> ORGANISM: Artificial Sequence
<220> FEATURE:
<223> OTHER INFORMATION: Synthetic: TPP-126 VL

<400> SEQUENCE: 296

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Arg Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Val Glu Ile Lys
            100                 105
```

<210> SEQ ID NO 297
<211> LENGTH: 117
<212> TYPE: PRT
<213> ORGANISM: Artificial Sequence
<220> FEATURE:
<223> OTHER INFORMATION: Synthetic: TPP-127 VH

<400> SEQUENCE: 297

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Asp Tyr
            20                  25                  30

Ile Ile Leu Trp Val Arg Gln Met Pro Gly Lys Gly Leu Glu Trp Met
        35                  40                  45

Gly His Ile Asp Pro Tyr Tyr Gly Ser Ser Asn Tyr Asn Leu Lys Phe
    50                  55                  60

Lys Gly His Val Thr Ile Ser Ala Asp Lys Ser Ile Ser Thr Ala Tyr
65                  70                  75                  80

Leu Gln Trp Ser Ser Leu Lys Ala Arg Thr Pro Pro Cys Ile Thr Val
                85                  90                  95

Arg Asp Ser Lys Arg Asp Tyr Phe Asp Tyr Trp Gly Gln Gly Thr Leu
            100                 105                 110

Val Thr Val Ser Ser
        115
```

<210> SEQ ID NO 298
<211> LENGTH: 107
<212> TYPE: PRT
<213> ORGANISM: Artificial Sequence
<220> FEATURE:
<223> OTHER INFORMATION: Synthetic: TPP-127 VL

<400> SEQUENCE: 298

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30
```

```
Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105
```

<210> SEQ ID NO 299
<211> LENGTH: 117
<212> TYPE: PRT
<213> ORGANISM: Artificial Sequence
<220> FEATURE:
<223> OTHER INFORMATION: Synthetic: TPP-128 VH

<400> SEQUENCE: 299

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Asp Tyr
            20                  25                  30

Ile Ile Leu Trp Val Arg Gln Met Pro Gly Lys Gly Leu Glu Trp Met
        35                  40                  45

Gly His Ile Asp Pro Tyr Tyr Gly Ser Ser Asn Tyr Asn Leu Lys Phe
    50                  55                  60

Lys Gly His Val Thr Ile Ser Ala Asp Lys Ser Ile Ser Thr Ala Tyr
65                  70                  75                  80

Leu Gln Trp Ser Ser Leu Lys Ala Arg Thr Pro Pro Cys Ile Thr Val
                85                  90                  95

Arg Asp Ser Lys Arg Asp Tyr Phe Asp Tyr Trp Gly Gln Gly Thr Leu
            100                 105                 110

Val Thr Val Ser Ser
        115
```

<210> SEQ ID NO 300
<211> LENGTH: 107
<212> TYPE: PRT
<213> ORGANISM: Artificial Sequence
<220> FEATURE:
<223> OTHER INFORMATION: Synthetic: TPP-128 VL

<400> SEQUENCE: 300

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gln Gly Thr Lys Leu Glu Ile Lys
```

```
            100                 105


<210> SEQ ID NO 301
<211> LENGTH: 117
<212> TYPE: PRT
<213> ORGANISM: Artificial Sequence
<220> FEATURE:
<223> OTHER INFORMATION: Synthetic: TPP-129 VH

<400> SEQUENCE: 301

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Asp Tyr
            20                  25                  30

Ile Ile Leu Trp Val Arg Gln Met Pro Gly Lys Gly Leu Glu Trp Met
        35                  40                  45

Gly His Ile Asp Pro Tyr Tyr Gly Ser Ser Asn Tyr Asn Leu Lys Phe
    50                  55                  60

Lys Gly His Val Thr Ile Ser Ala Asp Lys Ser Ile Ser Thr Ala Tyr
65                  70                  75                  80

Leu Gln Trp Ser Ser Leu Lys Ala Arg Thr Pro Pro Cys Ile Thr Val
                85                  90                  95

Arg Asp Ser Lys Arg Asp Tyr Phe Asp Tyr Trp Gly Gln Gly Thr Leu
            100                 105                 110

Val Thr Val Ser Ser
        115


<210> SEQ ID NO 302
<211> LENGTH: 107
<212> TYPE: PRT
<213> ORGANISM: Artificial Sequence
<220> FEATURE:
<223> OTHER INFORMATION: Synthetic: TPP-129 VL

<400> SEQUENCE: 302

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 303
<211> LENGTH: 117
<212> TYPE: PRT
<213> ORGANISM: Artificial Sequence
<220> FEATURE:
<223> OTHER INFORMATION: Synthetic: TPP-130 VH

<400> SEQUENCE: 303

Gln Met Gln Leu Val Gln Ser Gly Ala Glu Val Lys Lys Thr Gly Ser
1               5                   10                  15
```

```
Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Ala Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 304
<211> LENGTH: 107
<212> TYPE: PRT
<213> ORGANISM: Artificial Sequence
<220> FEATURE:
<223> OTHER INFORMATION: Synthetic: TPP-130 VL

<400> SEQUENCE: 304

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Arg Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Val Glu Ile Lys
            100                 105


<210> SEQ ID NO 305
<211> LENGTH: 117
<212> TYPE: PRT
<213> ORGANISM: Artificial Sequence
<220> FEATURE:
<223> OTHER INFORMATION: Synthetic: TPP-131 VH

<400> SEQUENCE: 305

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Ala Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
```

```
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 306
<211> LENGTH: 107
<212> TYPE: PRT
<213> ORGANISM: Artificial Sequence
<220> FEATURE:
<223> OTHER INFORMATION: Synthetic: TPP-131 VL

<400> SEQUENCE: 306

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 307
<211> LENGTH: 117
<212> TYPE: PRT
<213> ORGANISM: Artificial Sequence
<220> FEATURE:
<223> OTHER INFORMATION: Synthetic: TPP-132 VH

<400> SEQUENCE: 307

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Ala Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 308
<211> LENGTH: 107
<212> TYPE: PRT
<213> ORGANISM: Artificial Sequence
<220> FEATURE:
```

<223> OTHER INFORMATION: Synthetic: TPP-132 VL

<400> SEQUENCE: 308

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Tyr Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 309
<211> LENGTH: 117
<212> TYPE: PRT
<213> ORGANISM: Artificial Sequence
<220> FEATURE:
<223> OTHER INFORMATION: Synthetic: TPP-133 VH

<400> SEQUENCE: 309

Gln Met Gln Leu Val Gln Ser Gly Ala Glu Val Lys Lys Thr Gly Ser
1 5 10 15

Ser Val Lys Val Ser Cys Lys Ala Ser Gly Tyr Ser Phe Thr Asp Tyr
20 25 30

Ile Ile Leu Trp Val Arg Gln Ala Pro Gly Gln Ala Leu Glu Trp Met
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Arg Ser Met Ser Thr Ala Tyr
65 70 75 80

Met Glu Leu Ser Ser Leu Arg Ser Glu Asp Thr Ala Met Tyr Tyr Cys
85 90 95

Ala Arg Ser Lys Arg Asp Tyr Phe Asp Tyr Trp Gly Gln Gly Thr Leu
100 105 110

Val Thr Val Ser Ser
115

<210> SEQ ID NO 310
<211> LENGTH: 107
<212> TYPE: PRT
<213> ORGANISM: Artificial Sequence
<220> FEATURE:
<223> OTHER INFORMATION: Synthetic: TPP-133 VL

<400> SEQUENCE: 310

Asp Ile Gln Met Thr Gln Ser Pro Ser Ser Val Ser Ala Ser Val Gly
1 5 10 15

Asp Arg Val Thr Ile Thr Cys Lys Ala Ser Gln Asp Ile Asn Ser Tyr
20 25 30

Leu Ser Trp Tyr Gln Gln Lys Pro Gly Lys Ala Pro Lys Leu Leu Ile
35 40 45

Tyr Arg Ala Asn Arg Leu Val Asp Gly Val Pro Ser Arg Phe Ser Gly

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 311
<211> LENGTH: 117
<212> TYPE: PRT
<213> ORGANISM: Artificial Sequence
<220> FEATURE:
<223> OTHER INFORMATION: Synthetic: TPP-134 VH

<400> SEQUENCE: 311

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Arg Gly Gln Arg Leu Glu Trp Ile
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Ser Lys Arg Asp Tyr Phe Asp Tyr Trp Gly Gln Gly Thr Leu
            100                 105                 110

Val Thr Val Ser Ser
        115


<210> SEQ ID NO 312
<211> LENGTH: 107
<212> TYPE: PRT
<213> ORGANISM: Artificial Sequence
<220> FEATURE:
<223> OTHER INFORMATION: Synthetic: TPP-134 VL

<400> SEQUENCE: 312

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Arg Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Val Glu Ile Lys
            100                 105


<210> SEQ ID NO 313
<211> LENGTH: 117
```

<212> TYPE: PRT
<213> ORGANISM: Artificial Sequence
<220> FEATURE:
<223> OTHER INFORMATION: Synthetic: TPP-135 VH

<400> SEQUENCE: 313

Gln Met Gln Leu Val Gln Ser Gly Pro Glu Val Lys Lys Pro Gly Thr
1 5 10 15

Ser Val Lys Val Ser Cys Lys Ala Ser Gly Tyr Ser Phe Thr Asp Tyr
20 25 30

Ile Ile Leu Trp Val Arg Gln Ala Arg Gly Gln Arg Leu Glu Trp Ile
35 40 45

Gly His Ile Asp Pro Tyr Tyr Gly Ser Ser Asn Tyr Asn Leu Lys Phe
50 55 60

Lys Gly Arg Val Thr Ile Thr Arg Asp Met Ser Thr Ser Thr Ala Tyr
65 70 75 80

Met Glu Leu Ser Ser Leu Arg Ser Glu Asp Thr Ala Val Tyr Tyr Cys
85 90 95

Ala Ala Ser Lys Arg Asp Tyr Phe Asp Tyr Trp Gly Gln Gly Thr Leu
100 105 110

Val Thr Val Ser Ser
115

<210> SEQ ID NO 314
<211> LENGTH: 107
<212> TYPE: PRT
<213> ORGANISM: Artificial Sequence
<220> FEATURE:
<223> OTHER INFORMATION: Synthetic: TPP-135 VL

<400> SEQUENCE: 314

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Ser Tyr
20 25 30

Leu Ser Trp Phe Gln Gln Lys Pro Gly Lys Ala Pro Lys Ser Leu Ile
35 40 45

Tyr Arg Ala Asn Arg Leu Val Asp Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Tyr Asp Glu Phe Pro Tyr
85 90 95

Thr Phe Gly Gln Gly Thr Lys Leu Glu Ile Lys
100 105

<210> SEQ ID NO 315
<211> LENGTH: 117
<212> TYPE: PRT
<213> ORGANISM: Artificial Sequence
<220> FEATURE:
<223> OTHER INFORMATION: Synthetic: TPP-136 VH

<400> SEQUENCE: 315

Gln Met Gln Leu Val Gln Ser Gly Pro Glu Val Lys Lys Pro Gly Thr
1 5 10 15

Ser Val Lys Val Ser Cys Lys Ala Ser Gly Tyr Ser Phe Thr Asp Tyr
20 25 30

Ile Ile Leu Trp Val Arg Gln Ala Arg Gly Gln Arg Leu Glu Trp Ile

```
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Ser Lys Arg Asp Tyr Phe Asp Tyr Trp Gly Gln Gly Thr Leu
            100                 105                 110

Val Thr Val Ser Ser
        115


<210> SEQ ID NO 316
<211> LENGTH: 107
<212> TYPE: PRT
<213> ORGANISM: Artificial Sequence
<220> FEATURE:
<223> OTHER INFORMATION: Synthetic: TPP-136 VL

<400> SEQUENCE: 316

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 317
<211> LENGTH: 117
<212> TYPE: PRT
<213> ORGANISM: Artificial Sequence
<220> FEATURE:
<223> OTHER INFORMATION: Synthetic: TPP-137 VH

<400> SEQUENCE: 317

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Arg Gly Gln Arg Leu Glu Trp Ile
        35                  40                  45

Gly His Ile Asp Pro Tyr Tyr Gly Ser Ser Asn Tyr Asn Leu Lys Phe
    50                  55                  60

Lys Gly Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Ser Lys Arg Asp Tyr Phe Asp Tyr Trp Gly Gln Gly Thr Leu
            100                 105                 110
```

```
Val Thr Val Ser Ser
        115


<210> SEQ ID NO 318
<211> LENGTH: 107
<212> TYPE: PRT
<213> ORGANISM: Artificial Sequence
<220> FEATURE:
<223> OTHER INFORMATION: Synthetic: TPP-137 VL

<400> SEQUENCE: 318

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 319
<211> LENGTH: 117
<212> TYPE: PRT
<213> ORGANISM: Artificial Sequence
<220> FEATURE:
<223> OTHER INFORMATION: Synthetic: TPP-138 VH

<400> SEQUENCE: 319

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 320
<211> LENGTH: 107
<212> TYPE: PRT
<213> ORGANISM: Artificial Sequence
<220> FEATURE:
<223> OTHER INFORMATION: Synthetic: TPP-138 VL

<400> SEQUENCE: 320

Asp Ile Gln Met Thr Gln Ser Pro Ser Ser Leu Ser Ala Ser Val Gly
```

```
1               5                   10                  15

Asp Arg Val Thr Ile Thr Cys Lys Ala Ser Gln Asp Ile Asn Ser Tyr
            20                  25                  30

Leu Ser Trp Tyr Gln Arg Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Val Glu Ile Lys
            100                 105


<210> SEQ ID NO 321
<211> LENGTH: 117
<212> TYPE: PRT
<213> ORGANISM: Artificial Sequence
<220> FEATURE:
<223> OTHER INFORMATION: Synthetic: TPP-139 VH

<400> SEQUENCE: 321

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 322
<211> LENGTH: 107
<212> TYPE: PRT
<213> ORGANISM: Artificial Sequence
<220> FEATURE:
<223> OTHER INFORMATION: Synthetic: TPP-139 VL

<400> SEQUENCE: 322

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 323
<211> LENGTH: 117
<212> TYPE: PRT
<213> ORGANISM: Artificial Sequence
<220> FEATURE:
<223> OTHER INFORMATION: Synthetic: TPP-140 VH

<400> SEQUENCE: 323

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115


<210> SEQ ID NO 324
<211> LENGTH: 107
<212> TYPE: PRT
<213> ORGANISM: Artificial Sequence
<220> FEATURE:
<223> OTHER INFORMATION: Synthetic: TPP-140 VL

<400> SEQUENCE: 324

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105


<210> SEQ ID NO 325
<211> LENGTH: 117
<212> TYPE: PRT
<213> ORGANISM: Artificial Sequence
<220> FEATURE:
<223> OTHER INFORMATION: Synthetic: TPP-141 VH
```

-continued

<400> SEQUENCE: 325

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Ser Phe Thr Asp Tyr
            20                  25                  30

Ile Ile Leu Trp Val Arg Gln Ala Pro Gly Gln Gly Leu Glu Trp Met
        35                  40                  45

Gly His Ile Asp Pro Tyr Tyr Gly Ser Ser Asn Tyr Asn Leu Lys Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ser Lys Arg Asp Tyr Phe Asp Tyr Trp Gly Gln Gly Thr Leu
            100                 105                 110

Val Thr Val Ser Ser
        115
```

<210> SEQ ID NO 326
<211> LENGTH: 107
<212> TYPE: PRT
<213> ORGANISM: Artificial Sequence
<220> FEATURE:
<223> OTHER INFORMATION: Synthetic: TPP-141 VL

<400> SEQUENCE: 326

```
Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Tyr Gln Gln Lys Pro Gly Lys Ala Pro Lys Leu Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gln Gly Thr Lys Leu Glu Ile Lys
            100                 105
```